United States Patent [19]
Ueda et al.

[11] Patent Number: 5,272,171
[45] Date of Patent: Dec. 21, 1993

[54] PHOSPHONOOXY AND CARBONATE DERIVATIVES OF TAXOL

[75] Inventors: Yasutsugu Ueda, Clinton; Henry Wong, Durham; Vittorio Farina, West Hartford, all of Conn.; Amarendra Mikkilineni, Easton, Pa.; Dolatrai M. Vyas, Madison; Terrence Doyle, Killingworth, both of Conn.

[73] Assignee: Bristol-Myers Squibb Company, New York, N.Y.

[21] Appl. No.: 981,151

[22] Filed: Nov. 24, 1992

Related U.S. Application Data

[63] Continuation-in-part of Ser. No. 836,621, Feb. 13, 1992, abandoned, and a continuation-in-part of Ser. No. 836,623, Feb. 13, 1992, abandoned.

[51] Int. Cl.$^5$ .................. A61K 31/335; C07D 305/14
[52] U.S. Cl. ..................................... 514/449; 549/60; 549/473; 549/510; 549/511
[58] Field of Search ................ 549/60, 473, 510, 511; 514/449

[56] References Cited

U.S. PATENT DOCUMENTS

| | | | |
|---|---|---|---|
| 4,814,470 | 3/1989 | Colin et al. | 514/449 |
| 4,876,399 | 10/1989 | Holton | 558/817 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,059,699 | 10/1991 | Kingston et al. | 540/511 |
| 5,136,060 | 8/1992 | Holton | 549/510 |

FOREIGN PATENT DOCUMENTS

400971A2 12/1990 European Pat. Off. .
522958A1 1/1993 European Pat. Off. .
524093A1 1/1993 European Pat. Off. .

OTHER PUBLICATIONS

G. I. Georg, et al, "Novel Biologically Active Taxol Analogues: Baccatin III 13-(N-(p-Chlorobenzoyl-)-2'R,3'S)-S'-phenylisoserinate) and Baccatin III 13-(-N-Benzoyl-(2'R,3'S)-3'-(p-chlorophenyl)isoserinate)", Bioorganic & Medical Chemistry Letters, vol. 2, No. 4, pp. 295-298, 1992.

I. Ojima, et al, "Efficient and Practical Asymmetric Synthesis of the Taxol C-13 Side Chain, N-Benzoyl-(2R,3S)-3-phenylisoserine, and Its Analogoues via Chiral 3-Hydroxy-4-aryl-β-lactams through Chiral Ester Enolate-Imine Cyclocondensation", J. Org. Chem., 56, pp. 1681-1683, 1991.

G. I. Georg, et al, "Semisynthesis and Biological Activity of Taxol Analogues: Baccatin III 13-(N-benzoyl-(2'R,3'S)-3'-(p-tolyl)isoserinate), Baccatin III 13-(N-(p-toluoyl)-(2'R,3'S)-3'-phenylisoserinate), Baccatin III 13-(N-benzoyl-(2'R,3'S)-3'-(p-trifluoromethylphenyl)isoserinate), and Baccatin III 13-(-N-(p-trifluoromethylbenzoyl)-(2'R,3'S)-3'--phenylisoserinate)", Bioorganic & Medical Chemistry Letters, vol. 2, No. 12, pp. 1751-1754, 1992.

Robert A. Holton et al, "A Synthesis of Taxusin," Journal of the American Chemical Society, 1988, vol. 110, pp. 6558-6560.

N. F. Magri and D. G. I. Kingston, "Modified Taxols. 2. Oxidation Products of Taxol", J. Org. Chem., 51, pp. 797-802, 1986.

N. F. Magri and D. G. I. Kingston, "Modified Taxols, 4. Synthesis and Biological Activity of Taxols Modified in the Side Chain", Journal of Natural Products, 51, No. 2, pp. 298-306, 1988.

D. G. I. Kingston, et al, "The Chemistry of Taxol, A Clinically Useful Anticancer Agent", Journal of Natural Products, 53, No. 1, pp. 1-12, 1990.

(List continued on next page.)

*Primary Examiner*—C. Warren Ivy
*Assistant Examiner*—Ba K. Trinh
*Attorney, Agent, or Firm*—William T. Han

[57] ABSTRACT

The present invention is directed to novel taxol derivatives useful as anti-tumor agents. Also provided by this invention is pharmaceutical formulations and methods of treating mammalian tumors with the compounds of this invention.

52 Claims, No Drawings

OTHER PUBLICATIONS

H. M. Deutsch, et al, "Synthesis of Congeners and Prodrugs. 3. Water-Soluble Prodrugs of Taxol with Potent Antitumor Activity", J. Med. Chem., 32, pp. 788–792, 1989.

K. L. Amsberry and R. T. Borchardt, "The Lactonization of 2'-Hydroxyhydrocinnamic Acid Amides: A Potential Prodrug or Amines", J. Org. Chem., 55, pp. 5867–5877, 1990.

G. T. Georg, et al, "Synthesis of Biologically Active Taxol Analogues with Modified Phenylisoserine Side Chains", J. Med. Chem., 35, pp. 4230–4237, 1992.

I. Ojima, et al, "New and Efficient Approaches to the Semisynthesis of Taxol and its C-13 Side Chain Analogs by means of B-Lactam Synthon Method", Tetrahedron, 48, No. 34, pp. 6985–7012, 1992.

A. E. Mathew, et al, "Synthesis and Evaluation of Some Water-Soluble Prodrugs and Derivatives of Taxol with Antitumor Activity", J. Med. Chem., 35, pp. 145–151, 1992.

Z. Zhao, et al., "Modified Taxols, 6. [1]Preparation of Water-Solublew Prodrugs of Taxol", Journal of Natural Products, 54, No. 6, pp. 1607–1611, 1991.

PHOSPHONOOXY AND CARBONATE DERIVATIVES OF TAXOL

CROSS REFERENCE

This application is a continuation-in-part of U.S. patent applications Ser. Nos. 07/836,621 now abandoned and 07/836,623 now abandoned, both filed on Feb. 13, 1992, which are herein incorporated by reference in their entirety.

FIELD OF INVENTION

The present invention provides compounds having antitumor activities.

BACKGROUND OF INVENTION

Taxol was first isolated from the stem bark of Western Yew, *Taxus brevifolia* Nut. (Taxaceae) and has the following structure (with the (C)2'-, 1-, 7-, 10- and 13th-positions indicated):

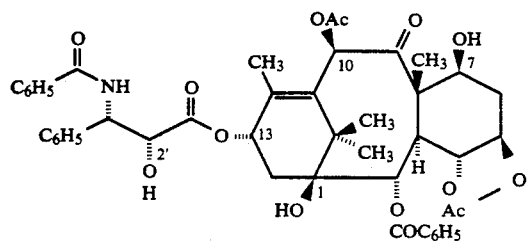

In ongoing clinical trials sponsored by the National Cancer Institute (NCI), taxol has shown promising results in fighting advanced cases of ovarian, breast, and other cancers.

Taxol is unique among antimitotic drugs in that it promotes the assembly of stable microtubules from tubulin even under otherwise unfavorable conditions. The drug binds to microtubules, stabilizing them from depolymerization, thus disrupting the tubulin-microtubule equilibrium and consequently inhibiting mitosis. The mechanism of action, toxicology, clinical efficacy, etc. of taxol are reviewed in a number of articles, such as in the article by Rowinsky et al. in Taxol: A Novel Investigational Antimicrotubule Agent, *J. Natl. Cancer Inst.*, 82: pp 1247-1259 (1990).

Since the discovery of its significant effectiveness in cancer treatment, many laboratories have launched programs to design taxol analogues in search of better pharmacological profiles. Out of such programs, for example, was the discovery of taxotere of the formula

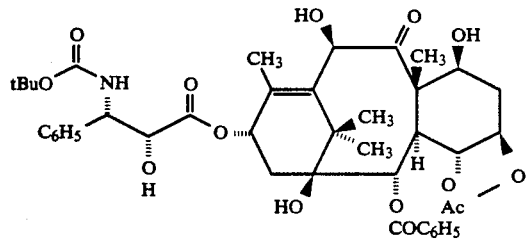

See, Biologically Active Taxol Analogues with Deleted A-Ring Side Chain Substitutents and Variable C-2' Configurations, *J. Med. Chem.*, 34, pp 1176-1184 (1991); Relationships between the Structure of Taxol Analogues and Their Antimitotic Activity, *J. Med. Chem.*, 34, pp 992-998 (1991).

One serious problem associated with taxol is that the compound is only very slightly soluble in water and this low solubility has created significant problems in developing suitable pharmaceutical formulations useful for human therapy. Some formulations for i.v. infusion have been developed which primarily utilize cremophore EL(R) as the drug carrier to overcome low water solubility problems. Cremophore, however, is itself somewhat toxic which could cause idiosyncratic histamine release and anaphylactoid like response. Thus, any improvement to increase water solubility by chemical modification is highly desired.

One approach to make taxol more water soluble has been to derivatize the 2'- and/or 7-hydroxy group with a hydrophilic group resulting in a bioreversible form known as a prodrug. Prodrugs, have been shown to improve the physicochemical (e.g. solubility, lipophilicity, etc.) and biological properties of many compounds. For example, U.S. Pat. No. 4,960,790, issued on Oct. 2, 1990 to Stella et al., discloses taxols with amino acid residues of alanine, leucine, isoleucine, valine, phenylalanine, proline, lysine, arginine or a group of the formula

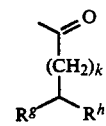

on the 2'- and/or 7-hydroxy group, wherein k is an integer of 1 to 3, and $R^h$ and $R^g$ are each hydrogen or an alkyl radical having from one to three carbon atoms.

Deutsch et al., in Synthesis of Congeners and Prodrugs. 3. Water-Soluble Prodrugs of Taxol with Potent Antitumor Activity, *Journal of Medicinal Chemistry*, 32, No. 4, pp 788-792 (1989), report an analogous approach for enhancing water solubility by derivatizing the 2'- and/or 7-position with a group such as —CO(CH$_2$)$_2$CO$_2$H, —CO(CH$_2$)$_3$CO$_2$H or —CO(CH$_2$)$_3$CONH(CH$_2$)$_3$N(CH$_3$)$_2$. Similarly, U.S. Pat. No. 5,059,699, issued to Kingston and Zhao on Oct. 22, 1991, discloses, inter alia, water soluble 2'-hydroxy derivatized taxols with a radical —CO—CHX—CHX-—SO$_2$O—M, —CO—(CH$_2$)$_s$—CO—NH—(CH$_2$-)$_z$—SO$_2$O—M or —CO—(CH$_2$)$_s$—CO—O—(CH$_2$-)$_z$—OH, wherein X is hydrogen, alkyl or aryl, M is an alkaline metal or hydrogen, s is 1 to 3, and z is 2 to 3.

We have discovered that water solubility of taxol can be increased by attaching a group containing hydrophilic phosphonooxy moiety to the 2'- and/or 7-hydroxy group. One example of such hydrophilic group is 3-(2'-phosphonooxy-4',6'-dimethylphenyl)-3,3-dimethylpropionyl. The use of structurally somewhat related 3-(2'-hydroxy-4',6'-dimethylphenyl)-3,3-dimethylpropionyl amides as potential prodrugs of corresponding amines has been reported by Amsberry et al. in The Lactonization of 2'-Hydroxyhydrocinnamic Acid Amides: A Potential Prodrug for Amines, *Journal of Organic Chemistry*, 55, pp 5867-5877 (1990). However, the use of the instant phosphonooxy containing groups to impart water solubility to taxol drug has never been reported.

There have been reports of other taxol derivatives acylated (as used herein, "acylation" also means the derivatization of a hydroxy group into a carbonate group) at the 2'- and/or 7-position. For example, N. F. Magri et al., in Modified Taxols. 2. Oxidation Products of Taxol, *Journal of Organic Chemistry*, 51, pp 797–802 (1986), disclose 2'-acetyltaxol and 2'-(2,2,2-trichloroethoxycarbonyl)taxol. Moreover, the same authors, in Modified Taxols. 4. Synthesis and Biological Activity of Taxols Modified in the Side Chain, *Journal of Natural Products*, 51, No. 2, pp 298–306 (1988), describe 2',7-diacetyl, 7-acetyl and 2',7-di(2,2,2-trichloroethoxycarbonyl)taxols. 2'-Chloroacetyltaxol has been reported by Kingston et al. in The Chemistry of Taxol, A Clinically Useful Anticancer Agent, *Journal of Natural Products*, 53, No. 1, pp 1–12 (1990). Furthermore, U.S. Pat. No. 5,059,699, issued to Kingston and Zhao on Oct. 22, 1991, discloses, inter alia, 2'-ethenylcarbonyltaxol.

The anti-tumor activities of some 2'- and/or 7-derivatized taxol have been discussed by Kingston et al. in The Chemistry of Taxol, A Clinically Useful Anticancer Agent, *Journal of Natural Products*, 53, No. 1, pp 1–12 (1990). It has been found that 2'-acetyltaxol, which is readily hydrolyzed to the parent taxol, retains respectable anti-tumor activity. On the other hand, it has been noted that taxol derivatives, such as 2'-(t-butyldimethylsilyl)taxol, which lack an accessible 2'-hydroxy group are much less active. It is generally accepted that carbonates are less readily hydrolyzed than their simple acyl counterparts. For example, (methyloxycarbonyl)oxy group is less readily hydrolyzed to the corresponding alcohol than methylcarbonyloxy group. Interestingly enough, we have also discovered that certain carbonate derivatives of taxol possess good anti-tumor activity in spite of the presence of less readily hydrolyzable carbonate groups. It is also the intention of this application to provide carbonate derivatives of taxol and water soluble versions thereof.

SUMMARY OF INVENTION

This invention relates to a taxol derivative of formula I

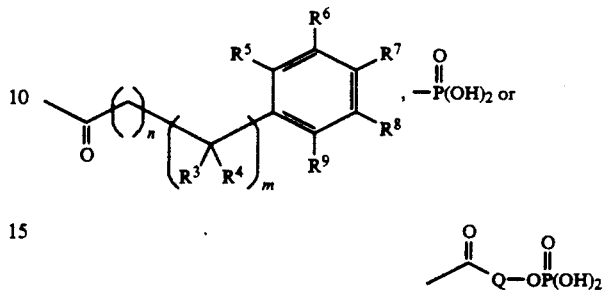

or a pharmaceutically acceptable salt thereof, in which $R^j$ is —COR$^z$ in which R$^z$ is t-butyloxy, C$_{1-6}$ alkyl, C$_{2-6}$ alkenyl, C$_{2-6}$ alkynyl, C$_{3-6}$ cycloalkyl, or phenyl, optionally substituted with one to three same or different C$_{1-6}$ alkyl, C$_{1-6}$ alkoxy, halogen or —CF$_3$ groups;

$R^y$ is C$_{1-6}$ alkyl, C$_{2-6}$ alkenyl, C$_{3-6}$ cycloalkyl, or a radical of the formula —W—R$^x$ in which W is a bond, C$_{2-6}$ alkenediyl, or —(CH$_2$)$_t$—, in which t is one to six; and R$^x$ is naphthyl, furyl, thienyl or phenyl, and furthermore R$^x$ can be optionally substituted with one to three same or different C$_{1-6}$ alkyl, C$_{1-6}$ alkoxy, halogen or —CF$_3$ groups;

$R^w$ is hydrogen, hydroxy, acetyloxy, —OC(=O)OY or —OZ;

$R^1$ is hydrogen, hydroxy, —OC(=O)OY or —OZ;
$R^2$ is hydroxy, —OC(=O)OY, —OC(=O)R or —OZ, with the proviso at least one of $R^1$, $R^2$ or $R^w$ is —OC(=O)OY or —OZ;

R is C$_{1-6}$ alkyl;

Z is of the formula

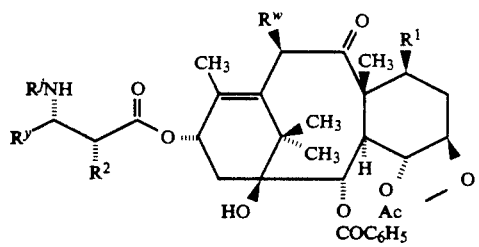

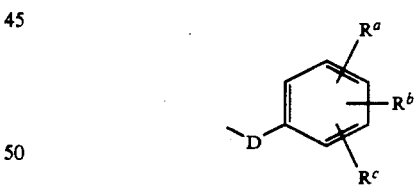

wherein $R^3$ and $R^4$ are independently hydrogen or C$_{1-6}$ alkyl, or $R^3$ and $R^4$ taken together with the carbon atom to which they are attached form C$_{3-6}$ cycloalkylidene;

$R^5$ is —OC(=O)R, —OP=O(OH)$_2$ or —CH$_2$OP=O(OH)$_2$;

$R^6$, $R^7$, $R^8$ and $R^9$ are independently halogen, C$_{1-6}$ alkyl, C$_{1-6}$ alkoxy or hydrogen; or one of $R^6$, $R^7$, $R^8$ and $R^9$ is —OC(=O)R, —OP=O(OH)$_2$ or hydroxy, and the others are independently halogen, C$_{1-6}$ alkyl, C$_{1-6}$ alkoxy or hydrogen; but when $R^5$ is —OC(=O)R, one of $R^6$, $R^7$, $R^8$ or $R^9$ must be —OP=O(OH)$_2$;

Q is —(CH$_2$)$_q$—, optionally substituted with one to six same or different C$_{1-6}$ alkyl or C$_{3-6}$ cycloalkyl, or a carbon atom of said —(CH$_2$)$_q$— group can also be a part of C$_{3-6}$ cycloalkylidene;

q is 2 to 6; n is 0, and m is 1 or 0 when $R^5$ is —CH$_2$OP=O(OH)$_2$; n is 1 or 0, and m is 1 when $R^5$ is —OC(=O)R or —OP=O(OH)$_2$;

Y is C$_{1-6}$ alkyl (optionally substituted with —OP=O(OH)$_2$ or one to six same or different halogen atoms), C$_{3-6}$ cycloalkyl, C$_{2-6}$ alkenyl or a radical of the formula

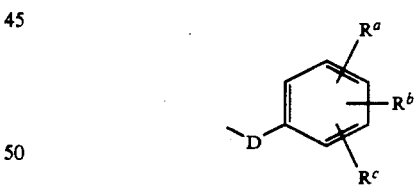

in which

D is a bond or —(CH$_2$)$_t$—, optionally substituted with one to six same or different C$_{1-6}$ alkyl; and R$^a$, R$^b$ and R$^c$ are independently hydrogen, amino, C$_{1-6}$ alkylamino, di-C$_{1-6}$ alkylamino, halogen, C$_{1-6}$ alkyl, or C$_{1-6}$ alkoxy; and with the further proviso that R$^2$ cannot be —OP=O(OH)$_2$; and Y cannot be —CH$_2$CCl$_3$.

Also provided by this invention is pharmaceutical formulations (compositions) and a method of treating mammalian tumors with a compound of formula I.

DETAILED DESCRIPTION OF THE INVENTION

This invention relates to a taxol derivative of formula I

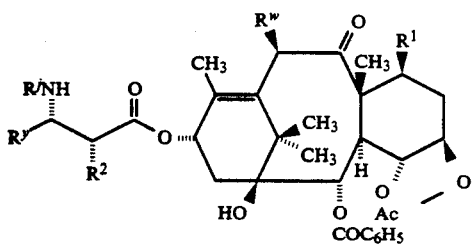

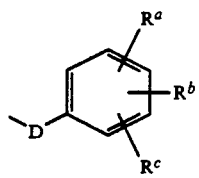

I or a pharmaceutically acceptable salt thereof, in which

R$^j$ is —COR$^z$ in which R$^z$ is t-butyloxy, C$_{1-6}$ alkyl, C$_{2-6}$ alkenyl, C$_{2-6}$ alkynyl, C$_{3-6}$ cycloalkyl, or phenyl, optionally substituted with one to three same or different C$_{1-6}$ alkyl, C$_{1-6}$ alkoxy, halogen or —CF$_3$ groups;

R$^y$ is C$_{1-6}$ alkyl, C$_{2-6}$ alkenyl, C$_{2-6}$ alkynyl, C$_{3-6}$ cycloalkyl, or a radical of the formula —W—R$^x$ in which W is a bond, C$_{2-6}$ alkenediyl, or —(CH$_2$)$_t$—, in which t is one to six; and R$^x$ is naphthyl, furyl, thienyl or phenyl, and furthermore R$^x$ can be optionally substituted with one to three same or different C$_{1-6}$ alkyl, C$_{1-6}$ alkoxy, halogen or —CF$_3$ groups;

R$^w$ is hydrogen, hydroxy, acetyloxy, —OC(=O)OY or —OZ;

R$^1$ is hydrogen, hydroxy, —OC(=O)OY or —OZ;
R$^2$ is hydroxy, —OC(=O)OY, —OC(=O)R or —OZ, with the proviso at least one of R$^1$, R$^2$ or R$^w$ is —OC(=O)OY or —OZ;

R is C$_{1-6}$ alkyl;
Z is of the formula

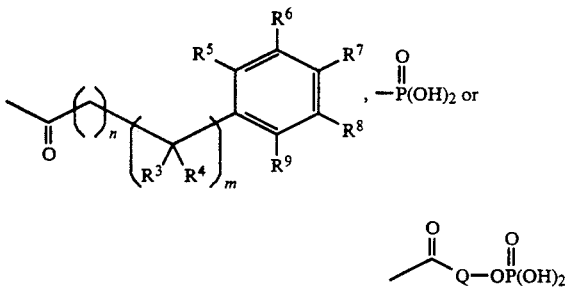

wherein
R$^3$ and R$^4$ are independently hydrogen or C$_{1-6}$ alkyl, or R$^3$ and R$^4$ taken together with the carbon atom to which they are attached form C$_{3-6}$ cycloalkylidene;

R$^5$ is —OC(=O)R, —OP=O(OH)$_2$ or —CH$_2$OP=O(OH)$_2$;

R$^6$, R$^7$, R$^8$ and R$^9$ are independently halogen, C$_{1-6}$ alkyl, C$_{1-6}$ alkoxy or hydrogen; or one of R$^6$, R$^7$, R$^8$ and R$^9$ is —OC(=O)R, —OP=O(OH)$_2$ or hydroxy, and the others are independently halogen, C$_{1-6}$ alkyl, C$_{1-6}$ alkoxy or hydrogen; but when R$^5$ is —OC(=O)R, one of R$^6$, R$^7$, R$^8$ or R$^9$ must be —OP=O(OH)$_2$;

Q is —(CH$_2$)$_q$—, optionally substituted with one to six same or different C$_{1-6}$ alkyl or C$_{3-6}$ cycloalkyl, or a carbon atom of said —(CH$_2$)$_q$— group can also be a part of C$_{3-6}$ cycloalkylidene;

q is 2 to 6; n is 0, and m is 1 or 0 when R$^5$ is —CH$_2$OP=O(OH)$_2$; n is 1 or 0, and m is 1 when R$^5$ is —OC(=O)R or —OP=O(OH)$_2$;

Y is C$_{1-6}$ alkyl (optionally substituted with —OP=O(OH)$_2$ or one to six same or different halogen atoms), C$_{3-6}$ cycloalkyl, C$_{2-6}$ alkenyl, or a radical of the formula $$\begin{array}{c} R^a \\ | \\ \text{—D—} \phantom{xx} R^b \\ | \\ R^c \end{array}$$

in which
D is a bond or —(CH$_2$)$_r$—, optionally substituted with one to six same or different C$_{1-6}$ alkyl; and R$^a$, R$^b$ and R$^c$ are independently hydrogen, amino, C$_{1-6}$ alkylamino, di-C$_{1-6}$ alkylamino, halogen, C$_{1-6}$ alkyl, or C$_{1-6}$ alkoxy; and with the further proviso that R$^2$ cannot be —OP=O(OH)$_2$; and Y cannot be —CH$_2$CCl$_3$.

In the instant application, the numbers in subscript after the symbol "C" define the number of carbon atoms a particular group can contain. For example, C$_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl, or the like alkyl groups; C$_{3-6}$ cycloalkylidene refers to cyclopropylidene, cyclobutylidene, cyclopentylidene or cyclohexylidene; C$_{2-6}$ alkenyl refers to straight or branched alkenyl groups such as vinyl, allyl, 1-propenyl, isopropenyl, 1-butenyl, 2-butenyl, 3-butenyl, methallyl, 1,1-dimethylallyl, 1-hexenyl, 2-hexenyl, or the like groups; C$_{3-6}$ cycloalkyl refers to cyclopropyl, cyclobutyl, cyclopentyl, or cyclohexyl; C$_{2-6}$ alkynyl refers to straight or branched alkynyl groups such as ethynyl, propargyl (2-propynyl), 1-propynyl, 2-butynyl, 3-butynyl, 1-hexynyl, 4-methyl-2-pentynyl, and the like groups; C$_{2-6}$ alkenediyl refers to groups such as ethylene-1,2-diyl (vinylene), 2-methyl-2-butene-1,4-diyl, 2-hexene-1,6-diyl, and the like groups; C$_{1-6}$ alkyloxy (alkoxy) refers to straight or branched alkyloxy groups such as methoxy, ethoxy, n-propoxy, i-propoxy, n-butoxy, t-butoxy (t-butyloxy), n-pentyloxy, n-hexyloxy, or 3-methylpentyloxy, to name a few; di-C$_{1-6}$ alkylamino refers to amino groups with two C$_{1-6}$ alkyl groups in which the two C$_{1-6}$ alkyl substituents may be the same or different, examples include groups such as dimethylamino, N-ethyl-N-methylamino, N-ethyl-N-propylamino, diethylamino, and the like groups; and halogen refers to fluorine, chlorine, bromine, or iodine. In the instant application all symbols once defined retain the same meaning until they are redefined.

Some compounds of formula I may also form pharmaceutically acceptable metal and amine salts in which the cation does not contribute significantly to the toxicity or biological activity of the salt. These salts are also part of the present invention. Suitable metal salts include the sodium, potassium, calcium, barium, zinc, and aluminum salts. The sodium or potassium salts are preferred. Amines which are capable of forming stable salts with the acidic phosphono group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine, or the like pharmaceutically acceptable amines.

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The synthesis of a compound of formula I can be accomplished by a wide variety of methods. The synthetic descriptions and specific examples that follow are only intended for the purpose of illustration, and are not to be construed as limiting in any manner ways to make compounds of the present invention by other methods.

A compound of formula XXXVII can serve as a common intermediate for making certain compounds within the scope of formula I,

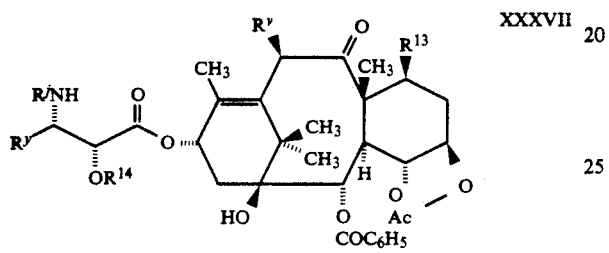

in which $R^v$ is hydrogen, hydroxy or acetyloxy; $R^{13}$ is hydrogen or hydroxy; and $R^{14}$ is hydrogen or —COR, with the proviso that at least one of $R^{13}$, —$OR^{14}$ or $R^v$ is hydroxy. It can be generalized that the reactivity of hydroxy groups (for example, toward an acylating group) in a compound of formula XXXVII in the decreasing order is C(2)'→C(7)→C(10)-. (The hydroxy group on C(1) is virtually unreactive to acylation.) These differences in reactivity among the hydroxy groups can be conveniently exploited to make the compounds of the instant invention. The following Schemes and Examples typify the syntheses of representative compounds. The methods that can be adapted to variations in order to produce other compounds embraced by this invention, but not specifically disclosed, will be obvious to anyone skilled in the art. In the Schemes that follow, preferred $R^y$ is phenyl, and preferred $R^j$ is benzoyl or t-butoxycarbonyl.

In one embodiment, a compound of formula $I^1$ can be made by acylating the 2'-hydroxy group of a compound of formula $XXXVII^1$ with a compound of the formula G—C(=O)OE, and removing $R^{10}$ if any from the product. See Scheme I. (Note: In Scheme I and in the subsequent Schemes, a radical of formula E is equal to a radical of formula Y when the former contains no —OP=O($OR^{10}$)$_2$. Consequently, for example, in Scheme I, if radical E contains no —OP=O($OR^{10}$)$_2$, no removal of $R^{10}$ is necessary to arrive at the compound of formula $I^1$.) The reaction of Step (a) can be conducted in any inert solvent such as methylene chloride, THF, acetonitrile, DMF, benzene, pyridine, p-dioxane, or the like solvents. The reaction is preferably conducted in the presence of a base. Examples of suitable base include triethylamine, N,N-diisopropylethylamine, pyridine, potassium carbonate, 4-dimethylaminopyridine, tetrabutylammonium hydroxide, benzyltriethylammonium hydroxide, etc.

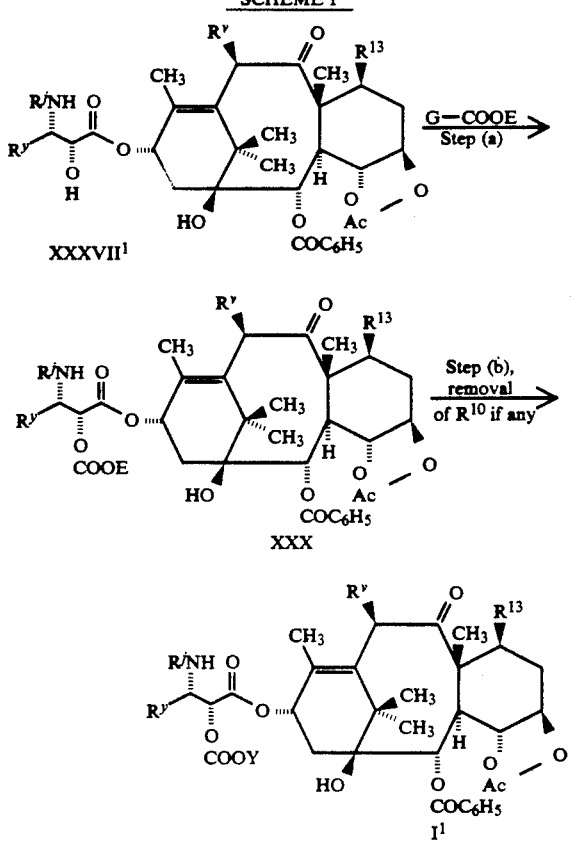

As used herein, G is a typical leaving group such as, but not limited to, chloro, bromo, fluoro or 1-imidazoyl; E is $C_{1-6}$ alkyl (optionally substituted with —OP=O($OR^{10}$)$_2$ or one to six same or different halogen atoms), $C_{3-6}$ cycloalkyl, $C_{2-6}$ alkenyl, or a radical of the formula

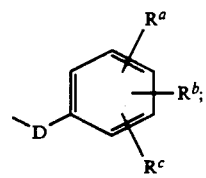

and $R^{10}$ is a conventional phosphonooxy hydroxy protecting group.

As used herein, conventional phosphonooxy hydroxy protecting groups are moieties which can be employed to block or protect the hydroxy function within the phosphonooxy group and they are well known to those skilled in the art. Preferably, said groups are those which can be removed by methods which result in no appreciable destruction to the remaining portion of the molecule. Examples of such readily removable phosphonooxy hydroxy protecting groups include benzyl, 2,2,2,-trichloroethyl or allyl. The removal of benzyl group can be accomplished by catalytic hydrogenolysis; the removal allyl group can be achieved by any one of the metal mediated removal processes well known in the art, such as by palladium tetrakistriphenylphosphine/tributyltin hydride/acetic acid or by sodium or potassium 2-ethylhexanoate/palladium tetrakistriphenylphosphine; and the removal of 2,2,2-trichloroethyl can be accomplished by $Zn/CH_3CO_2H\text{-}MeOH$.

The 7-hydroxy group of a compound of formula $XXX^1$ can be further acylated with a carboxylic acid of formula IX or XXV (an acid of formula IX or XXV is esterified to the 7-hydroxy group) or phosphorylated with an anhydride of formula XXIV,

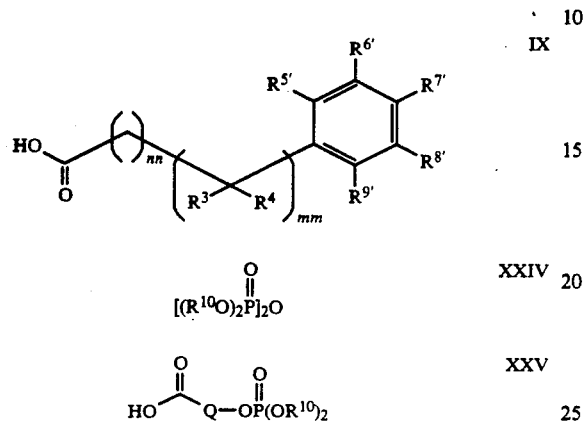

IX $$[(R^{10}O)_2P]_2O \quad XXIV$$

$$HO\overset{O}{\underset{\|}{C}}-Q-\overset{O}{\underset{\|}{O}P}(OR^{10})_2 \quad XXV$$

and subsequent removal of all $R^{10}$ groups from the addition product of formula XXXI affords a compound of formula $I^2$, which is within the scope of formula I compounds. See Scheme II.

SCHEME II

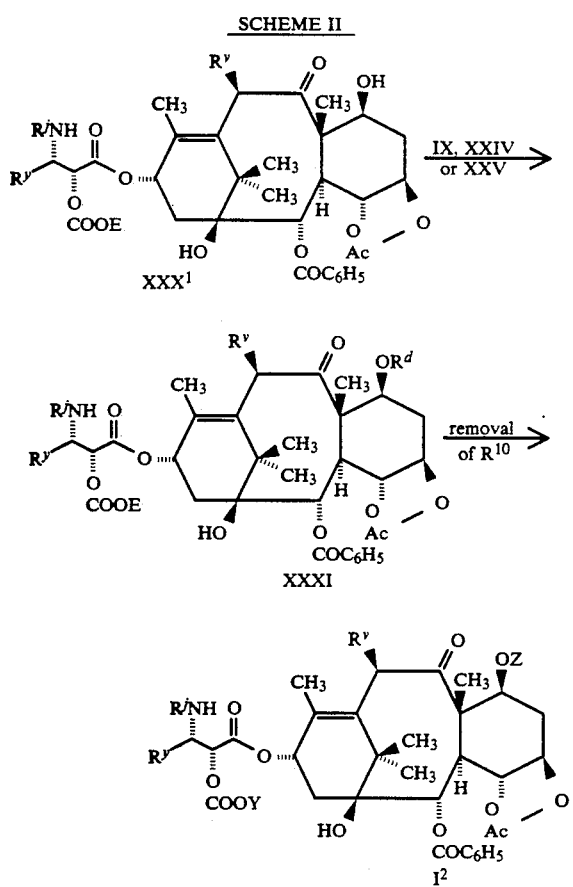

As used herein, $R^d$ is a radical of the formula

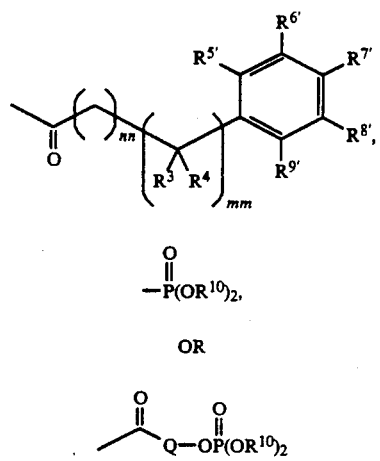

wherein $R^{5'}$ is —OC(=O)R, —OP=O(OR$^{10}$)$_2$ or —CH$_2$OP=O(OR$^{10}$)$_2$; $R^{6'}$, $R^{7'}$, $R^{8'}$ and $R^{9'}$ are independently halogen, $C_{1-6}$ alkyl, $C_{1-6}$ alkoxy or hydrogen; or one of $R^{6'}$, $R^{7'}$, $R^{8'}$ and $R^{9'}$ is —OC(=O)R, —OP=O(OR$^{10}$)$_2$ or hydroxy, and the others are independently halogen, $C_{1-6}$ alkyl, $C_{1-6}$ alkoxy or hydrogen; but when $R^{5'}$ is —OC(=O)R, one of $R^{6'}$, $R^{7'}$, $R^{8'}$ or $R^{9'}$ is —OP=O(OR$^{10}$)$_2$; nn is O, and mm is 1 or 0 when $R^{5'}$ is —CH$_2$OP=O(OR$^{10}$)$_2$; nn is 1 or 0, and mm is 1 when $R^{5'}$ is —OC(=O)R or —OP=O(OR$^{10}$)$_2$.

The art of acylating a hydroxy group with a carboxylic acid is well known in the art. Particularly useful to the present invention are those that employ dehydrating agents such as dicyclohexylcarbodiimide (DCC), alkyl chloroformate and triethylamine, pyridinium salts-Bu$_3$N, phenyl dichlorophosphate, DCC and an aminopyridine, 2-chloro-1,3,5-trinitrobenzene and pyridine, polyphosphate ester, chlorosulfonyl isocyanate, chlorosilanes, MeSO$_2$Cl-triethylamine, Ph$_3$P-CCl$_4$-triethylamine, or N,N'-carbonyldiimidazole, to name a few. References to these reagents can be found in "Advanced Organic Chemistry", 3rd Ed., by Jerry March, pp 348–351 (1985, John Wiley & Sons). More particularly advantageous dehydrating system is comprised of DCC and 4-dimethylaminopyridine (4-DMAP).

The phosphorylation with a compound of formula XXIV is conducted in an inert solvent such as diethyl ether, 1,4-dioxane, diglyme, chloroform, DMF, THF, or methylene chloride, and also in the presence of an amine base such as imidazole, 1H-tetrazole, 4-dimethylaminopyridine, or triethylamine, N,N-diisopropylethylamine, or any other tri(C$_{1-6}$)alkylamines. A stronger base such as lithium diisopropylamide or C$_{1-6}$ alkyl lithium can also be employed.

As a variation of steps in Scheme II, a compound of formula $XXX^1$ can be further reacted with a compound of formula G-COOE, in which E is the same or different radical from radical E of formula $XXX^1$, to afford a compound of formula XLIII and the removal of $R^{10}$, if any, from the product affords an additional compound ($I^7$) within the scope of formula I. See Scheme IIa.

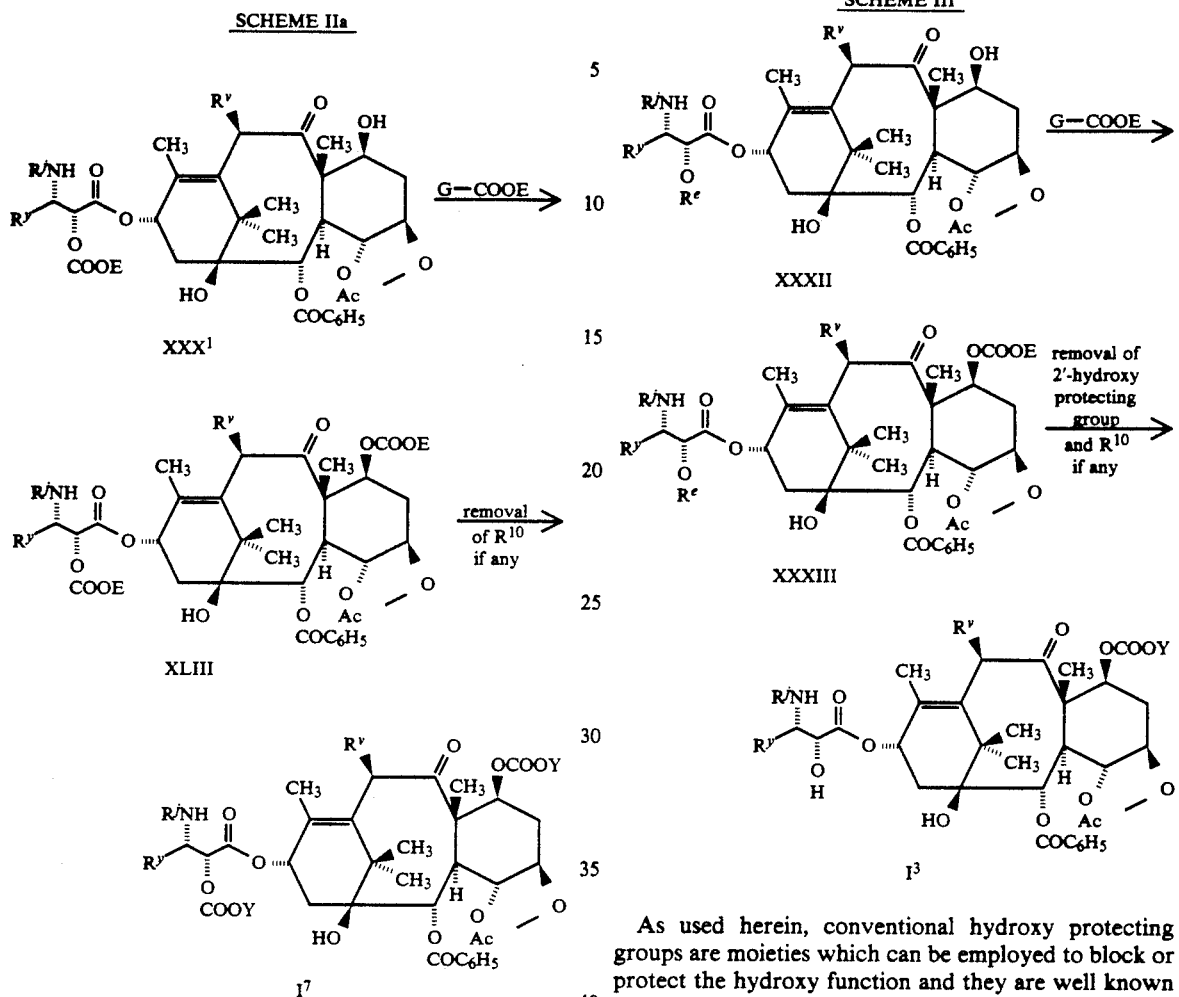

As another embodiment, the 2'-hydroxy group of a compound of formula XXXVII² can be protected with a conventional hydroxy protecting group R$^e$. Subsequent acylation of the 7-hydroxy group with a compound of formula G-COOE and the removal of the hydroxy protecting group R$^e$ and R$^{10}$, if any, affords a compound of formula I³, which is further within the scope of formula I compounds. See Scheme III.

As used herein, conventional hydroxy protecting groups are moieties which can be employed to block or protect the hydroxy function and they are well known to those skilled in the art. Preferably, said groups are those which can be removed by methods which result in no appreciable destruction to the remaining portion of the molecule. Examples of such readily removable hydroxy protecting groups include chloroacetyl, methoxymethyl, 2,2,2-trichloroethyoxymethyl, 2,2,2-trichloroethyloxycarbonyl, tetrahydropyranyl, tetrahydrofuranyl, t-butyl, benzyl, p-nitrobenzyl, p-methoxybenzyl, diphenylmethyl, triC$_{1-6}$alkylsilyl, triphenylsilyl, and the like. Preferred protecting groups for the 2'-hydroxy group of taxol and a derivative thereof are triethylsilyl, 2,2,2-trichloroethyloxycarbonyl and benzyloxycarbonyl; even more preferred group is benzyloxycarbonyl, which can be removed conveniently by catalytic hydrogenolysis. Other suitable protecting groups which can be used are found in Chapter 2 of "Protecting Groups in Organic Synthesis", Second Ed., by Theodora W. Greene and Peter G. M. Wuts (1991, John Wiley & Sons); the disclosure thereof is herein incorporated by reference.

As a further embodiment, a hydroxy protecting group R$^e$ can be removed from a compound of formula XXXIII to afford a compound of formula XXXIV. The 2'-hydroxy group of a compound of formula XXXIV can be acylated with an acid of formula IX or XXV to yield a compound of formula XXXV, and subsequent removal of phosphonooxy protecting groups R$^{10}$ from the product yields a compound of formula I⁴. See Scheme IV. As used herein, $R^f$ is a radical of the formula

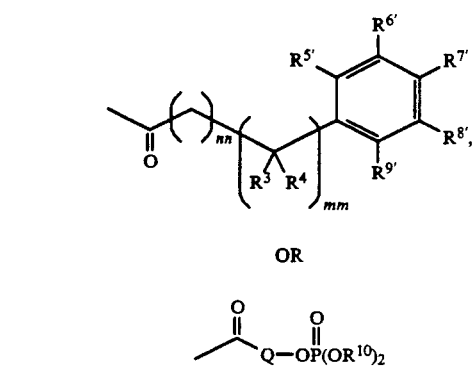

OR

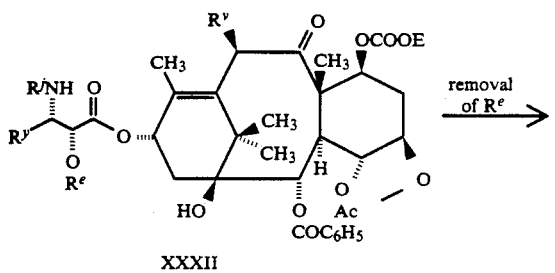

SCHEME IV

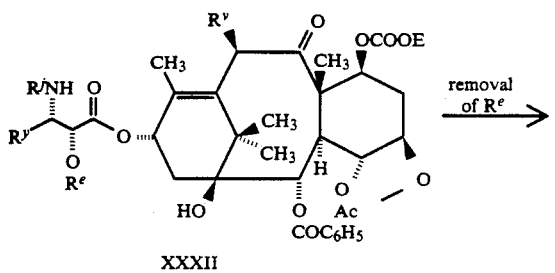

XXXII

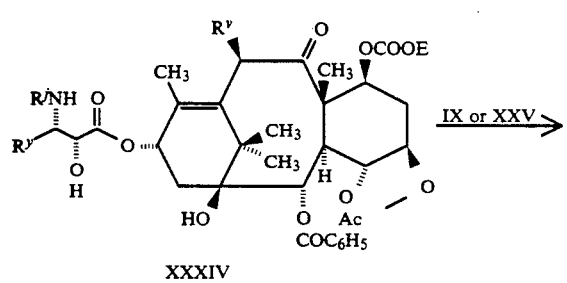

XXXIV

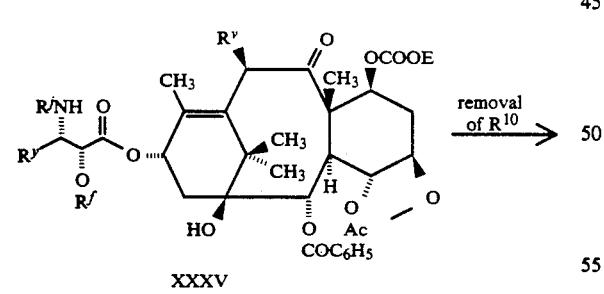

XXXV

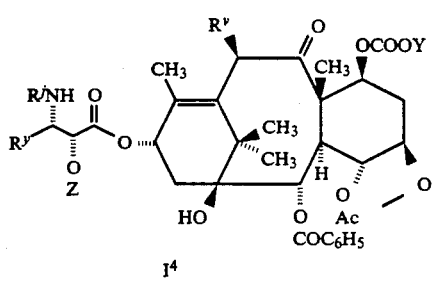

$I^4$

SCHEME V

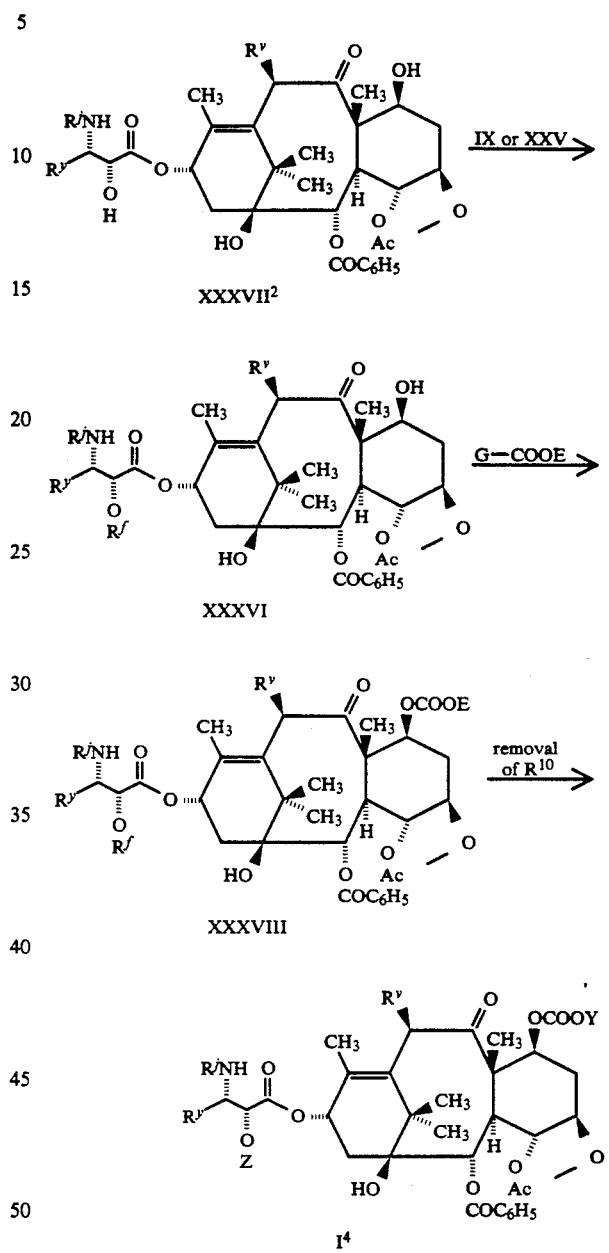

An alternative method of obtaining a compound of formula $I^4$ is through a series of steps as shown in Scheme V. In the Scheme, the 2'-hydroxy group of a compound of formula XXXVII² is acylated with an acid of formula IX or XXV to afford a compound of formula XXXVI. A radical of the formula —COOE is subsequently introduced onto the 7-hydroxy group by acylation with a compound G-COOE to afford a compound of formula XXXVIII. Removal of phosphonooxy protecting groups $R^{10}$ from a compound of formula XXXVIII affords a compound of formula $I^4$.

SCHEME VI

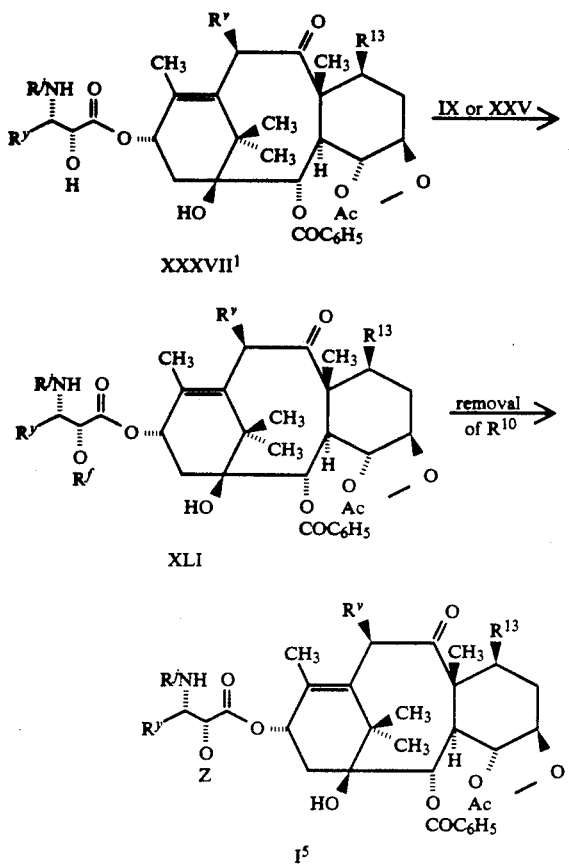

A compound of formula I⁵ can be obtained by acylating the 2'-hydroxy group of a compound of formula XXXVII¹ with an acid of formula IX or XXV to afford a compound of formula XLI and, subsequently, removing $R^{10}$ from a compound of formula XLI. See Scheme VI.

As another variation, the synthesis of a compound of formula I in which $R^1$ and $R^2$ are both identical radicals of formula —OZ (with the proviso that both $R^1$ and $R^2$ are not —OP(=O)(OH)₂) can be made by simultaneous acylation of the 2'- and 7-hydroxy groups in a compound of formula XXXVII² with about two equivalents of an acid of formula IX or XXV, followed by the removal of $R^{10}$ protecting groups. On the other hand, for making a compound of formula I in which $R^1$ and $R^2$ are non-identical radicals of formula —OZ, the acylation of the 2'- and 7-hydroxy groups is preferably effected in a stepwise manner, i.e., by first acylating the 2'-hydroxy group with a compound of formula IX or XXV, followed by phosphorylating the 7-hydroxy group with an anhydride of formula XXIV or acylating the 7-hydroxy group with a different reagent of formula IX or XXV, and further followed by the removal of $R^{10}$ radicals.

Yet as another variant, the 7-hydroxy group of a compound of formula XLII, in which $R^{15}$ is a conventional hydroxy protecting group or —COR, can be acylated with a compound of formula IX or XXV or phosphorylated with an anhydride of formula XXIV to afford a compound of formula XL. Upon removal of 2'-hydroxy protecting group, if any, and $R^{10}$ from a compound of formula XL, a compound of formula I⁶ can be obtained. See Scheme VII.

Similarly, the 7-hydroxy group of a compound of formula XXXVII³ can be reacted with a compound of formula G-COOE to afford a compound of formula XLIV. Upon removal of $R^{10}$, if any, from a compound of formula XLIV, a compound of formula I⁸ can be obtained. See Scheme VIIa.

A compound within the scope of formula I in which $R^w$ is —OZ or —OC(=O)OY can be made from a compound of formula XXXVII⁷ by modification of the earlier described processes which exploits the difference in reactivity of hydroxy groups in a compound of formula XXXVII⁷: the reactivity in the decending order is C(2')→C(7)→C(13)→>C(1)-hydroxy. As an illustration, a compound of formula I⁹ can be made by a process of Scheme VIIb. In the Scheme, the 2'- and 7-hydroxy groups of a compound of formula XXXVII⁷ are protected with a conventional hydroxy protecting group $R^e$. The product of formula LXXVIII is acylated or phosphorylated with a compound of formula IX, XXIV, XXV or G-COOE to afford a compound of formula LXXIX, in which $R^o$ is —OR$^d$ or —OCOOE, from which $R^e$ and $R^{10}$, if any, are removed to afford a compound of formula I⁹, in which $R^r$ is —OZ or —OCOOY.

SCHEME VII

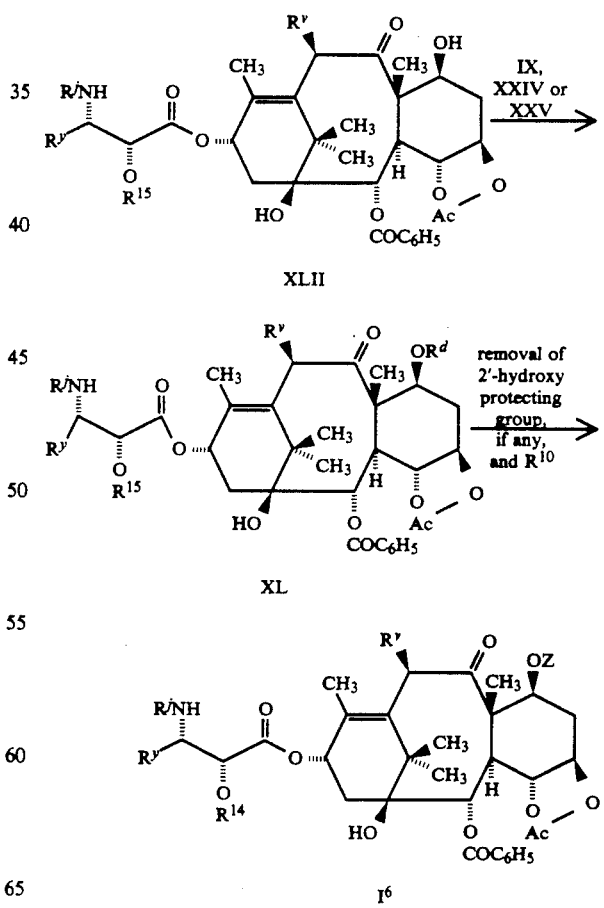

SCHEME VIIa

-continued

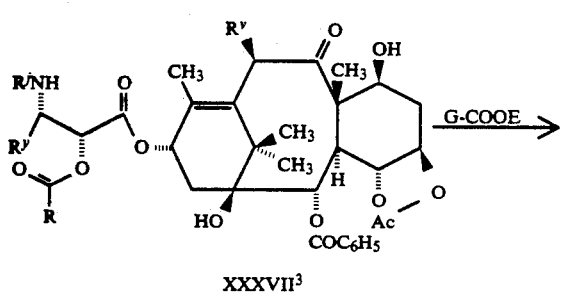

XXXVII³

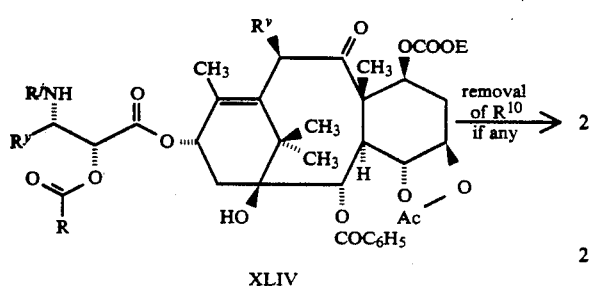

XLIV

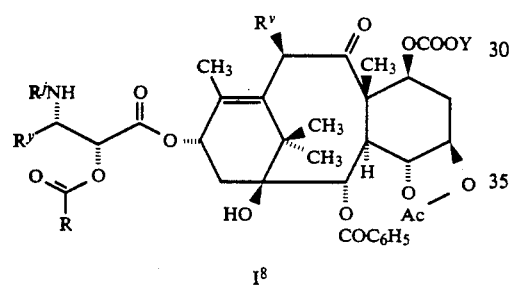

I⁸

SCHEME VIIb

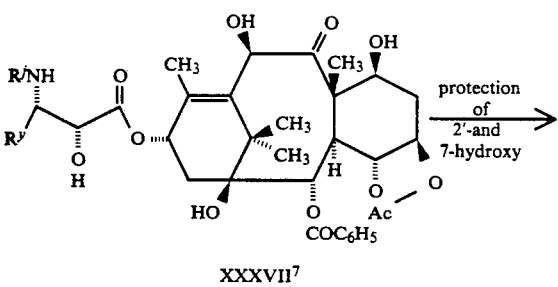

XXXVII⁷

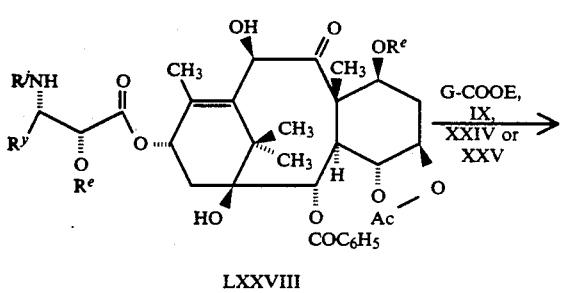

LXXVIII

-continued

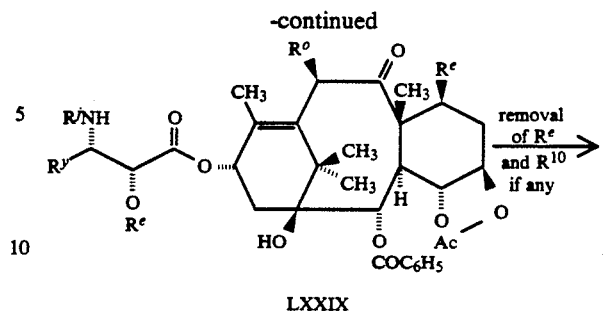

LXXIX

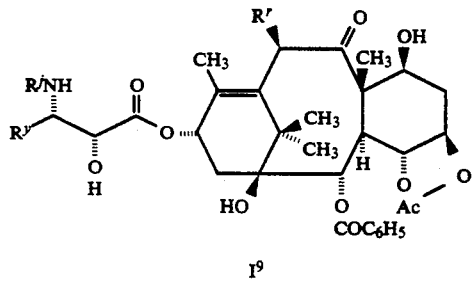

I⁹

It is well within those skilled in the art that when the removal of phosphonooxy protecting groups $R^{10}$ at any step in the foregoing Schemes is conducted in the presence of a base, the corresponding salt of phosphonooxy group can be obtained. For example, the presence of sodium bicarbonate during the removal affords the sodium salt.

The compounds of formulas IX, XXIV and XXV can be made by a wide variety of conventional methods employing conventional starting materials. For example, as a matter of illustration, synthesis of an acid of formula IX', which is within the scope of acids of formula IX, can be made by the sequence of steps as shown in Scheme A. In the Scheme, $R^{6'}$, $R^{7'}$, $R^{8'}$, and $R^{9'}$, preferably, are independently hydrogen or $C_{1-6}$ alkyl.

The methods described by Amsberry et al., *Journal of Organic Chemistry*, 55, pp 5867–5877 (1990), for making certain compounds of formula III and IV in which $R^{6'}$ and $R^{8'}$ are hydrogen, $R^{7'}$ is methyl or hydrogen, and $R^{9'}$ is methyl can be adapted to make additional compounds of formula III and IV. More specifically, Step (a) involves acid promoted transesterification of an acrylic acid ester with a phenol derivative of formula II and subsequent ring cyclization to afford a compound of formula III. The reaction is usually conducted in an inert organic solvent such as benzene, toluene or xylene, and the preferred catalyst is concentrated sulfuric acid. The reaction is normally conducted at an elevated temperature, preferably at or above the boiling point of benzene.

In Step (b), a lactone of formula III is being reduced. The reduction is normally conducted in an inert solvent such as 1,4-dioxane, diglyme, tetrahydrofuran (THF) or diethyl ether. A suitable reducing agent is lithium aluminum hydride. Other metal aluminum hydrides known to reduce lactones to alcohols can be employed as well. Step (c) involves the protection of the free alkylhydroxy group in a compound of formula IV to afford a compound of formula V in which $R^{12}$ (like $R^{e}$) is a conventional hydroxy protecting group. Some examples of conventional hydroxy protecting groups are given above. A more desirable group for $R^{12}$ is t-butyldimethylsilyl. The attachment of t-butyldimethylsilyl group on a hydroxy group can be accomplished by the method described by Corey and Venkateswarlu, in the *J. Amer. Chem. Soc.*, 94, p. 6190 (1972). Or more generally by reacting the hydroxy group with t-butyldimethylsilyl chloride in an inert solvent such as diethyl ether, 1,4-dioxane, diglyme, chloroform, DMF, THF, or methylene chloride, and also in the presence of an amine base such as imidazole, 4-dimethylaminopyridine, or tri($C_{1-6}$)alkylamine, such as triethylamine, N,N-diisopropylethylamine, or any other tri($C_{1-6}$)alkylamines.

In Step (d), the phenolic hydroxy group of a compound of formula V is phosphorylated with a compound of formula XXIV to afford a compound of formula VI in which $R^{10}$ is a phosphonooxy protecting group defined above. A preferred $R^{10}$ radical is benzyl. As an example, the addition of dibenzylphosphono group is effected by reacting a phenolic salt of a compound of formula V with tetrabenzylpyrophosphate that in turn can be made from dibenzylphosphate and about 0.5 equivalent of DCC. Step (d) is normally conducted in an inert aprotic solvent, such as 1,4-dioxane, diglyme, DMF or THF. The cation of the phenolic salt of a compound of formula V can be sodium, potassium, lithium, calcium, benzyltriethylammonium or tetraethylammonium, tetrabutylammonium or any other tetra($C_{1-6}$)alkylammonium cations. The formation of the phenolic salt can be effected by removing the phenolic proton by a base such as $C_{1-6}$alkyl lithium, potassium carbonate, potassium hydroxide, potassium hydride, sodium hydride, sodium hydroxide, sodium carbonate, or a quaternary ammonium hydroxide such as, but not limited to, tetrabutylammonium hydroxide or benzyltriethylammonium hydroxide.

In Step (e), the hydroxy protecting group $R^{12}$ is removed. When $R^{12}$ is t-butyldimethylsilyl, fluoride ion or mineral acid in alcohol or acetonitrile can be used for its removal. The source of fluoride ion can be from tetrabutylammonium fluoride. The removal with fluoride is conducted in an inert solvent such as THF, methylene chloride, 1,4-dioxane, DMF, chloroform, or in the like inert solvent; and preferably the reaction medium is buffered by a weak acid such as acetic acid. An example of mineral acid in alcohol is hydrochloric acid in isopropanol.

Step (f) entails the oxidation of the hydroxy group to the aldehyde group. A wide array of reagents well known to those skilled in the art are available for oxidizing a primary alcohol to an aldehyde, which can also be used to effect Step (f). Some examples include: dipyridine Cr(VI) oxide (Collin's reagent), pyridinium chlorochromate (PCC), pyridinium dichromate (PDC), ceric ammonium nitrate (CAN), $Na_2Cr_2O_7$ in water, N-iodosuccinimide and $Bu_4N^+I^-$, $Ag_2CO_3$-on-Celite, N-methylmorpholine-n-oxide, a Ru complex, etc. References to the aforementioned reagents and to some other reagents for the oxidation can be found in such text as "Advanced Organic Chemistry", 3rd Ed., by Jerry March, pp 1057–1060 and 1081–1082 (1985, John Wiley & Sons). A preferable reagent for Step (f) is pyridinium chlorochromate (PCC) in methylene chloride.

Step (g) involves a further oxidation of an aldehyde of formula VIII into an acid of formula IX'. Many reagents are known to convert an aldehyde to an acid. Some examples include: potassium permanganate, $Ag_2O$-water, m-chloroperbenzoic acid, Jones reagent (chromic and sulfuric acid in water), etc. The oxidation in Step (g) is preferably done using the Jones reagent in acetone.

In a more preferred embodiment, a compound of formula IV can be directly converted to a compound of formula VII by employing the method specified above for Step (d). Furthermore, a compound of formula VII can be directly converted to a compound of formula IX' with the Jones reagent.

As another example, the synthesis of acids of formula IX", within the scope of formula IX compounds, can be made by a series of steps as shown in Scheme B. In the Scheme, $R^{6'}$, $R^{7'}$, and $R^{9'}$ preferably are independently hydrogen or $C_{1-6}$alkyl. In Step (a), a quinone of formula X is reduced to a hydroquinone of formula XI by a standard quinone reduction method such as by employing sodium hydrosulfite. The annulation in Step (b) can be effected using the same or substantially the same condition described for Step (a) of Scheme A. The phenolic hydroxy group in a compound of formula XII is protected in Step (c) to afford a compound of formula XIII. A suitable phenol protecting group $R^{11}$ for the purpose of Step (c) is benzyl. Other well-known phenol protecting groups such as those enumerated in pp. 144–170 of "Protecting Groups in Organic Synthesis", Second Ed., by Theodora W. Greene and Peter G. M. Wuts (1991, John Wiley & Sons), may also be used. The reduction in Step (d) can be conducted in the same or substantially the same manner as described for Step (b) of Scheme A. The protection of the alkyl hydroxy group in a compound of formula XIV with $R^{12}$ is conducted in the same or substantially the same way as described for Step (c) in Scheme A. The phenolic hydroxy group in a compound of formula XV is subsequently acylated in Step (f). The acylation methodologies which are useful to the instant invention have been described hereinabove. In addition, acylation using a carboxylic anhydride of the formula (RC=O)$_2$O can also be particularly useful for Step (f). In Step (g), the phenolic hydroxy protecting group $R^{11}$ is removed. When $R^{11}$ is benzyl, it can be removed by catalytic hydrogenolysis. In Step (h), the conversion of a compound of formula XVII to a compound of formula XVIII can be effected in the same or substantially the same way as described for Step (d) of Scheme A. A preferred $R^{10}$ radical for steps in Scheme B is benzyl. The removal of $R^{12}$ hydroxy protecting group from a compound of formula XVIII can be carried out in the same or substantially the same manner as described for Step (e) of Scheme A. The oxidation of the alcohol group to the carboxylic group in Step (j) can be done with the Jones reagent.

As a further example, the synthesis of acids of formula IX''', within the scope of formula IX compounds, can be made by a series of steps as shown in Scheme C. In the Scheme, $R^{6'}$, $R^{7'}$, $R^{8'}$, and $R^{9'}$ preferably are independently $C_{1-6}$ or hydrogen. The same or substantially the same reaction conditions described for Steps (c) and (e) of Scheme A can be employed to effect Steps (a) and (c), respectively, of Scheme C. For making a compound formula XXII in which $R^{10}$ is allyl or benzyl, a compound of formula XXI can be reacted with bis(allyloxy)(diisopropylamino)phosphine or dibenzyloxy(diisopropylamino)phosphine in the presence of a base, such as 1H-tetrazole [see: Bannwarth and Kunig, *Tetrahedron Letters*, 30, p. 4219 (1989) and Yu and Fraser-Reid, *Tetrahedron Letters*, 29, p. 979 (1988)]; and the resulting addition product is subsequently oxidized, for example by m-chloroperbenzoic acid. The oxidation of Step (d) can be accomplished with the Jones reagent.

As shown in Scheme D, a slight modification of processes of Schemes A, B, and C affords a compound of formulas IX''''. For example, Steps (a), (c) and (d) of Scheme D can be conducted in the same or substantially the same way as Steps (a), (c) and (d) of Scheme C, respectively. Step (b) of Scheme D can be the same or substantially the same as Step (d) of Scheme A.

The synthesis of acids of formula XXV can be achieved by a wide array of methods. For example, as a matter of illustration, a series of steps in Scheme E can be used to make a compound of formula XXV. In the Scheme, one hydroxy group of a diol of formula XXVI is protected with an earlier defined $R^{12}$ radical to afford a compound of formula XXVII; a prefered $R^{12}$ radical is t-butyldimethylsilyl. A phosphonooxy group protected with $R^{10}$ radicals can be introduced by the same or substantially the same method that was described for Step (b) of Scheme C. The same or substantially the same method of Step (e) of Scheme A can be used to remove $R^{12}$ from a compound of formula XXVIII. Oxidation of a compound of formula XXIX using the Jones reagent affords a formula XXV compound.

-continued

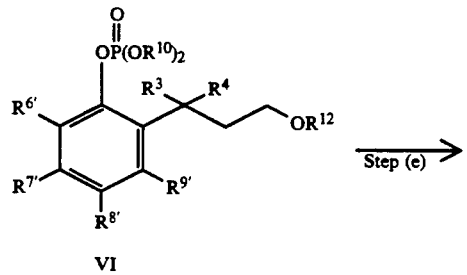
VI

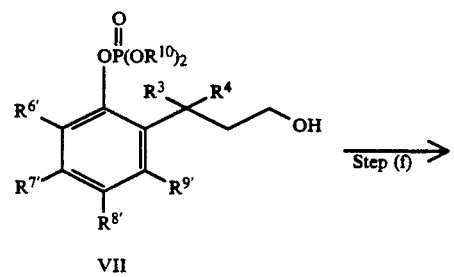
VII

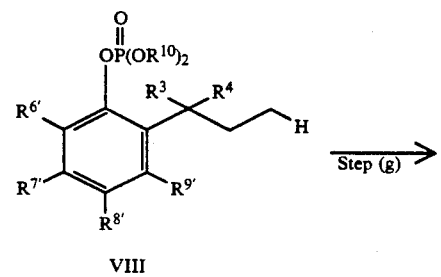
VIII

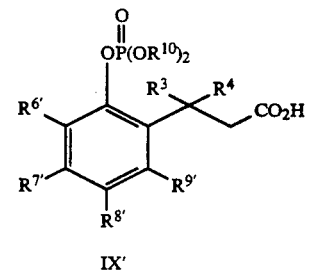
IX'

SCHEME A

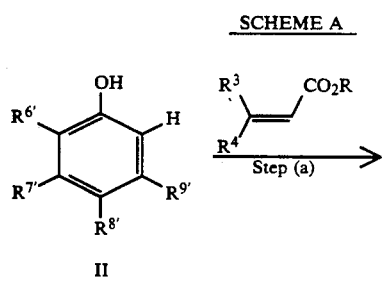
II

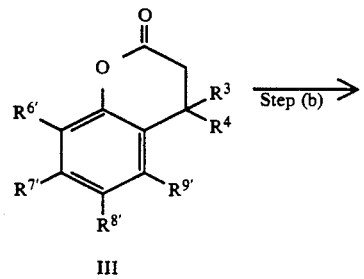
III

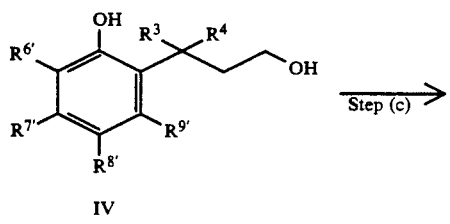
IV

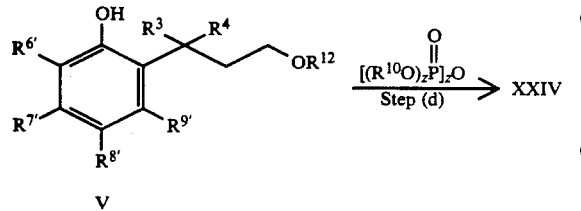
V

SCHEME B

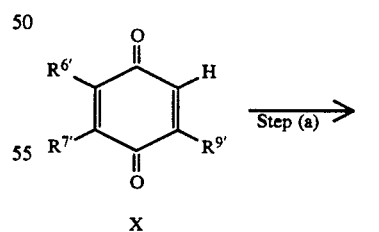
X

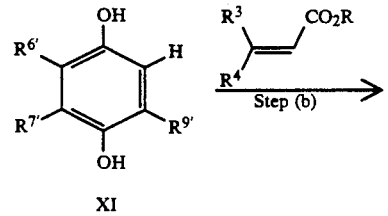
XI

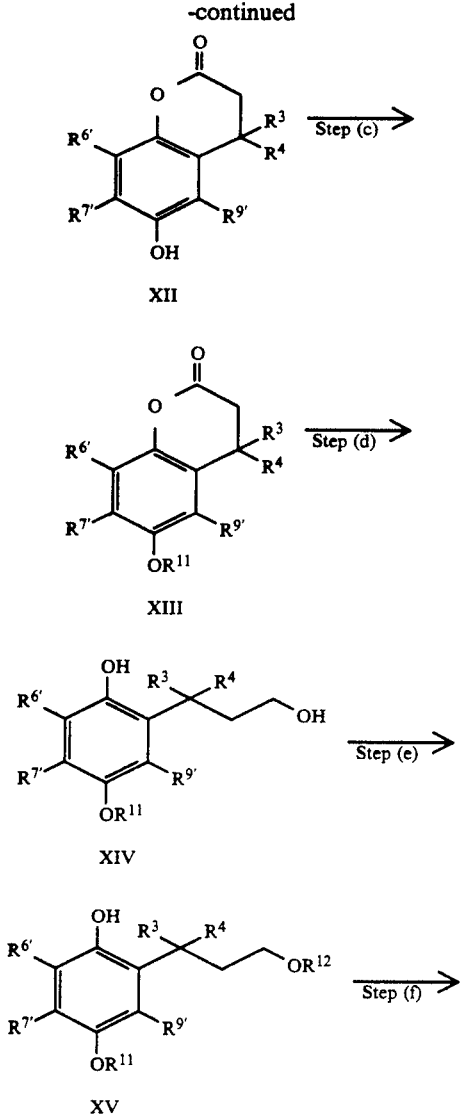
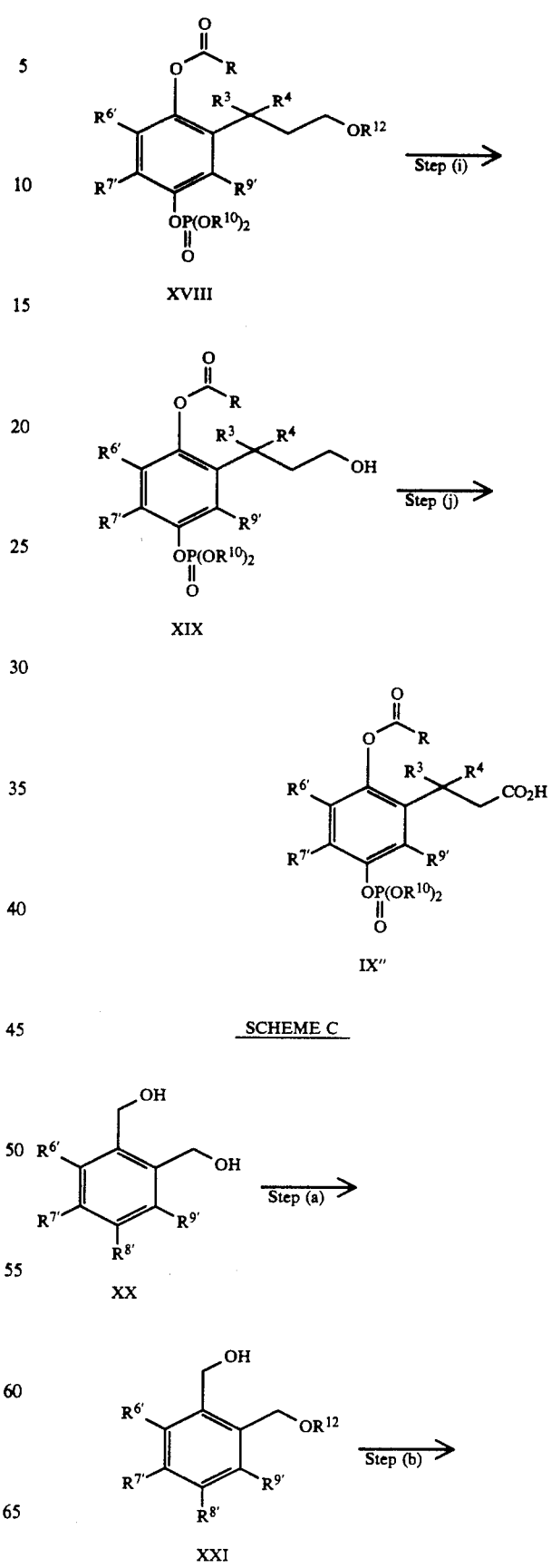
SCHEME C

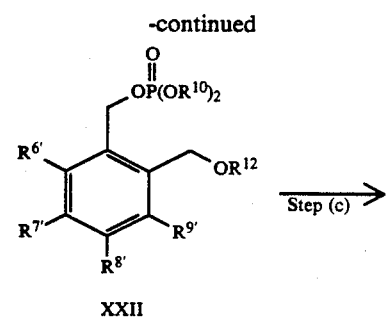

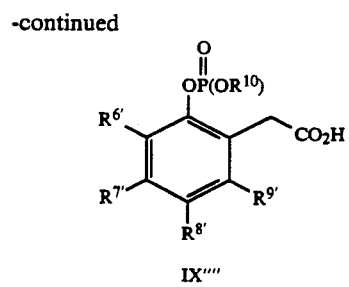

SCHEME E

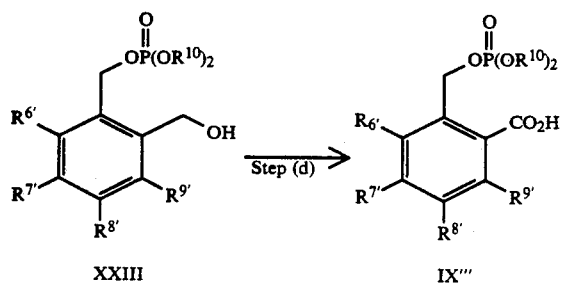

SCHEME D

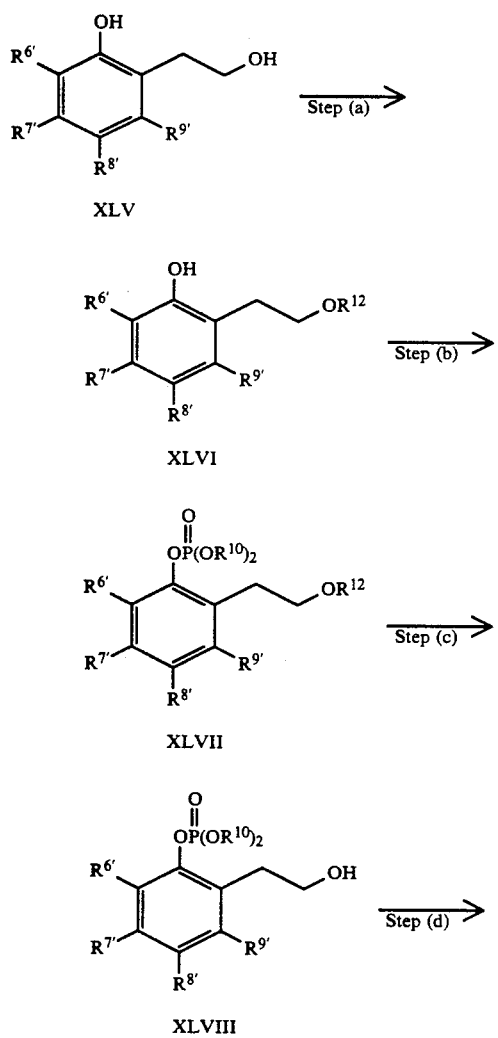

The compounds represented by general formula XXXVII are either already known or can be made by conventional methods employing conventional starting materials. For example, a compound of formula XXXVII in which $R^{14}$ is —COR can be made by acylating the 2'-hydroxy group of a compound of formula XXXVII[1] with an acid RCOOH or a reactive derivative thereof.

A compound of formula XXXVII[4] in which $R^{16}$ is acetyloxy or hydrogen can be made by the process shown in Scheme VIII.

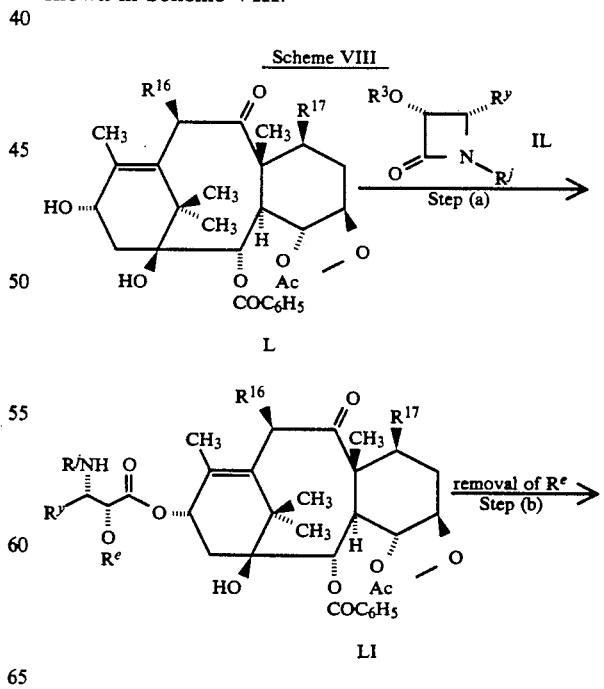

-continued
Scheme VIII

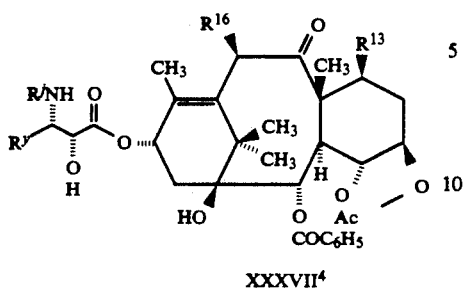

XXXVII⁴

In Step (a) of Scheme VIII, an azetidinone IL is reacted with a compound of formula L (a baccatin III derivative) to afford a compound of formula LI, in which $R^{17}$ is hydrogen or a radical $R^eO-$, wherein $R^e$ is the same or different hydroxy protecting group $R^e$ of formula IL. The general class of azetidinones of formula IL are known. Their syntheses or syntheses of their precursors have been reported such as by Holton in European Patent Application 0,400,971 A2 published on Dec. 5, 1990; by Ojima et al. in *Tetrahedron*, 48, No. 34, pp 6985–7012 (1992); *Journal of Organic Chemistry*, 56, pp 1681–1683 (1991); and *Tetrahedron Letters*, 33, No. 39, pp 5737–5740 (1992); and by Palomo et al. in *Tetrahedron Letters*, 31, No. 44, pp 6429–6432 (1990); all five disclosures are herein incorporated by reference in their entirety. The methods that can be adapted to variations in order to produce other azetidinones within the scope of formula IL, but not specifically disclosed herein or in the above five references or reported elsewhere, will be obvious to anyone skilled in the art. Furthermore, European Patent Application 0,400,971 A2 and *Tetrahedron*, 48, No. 34, pp 6985–7012 (1992) also describe processes whereby the class of azetidinones of formula IL are reacted with (C)13-hydroxy group of baccatin III derivatives or sodium alkoxide thereof to afford taxol analogues with a variety of (C)13-side chains. In Step (a) of Scheme VIII, it is advantageous to convert the hydroxy group on the (C)13-carbon into a metal alkoxide before the coupling. The metal cation of said metal alkoxide is preferably selected from Group Ia or IIa metals. The formation of a desired metal alkoxide may be done by reacting a compound of formula L with a strong metal base, such as lithium diisopropylamide, $C_{1-6}$ alkyllithium, lithium bis(trimethylsilyl)amide, phenyllithium, sodium hydride, potassium hydride, lithium hydride, or the like base. For example when lithium alkoxide is desired, a compound of formula L may be reacted with n-butyllithium in an inert solvent such as tetrahydrofuran. Removal of $R^e$ from a compound of formula LI in Step (b), affords a compound of formula XXXVII⁴. The process of Scheme VIII can be readily adapted to make other compounds within the scope of formula XXXVII.

The numbering on a baccatin III derivative of formula L as used in this application is as follows:

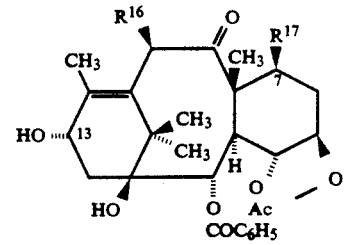

L

As a further illustration, a compound of formula XXXVII⁵ can be made by a process of Scheme IX. In Step (a), when a compound of formula XXXVII⁶ is treated with about one and half to two equivalents of a conventional hydroxy protecting reagent, preferably trichloroethyl chloroformate, a compound of formula LII is obtained. A compound of formula LII is subsequently reacted with 1,1,2-trifluoro-2-chlorotriethylamine in Step (b) to afford a dieneone of formula LIII. In Step (c), protecting groups $R^e$ are removed. (The removal of trichloroethyloxycarbonyl group can be done by zinc dust in acetic acid.) In Step (d), the diene moiety of a compound of formula LIV is catalytically hydrogenated to afford a compound of formula XXXVII⁵.

SCHEME IX

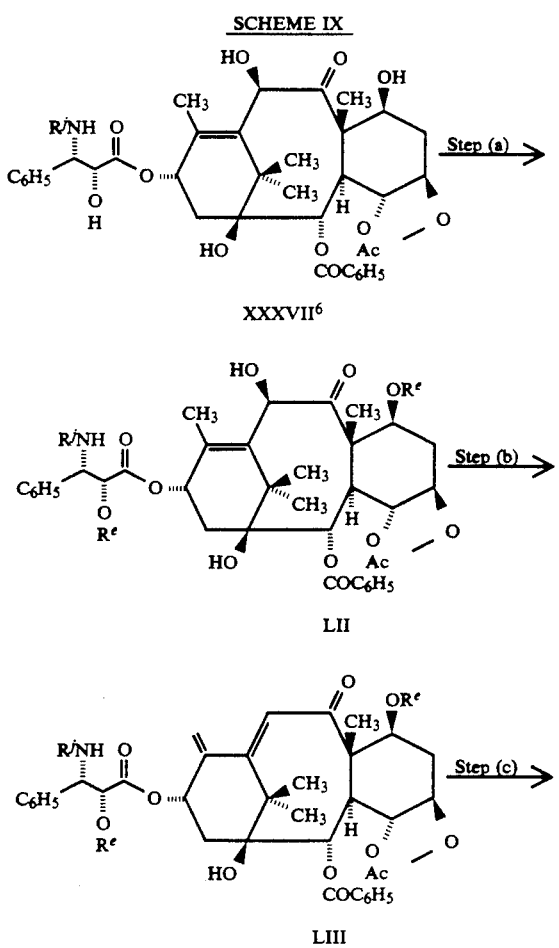

-continued
SCHEME IX

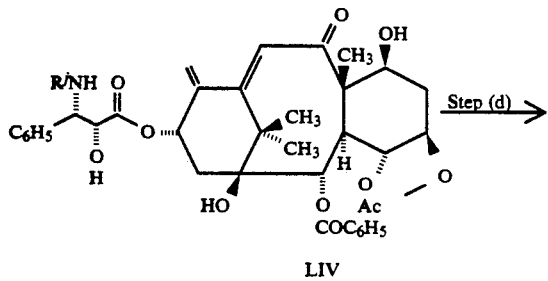
LIV

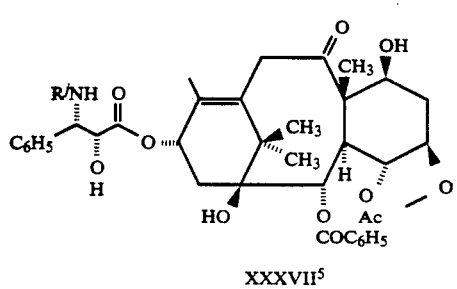
XXXVII[5]

Scheme VIIIa

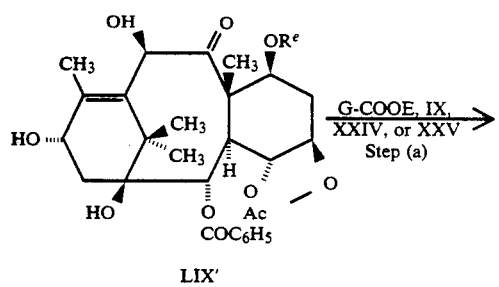
LIX'

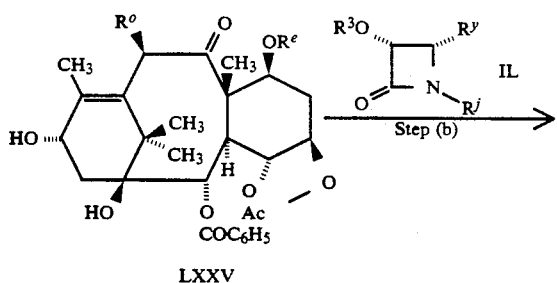
LXXV

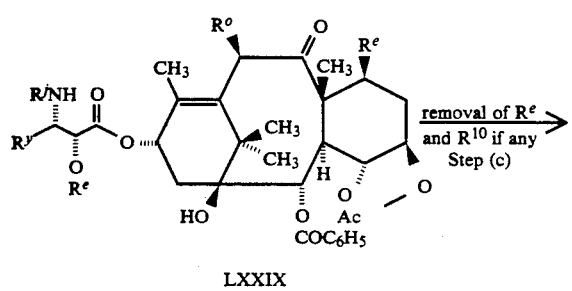
LXXIX

-continued
Scheme VIIIa

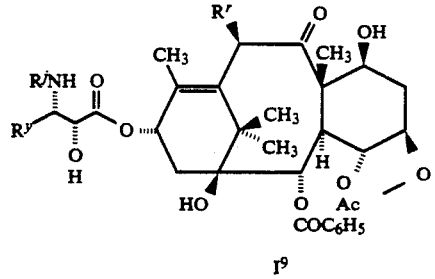
I[9]

As an adaptation of Scheme VIII process, a compound of I[9] also can be made by a process of Scheme VIIIa. In the Scheme, a compound of formula LIX' is acylated or phosphorylated with a compound of formula IX, XXIV, XXV or G-COOE thereby affording a compound of formula LXXV. (Note: A compound of formula LIX' in which R[e] is triethylsilyl is already known and other compounds with different R[e] groups can be similarly prepared.) Step (b) is carried out in the same or substantially the same way as Step (a) of Scheme VIII. Removal of R[e] and R[10], if any, from a compound of formula LXXIX affords a compound of formula I[9].

DESCRIPTION OF SPECIFIC EMBODIMENTS

The specific examples which follow illustrate the synthesis of representative compounds of the instant invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are:

MS: mass spectrometry
HRMS: high resolution mass spectrometry
DMF: dimethylformamide
Ac: acetyl DMSO: dimethyl sulfoxide
Ph: phenyl
Ar: aryl
DCI: desorption chemical ionization
Y: yield
v/v: volume/volume
FAB: fast atom bombardment
NOBA: m-nitrobenzylalcohol
Rt: retention time
min: minute(s)
h: hour(s)
tlc: thin layer chromatography
tBu: tertiarybutyl
i-PrOH: isopropylalcohol
Cbz (or CBZ): benzyloxycarbonyl
Bz: benzoyl In the examples that follow, hexane and hexanes may be used interchangeably.

In the following examples pertaining to the phosphonooxy salts, the ratios of cations to the parent compounds indicated, for example in the structural formulas, are approximations. It is well understood in the art that the outcome of ratios of cations to the parent compound is dependent upon a particular isolation condition being employed. Furthermore, the structural formulas of salts are only meant to indicate the ratios of cations to the parent molecule, i.e., a monosodium salt may also exist as a mixture of disodium, monosodium and free acid forms.

EXAMPLE 1

4,4,5,7-Tetramethyl-3,4-dihydrocoumarin (IIIa)

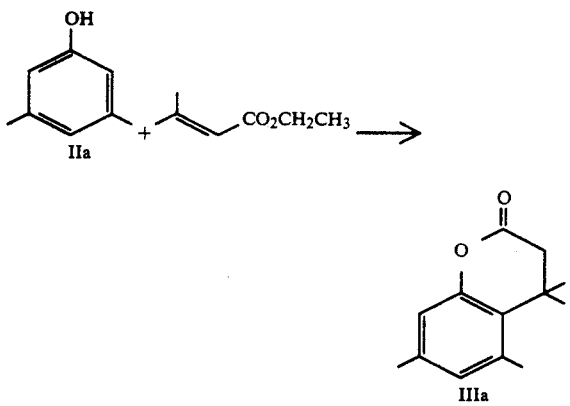

3,5-Dimethylphenol (IIa) (3.2 g, 26.2 mmol), ethyl 3,3-dimethylacrylate (5 mL, 36 mmol, 1.4 eq.) and concentrated sulfuric acid (1.5 mL) were dissolved in anhydrous benzene (30 mL), and the reaction mixture was heated to reflux for 2 h. The reaction mixture was cooled to room temperature and washed successively with water (2×40 mL), 5% aqueous $NaHCO_3$ solution (2×20 mL), brine (2×20 mL) and dried over anhydrous sodium sulfate. After filtering off the desiccant, the solvent was removed under vacuum to obtain a dark brown gummy material. To this gummy material was added anhydrous ether (5 mL) and boiled for 2 min on a steam bath. The title compound, IIIa, (3.34 g, 16.4 mmol, Y: 62.4%) was crystallized out from the mixture upon cooling in an ice bath; mp, 95.8–96.3° C.; $^1$H-NMR (300 MHz, acetone-d$_6$) δ ppm: 1.41 (6H, s, 4,4-Me$_2$), 2.24 (3H, s, 5-Me), 2.46 (3H, s, 7-Me), 2.61 (2H, s, 3-H$_2$), 6.68 (1H, s, Ar-H), 6.76 (1H, s, Ar-H); MS (Isobutane-DCI) m/e: 205 (M+H)$^+$; IR (KBr) ν max: 1770, 1250, 1190, 870 cm$^{-1}$.

Anal. calcd for $C_{13}H_{16}O_2$: C, 76.45; H, 7.90. Found: C, 76.63; H, 7.83.

EXAMPLE 2

3-(2'-Hydroxy-4',6'-dimethylphenyl)-3,3-dimethylpropanol (IVa)

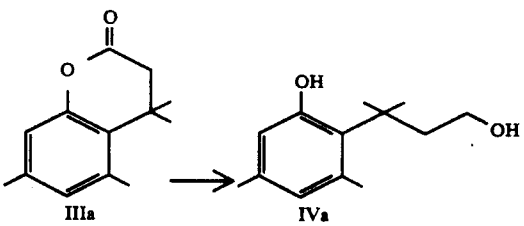

A solution of compound IIIa (27 g, 132.2 mmol) in dry tetrahydrofuran (THF, 100 mL) was added dropwise to a stirred suspension of 95% lithium aluminum hydride (LAH, 5.3 g, 132.5 mmol) in dry THF (250 mL) in 30 min period, so that the temperature did not rise for the suspension to reflux. The reaction mixture was stirred vigorously using a mechanical stirrer for 30 min. The excess LAH was quenched with 10% aqueous HCl solution (15 mL). The insoluble material was filtered off and washed with EtOAc. The solvent was evaporated in vacuo from the combined filtrate and EtOAc washing. The residue, thus obtained, was taken into EtOAc (150 mL). The ethyl acetate layer was washed with brine (2×50 mL) and dried over anhydrous sodium sulfate. The desiccant was filtered off and the filtrate was concentrated in vacuo to obtain a gummy material. To this gummy material was added hexane/acetone (20 mL, 9:1, v/v) and boiled for 2 min on a steam bath. The title compound, IVa, (23.3 g, 111.9 mmol, Y: 84.6%) crystallized out from the mixture upon cooling in an ice bath; mp, 116–117° C.; $^1$H-NMR (300 MHz, acetone-d$_6$) δ ppm: 1.52 (6H, s, 3,3-Me$_2$), 2.1 (3H, s, 6'-Me), 2.17 (2H, t, J=7.7 Hz, 2-H$_2$), 2.43 (3H, s, 4'-Me), 3.14 (1H, t, J=5.2 Hz, 1-OH, exchanged with D$_2$O), 3.39–3.45 (2H, m, 1-H$_2$), 6.37 (1H, s, Ar-H), 6.49 (1H, s, Ar-H) 7.98 (1H, s, 2'-OH, exchanged D$_2$O); MS (Isobutane-DCI) m/e: 209 (M+H)$^+$; IR (KBr) ν max: 3510, 3230, 1310, 850 cm$^{-1}$.

Anal. calcd for $C_{13}H_{20}O_2$: C, 74.97; H, 9.68. Found: C, 75.35; H, 9.92.

EXAMPLE 3

1-O-t-Butyldimethylsilyl-3-(2'-hydroxy-4',6'-dimethylphenyl)-3,3-dimethylpropanol (Va)

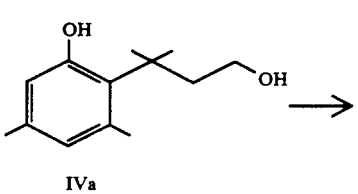

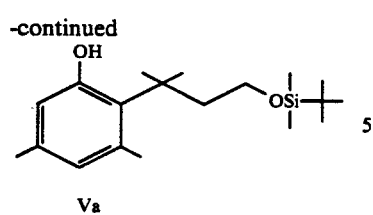

Va

A mixture of compound IVa (6 g, 28.8 mmol), t-butyldimethylsilyl chloride (5.2 g, 34.5 mmol, 1.2 eq.), and imidazole (4.9 g, 71.97 mmol, 2.5 eq.) in anhydrous DMF (30 mL) was stirred overnight at room temperature. The reaction mixture was diluted with EtOAc (50 mL), washed with brine (5×40 mL) and dried over anhydrous sodium sulfate. The desiccant was filtered off and the filtrate was concentrated in vacuo to obtain a white solid which was recrystallized from hexane giving 8.9 g (27.59 mmol, Y: 96%) of the title compound, Va, as a white crystalline material; mp, 117–118° C.; $^1$H-NMR (300 MHz, acetone-$d_6$) δ ppm: −0.15 (6H, s, Si-Me$_2$), 0.83 (9H, s, tBu), 1.53 (6H, s, 3,3-Me$_2$), 2.10 (3H, s, 6'-Me), 2.19 (2H, t, J=7.5 Hz, 2-H$_2$), 2.43 (3H, s, 4'-Me), 3.51 (2H, t, J=7.5 Hz, 1-H$_2$), 6.37 (1H, s, Ar-H), 6.50 (1H, s, Ar-H), 8.0 (1H, s, 2'-OH, exchanged with D$_2$O); MS (Isobutane-DCI) m/e: 323 (M+H)$^+$; IR (KBr) ν max: 3308 (OH), 2856, 1614, 1390, 1260 cm$^{-1}$; UV (MeOH:H$_2$O, 1:1) λ max: 196 (ε 3.3×10$^4$), 284 nm (ε 1.9×10$^2$).

Anal calcd for C$_{19}$H$_{34}$O$_2$Si: C, 70.75; H, 10.63. Found: C, 70.52; H, 10.83.

EXAMPLE 4

Tetrabenzylpyrophosphate (XXIVa)

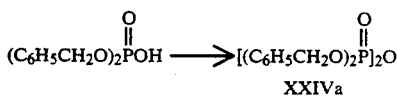

Dibenzylphosphate (55.6 g, 0.2 mol) was dissolved in 400 mL THF; the solution was stirred and 1,3-dicyclohexylcarbodiimide (24.8 g, 0.12 mol) was added. Stirring was continued for an additional 20 h.[1] The reaction mixture was filtered to remove 1,3-dicyclohexylurea and the filtrate concentrated to a viscous residue. This residue was suspended in a minimum amount of THF and filtered again to remove insoluble material. The filtrate was again concentrated and 200 mL of hexanes was added. The suspension was transferred to an Erlenmeyer flask. A small amount of THF was used to assist the transfer. The suspension was triturated with sonication.[2] The crystals were collected washed with hexanes and vacuum dried. 51.9 g (Y: 96%) of off-white crystals were obtained; mp, 59–61° C.[3] (Lit.* mp, 60–61° C.).

*Reference: H. G. Khorana, A. R. Todd, J. Chem. Soc., p. 2257 (1953).

Notes

1. The reaction time can be shortened to 4 h with no loss in yield.
2. Very good agitation is necessary during the crystallization to prevent a solid mass from forming. Sonication works very well.
3. The product can be expected to be moisture sensitive. Prolonged storage should probably be avoided. Slight deterioration of the pyrophosphate was noted upon storing in a desiccator with occasional use for a period of approximately 2 months.

EXAMPLE 5

1-O-t-Butyldimethylsilyl-3-(2'-dibenzylphosphonooxy-4',6'-dimethylphenyl)-3,3-dimethylpropanol (VIa)

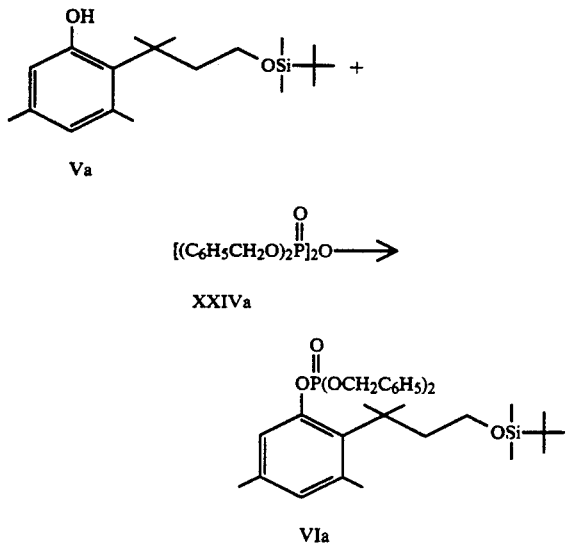

Sodium hydride (60% in mineral oil, 860 mg, 21.5 mmol, 1.2 eq.) was washed with hexanes, dried under nitrogen and suspended in anhydrous DMF (70 mL). To this suspension was added compound Va (5.8 g, 18 mmol), and the mixture was stirred in an oil bath at 65° C. for 5 min. To this warm reaction mixture was added tetrabenzylpyrophosphate (XXIVa) (14.5 g, 26.93 mmol, 1.5 eq.) all at once. The reaction mixture was continued to be stirred at 65° C. for 10 min. Subsequently, it was diluted with EtOAc (300 mL), washed with brine (4×100 mL) and dried over anhydrous sodium sulfate. It was filtered and the filtrate was concentrated in vacuo to obtain compound VIa as a crude product which was purified on a silica gel column. The column was eluted with 10% EtOAc in hexanes to yield 10 g (17.16 mmol, Y: 95%) of the title compound, VIa, as a gummy material; $^1$H-NMR (300 MHz, acetone-$d_6$) δ ppm: −0.57 (6H, s, Si-Me$_2$), 0.82 (9H, s, tBu), 1.52 (6H, s, 3,3-Me$_2$), 2.11 (2H, t, J=7.3 Hz, 2-H$_2$), 2.14 (3H, s, 6'-Me), 2.5 (3H, s, 4'-Me), 3.51 (2H, t, J=7.3 Hz, 1-H$_2$), 5.13–5.21 (4H, 2 ABq, CH$_2$Ph), 6.75 (1H, Ar-H), 7.12 (1H, s, Ar-H), 7.33–7.4 (10H, m); MS (Isobutane-DCI) m/e: 583 (M+H)$^+$; IR (NaCl film) ν max: 1280 (P=O), 1260, 1018 (P—O) cm$^{-1}$; UV (MeOH:H$_2$O, 1:1) λ max: 196 nm (ε 3.95×10$^3$).

Anal. calcd for C$_{33}$H$_{47}$O$_5$PSi: C, 68.02; H, 8.13. Found: C, 68.19; H, 7.94.

Alternate Run

Compound Va (21.7 g, 67.2 mmol) was dissolved in 330 mL of dry THF under N$_2$ and cooled in an ice bath. With stirring, 26.9 mL (67.2 mmol) of 2.5M n-butyllithium in hexanes was added over a period of 10 min. To this was added pyrophosphate XXIVa (39.8 g, 74 mmol) and the cooling bath was removed. After stirring for 1 h the precipitate was removed by filtration and the filtrate concentrated to leave a yellow oily residue. This was purified by silica gel column chromatography (being eluted with 9:1 hexanes/EtOAc) to obtain 33.7 g (Y: 86%) of purified VIa as a clean colorless oil; Rf: 0.55 (9:1 hexanes/EtOAc).

EXAMPLE 6

3-(2'-Dibenzylphosphonooxy-4',6'-dimethylphenyl)-3,3-dimethylpropanol (VIIa)

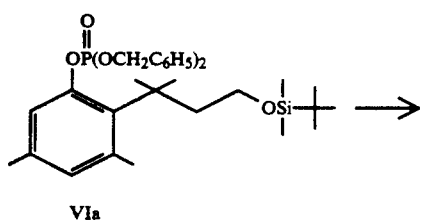

VIa

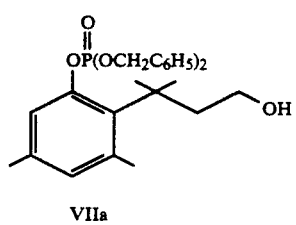

VIIa

To a solution of compound VIa (10 g, 17.2 mmol) in dry THF (250 mL) was added successively AcOH (6.2 mL, 108.3 mmol, 6.3 eq.) and tetrabutylammonium fluoride (TBAF) hydrate (13.5 g) at room temperature. The reaction mixture was stirred at room temperature for 3 days. The solvent was pumped off from the reaction mixture and the gummy residue was taken into EtOAc (300 mL), washed with brine (4×100 mL) and dried over anhydrous sodium sulfate. The desiccant was filtered off and the filtrate was concentrated in vacuo to obtain a crude product which was purified on a silica gel column. The column was eluted with EtOAc/hexanes (1:1, v/v) to obtain 5.8 g (12.38 mmol, Y: 72%) of the title compound, VIIa, as a gummy material; 1H-NMR (300 MHz, acetone-d6) δ ppm: 1.51 (6H, s, 3,3-Me2), 1.2 (2H, t, J=7.5 Hz, 2-H2), 2.13 (3H, s, 6'-Me), 2.49 (3H, s, 4'-Me), 3.31 (1H, t, J=5.15 Hz, 1-OH, exchanged with D2O), 3.39-3.46 (2H, m, 1-H2), 5.17 (4H, ABq, CH2Ph), 6.74 (1H, s, Ar-H), 7.1 (1H, s, Ar-H), 7.3-7.42 (10H, m); MS (Isobutane-DCI) m/e: 469 (M+H)+; IR (NaCl film) ν max: 3442 (OH), 1275 (P=O), 1260, 1018 (P—O) cm−1.

Anal. calcd for C27H31O5P: C, 69.21; H, 7.10.
Found: C, 68.94; H, 7.06.

Alternate Run

Compound VIa (33.6 g, 57.6 mmol) was dissolved in 330 mL of 2-propanol and with stirring was treated with 25 mL of 6N HCl. After stirring for 1 h at room temperature, the reaction mixture was concentrated without warming. The residue was dissolved in 300 mL of EtOAc and washed with water (2×150 mL) and saturated brine (150 mL). The EtOAc layer was dried over anhydrous sodium sulfate, filtered and concentrated to leave 28 g of compound VIIa (somewhat contaminated with some silylated by-products) as a clean oil; Rf: 0.45 (SiO2, 1:1 EtOAc/Hexanes).

EXAMPLE 7

3-(2'-Dibenzylphosphonooxy-4',6'-dimethylphenyl)-3,3-dimethylpropionaldehyde (VIIIa)

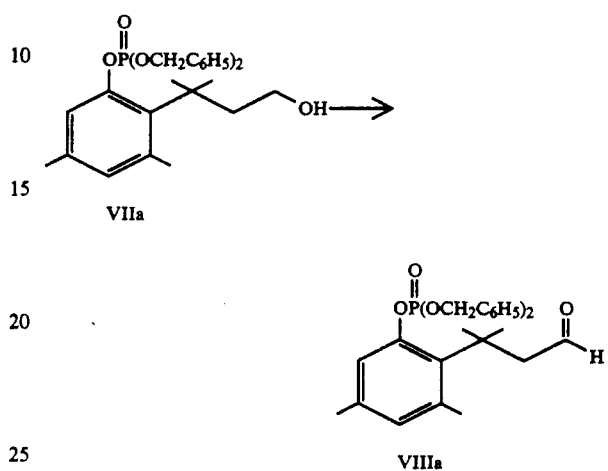

To a solution of compound VIIa (3.5 g, 7.5 mmol) in anhydrous CH2Cl2 (100 mL) was added pyridinium chlorochromate (PCC, 3.24 g, 15.03 mmol, 2 eq.) all at once at room temperature. The reaction mixture was allowed to be stirred at room temperature for 1 h. The volume of the reaction mixture was reduced to 10 mL by evaporating the solvent in vacuo. The resultant crude reaction product was purified on a silica gel column, being eluted with 40% EtOAc in hexanes, to obtain 2.74 g (5.87 mmol, Y: 78%) of the title compound, VIIIa, as a yellow viscous oil; 1H-NMR (300 MHz, acetone-d6) δ ppm: 1.57 (6H, s, 3,3-Me2), 2.14 (3H, s, 6'-Me), 2.51 (3H, s, 4'-Me), 2.91 (2H, d, J=2 3 Hz, 2-H2), 5.11-5.23 (4H, 2 ABq, CH2Ph), 6.78 (1H, s, Ar-H), 7.12 (1H, s, Ar-H), 7.35-7.39 (10H, m), 9.49 (1H, t, J=2.3 Hz, CHO); MS (Isobutane-DCI) m/e: 467 (M+H)+; IR (NaCl film) ν max: 1740 (C=O), 1280 (P=O), 1020 (P—O) cm−1; UV (MeOH:H2O, 1:1) λ max: 200 (ε 3.7×10^4), 264 nm (ε 3.6×10^2).

Anal. calcd for C27H31O5P: C, 69.51; H, 6.70.
Found: C, 69.76; H, 6.73.

EXAMPLE 8

3-(2'-Dibenzylphosphonooxy-4',6'-dimethylphenyl)-3,3-dimethylpropionic acid (IXa)

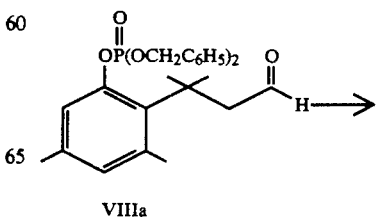

VIIIa

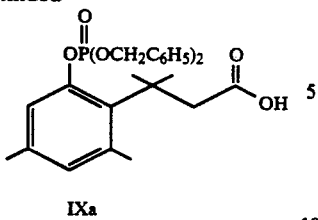

IXa

To a solution of compound VIIIa (1.46 g, 3.13 mmol) in acetone (40 mL) was added Jones reagent* (3 mL) at room temperature. The reaction mixture was stirred at room temperature for 20 min. The insoluble material was filtered off and the filtrate was concentrated in vacuo. The residue thus obtained was taken into EtOAc and purified on a silica gel column, being eluted with EtOAc/CH$_2$Cl$_2$ (1:1, v/v), to obtain 1.0 g (2.07 mmol, Y: 66%) of the title compound, IXa, as a gummy material; $^1$H-NMR (300 MHz, acetone-d$_6$) δ ppm: 1.6 (6H, s, 3,3-Me$_2$), 2.12 (3H, s, 6'-Me), 2.52 (3H, s, 4'-Me), 2.93 (2H, s, 2-H$_2$) 5.15–5.18 (4H, 2ABq, CH$_2$Ph), 6.72 (1H, s, Ar-H), 7.08 (1H, s, Ar-H), 7.33–7.4 (10H, m); MS (Isobutane-DCI) m/e: 483 (M+H)$^+$; IR (NaCl film) ν max: 1715 (C=O), 1260 (P=O), 1020 (P—O) cm$^{-1}$; UV (MeOH:H$_2$O, 1:1) λ max: 202 (ε 4.2×10$^4$), 258 nm (ε 8.3×10$^2$).

*Note: The Jones reagent was prepared by dissolving CrO$_3$ (26.72 g) in "concentrated sulfuric acid (23 mL) and diluted with water to a volume of 100 mL" (see Fieser and Fieser "Reagents for Organic Synthesis" Vol 1, p 142, John Wiley, New York, 1967).

Anal. calcd for C$_{27}$H$_{31}$O$_6$P: C, 67.21; H, 6.48. Found: C, 66.75; H, 6.29.

EXAMPLE 9

3-(2'-Dibenzylphosphonooxy-4',6'-dimethylphenyl)-3,3-dimethylpropanol (VIIa)

Sodium hydride (NaH, 1.20 g, 30 mmol; 60% in mineral oil, Aldrich) was washed with anhydrous hexanes, dried under dry nitrogen and suspended in anhydrous DMF (100 mL; Aldrich Sure Seal). To this suspension was added compound IVa (5.20 g, 25.0 mmol) and the mixture was heated at 65° C. for 5 min. To this warm mixture was added tetrabenzylpyrophosphate (XXIVa) (20.2 g, 37.5 mmol) all at once. The reaction mixture was heated at 65° C. for 1½ h. The cooled reaction mixture was diluted with EtOAc (450 mL), washed with H$_2$O (150 mL×3) and then with brine (150 mL). The organic phase was dried (Na$_2$SO$_4$) and concentrated. The residue was purified by silica column chromatography, being eluted with 35% EtOAc in hexanes, to obtain 4.70 g (10 mmol, Y: 40.1%) of the title compound, VIIa, as a gummy oil. This material was identical to the product obtained in Example 6 as determined by $^1$H-NMR (300 MHz, acetone-d$_6$).

EXAMPLE 10

3-(2'-Dibenzylphosphonooxy-4',6'-dimethylphenyl)-3,3-dimethylpropionic acid (IXa)

To a solution of the alcohol VIIa (4.90 g, 10.5 mmol) in acetone (75 mL) was added Jones reagent (10 mL) at room temperature. The reaction mixture was stirred at room temperature for 20 min. The insoluble material was filtered and the filtrate concentrated in vacuo. The residue was taken into EtOAc and purified by silica gel column chromatography, being eluted with 50% EtOAc in CH$_2$Cl$_2$, to obtain 3.20 g (6.64 mmol 63.5%) of the title compound, IXa, as a yellowish oily solid; Rf: 0.44 (50% EtOAc in hexane); $^1$H-NMR (300 MHz, acetone-d$_6$) indicated that this material was identical to the product obtained in Example 8.

Alternate Run

Compound VIIa (26 g, 55.4 mmol) was dissolved in 350 mL acetone and was carefully treated with 36 mL of Jones Reagent under stirring. After stirring for 30 min, 15 mL 2-propanol was added and stirring was continued for an additional 15 min. The reaction mixture was concentrated to half the volume and 400 mL EtOAc and 200 mL water were added. The layers were separated, and the aqueous layer was extracted further with 100 mL EtOAc. The combined EtOAc layers were then washed with water (2×200 mL) and saturated brine (200 mL). After drying over anhydrous sodium sulfate, filtration and concentration, 27 g of a yellow/green oil was obtained. The oil was crystallized from Et$_2$O/hexane to give 20.7 g (Y: 77.5%) of the title product, IXa; mp, 79.5–80.5° C.

EXAMPLE 11

1.4-Dihydroxy-2,6-dimethylbenzene (XIa)

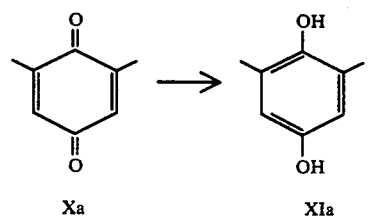

Xa                XIa

A solution of 2,6-dimethyl-1,4-benzoquinone (Xa) (5.66 g, 42 mmol, Aldrich) in Et$_2$O (200 mL) was shaken vigorously in a separatory funnel with two 200 mL portions of aqueous sodium hydrosulfite solution (sodium dithionite, Na$_2$S$_2$O$_4$, 14.5 g, 83.3 mmol) until the Et$_2$O layer turned bright yellow. The ether layer was washed with brine (200 mL×2), dried (MgSO$_4$) and concentrated in vacuo to obtain 4.865 g (35.3 mmol, Y: 83.9%) of the title compound as a white solid; mp, 148–150° C. (acetone-hexane) [mp reported by L. A. Carpino, S. A. Triolo, and R. A. Berglund in *J. Org. Chem.*, 54, p. 3303 (1989): 145–148° C.]; Rf: 0.47 (10% EtOAc in CH$_2$Cl$_2$); IR(KBr) 3312 cm$^{-1}$ (OH); $^1$H-NMR (300 MHz, acetone-d$_6$) δ ppm: 2.15 (6H, s, Me), 6.45 (2H, s, Ar-H), 6.58 (1H, s, OH), 7.47 (1H, s, OH); $^{13}$C-NMR (75 MHz, acetone-d$_6$) δ ppm: 16.84, 116.00, 126.45, 147.46, 151.54; MS (isobutane-DCI) m/e: 139 (MH$^+$).

EXAMPLE 12

6-Hydroxy-4,4,5,7-tetramethylhydrocoumarin (XIIa)

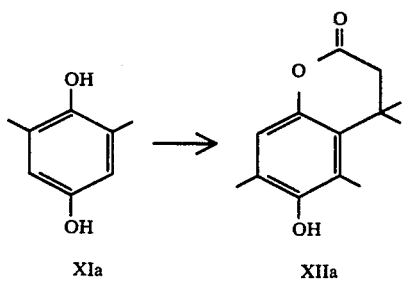

XIa                XIIa

A mixture of 1,4-dihydroxy-2,6-dimethylbenzene (XIa) (4.83 g, 35 mmol), ethyl β,β-dimethylacrylate (5.38 g, 42 mmol; Aldrich) and concentrated sulfuric acid (2 mL) in toluene (200 mL) was heated at reflux for 3.5 h. After the mixture had cooled, it was washed successively with $H_2O$ (200 mL×2), 5% aqueous NaHCO$_3$ solution (200 mL×2), and then with brine (200 mL). The toluene solution was dried (MgSO$_4$) and concentrated in vacuo. The residual solid was crystallized from toluene to obtain 4.637 g (21.1 mmol, Y: 60.2%) of the title compound as an off-white solid; mp, 141–142° C. [mp reported by K. L. Amsberry and R. T. Borchardt in *Pharmaceutical Res.*, 8, p. 323 (1991): 140–142° C.]; Rf: 0.67 (10% EtOAc in $CH_2Cl_2$); IR(KBr) 3418(OH), 1742 cm$^{-1}$ (lactone); $^1$H-NMR (300 MHz, acetone-d$_6$) δ ppm: 1.43 (6H, s, gem-Me), 2.22 (3H, s, Ar-Me), 2.38 (3H, s, Ar-Me), 2.56 (2H, s, $CH_2$), 6.66 (1H, s, Ar-H), 7.19 (1H, s, OH); $^{13}$C-NMR (75 MHz, acetone-d$_6$) δ ppm: 15.12, 16.64, 27.94, 36.15, 46.56, 117.56, 124.49, 125.26, 129.79, 146.16, 151.45, 169.15; MS (isobutane-DCI) m/e: 221 (MH+).

Anal. calcd for $C_{13}H_{16}O_3$: C, 70.89; H, 7.33. Found: C, 71.21; H, 7.43.

EXAMPLE 13

6-Benzyloxy-4,4,5,7-tetramethylhydrocoumarin (XIIIa)

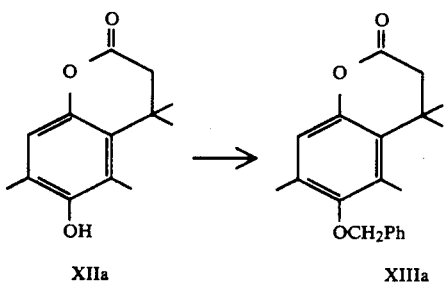

A mixture of hydroxyhydrocoumarin XIIa (1.10 g, 5 mmol), benzyl bromide (1.28 g, 7.5 mmol; Aldrich) and anhydrous potassium carbonate (1.38 g, 10 mmol) in anhydrous DMF (10 mL; Aldrich Sure Seal) was stirred under dry nitrogen atmosphere for 3 days. The mixture, diluted with EtOAc (30 mL) and $H_2O$ (10 mL), was washed successively with 2N hydrochloric acid (14 mL), $H_2O$ (10 mL), 5% aqueous NaHCO$_3$ solution (10 mL), and then with brine (15 mL). The EtOAc layer was dried (Na$_2$SO$_4$) and concentrated in vacuo to dryness. The resulting solid was triturated with hexane to obtain 1.359 g (4.38 mmol, Y: 87.7%) of the title compound as an off-white solid; mp, 94–96° C. (recrystallized from isopropyl alcohol); Rf: 0.57 (30% EtOAc in hexane); IR(KBr) 1768 cm$^{-1}$ (lactone); $^1$H-NMR (300 MHz, CDCl$_3$) δ ppm: 1.43 (6H, s, gem-Me), 2.26 (3H, s, Ar-Me), 2.40 (3H, s, Ar-Me), 2.56 (2H, s, $CH_2$), 4.73 (2H, s, $OCH_2$), 6.76 (1H, s, Ar-H), 7.3–7.5 (5H, m, Ar-Hs); $^{13}$C-NMR (75 MHz, CDCl$_3$) δ ppm: 15.15, 16.54, 27.87, 35.78, 46.15, 74.85, 118.00, 128.38, 128.72, 129.12, 129.17, 130.31, 131.55, 137.88, 148.02, 153.44, 169.15; MS (isobutane-DCI) m/e: 311 (MH+), 91.

Anal. calcd for $C_{20}H_{22}O_3$: C, 77.40; H, 7.15. Found: C, 77.37; H, 7.13.

EXAMPLE 14

3-(2'-Hydroxy-5'-benzyloxy-4',6'-dimethylphenyl)-3,3-dimethylpropanol (XIVa)

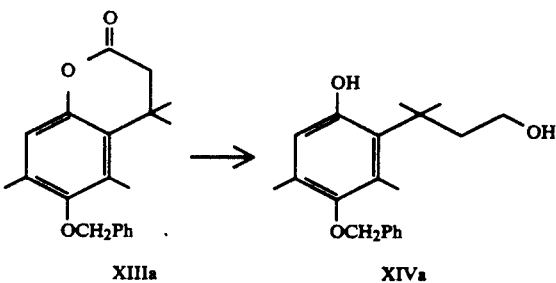

A solution of benzyloxyhydrocoumarin XIIIa (1.147 g, 3.70 mmol) in anhydrous THF (7 mL) was carefully added to a stirred suspension of LiAlH$_4$ (281 mg, 7.4 mmol) in anhydrous THF (15 mL). The mixture was stirred at room temperature under dry nitrogen atmosphere for 20 min and then heated at reflux for 30 min by which time tlc (30% EtOAc in hexane) indicated that the reaction was complete. The mixture was cooled in an ice-bath and to this mixture was added carefully and successively EtOAc (15 mL), 6N hydrochloric acid (5 mL), and $H_2O$ (15 mL). The EtOAc layer was collected and the aqueous layer was extracted with EtOAc (25 mL). Both EtOAc layers were combined and washed successively with 1N hydrochloric acid (25 mL), saturated aqueous NaHCO$_3$ solution (25 mL), and brine. The EtOAc layer was dried (Na$_2$SO$_4$) and concentrated in vacuo to dryness to obtain 1.10 g (3.35 mmol, Y: 90.6%) of the title compound as a white solid; mp, 90–91° C.; Rf: 0.15 (30% EtOAc in hexane); IR(KBr) 3462, 3262, 1601 cm$^{-1}$; $^1$H-NMR (300 MHz, acetone-d$_6$) δ ppm: 1.58 (6H, s, gem-Me), 2.16 (3H, s, Ar-Me), 2.21 (2H, t, J=7.8 Hz, $CH_2$), 2.46 (3H, s, Ar-Me), 3.17 (1H, t, J=5 Hz, OH), 3.45–3.52 (2H, m, $CH_2O$), 4.69 (2H, s, $OCH_2Ph$), 6.55 (1H, s, Ar-H), 7.3–7.55 (5H, m, Ph-Hs), 7.85 (1H, s, Ar-OH); $^{13}$C-NMR (75 MHz, acetone-d$_6$) δ ppm: 16.47, 32.73, 41.00, 46.39, 61.15, 75.02, 118.03, 127.90, 129.01, 129.11, 129.46, 129.68, 131.86, 132.40, 139.68, 150.92, 153.88; MS(FAB/NOBA+NaI+KI) m/e: 353 (MK+), 337 (MNa+), 314 (M+), 229, 223.

Anal. calcd for $C_{20}H_{26}O_3$: C, 76.41; H, 8.34. Found: C, 76.28; H, 8.25.

EXAMPLE 15

1-O-t-Butyldimethylsilyl-3-(5'-benzyloxy-4',6'-dimethyl-2'-hydroxyphenyl)-3,3-dimethylpropanol (XVa)

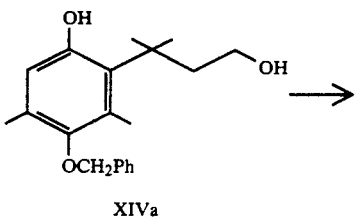

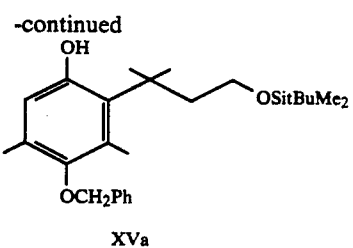

XVa

A mixture of diol XIVa (1.017 g, 3.10 mmol), t-butyldimethylsilyl chloride (561 mg, 3.72 mmol; Aldrich) and imidazole (527 mg, 7.75 mmol) in DMF (5 mL; Aldrich, Sure Seal) was stirred at room temperature under nitrogen atmosphere for 18 h. This mixture was diluted with EtOAc (20 mL) and successively washed with H$_2$O (15 mL×3) and brine (15 mL). The EtOAc phase was dried (Na$_2$SO$_4$) and concentrated in vacuo to give 1.38 g (3.16 mmol, Y: ≧100%) of the title compound as a crude oil; Rf: 0.72 (30% EtOAc in hexane); IR (film) 3380 cm$^{-1}$(OH); $^1$H-NMR (300 MHz, acetone-d$_6$) δ ppm: −0.03 (6H, s, SiMe$_2$), 0.84 (9H, s, SitBu), 1.56 (6H, s, gem-Me), 2.15 (3H, s, Ar-Me), 2.20 (2H, t, J=7.5 Hz, CH$_2$), 2.45 (3H, s, Ar-Me), 3.56 (2H, t, J=7.5 Hz, CH$_2$OSi), 4.67 (2H, s, OCH$_2$Ph), 6.54 (1H, s, Ar-H), 7.3-7.5 (5H, m, Ph-Hs), 7.88 (1H, s, Ar-OH); MS (isobutane-DCI) m/e: 429 (MH+), 337, 297, 201.

EXAMPLE 16

1-O-t-Butyldimethylsilyl-3-(2'-acetoxy-5'-benzyloxy-4',6'-dimethylphenyl)-3,3-dimethylpropanol (XVIa)

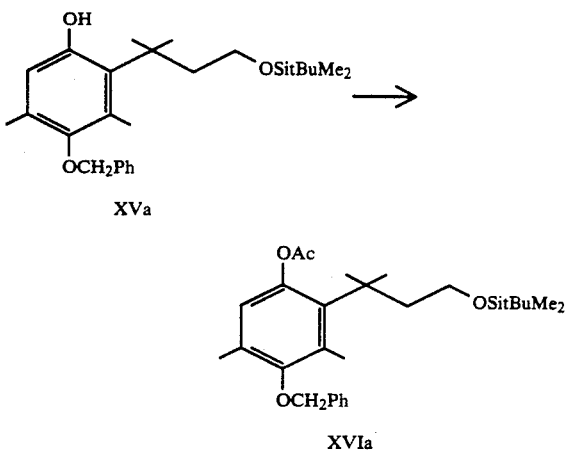

To a solution of phenol XVa (1.38 g, 3.10 mmol; crude) in pyridine (2 mL; dried over NaOH) was added acetic anhydride (1 mL, 10.6 mmol) and the solution was stirred at room temperature for 15 h. The volatiles were evaporated in vacuo and the residue, diluted with CH$_2$Cl$_2$ (20 mL), was successively washed with H$_2$O (15 mL×2) and brine (15 mL). The CH$_2$Cl$_2$ phase was dried (Na$_2$SO$_4$) and concentrated in vacuo. The residue was purified by silica gel column chromatography (SiO$_2$, 100 g), being eluted with 12% EtOAc in hexane, to obtain 1.24 g (2.64 mmol, Y: 85.2%) of the title compound as a clear oil; Rf: 0.23 (10% EtOAc in hexane); IR (film): 1760 cm$^{-1}$ (OAc); $^1$H-NMR (300 MHz, CDCl$_3$) δ ppm: −0.03 (6H, s, SiMe$_2$), 0.83 (9H, s, SitBu), 1.47 (3H, s, Ar-Me), 2.05 (2H, t, J=7.5 Hz, CH$_2$), 2.23 (3H, s, Ar-Me), 2.25 (3H, s, OAc), 2.47 (3H, s, Ar-Me), 3.50 (2H, t, J=7.5 Hz, CH$_2$OSi), 4.72 (2H, s, OCH$_2$Ph), 6.58 (1H, s, Ar-H), 7.2-7.5 (5H, m, Ph-Hs); MS (isobutane-DCI) m/e: 471 (MH+), 413, 385, 201.

Anal. calcd for C$_{28}$H$_{42}$O$_4$Si: C, 71.45, H, 9.00. Found: 71.47; H, 9.21.

EXAMPLE 17

1-O-t-Butyldimethylsilyl-3-(2'-acetoxy-4',6'-dimethyl-5'-hydroxyphenyl)-3,3-dimethylpropanol (XVIIa)

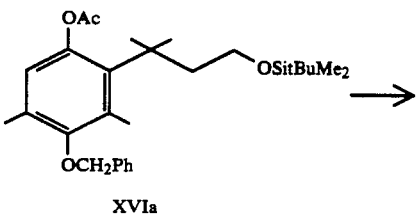

XVIa

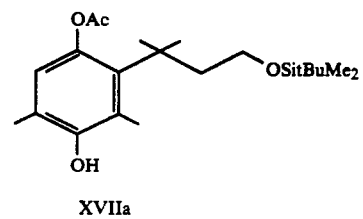

XVIIa

To a solution of benzyl ether XVIa (1.19 g, 2.53 mmol) in absolute EtOH (100 mL) was added 10% Pd on carbon (400 mg, Aldrich), and the mixture was stirred in a Parr apparatus under hydrogen atmosphere (30 psi) at room temperature for 2 h. The catalyst was removed by filtration through Celite and the filtrate was concentrated. The residue was purified by silica gel column chromatography (SiO$_2$, 15 g), being eluted with 20% EtOAc in hexane, to obtain 863 mg (2.27 mmol, Y: 97.1%) of the title compound as white solid; mp, 87-88° C. (recrystallized from EtOAc/hexane); Rf: 0.34 (20% EtOAc in hexane); IR(KBr) 3490 (OH), 1734, 1232 cm$^{-1}$ (OAc); $^1$H-NMR (300 MHz, acetone-d$_6$) δ ppm: −0.03 (6H, s, SiMe$_2$), 0.84 (9H, s, tBu), 1.46 (6H, s, gem-Me), 2.05 (2H, t, J=7.5 Hz, CH$_2$O), 2.16 (3H, s, Ar-Me), 2.19 (3H, s, OAc), 2.40 (3H, Ar-Me), 3.53 (2H, t, J=7.5 Hz, CH$_2$O), 6.50 (1H, s, Ar-H), 7.10 (1H, s, Ar-OH); MS (isobutane-DCI) m/e: 381 (MH+), 323, 295, 201, 145.

Anal. calcd for C$_{21}$H$_{36}$O$_4$Si: C, 66.28; H, 9.54. Found: C, 66.28; H, 9.83.

EXAMPLE 18

1-O-t-Butyldimethylsilyl-3-(2'-acetoxy-5'-dibenzylphosphonooxy-4',6'-dimethylphenyl)-3,3-dimethylpropanol (XVIIIa)

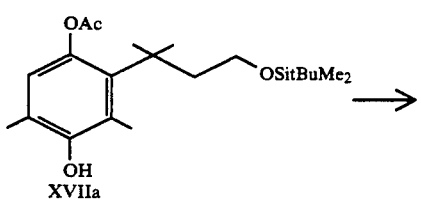

XVIIa

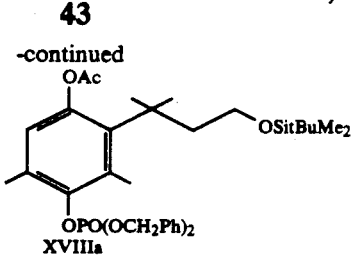

NaH (120 mg, 3.0 mmol; 60% dispersion, Aldrich) was washed with anhydrous hexane to remove the oil. To a suspension of the residue in anhydrous DMF (10 mL; Aldrich Sure Seal) was added a solution of phenol XVIIa (760 mg, 2.0 mmol) in DMF (5 mL). The mixture was heated at 60–70° C. under dry nitrogen atmosphere for 15 min and to this was added tetrabenzylpyrophosphate (XXIVa) (1.61 g, 3.0 mmol). The mixture was continued to be heated at 60–70° C. for 30 min. The mixture was subsequently cooled, diluted with EtOAc (30 mL), and successively washed with $H_2O$ (20 mL×3) and brine (20 mL). The organic phase was dried ($Na_2SO_4$) and concentrated. The residue was purified by silica gel column chromatography ($SiO_2$, 100 g), being eluted with 20% EtOAc in hexane, to obtain 1.04 g (1.63 mmol, Y: 81.6%) of the title compound as an oil; Rf: 0.23 (20% EtOAc in hexane); IR (film) 1760 cm$^{-1}$ (OAc); $^1$H-NMR (300 MHz, $CDCl_3$) δ ppm: −0.04 (6H, s, $SiMe_2$), 0.83 (9H, s, tBu), 1.42 (6H, s, gem-Me), 2.00 (2H, t, J=7.5 Hz, $CH_2$), 2.24 (3H, s, Ar-Me), 2.25 (3H, s, OAc), 2.43 (3H, s, Ar-Me), 3.54 (2H, t, J=7.5 Hz, $CH_2OSi$), 5.03 (2H, s, $OCH_2Ph$), 5.06 (2H, s, $OCH_2Ph$), 6.55 (1H, s, Ar-H), 7.2–7.4 (10H, m, Ph-Hs); MS (isobutane-DCI) m/e: 641 (MH+), 583, 441.

Anal. calcd for $C_{35}H_{49}O_7PSi$: C, 65.61; H, 7.71. Found: C, 65.68; H, 7.64.

EXAMPLE 19

3-(2'-Acetoxy-5'-dibenzylphosphonooxy-4',6'-dimethylphenyl)-3,3-dimethylpropanol (XIXa)

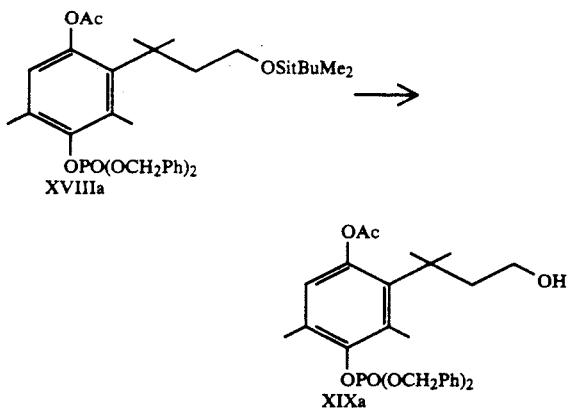

To a solution of silylether XVIIIa (960 mg, 1.5 mmol) in anhydrous THF (30 mL; distilled from benzophenone ketyl) was added HOAc (0.6 mL, 10.5 mmol; glacial) followed by tetrabutylammonium fluoride hydrate (1.59 g; Aldrich). The resultant mixture was stirred at room temperature for 1.5 h. The mixture was diluted with EtOAc (50 mL) and was successively washed with $H_2O$ (x2) and brine. The organic phase was dried ($Na_2SO_4$) and concentrated. The residue was purified by silica gel column chromatography ($SiO_2$, 90 g), being eluted with 30% EtOAc in hexane, to obtain 255 mg (0.398 mmol, Y: 26.5%) of the starting silylether, XVIIIa, and 254 mg (0.483 mmol, Y: 32.2%) of the title compound, XIXa, as an oil; Rf: 0.23 (50% EtOAc in hexane); IR (film) 3440 (OH), 1758 cm$^{-1}$ (OAc); $^1$H-NMR (300 MHz, acetone-$d_6$) δ ppm: 1.46 (6H, s, gem-Me), 2.24 (3H, s, OAc), 2.25 (3H, s, Ar-Me), 2.48 (3H, s, Ar-Me), 3 28 (2H, t, J=5.2 Hz, OH), 3.44 (2H, m, $CH_2OH$), 5.12 (2H, s, $OCH_2Ph$), 5.15 (2H, s, $OCH_2Ph$), 6.66 (1H, s, Ar-H), 7.36 (10H, s, Ph-Hs); MS (isobutane-DCI) m/e: 527 (MH+).

EXAMPLE 20

3-(2'-Acetoxy-5'-dibenzylphosphonooxy-4',6'-dimethylphenyl)-3,3-dimethylpropionic acid (IXb)

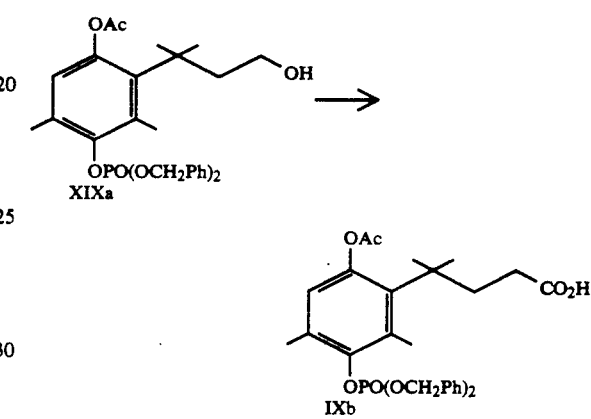

To a solution of alcohol XIXa (250 mg, 0.47 mmol) in acetone (5 mL) was added at 0–5° C. (ice-bath) Jones reagent (0.4 mL). The mixture was stirred for 30 min and the reaction was quenched by addition of isopropyl alcohol. To this green mixture was added EtOAc and $H_2O$. The aqueous phase was extracted with EtOAc (15 mL×3). The EtOAc extracts were combined, successively washed with $H_2O$ (15 mL) and brine (15 mL), dried ($Na_2SO_4$), and concentrated to obtain 226 mg (0.419 mmol, crude yield 89%) of the title compound as a crude oil. A portion of this oil (53 mg) was purified by silica gel column chromatography ($SiO_2$, 8 g), being eluted with 50% EtOAc in $CH_2Cl_2$, to obtain 24 mg (0.044 mmol, Y: 40%) of the title compound, IXb, as an oil; Rf: 0.17 (20% EtOAc in $CH_2Cl_2$) IR (film) ~3000 (broad), 1758 (OAc), 1728 cm$^{-1}$ ($CO_2H$); $^1$H-NMR (300 MHz, $CDCl_3$) δ ppm: 1.54 (6H, s, gem-Me), 2.23 (3H, s, Ar-Me), 2.27 (3H, s, OAc), 2.45 (3H, s, Ar-Me), 2.79 (2H, s, $CH_2$), 5.03 (2H, s, $OCH_2Ph$), 5.06 (2H, s, $OCH_2Ph$), 6.57 (1H, s, Ar-H), 7.25–7.33 (10H, m, Ph-Hs); MS (isobutane-DCI) m/e: 541 (MH+), 481 (MH-HOAc).

EXAMPLE 21

1-(t-Butyldimethylsilyloxy)methyl-2-(hydroxymethyl)-benzene (XXIa)

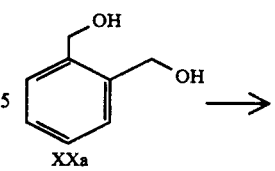

-continued

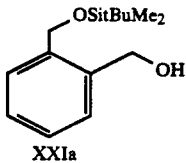

XXIa

The following silylation was performed using the condition reported by Corey and Venkateswarlu. *J. Am. Chem. Soc.*, 94, p. 6190 (1972). A mixture of diol XXa (1.38 g, 10 mmol; Aldrich), t-butyldimethylsilyl chloride (1.81 g, 12 mmol; Aldrich) and imidazole (1.7 g, 25 mmol) in anhydrous DMF (10 mg; Aldrich Sure Seal) was stirred at room temperature for 18 h. To the mixture was added EtOAc (15 mL) and H$_2$O (15 mL). The EtOAc phase was washed with H$_2$O (15 mL×2) and then with brine, dried (Na$_2$SO$_4$), and concentrated in vacuo. The crude residue was purified by silica gel column chromatography (SiO$_2$, 100 g), being eluted with 20% EtOAc in hexanes, to obtain 1.018 g (4.04 mmol, Y: 40.4%) of the title compound as a clear oil; Rf: 0.53 (30% EtOAc in hexane); IR (film) 3380 cm$^{-1}$ (OH); $^1$H-NMR (300 MHz, acetone-d$_6$) δ ppm: 0.10 (6H, s, SiMe$_2$), 0.92 (9H, s, SitBu), 4.05 (1H, t, J=5.7 Hz, OH), 4.67 (2H, d, J=5.5 Hz, CH$_2$OH, 4.84 (2H, s, CH$_2$OSi), 7.24 (2H, m, ArHs), 7.42 (2H, m, ArHs); MS (isobutane-DCI) m/e 253 (MH+), 235, 121; HRMS (FAB/NOBA) calcd for C$_{14}$H$_{24}$O$_2$Si(MH+): 253.1624, Found: 253.1615.

Anal. calcd for C$_{14}$H$_{23}$O$_2$Si: C, 66.88; H, 9.22. Found: C, 66.59; H, 9.58.

EXAMPLE 22

1-(Bisallylphosphonooxy)methyl-2-[(t-butyldimethyl-silyloxy)methyl]benzene (XXIIa)

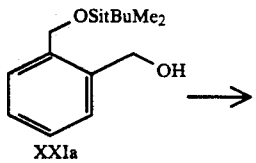

XXIa

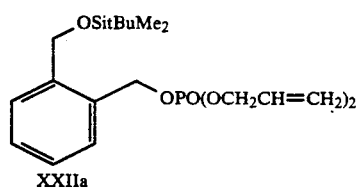

XXIIa

To a solution of siloxymethylbenzylalcohol XXIa (252 mg, 1 mmol) in CH$_2$Cl$_2$ (10 mL; Aldrich Sure Seal) was added 1H-tetrazole (210 mg, 3 mmol; Aldrich) and then bis(allyloxy)(diisopropylamino)phosphine (520 mg, 1.5 mmol; prepared by the method of Bannwarth and Kunig, *Tet. Lett.*, 30, p. 4219 (1989)) at room temperature. The mixture was stirred under nitrogen atmosphere at room temperature for 4 h. The mixture was cooled to −40° C. and to this mixture was added at −40° C. a solution of m-chloroperbenzoic acid (240 mg, 1.11 mmol; Aldrich, 80–85%) in CH$_2$Cl$_2$ (3 mL). The resulting mixture was stirred at 0–5° C. for 1 h and washed successively with aqueous NaHSO$_3$, saturated NaHCO$_3$ and brine, dried (Na$_2$SO$_4$), and concentrated. The residue was purified by silica gel column chromatography (SiO$_2$, 40 g), being eluted with 30% EtOAc in hexanes, to obtain 269 mg (0.655 mmol, Y: 65.5%) of the title compound as a colorless oil*; Rf: 0.35 (30% EtOAc in hexane); $^1$H-NMR (300 MHz, acetone-d$_6$) δ ppm: 0.126 (6H, s, SiMe$_2$), 0.957 (9H, s, tBu), 4.53 (4H, m, OCH$_2$C=), 5.16 (2H, s, CH$_2$OSi), 5.2 (4H, m, =CH$_2$and CH$_2$OP), 5.36 (2H, bd, J=17 Hz, =CH$_2$), 5.95 (2H, m, CH=), 7.3–7.5 (4H, m, Ar-Hs); MS (isobutane-DCI) m/e: 413 (MH+), 235; HRMS (FAB/-NOBA) calcd for C$_{20}$H$_{34}$O$_5$PSi (MH+) 413.1913, Found: 413.1897.

*This was also run on 10 mmol scale, yielding 77.1% of the title compound, XXIIa.

Anal. calcd for C$_{20}$H$_{33}$O$_5$PSi: C, 58.23; H, 8.06; P, 7.51.

Found: C, 58.03; H, 8.05; P, 7.50.

EXAMPLE 23

2-[(Bisallylphosphonooxy)methyl]benzyl alcohol (XXIIIa)

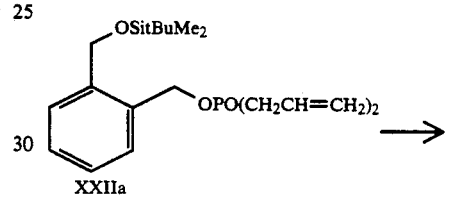

XXIIa

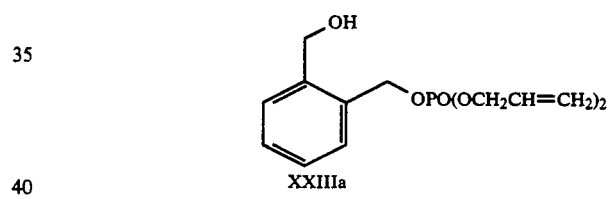

XXIIIa

To a solution of the silylether XXIIa (2.06 g, 5.00 mmol) in isopropanol (30 mL) was added 6N HCl (2.0 mL, 12 mmol) and the mixture stirred at room temperature for 3 h. The solvent was evaporated in vacuo without heat and the residue was diluted with EtOAc. This mixture was washed with H$_2$O (x2), brine and dried (Na$_2$SO$_4$). Evaporation of the solvent gave a crude oil which was purified by silica gel column chromatography (SiO$_2$, 100 g), being eluted with 50% EtOAc in CH$_2$Cl$_2$, to obtain 1.33 g (4.46 mmol, Y: 89.2%) of the title compound as a colorless oil; Rf: 0.3 (50% EtOAc in CH$_2$Cl$_2$); IR (film) 3406 (OH), 1264 cm$^{-1}$; $^1$H-NMR (300 MHz, acetone-d$_6$) δ ppm: 4.26 (1H, t, J=5.5 Hz, OH), 4.51 (4H, m, OCH$_2$), 4.74 (2H, d, J=5.2 Hz, CH$_2$OH), 5.15–5.22 (4H, m, CH$_2$OP and =CH$_2$), 5.32 (2H, qd, J=1.5, 17.2 Hz, =CH$_2$), 5.85–6.01 (2H, m, CH=), 7.29–7.48 (4H, m, ArHs); MS (isobutane-DCI) m/e: 299 (MH+), 281, 179; HRMS (FAB/NOBA) calcd for C$_{14}$H$_{20}$O$_5$P(MH+): 299.1048, Found: 299.1049.

Anal. calcd for C$_{14}$H$_{19}$O$_5$P: C, 56.38; H, 6.43. Found: C, 56.21; H, 6.44.

EXAMPLE 24

2-[(Bisallylphosphonooxy)methyl]benzoic acid (IXc)

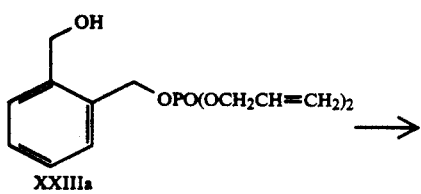

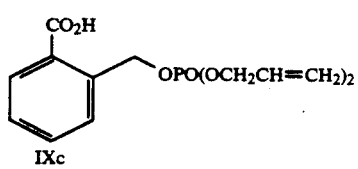

To a solution of the benzylalcohol XXIIIa (1.31 g, 4.40 mmol) in acetone (30 mL) was added at room temperature Jones reagent (3 mL). The mixture was stirred at room temperature for 0.5 h and the reaction was quenched by addition of i-PrOH (0.5 mL). To this green colored mixture was added EtOAc (50 mL) and then H$_2$O (30 mL). The mixture was stirred to obtain a clear two-phase solution. The aqueous phase was extracted with EtOAc (20 mL). The organic phases were combined, washed with H$_2$O (x2) and brine, dried (Na$_2$SO$_4$), and concentrated to dryness in vacuo to obtain 1.347 g (4.32 mmol, Y: 98.1%) of the title compound as a viscous oil; Rf: 0.18 (EtOAc); IR (film) ~3000 (CO$_2$H), 1712 (CO$_2$H), 1260, 1226 cm$^{-1}$; $^1$H-NMR (300 MHz, CDCl$_3$) δ ppm: 4.61 (4H, m, OCH$_2$), 5.24 (2H, dd, J=1.2, 10.5 Hz, =CH$_2$), 5.36 (2H, qd, J=1.5, 17.1 Hz, =CH$_2$), 5.66 (2H, d, J=6.9 Hz, CH$_2$OP), 7.38 (1H, t, J=7.3 Hz, 4-H), 7.57 (1H, t, J=7.6 Hz, 4-H), 7.69 (1H, d, J=7.8 Hz, 3-H), 8.07 (1H, dd, J=1.3, 7.7 Hz, 6-H); MS (isobutane-DCI) m/e: 313 (MH+), 179, 135; HRMS (FAB/NOBA) calcd for C$_{14}$H$_{18}$O$_6$P(MH+) 313.0841, Found: 313.0849.

Anal. calcd for C$_{14}$H$_{17}$O$_6$P: C, 53.85; H, 5.49. Found: C, 53.63; H, 5.50.

EXAMPLE 25

1-Dibenzylphosphonooxy-4-(t-butyldimethylsilyloxy)-butane (XXVIIIa)

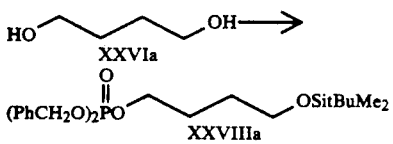

A solution of 1,4-butanediol (10.54 g, 0.117 mol) in dry THF (100 mL) was treated with t-butyl dimethylsilylchloride (17.30 g, 0.114 mol) and imidazole (7.80 g, 0.114 mol). After 2 h at room temperature, work-up with ethyl acetate and water, followed by drying the organic phase and concentration, gave a crude product that was purified by silica gel flash chromatography (being eluted with 20% ethyl acetate in hexane) to yield 15.5 g (Y: 65%) of 4-(t-butyldimethylsilyloxy)-1-butanol (XXVIIa) as a colorless oil; $^1$H-NMR (CDCl$_3$, 300 MHz) δ ppm: 3.58 (m, 4H) 1.58 (m, 4H) 0.84 (s, 9H) 0.01 (s, 6H).

This oil (171.1 mg, 0.908 mmol) in dry dichloromethane (10 mL) was treated with dibenzyloxy(diisopropylamino)phosphine [prepared as in Bannwarth, W.; Trzeciak, A. Helv. Chim. Acta, 70, p. 175 (1987)] (399 mg, 1.120 mmol) and 1H-tetrazole (191 mg, 2.270 mmol). After 3 h at room temperature the suspension was cooled to −40° C., and solid m-chloroperbenzoic acid (50–60%, 570 mg, 1.82 mmol) was added. After 1 h the temperature of the mixture reached 0° C. Work-up with ethyl acetate and 5% aqueous sodium bicarbonate solution gave a crude product that was purified by silica gel flash chromatography (being eluted with 25% ethyl acetate in hexane) to yield the title compound as a yellow oil (185 mg, Y: 45%); $^1$H-NMR (CDCl$_3$, 300 MHz) δ ppm: 7.40–7.26 (m, 10H) 5.00 (m, 4H) 4.01 (q, 2H) 3.57 (t, 2H) 1.72–1.47 (m, 4H) 0.87 (s, 9H) 0.02 (s, 6H); HRMS calcd for MH+: 465.2226, found: 465.2216.

EXAMPLE 26

4-Dibenzylphosphonooxy-1-butanol (XXIXa)

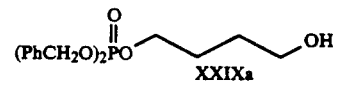

Compound XXVIIIa (90 mg, 0.201 mmol) in dry THF (1 mL) was treated with tetrabutylammonium fluoride (1M in THF, 0.4 mL, 0.4 mmol). After 3 h at room temperature, the mixture was partitioned between water and EtOAc, dried, and loaded on a silica gel flash column (being eluted with 40% ethyl acetate in hexane with 2% methanol) to give 64.4 mg (Y: 92%) of the title compound as an oil; $^1$H-NMR (CDCl$_3$, 300 MHz) δ ppm: 7.38–7.28 (m, 10H) 5.01 (m, 4H) 4.02 (q, 2H) 3.59 (t, 2H) 1.73–1.51 (m, 4H); HRMS calcd for MH+: 351.1361, found: 351.1371.

EXAMPLE 27

4-(Dibenzylphosphonooxy)butanoic acid (XXVa)

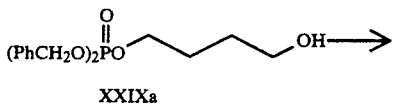

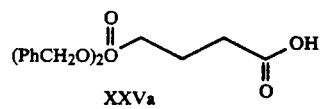

Alcohol XXIXa (772 mg, 2.200 mmol) in acetone (6 mL) at 0° C. was treated with chromic acid (Jones' reagent, 2.7M, 4.15 mL, 11 mmol). After 16 h at room temperature, the mixture was diluted with water and extracted with ethyl acetate. The organic layer was washed with 10% aqueous sodium thiosulfate, dried and concentrated to yield the title compound as a colorless oil (746.8 mg, Y: 93%). This oil was used directly in a subsequent step without further purification; $^1$H-NMR (CDCl$_3$, 300 MHz) δ ppm: 7.53–7.27 (m, 10H) 4.99 (m, 4H) 3.97 (q, 2H) 2.31 (t, 2H) 1.84 (m, 2H); HRMS calcd for MH+: 365.1154, found: 365.1132.

EXAMPLE 28

1-Dibenzylphosphonooxy-3,3,-dimethyl-4-(t-butyl-dimethylsilyloxy)butane (XXVIIIb)

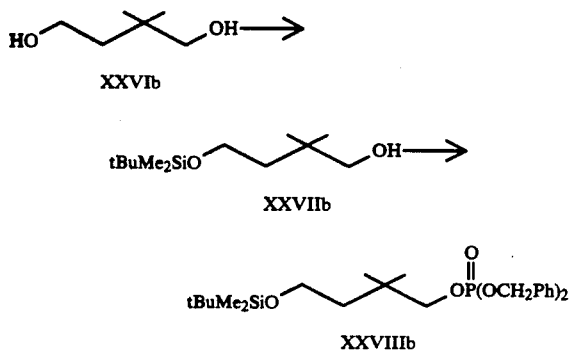

A solution of 2,2-dimethyl-1,4-butanediol (8.01 g, 67.8 mmol) in dry THF (80 mL) was treated with t-butyldimethylsilyl chloride (10.2 g, 67.8 mmol) and imidazole (4.60 g, 67.6 mmol). After 24 h at room temperature, work-up with ethyl acetate and water followed by drying the organics and concentration gave a crude product, which was purified by silica gel flash chromatography (being eluted with 5% ethyl acetate in hexane) to afford 11.0 g (Y: 70%) of 4-t-butyldimethylsilyloxy-2,2-dimethyl-1-butanol (XXVIIb) as a colorless oil; $^1$H-NMR (DMSO-d$_6$) δ ppm: 4.43 (t, 1H) 3.61 (t, 2H) 3.05 (d, J=2.7 Hz, 2H) 1.38 (t, 2H) 0.83 (s, 9H) 0.78 (s, 6H) 0.00(s, 6H); HRMS Calcd for C$_{12}$H$_{29}$O$_2$Si (MH+): 233.1937, found: 233.1930.

This oil (6.19 g, 26.6 mmol) in dry dichloromethane (110 mL) was treated with 1H-tetrazole (5.60 g, 79.9 mmol) followed by a solution of dibenzyloxy(diisopropylamino)phosphine (14.2 g, 39.9 mmol) in dry dichloromethane (10 mL). After 2 h at room temperature, the suspension was cooled to −40° C., and solid m-chloroperbenzoic acid (50–60%, 16.7 g, 53.5 mmol) was added. The resulting mixture was allowed to warm up to 0° C., then it was worked up by addition of 5% aqueous sodium bicarbonate, phase separation, and washing the organics with 10% sodium thiosulfate followed by water. The organic phase was dried and evaporated. The residue was chromatographed on silica gel (being eluted with 25% ethyl acetate in hexane) to yield 11.5 g (Y: 89%) of the title compound as a colorless oil; $^1$H-NMR (CDCl$_3$) δ ppm: 7.34–7.27 (m, 10H) 5.01 (d, J=8.4 Hz, 4H) 3.67 (d, J=4.2 Hz, 2H) 3.61 (t, 2H) 1.46 (t, 2H) 0.88 (s, 6H) 0.85 (s, 9H) 0.00 (s, 6H); HRMS Calcd for C$_{26}$H$_{42}$O$_5$PSi (MH+): 493.2539, found: 293.2534.

EXAMPLE 29

4-Dibenzylphosphonooxy-3,3-dimethyl-1-butanol (XXIXb)

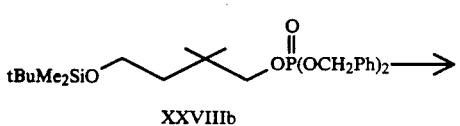

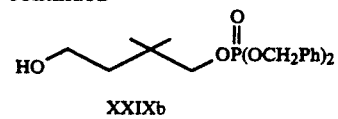

Tetrabutylammonium fluoride (1M in THF, 24.1 mL, 24.1 mmol) was added to a solution of compound XXVIIIb (10.8 g, 21.9 mmol) in dry THF (100 mL). After 4 h at room temperature, the reaction was worked up by addition of ethyl acetate and water. Following separation of the two layers, the organic phase was dried and concentrated. The residue was purified by silica gel chromatography (being eluted with 65% ethyl acetate in hexane) to give 7.35 g (Y: 89%) of the title product as a colorless oil; $^1$H-NMR (DMSO-d$_6$) δ ppm: 7.41–7.30 (m, 10H) 5.01 (d, J=9 Hz, 4H) 4.33 (t, 1H) 3.64 (d, J=6 Hz, 2H) 3.45–3.38 (m, 2H) 1.37 (t, 2H) 0.82 (s, 6H).

EXAMPLE 30

4-Dibenzylphosphonooxy-3,3-dimethylbutanoic acid (XXVb)

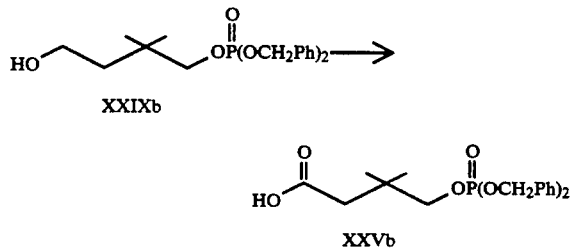

Chromic acid (Jones reagent, 2.7M, 7.5 mL, 20.2 mmol) was added to a solution of compound XXIXb (1.53 g, 4.04 mmol) in acetone (30 mL). After 5 h at room temperature, the solids were removed by filtration and the filtrate diluted with ethyl acetate. The diluted filtrate was washed with water followed by 10% aqueous sodium thiosulfate. The organic layer was dried and concentrated to give 1.43 g (89% yield) of the title product as a colorless oil which was used without further purification; $^1$H-NMR (CDCl$_3$) δ ppm: 7.34–7.29 (m, 10H) 5.02 (dd, J=8.4 Hz, J'=1.2 Hz, 4H) 3.79 (d, J=6 Hz, 2H) 2.24 (s, 2H) 0.97 (s, 6H); HRMS Calcd for C$_{20}$H$_{26}$O$_6$P (MH+) 393.1467, found: 393.1455.

EXAMPLE 31

2-[2-(t-Butyldimethylsiloxy)ethyl]phenol (XLVIa)

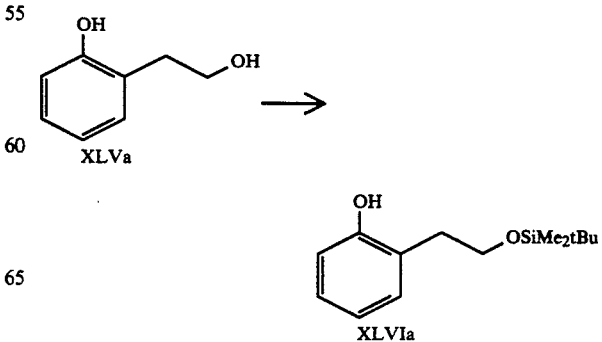

2-Hydroxyethylphenol (XLVa) (15.2 g, 0.11 mol) and t-butyldimethylsilyl chloride (18.2 g, 0.121 mol) were placed together in DMF (120 mL; Aldrich Sure Seal). While the solution was being stirred, imidazole (16.5 g, 0.242 mol) was added portionwise (slightly exothermic). After stirring for 3 h at room temperature, EtOAc (200 mL) was added and the resultant solution was washed with water (3×200 mL) and brine (200 mL). The EtOAc layer was dried over anhydrous sodium sulfate, filtered and concentrated to leave a yellow oil which was purified by silica gel column chromatography (being eluted with 19:1 hexanes/EtOAc) to obtain 27.7 g (0.11 mol, Y: 100%) of the title compound as an oil; Rf: 0.40 (19:1 hexanes/EtOAc); $^1$H-NMR (CDCl$_3$) δ ppm: 0.067 (6H, s, SiMe$_2$), 0.893(9H, s, SitBu), 2.87 (2H, t, J=5 Hz, ArCH$_2$), 3.91 (2H, t, J=5 Hz, CH$_2$OSi), 6.80 (1H, dt, J=1.3, 7.4 Hz, 5'-H), 6.90 (1H, dd, J=1.2, 8 Hz, 2'-H), 7.00 (1H, dd, J=1,5, 7.3 Hz, 6'-H), 7.12 (1H, dt, J=1.6, 7.5 Hz, 4'-H), 8.29 (1H, s, OH, D$_2$O exchanged); IR (film) 3300 (OH), 1616 cm$^{-1}$; MS (FAB/NOBA) m/e: 253 (MH+), 237, 209.

Anal. calcd for C$_{14}$H$_{24}$O$_2$Si: C, 66.61; H, 9.59. Found: C, 66.53: H, 9.64.

EXAMPLE 32

1-(t-Butyldimethylsilyloxy1ethyl-2-(dibenzylphosphonooxy)benzene (XLVIIa)

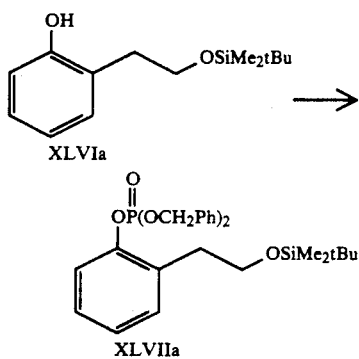

To a solution of siloxyphenol XLVIa (15.3 g, 60.6 mmol) in anhydrous THF (140 mL) in an ice-bath was added under nitrogen atmosphere a solution of 2.5M n-BuLi in hexanes (24.3 mL, 60.8 mmol) over a period of 15 min. To this was added tetrabenzylpyrophosphate (XXIVa) (35.5 g, 67 mmol) and the cooling bath was removed. After the mixture was stirred for 2 h, the precipitate was removed by filtration and the filtrate concentrated to leave an oily residue. This was purified by silica gel column chromatography (being eluted with 9:1 hexanes/EtOAc) to obtain 31 g (60.5 mmol, Y: 99.8%) of the title compound as an oil; Rf: 0.4 (9:1 hexanes/EtOAc); $^1$H-NMR (CDCl$_3$) δ ppm: −0.08 (6H, s, SiMe$_2$), 0.817 (9H, s, SitBu), 2.82 (2H, t, J=7 Hz, ArCH$_2$), 3.73 (2H, t, J=7 Hz, CH$_2$OSi), 5.10 (4H, ABq, OCH$_2$), 7–7.3 (14H, m, Ar-Hs); IR (film) 1492, 1456 cm$^{-1}$; MS (FAB/NOBA) m/e: 513 (MH+), 455.

Anal. calcd for C$_{28}$H$_{37}$O$_5$SiP: C, 65.60; H, 7.27. Found: C, 65.65; H, 7.34.

EXAMPLE 33

2-[2-(Dibenzylphosphonooxy)phenyl]ethanol (XLVIIIa)

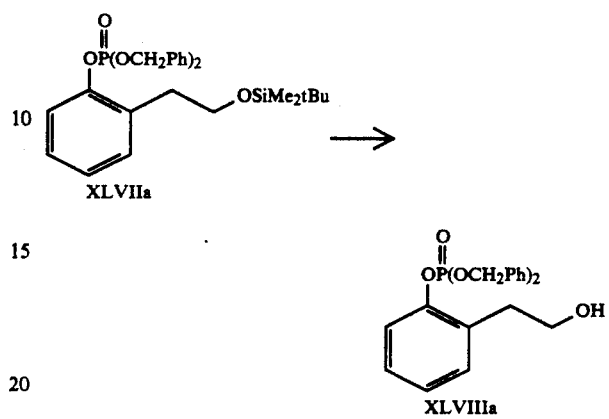

A solution of siloxy phosphate compound XLVIIa (54 g, 0.105 mol) in 2-propanol (600 mL) was treated with 6N HCl (45 mL). After the reaction mixture was stirred for 1 h at room temperature, the reaction mixture was concentrated in vacuo without warming. The residue was dissolved in EtOAc (400 mL) and washed successively with water (2×300 mL) and brine (300 mL). After drying over anhydrous sodium sulfate, filtration and concentration, 43 g (0.108 mol, Y: >100%) of the title compound crystallized as white crystals from an oily residue upon standing. An analytical sample was obtained by trituration with hexane; mp, 65°–66° C.; Rf: 0.35 (1:1 hexanes/EtOAc); $^1$H-NMR (CDCl$_3$) δ ppm: 2.83 (2H, t, J=6.5 Hz, ArCH$_2$), 3.77 (2H, t, J=6.5 Hz, CH$_2$OH), 5.10 (4H, d, J=8.5 Hz, OCH$_2$Ph), 7.05–7.36 (14H, m, Ar-Hs); IR (KBr) 3436 (OH), 1490, 1458 cm$^{-1}$; MS (FAB/NOBA) m/e: 399 (MH+), 381, 277.

Anal. calcd for C$_{22}$H$_{23}$O$_5$P: C, 66.33; H, 5.82. Found: C, 66.56; H, 5.86.

EXAMPLE 34

2-(Dibenzylphosphonooxy)phenylacetic acid (IXd)

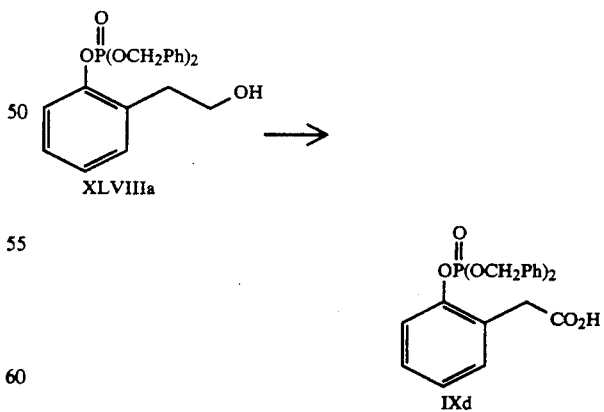

To a stirred solution of phenylethanol XLVIIIa (41.3 g, 0.104 mol) in acetone (500 mL) was added the Jones reagent (65 mL). The resultant mixture was stirred further at ambient temperature for 45 min and then 2-propanol (40 mL) was added. Stirring was continued for 20 min. Then EtOAc (400 mL) and water (400 mL)

were added with stirring and the layers were separated. The aqueous layer was extracted further with EtOAc (200 mL). The combined EtOAc layers were washed with water (2×300 mL), and brine (300 mL), dried over anhydrous sodium sulfate and filtered. Concentration of the filtrate in vacuo gave crystals which were triturated with 1:1 EtOAc/hexanes (300 mL) to give after drying 24.4 g (59.2 mmol, Y: 56.9%) of the title compound as white crystals; mp, 114°–116° C.; Rf: 0.35 (EtOAc); $^1$H-NMR (CDCl$_3$) δ ppm: 3.61 (2H, s, CH$_2$Ar), 5.07 (4H, d, J=8 Hz, OCH$_2$), 7.05–7.35 (14H, m, Ar-Hs); IR (KBr) 3065 (br, CO$_2$H), 1722 (CO$_2$H) cm$^{-1}$; MS (FAB/NOBA) m/e: 413 (MH+), 277.

Anal. calcd for C$_{22}$H$_{21}$O$_6$P: C, 64.08; H, 5.13. Found: C, 64.30; H, 5.18.

EXAMPLE 35

2'-O-[3''-(2'''-Dibenzylphosphonooxy-4''',6'''-dimethylphenyl)-3'',3''-dimethylpropionyl]taxol (XLIa)

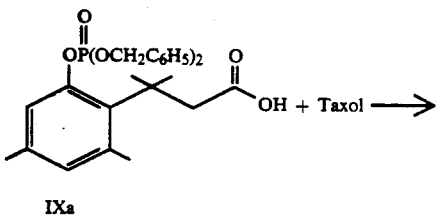

IXa

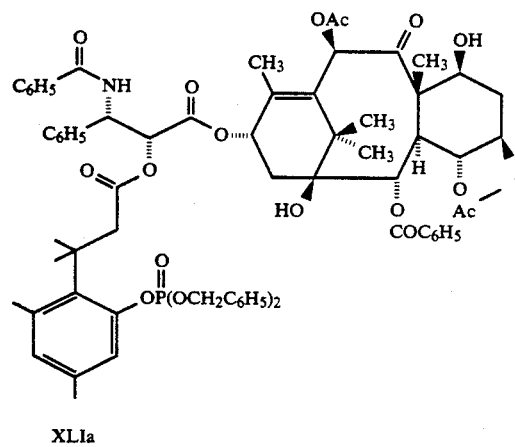

XLIa

To a solution of compound IXa (65 mg, 0.13 mmol, 1.1 eq.) in anhydrous CH$_2$Cl$_2$ (8 mL) was added N,N-dicyclohexylcarbodiimide (DCC, 40 mg, 0.19 mmol, 1.6 eq.) and 4-DMAP (14 mg, 0.11 mmol, 1 eq.). The reaction mixture was stirred at room temperature for 10 min under nitrogen. To this mixture was added taxol (100 mg, 0.12 mmol) and the stirring was maintained at room temperature for 4.5 h. The solvent was pumped off from the reaction mixture and the residue was taken into acetone (5 mL). The undissolved material was filtered off and the filtrate was concentrated in vacuo to obtain 190 mg of the title product, XLIa, as a crude solid. The crude product, thus obtained, was purified on a silica gel column, being eluted with 40% EtOAc in hexanes, to obtain 100 mg (0.076 mmol, Y: 69%) of the title compound as a white powder; mp, 110–120° C. (decomposition); [α]$_D^{20}$−35.5° (c=0.22, 95% EtOH); $^1$H-NMR (300 MHz, acetone-d$_6$) δ ppm: 1.17 (6H, s, 16-H$_3$ and 17-H$_3$), 1.52 (3H, s, 3''-Me), 1.56 (3H, s, 3''-Me), 1.64 (3H, s, 19-H$_3$), 1.86 (3H, s, 18-H$_3$), 2.05 (3H, s, 10-OAc), 2.16 (3H, s, 6'''-Me), 2.39 (3H, s, 4-OAc), 2.43 (3H, s, 4'''-Me), 2.92–2.97–3.01–3.06 (2H, ABq, 2''-H$_2$), 3.48 (1H, d, J=5.8 Hz, 7-OH, exchanged with D$_2$O), 3.81 (1H, d, J=7.1 Hz, 3-H), 3.89 (1H, s, 1-OH, exchanged with D$_2$O), 4.15 (2H, ABq, 20-H$_2$), 4.39 (1H, m, 7-H), 4.93 (1H, d, J=8.1 Hz, 5-H), 5.14 (2H, ABq, CH$_2$Ph), 5.1–5.13 (2H, m, CH$_2$Ph), 5.44 (1H, d, J=5.4 Hz, 2'-H), 5.66 (1H, d, J=7.1 Hz, 2-H), 5.88 (1H, dd, J=5.4, 8.9 Hz, 3'-H), 6.11 (1H, bt, J=9.5 Hz, 13-H), 6.39 (1H, s, 10-H), 6.65 (1H, s, Ar-H), 7.0 (1H, s, Ar-H), 7.21–7.68 (21H, m), 7.85 (2H, "d", J=8 Hz, 3'-NHCOPh), 8.10 (2H, "d", J=8 Hz, 2-CO$_2$Ph), 8.31 (1H, d, J=8.9 Hz, NH, exchanged with D$_2$O); MS (FAB-NOBA) m/e: 1318 (M+H)+, 1340 (M+Na)+, 1356 (M+K); IR (KBr) ν max: 3440, 1740 (C=O), 1665 (CONH), 1275 (P=O), 1250 (C—O), 1020 (P—O) cm$^{-1}$; UV (MeOH:-H$_2$O, 1:1) λ max: 196 nm (ε 1.35×10$^4$); HRMS calcd for C$_{74}$H$_{81}$NO$_{19}$P (MH+): 1318.5140, found: 1318.5187.

Anal. calcd for C$_{74}$H$_{80}$NO$_{19}$P.H$_2$O: C, 66.51; H, 6.19; N, 1.05. Found: C, 66.65; H, 6.26; N, 1.06.

EXAMPLE 36

2'-O-[3''-(2'''-Phosphonooxy-4''',6'''-dimethylphenyl)-3'',3''-dimethylpropionyl]taxol (Ia)

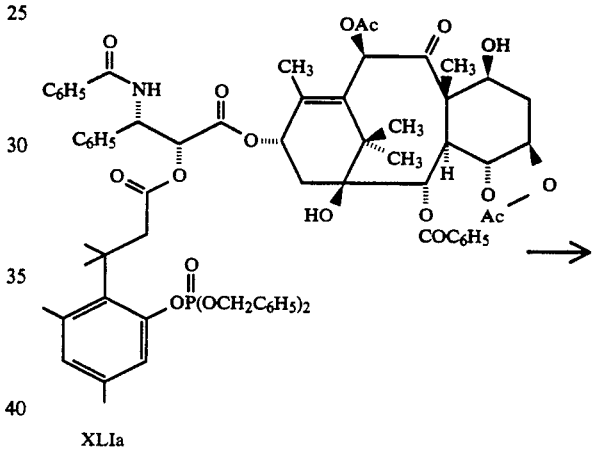

XLIa

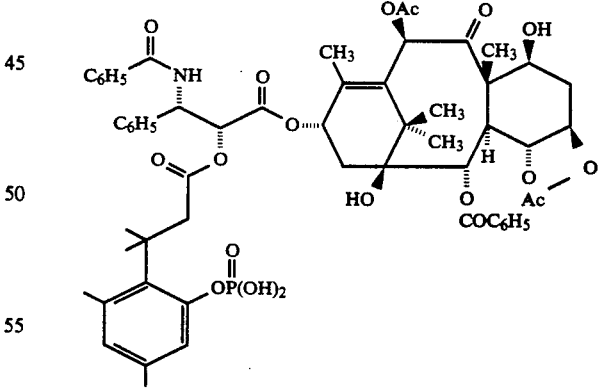

Ia

A mixture of compound XLIa (60 mg, 0.046 mmol) and 10% Pd on activated carbon (20 mg) in absolute EtOH (10 mL) was stirred under 40 psi of hydrogen atmosphere in a Parr apparatus for 3.5 h. The catalyst was filtered through Celite and the filtrate was concentrated in vacuo to yield a solid. The solid was triturated with anhydrous ether to obtain 50 mg (0.044 mmol, Y: 96%) of the title compound, Ia, as a white powder; mp, 158–163° C. (decomposition); [α]$_D^{20}$ −41.4° (c=0.22, 95% EtOH); $^1$H-NMR (300 MHz, acetone-d$_6$) δ ppm: 1.15 (3H, s, 17-H$_3$), 1.16 (3H, s, 16-H$_3$), 1.56 (3H, s, 3″-Me), 1.58 (3H, s, 3″-Me), 1.63 (3H, s, 19-H$_3$), 1.88 (3H, s, 18-H$_3$), 2.05 (3H, s, 10-OAc), 2.15 (3H, s, 6‴-Me), 2.38 (3H, s, 4-OAc), 2.43 (3H, s, 4‴-Me), 2.30-3.-05-3.21-3.26 (2H, ABq, 2″-H$_2$), 3.79 (1H, d, J=7.1 Hz, 3-H), 4.13 (2H, s, 20-H$_2$), 4.38 (1H, dd, J=10.5, 6.5 Hz, 7-H), 4.92 (1H, d, J=9.6 Hz, 5-H), 5.39 (1H, d, 6.6 Hz, 2′-H), 5.64 (1H, d, J=7.1 Hz, 2-H), 5.78 (1H, "t", J=7.5 Hz, 3′-H), 6.05 (1H, "t", J=8.8 Hz, 13-H), 6.39 (1H, s, 10-H), 6.54 (1H, s, Ar-H), 7.17–7.69 (12H, m), 7.94 (2H, "d", J=7 Hz, 3′-NHCOPh), 8.10 (2H, "d" J=8 Hz, 2-CO$_2$Ph), 8.62 (1H, d, J=8.7 Hz, NH, exchanged with D$_2$O); MS (FAB-NOBA/KI+NaI) m/e: 1138 (M+H)$^+$, 1160 (M+Na)$^+$, 1176 (M+K)$^+$, 1182 (M+2Na-H)$^+$, 1198 (M+K+Na-H)$^+$, 1214 (M+2K-H)$^+$; IR (KBr) ν max: 3438, 1730, 1665, 1270, 1250, 980 (P—OH) cm$^{-1}$; UV (MeOH:H$_2$O, 1:1) λ max: 198 (ε 9.3×10$^4$), 227 nm (ε 3.2×10$^4$); HRMS calcd for C$_{60}$H$_{68}$NO$_{19}$P (MH+): 1138.4201, found: 1138.4158.

Anal. calcd for C$_{60}$H$_{68}$NO$_{19}$P.3H$_2$O: C, 60.45; H, 6.26; N, 1.18. Found: C, 60.12; H, 6.02; N, 1.12.

EXAMPLE 37

2′-O-[3″-(2‴-Phosphonooxy-4‴,6‴-dimethylphenyl)-3″,3″-dimethylpropionyl]taxol disodium salt (Ib)

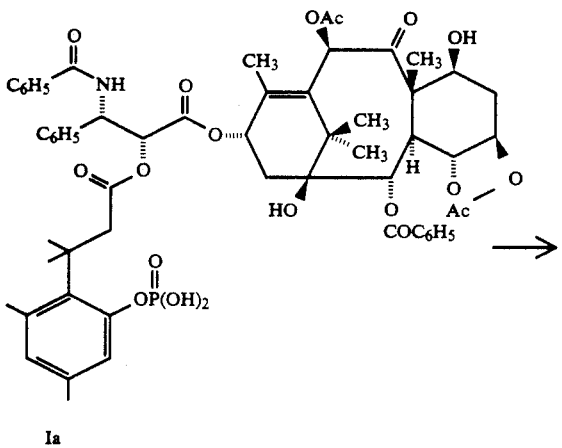

Ia

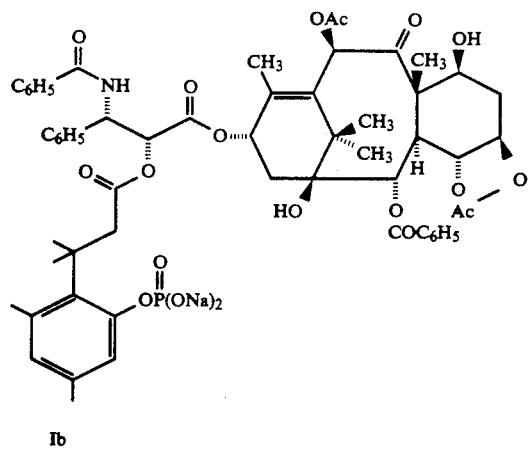

Ib

To a suspension of compound Ia (70 mg, 0.062 mmol) in water was added sodium hydrogen carbonate (11 mg. 0.13 mmol, 2.1 eq.). This mixture was sonicated at room temperature for 5 min to obtain a clear solution. This solution was passed through C-18 reverse phase column (Lichroprep RP-18, EM Science). The column was successively eluted with water (150 mL), 5% CH$_3$CN in H$_2$O (100 mL), 10% CH$_3$CN in H$_2$O (100 mL) and then with 25% CH$_3$CN in H$_2$O. The fractions containing the desired material, Ib, were combined; CH$_3$CN was pumped off; and the remaining aqueous portion was lyophilized to obtain 57 mg (0.048 mmol, Y: 77%) of the title compound, Ib, as a white puffy material; HPLC Rt: 3.15 min (purity>99%; C$_{18}$ Waters radial pack column; flow rate: 2 mL/min; eluent: 35/65 of A/B, A=0.05M, pH 6.1 ammonium phosphate buffer, B=80% CH$_3$CN in H$_2$O; UV detection at 254 nm); taxol Rt: 5.37 min; [α]$_D^{20}$ −35.9 (c=0.39, 95% EtOH); $^1$H-NMR (300 MHz, acetone-d$_6$/D$_2$O) δ ppm: 1.1 (6H, s, 16-H$_3$ & 17-H$_3$), 1.55 (3H, s, 3″-Me), 1.56 (3H, s, 3″-Me), 1.57 (3H, s, 19-H$_3$), 1.78 (3H, s, 18-H$_3$), 2.04 (3H, s, 10-OAc), 2.14 (3H, s, 6‴-Me), 2.31 (3H, s, 4-OAc), 2.32 (3H, s, 4‴-Me), 3.12–3.17–3.35–3.40 (2H, ABq, 2″-H$_2$), 3.7 (1H, d, J=7.2 Hz, 3-H), 4.1 (2H, s, 20-H$_2$), 4.29 (1H, dd, J=6.3, 10.5 Hz, 7-H), 4.94 (1H, d, J=8.1 Hz, 5-H), 5.31 (1H, d, 7.5 Hz, 2′-H), 5.57 (1H, d, J=7.2 Hz, 2-H), 5.64 (1H, d, J=7.8 Hz, 3′-H), 5.94 (1H, bt, J=9 Hz, 13-H), 6.24 (1H, s, 10-H), 6.24 (1H, s, Ar-H), 7.14–7.72 (12H, m), 7.81 (2H, "d", J=8.1 Hz, 3′-NHCOPh), 8.04 (2H, "d", J=8.4 Hz, 2-CO$_2$Ph); MS (FAB-NOBA/-NaI+KI) m/e: 1160 (M+Na)$^+$, 1182 (M+2Na-H)$^+$, 1198 (M+K+Na-H)$^+$, 1220 (M+2Na+K-2H)$^+$; IR (KBr) ν max: 3446, 1730, 1270, 1250, 1170, 975 cm$^{-1}$; UV (MeOH:H$_2$O, 1:1) λmax: 200 (ε 9.02×10$^4$), 226 nm (ε 3.23×10$^4$); Solubility: >1 mg/50 μL deionized water at 22° C. (clear solution); HRMS calcd for C$_{60}$H$_{67}$NO$_{19}$PNa$_2$ (MH+): 1182.3840, found: 1182.3886.

EXAMPLE 38

2′-O-(Benzyloxycarbonyl)taxol (Ic)

Taxol ⟶

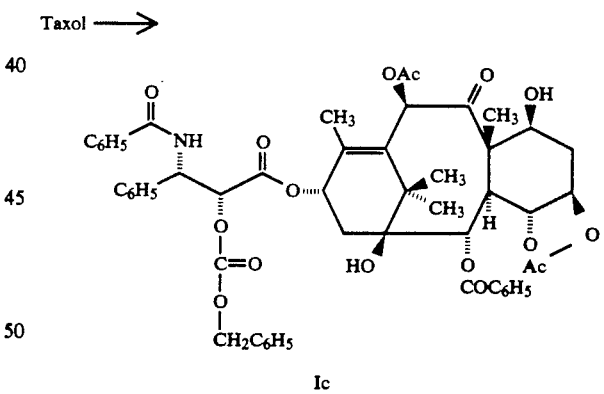

Ic

To a stirred, room temperature solution of taxol (150 mg, 0.176 mmol) and N,N-diisopropylethylamine (93 μL, 0.534 mmol, 3 eq.) in anhydrous CH$_2$Cl$_2$ (4 mL) was added benzyl chloroformate (75 μL, 0.525 mmol, 3 eq.) at room temperature. The reaction mixture was stirred at room temperature for 3 h. The reaction mixture was concentrated to 2 mL in volume and the product was purified on a silica gel column, using 1:1 of EtOAc/hexanes as eluent, to obtain 150 mg (0.152 mmol, Y:86%) of the title compound, Ic, as a white powder; mp, 140–150° C. (decomposition); [α]$_D^{20}$−53.5° (c=0.2, 95% EtOH); $^1$H-NMR (300 MHz, acetone-d$_6$) δ ppm: 1.18 (3H, s, 17-H$_3$), 1.92 (3H, s, 16-H$_3$), 1.66 (3H, s, 19-H$_3$), 1.96 (3H, s, 18-H$_3$), 2.16 (3H, s, 10-OAc), 2.5 (3H, s, 4-OAc), 3.53 (1H, d, J=5.89

Hz, 7-OH, exchanged with D₂O), 3.85 (1H, d, J=7.19 Hz, 3-H), 3.9 (1H, s, 1-OH, exchanged with D₂O), 4.17 (2H, ABq, 20-H₂), 4.25 (1H, m, 7-H), 4.97 (1H, d, J=9.56 Hz, 5-H), 5.19 (2H, ABq, OCH₂C₆H₅), 5.54 (1H, d, J=5.5 Hz, 2'-H), 5.68 (1H, d, J=7.13 Hz, 2-H), 6.01 (1H, dd, J=5.5, 9.05 Hz, 3'-H), 6.17 (1H, bt, J=9.0 Hz, 13-H), 6.42 (1H, s, 10-H), 7.28–7.69 (16H, m), 7.87 (2H, "d", J=8 Hz, 3'-NHCOPh), 8.14 (2H, "d", J=8 Hz, 2-CO₂Ph), 8.55 (1H, d, J=9.06 Hz, NH, exchanged with D₂O); MS (FAB-NOBA/NaI+KI) m/e: 988 (M+H)⁺, 1010 (M+Na)⁺, 1026 (M+K)⁺; IR (KBr) ν max: 3448, 1748 (C=O), 1726 (CONH), 1250 (C—O) cm⁻¹; UV (MeOH:H₂O, 1:1) λ max: 198 (ε 7.3×10⁴), 230 nm (ε 2.7×10⁴); HRMS calcd for C₅₅H₅₈NO₁₆ (MH⁺): 988.3756, found: 988.3766.

Anal. calcd for C₅₅H₅₇NO₁₆·H₂O: C, 65.67; H, 5.92; N, 1.40. Found: C, 65.99; H, 5.64; N, 1.33.

EXAMPLE 39

2'-O-Benzyloxycarbonyl-7O-[3''-(2''''-dibenzylphosphonooxy-4''',6'''-dimethylphenyl)-3'',3''-dimethylpropionyl]taxol (XLa)

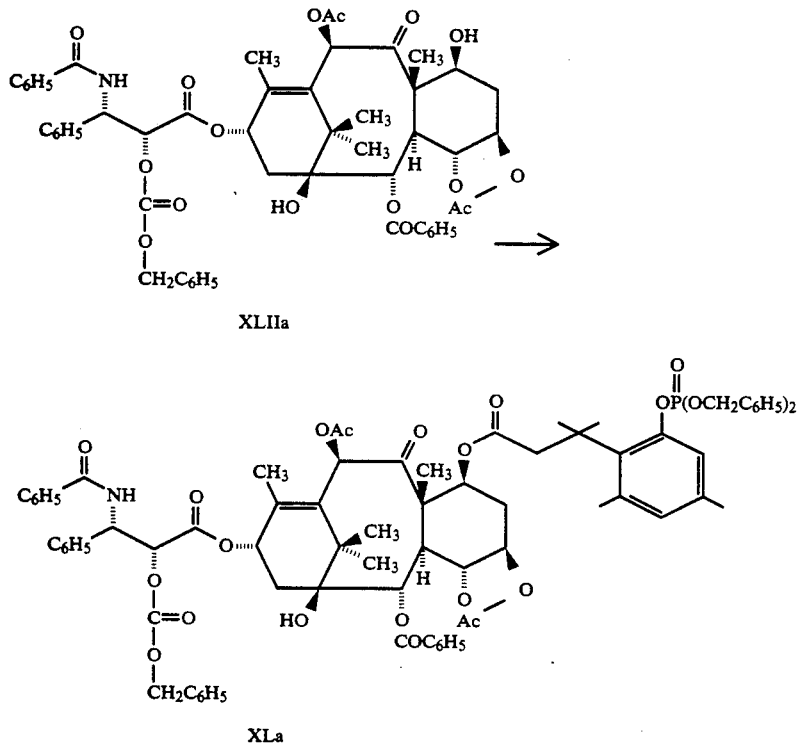

XLIIa

XLa

To a stirred mixture (15 min at room temperature) of compound IXa (95 mg, 0.2 mmol, 1.3 eq.), DCC (53 mg, 0.26 mmol, 1.7 eq.), and 4-DMAP (20 mg, 0.16 mmol, 1.1 eq.) in anhydrous CH₂Cl₂ (6 mL) was added compound XLIIa (150 mg, 0.15 mmol). The reaction mixture was stirred continuously at room temperature for 2.5 days. The solvent was evaporated off from the reaction mixture and the resultant residue was taken into acetone. The insoluble material was filtered off and the filtrate was concentrated in vacuo to obtain a solid which was purified on a silica gel column using 10% EtOAc in CH₂Cl₂ as eluent to obtain 70 mg (0.048 mmol, Y: 32%) of the title compound, XLa, as a white powder; mp, 87–95° C. (decomposition); [α]$_D^{20}$ −38.49° (c=0.265, CH₂Cl₂); ¹H-NMR (300 MHz, acetone-d₆) δ ppm: 1.14 (3H, s, 17-H₃), 1.17 (3H, s, 16-H₃), 1.52 (3H, s, 19-H₃), 1.65 (6H, s, 3'',3''-Me₂), 1.91 (3H, 18-H₃), 2.06 (3H, s, 10-OAc), 2.09 (3H, s, 6'''-Me), 2.63 (3H, s, 4'''-Me), 2.68 (3H, s, 4-OAc), 2.63–2.69–3.14–3.19 (2H, ABq, 2''-H₂), 3.85 (1H, d, J=7.09 Hz, 3-H), 3.95 (1H, s, 1-OH, exchanged with D₂O), 4.11 (2H, ABq, 20-H₂), 4.78 (1H, d, J=9.93 Hz, 5-H), 5.12–5.26 (6H, m), 5.45 (1H, m, 7-H), 5.51 (1H, d, J=5.56 Hz, 2'-H), 5.63 (1H, d, J=6.9 Hz, 2-H), 5.95 (1H, dd, J=6.5, 8.9 Hz, 3'-H), 6.12 (1H, bt, J=9 Hz, 13-H), 6.22, (1H, s, 10-H), 6.7 (1H, s, Ar-H), 7.08 (1H, s, Ar-H), 7.30–7.67 (26H, m), 7.86 (2H, "d", J=8.5 Hz, 3'-NHCOPh), 8.12 (2H, "d", J=8.5 Hz, 2-CO₂Ph), 8.54 (1H, d, J=8.93 Hz, NH, exchanged with D₂O); MS (FAB) m/e: 1453 (M+H)⁺; IR (KBr) ν max: 3432, 1750, 1665, 1240, 1025 (P-O) cm⁻¹; HRMS calcd for C₈₂H₈₇NO₂₁P (MH⁺): 1452.5508, found: 1452.5693.

Anal. calcd for C₈₂H₈₆NO₂₁P: C, 67.81; H, 5.97; N, 0.97.

Found: C, 67.97; H, 6.38; N, 1.18.

The starting material XLIIa (65 mg, 0.066 mmol, Y: 43%) was also recovered from the column as a white powder.

ALTERNATE RUN

To a stirred mixture of compound IXa (1.05 g, 2.18 mmol, 1.3 eq.) and compound XLIIa (1.66 g, 1.68 mmol) in anhydrous CH₂Cl₂ (40 mL) was added 4-DMAP (427 mg, 1.85 mmol, 1.1 eq.) and DCC (381 mg, 1.85 mmol, 1.1 eq.). The reaction mixture was allowed to be stirred at room temperature for 2 days. The reaction appeared to be incomplete. The additional amounts of DCC (200 mg, 0.971 mmol, 0.58 eq.), acid IXa (412 mg, 0.854 mmol, 0.51 eq.) and DMAP (167 mg, 0.723 mmol, 0.43 eq.) were added and the mixture stirred for an additional 4 days. The solvent was evaporated off from the reaction mixture and the residue was taken into acetone. The insoluble material (presumably DCU) was filtered off and the filtrate was concentrated in vacuo to obtain a solid which was purified by silica gel column, being eluted with 50% EtOAc in hexane to obtain 1.76 g (1.21 mmol, Y: 72.1%) of the title compound, XLa, as a white powder; mp, 135-148° C. (dec. from acetone-hexane). The $^1$H-NMR, IR and MS spectra were essentially identical to those reported above.

EXAMPLE 40

7-O-[3''-(2'''-Phosphonooxy-4''',6'''-dimethylphenyl)-3'',3''-dimethylpropionyl]taxol disodium salt (Id)

form of Id) amount of the title compound was obtained as a white puffy powder after lyophilization (total combined yield: 92%); HPLC Rt: 2.4 min (purity >98%; $C_{18}$ Waters radial pack column; flow rate: 2 mL/min; eluent: 35/65 of A/B, A=0.05M, pH 6.0 ammonium phosphate buffer, B=80% $CH_3CN$ in $H_2O$; UV detection at 254 nm); taxol Rt: 3.54 min; $[\alpha]_D^{20}$ −22.99° (c=0.335, 95% EtOH); $^1$H-NMR (300 MHz, acetone-$d_6$/$D_2O$) δ ppm: 1.05 (3H, s, 17-$H_3$), 1.09 (3H, s, 16-$H_3$), 1.50 (3H, s, 3''-Me) 1.55 (3H s, 3''-Me) 1.58 (3H s, 9-$H_3$), 1.8 (3H, s, 18-$H_3$), 2.12 (3H, s, 6'''-Me), 2.29 (3H, s, 10-OAc), 2.41 (3H, s, 4'''-Me), 2.61 (3H, s, 4-OAc),

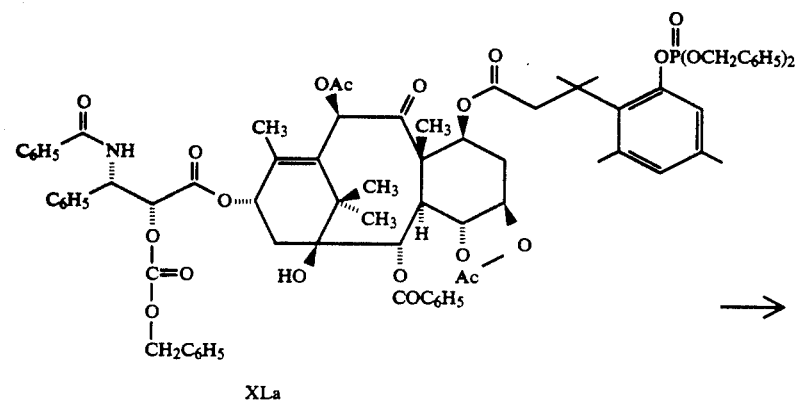

XLa

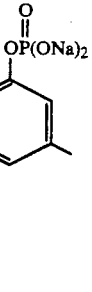

A mixture of compound XLa (70 mg, 0.048 mmol) and 10% palladium on activated carbon (25 mg) in absolute EtOH (6 mL) was stirred under 40 psi of hydrogen atmosphere in a Parr apparatus for 2 h. The catalyst was filtered through Celite and the filtrate was concentrated in vacuo. The gummy residue, thus obtained, was triturated with anhydrous ether to obtain 50 mg (0.044 mmol, 92%) of the free acid form of compound Id as a white powder. This powder was suspended in water (5 mL) and sodium hydrogen carbonate (7.5 mg, 0.89 mmol, 2 eq.) was added. The mixture was sonicated for 5 min at room temperature. The mixture was still found to be cloudy, but it turned into a clear solution by the addition of 5 drops 5 of $CH_3CN$. This solution was passed through C-18 reverse phase column. The column was successively eluted with water (800 mL), 15% $CH_3CN$ in $H_2O$ (100 mL) and 25% $CH_3CN$ in $H_2O$. The fractions containing the desired compound were combined; $CH_3CN$ was removed by evaporation; and the remaining aqueous portion was lyophilized to obtain 37 mg (0.031 mmol, Y: 71%, based on the free acid form of compound Id) of the title compound as a white puffy powder. When the column was further eluted with 50% $CH_3CN$ in $H_2O$, an additional (11 mg, 0.009 mmol, Y: 21%, based on the free acid 2.71-2.76-3.28-3.33 (2H, ABq, 2''-$H_2$), 3.74 (1H, d, J=6.9 Hz, 3-H), 4.05 (2H, ABq, 20-$H_2$), 4.75 (1H, d, J=6.26 Hz, 2'-H), 4.81 (1H, d, J=8.67 Hz, 5-H), 5.36 (1H, m, 7-H), 5.53 (1H, d, J=7.13 Hz, 2-H), 5.58 (1H, d, J=6.25 Hz, 3'-H), 6.02 (1H, bt, J=8 Hz, 13-H), 6.17 (1H, s, 10-H), 6.34 (1H, s, Ar-H), 7.18-7.67 (12H, m), 7.86 (2H, "d", J=8.25 Hz, 3'-NHCOPh), NHCOPh), 8.0 (2H, "d", J=8 Hz, 2-$CO_2$Ph); MS (FAB) m/e: 1160 (M-Na+2H)$^+$, 1182 (M+H)$^+$; IR (KBr) ν max: 3432, 1740, 1720, 1648, 1270, 1250 cm$^{-1}$; UV (MeOH:$H_2O$, 1:1) λ max: 200 (ε 7.85×10$^4$), 228 nm (ε 2.76×10$^4$); Solubility: >1 mg/50 μL deionized water at 22° C. (clear solution); HRMS calcd for $C_{60}H_{67}NO_{19}PNa_2$: 1182.3840, found: 1182.3864.

EXAMPLE 41

2'-O-(Ethoxycarbonyl)taxol (Ie)

Taxol ⟶

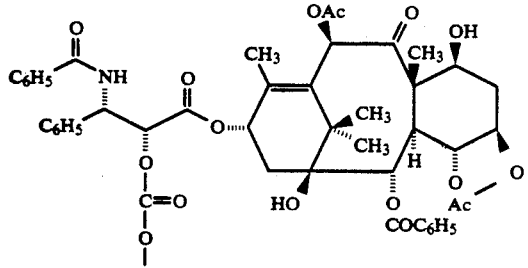

Ie

To a solution of taxol (1.1 g, 1.29 mmol) in anhydrous CH$_2$Cl$_2$ (25 mL) was added N, N-diisopropylethylamine (0.68 mL, 3.9 mmol, 3 eq.) at room temperature. The reaction mixture was stirred at room temperature for 10 min and then cooled to 0° C. To this cooled solution was added ethyl chloroformate (0.38 mL, 3.9 mmol, 3 eq.). The mixture was allowed to be stirred at 0° C. for 3 h. Subsequently, it was washed with brine and dried over anhydrous MgSO$_4$. The desiccant was filtered off and the filtrate was concentrated in vacuo to yield a white powder which was purified by silica gel chromatography, being eluted with 40% EtOAc in hexanes, to obtain 850 mg (0.92 mmol, Y: 71.3%) of the title compound as a white crystalline solid; mp, 157–162° C. (decomposition); $[\alpha]_D^{20}$ −48.3° (c=0.17 EtOH); $^1$H-NMR (acetone-d$_6$) $\delta$ ppm: 1.18 (3H, s, 17-H$_3$), 1.19 (3H, s, 16-H$_3$), 1.24 (3H, t, J=7.05 Hz, 2'-OCO$_2$CH$_2$CH$_3$), 1.65 (3H, s, 19-H$_3$), 1.95 (3H, s, 18-H$_3$), 2.15 (3H, s, 10-OAc), 2.49 (3H, s, 4-OAc), 3.53 (1H, d, J=5.89, 7-OH, exchanged with D$_2$O), 3.84 (1H, d, J=7.25 Hz, 3-H), 3.92 (1H, s, 1-OH, exchanged with D$_2$O), 4.1–4.25 (4H, m, 20-H$_2$ and 2'-CO$_2$CH$_2$), 4.42 (1H, m, 7-H), 4.96 (1H, d, J=9.45 Hz, 5-H), 5.5 (1H, d, J=5.7 Hz, 2'-H), 5.68 (1H, d, J=7.24 Hz, 2-H), 6.0 (1H, dd, J=5.65, 8.98 Hz, 3'H), 6.16 (1H, bt, J=8.97 Hz, 13-H), 6.41 (1H, s, 10-H), 7.28–7.7 (11H, m) 7.88 (2H, d, J=8.52 Hz, 3'-NHCOPh), 8.14 (2H, d, J=8.53, 2-CO$_2$Ph), 8.52 (1H, d, J=9.15 Hz NH, exchanged with D$_2$O); MS (FAB-NOBA/NaI+KI) m/e: 926 (M+H)$^+$, 948 (M+Na)$^+$, 964 (M+K)$^+$; IR (KBr) $\nu_{max}$: 1750 (C=O), 1726 (CONH), 1244 (C—O) cm$^{-1}$; UV (MeOH:H$_2$O 1:1) $\lambda_{max}$: 198 ($\epsilon$ 4.8×10$^4$), 232 ($\epsilon$ 2.3×10$^4$); HRMS calcd for C$_{50}$H$_{56}$NO$_{16}$ (MH$^+$): 926.3599, found: 926.3626.

Anal. calcd for C$_{50}$H$_{55}$NO$_{16}$.1H$_2$O: C, 63.62; H, 6.09; N, 1.49. Found: C, 63.48; H, 5.96; N, 1.40.

ALTERNATE RUN

To a solution of taxol (9.4 g, 11 mmol) in anhydrous CH$_2$Cl$_2$ (20 was added N,N-diisopropylethylamine (4.28 g, 33 mmol, 3 eq.) at room temperature. The reaction mixture was stirred at room temperature for a few minutes and then cooled to 0° C. To this cooled solution was added ethyl chloroformate (3.58 g, 33 mmol, 3 eq.) dropwise over period of a few minutes and the reaction mixture was continued to be stirred at 0° C. for 3 h. The reaction mixture was washed with brine and dried over anhydrous MgSO$_4$. The desiccant was filtered off and the filtrate was concentrated in vacuo to obtain a white powder which was purified by crystallization from acetone-95% EtOH to obtain 8.3 g (9.0 mmol, Y: 81%) of the title compound as a white crystalline solid; mp, 197–199° C. (decomposition); $[\alpha]_D^{20}$ −61.84° (c=0.76, CH$_2$Cl$_2$).

Anal calcd for C$_{50}$H$_{55}$NO$_{16}$.¼EtOH: C, 64.70; H, 6.08; N, 1.49. Found: C,64.30; H, 6.08; N, 1.44.

EXAMPLE 42

2'-O-(Allyloxycarbonyl)taxol (If)

Taxol →

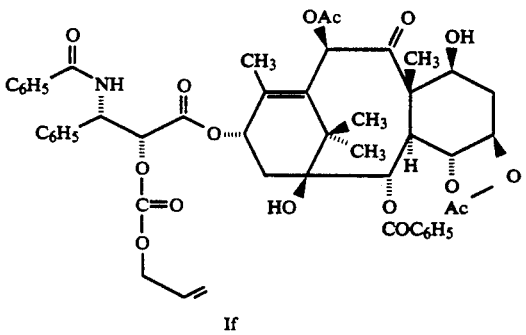

If

Taxol (169 mg, 0.198 mmol) in dry methylene chloride (3 mL) was treated with pyridine (0.02 mL) and allyl chloroformate (0.12 mL added in three batches over 36 h). After 120 h at room temperature, the mixture was diluted with ethyl acetate, washed with water and brine, and was loaded onto a silica gel column (being eluted with 50:50, ethyl acetate-hexane) to afford the title product (103 mg, Y: 62%) and unreacted taxol (18 mg). The NMR spectrum was consistent for the structure; HRMS calcd for M+K: 376.3158, found: 976.3177.

EXAMPLE 43

2'-O-[(Chloromethoxy)carbonyl]taxol (Ig)

Taxol →

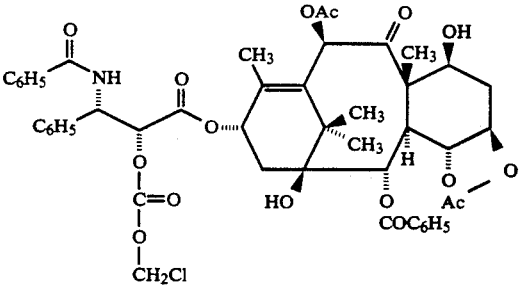

Ig

Taxol (1.160 g, 1.360 mmol) in dry methylene chloride (30 mL) was treated with N,N-diisoproylethylamine (2 mL) and then chloromethyl chloroformate (0.35 g, 2.720 mmol) at 0° C. for 3 h. Standard work up (as in Example 41 or 42) and chromatography gave the title product as a white solid (820 mg, 64%); mp, 173–6°C. (recrystallized from ether). The NMR spectrum was consistent for the structure.

EXAMPLE 44

2'-O-[(1-Chloroethoxy)carbonyl]taxol (Ih)

Taxol ⟶

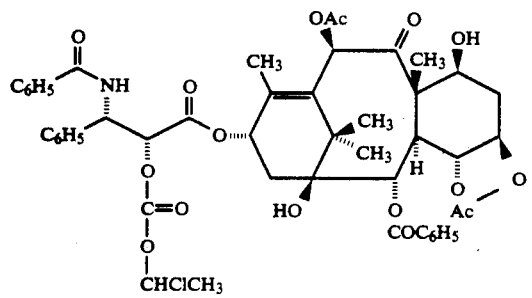

Ih

Taxol (1.000 g, 1.289 mmol) in dry methylene chloride (30 mL) was treated with N,N-diisoproylethylamine (2 mL) and then with 1-chloroethyl chloroformate (0.37 g, 2.579 mmol) at 0° C. The resulting mixture was allowed to be stirred for 3 h. Standard work up (as in Example 41 or 42) and chromatography gave the title product (875 mg, Y: 71%) as a white solid; mp, 181-3° C. (recrystallized from ether). The NMR spectrum was consistent for the structure.

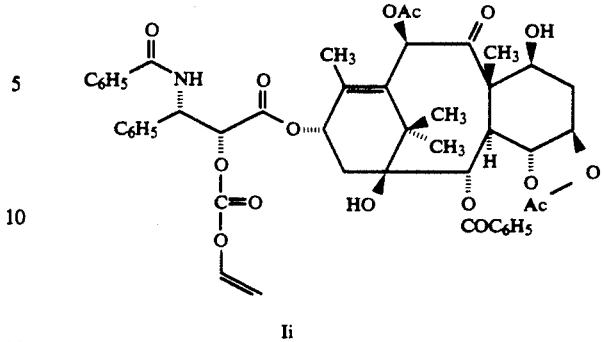

Ii

Taxol (0.850 g, 0.998 mmol) in dry methylene chloride (30 mL) was treated with N,N-diisopropylethylamine (0.6 mL) and vinyl chloroformate (0.213 g, 2.00 mmol) at 0° C. The resulting mixture was allowed to be stirred for 30 min. Standard work up (as in Example 41 or 42) and triturating the product with ether yielded the title product as a white powder (0.923 g, Y: 100%); mp, 168-71° C. The NMR spectrum was consistent for the structure.

EXAMPLE 46

2'-O-Ethoxycarbonyl-7-O-[3''-(2'''-dibenzylphosphonooxy-4''',6'''-dimethylphenyl)-3'',3''-dimethylpropionyl]taxol (XXXIa)

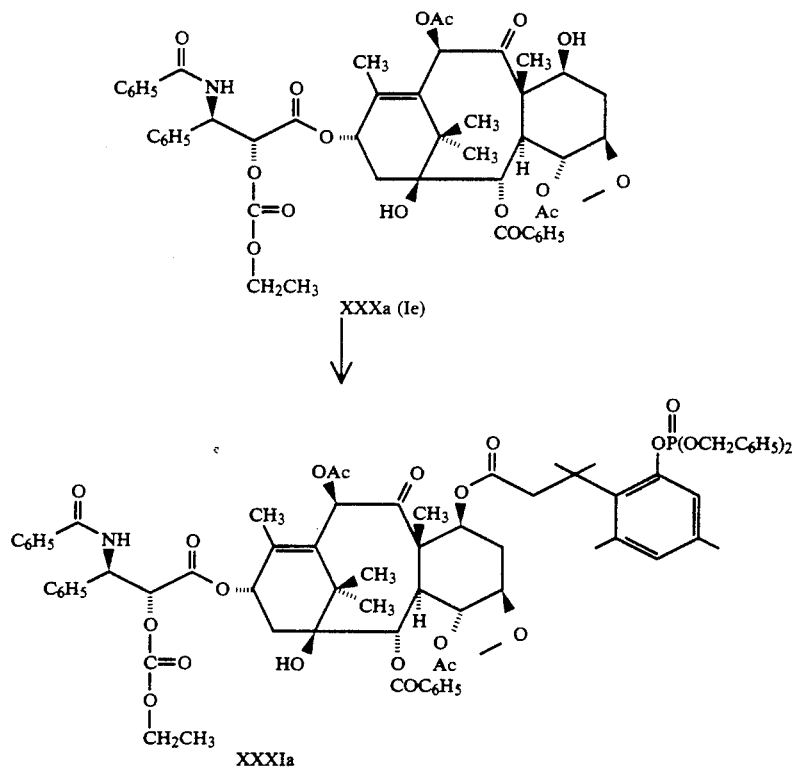

EXAMPLE 45

2'-O-(Vinyloxycarbonyl)taxol (Ii)

Taxol ⟶

To a stirred mixture (15 min at room temperature) of compound IXa (508 mg, 1.05 mmol, 1.5 eq.), DCC (247 mg, 1.12 mmol, 1.7 eq.), and 4-DMAP (94 mg, 0.77 mmol, 1.1 eq.) in anhydrous $CH_2Cl_2$ (20 mL) was added compound XXXa (650 mg, 0.702 mmol). The reaction mixture was allowed to be stirred at room temperature for 3 days under nitrogen atmosphere. The solvent was evaporated from the reaction mixture and the residue was taken into acetone. The insoluble material (presumably DCU) was filtered off and the filtrate was concentrated in vacuo to obtain a solid which was purified on a silica gel column, being eluted with 6% EtOAc in $CH_2Cl_2$, to obtain 460 mg (0.331 mmol, Y: 47%) of the title compound as a white powder; mp, 118-123° C. (decomposition); $[\alpha]_D^{20} = -44.71°$ (c=0.26, $CH_2Cl_2$); $^1$H-NMR (acetone-d$_6$) δ ppm: 1.14 (3H, s, 17-H$_3$), 1.17 (3H, s, 16-H$_3$), 1.23 (3H, t, J=7 Hz, 2'-OCO$_2$CH$_2$CH$_3$), 1.52 (3H, s, 19-H$_3$), 1.65 (6H, s, 3",3"-Me$_2$), 1.91 (3H, 18-H$_3$), 2.06 (3H, s, 10-OAc), 2.13 (3H, s, 6'''-Me), 2.44 (3H, s, 4'''-Me), 2.51 (3H, s, 4-OAc), 2.63-2.68-3.-13-3.18 (2H, ABq, 2"-H$_2$), 3.85 (1H, d, J=7 Hz, 3-H), 3.95 (1H, s, 1-OH, exchanged with D$_2$O), 4.11 (2H, bs, 20-H$_2$), 4.17 (2H, m, 2'-CO$_2$CH$_2$CH$_3$), 4.79 (1H, d, J=8 Hz, 5-H), 5.18-5.19-5.21-5.22 (2H, ABq, OCH$_2$Ph), 5.24 (2H, d, J=7.8 Hz, OCH$_2$Ph), 5.45 (1H, t, J=6.9 Hz, 7-H), 5.47 (1H, d, J=5.7 Hz, 2'-H), 5.63 (1H, d, J=7.1 Hz, 2-H), 5.96 (1H, dd, J=5.8, 8.9 Hz, 3'-H), 6.12 (1H, bt, J=9 Hz, 13-H), 6.21 (1H, s, 10-H), 6.71 (1H, s, Ar-H), 7.08 (1H, s, Ar-H), 7.30-7.67 (21H, m), 7.89 (2H, "d", J=8.5 Hz, 3'-NHCOPh), 8.12 (2H, "d", J=8.5 Hz, 2-OCOPh), 8.50 (1H, d, J=9.0 Hz, NH, exchanged with D$_2$O); MS(FAB/NOBA+NaI+KI) m/e: 1390 (M+H)+, 1412 (M+Na)+, 1428 (M+K)+; IR(KBr) ν max: 3432, 1750, 1730 (shoulder), 1244, 1020 (P—O)cm$^{-1}$; HRMS calcd for $C_{77}H_{85}NO_{21}P$(MH+): 1390.5352, found: 1390.5344.

Anal. calcd for $C_{77}H_{84}NO_{21}P \cdot H_2O$: C, 65.67; H, 6.16; N, 1.00. Found: C, 65.67; H, 6.10; N, 0.97.

ALTERNATE RUN

To a stirred mixture (15 min at room temperature) of phosphonooxyphenylpropionic acid IXa (2.17 g, 5.25 mmol, 1.75 eq.), DCC (1.19 g, 5.78 mmol, 1.93 eq.), and 4-DMAP (503 mg, 4.12 mmol, 1.37 eq.) in anhydrous $CH_2Cl_2$ (60 mL) was added compound XXXa (2.78 g, 3.00 mmol). The reaction mixture was continued to be stirred at room temperature for 3 days under nitrogen atmosphere. The solvent was evaporated from the reaction mixture, and the residue was taken into acetone. The insoluble material (presumably DCU) was filtered off and the filtrate was concentrated in vacuo to obtain a solid which was purified on a silica gel column, being eluted with 20-25% EtOAc in $CH_2Cl_2$, to obtain 2.60 g (1.87 mmol, Y: 62 %) of the title compound as a white sticky powder. This was triturated with anhydrous Et$_2$O (ca. 50 mL) using a sonicator to obtain 2.3 g (1.65 mmol, Y: 55%) of the title compound as a white solid; HPLC purity: >99%; mp, 148-150° C.; $[\alpha]_D^{20} = -40.0°$ (c=0.62, $CH_2Cl_2$);

Anal. calcd for $C_{77}H_{84}NO_{21}P$: C, 66.51; H, 6.09; N, 1.01.

Found: C, 66.33; H, 6.05; N, 0.99.

EXAMPLE 47

2'-O-Ethoxycarbonyl-7-O-[3"-(2'''-phosphonooxy-4''',6'''-dimethylphenyl)-3",3"-dimethylpropionyl]taxol (Ij)

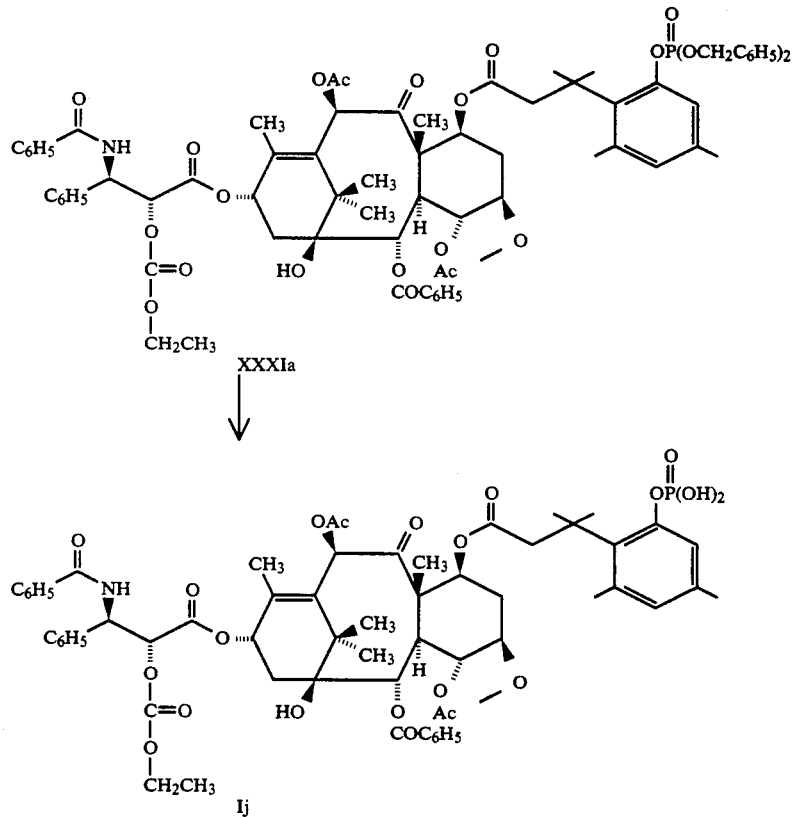

A mixture of compound XXXIa (2.1 g, 1.51 mmol) and 10% palladium on activated carbon (200 mg) in absolute EtOH (200 mL) and EtOAc (100 mL) was stirred under 40 psi of hydrogen atmosphere using a Parr apparatus for 5 h. The catalyst was filtered off. The filtrate was concentrated under vacuum. The gummy residue, thus obtained, was triturated with anhydrous Et$_2$O containing a small amount of EtOAc to obtain 1.5 g (1.24 mmol, Y: 82%) of the title compound: mp, 179-180.5° C.; $[\alpha]_D^{20} = -42.82°$ (c=0.425, $CH_2Cl_2$); $^1$H-NMR (acetone-$d_6$) δ ppm: 1.14 (3H, s, $CH_3$), 1.17 (3H, s, $CH_3$), 1.23 (3H, t, J=7 Hz, 2'-OCO$_2$CH$_2$CH$_3$), 1.54 (3H, s, Me), 1.65 (6H, s, Me), 1.92 (3H, s, 18-H$_3$), 2.12 (3H, s, Me), 2.13 (3H, s, 10-OAc), 2.43 (3H, s, 4-OAc), 2.52 (3H, s, Me), 2.68-2.73-3.08-3.13 (2H, ABq, 2"-H$_2$), 3.85 (1H, d, J=7 Hz, 3-H), 4.11 (2H, bs, 20-H$_2$), 4.2 (2H, m, 2'-OCO$_2$CH$_2$CH$_3$), 4.83 (1H, d, J=8.2 Hz, 5-H), 5.45 (1H, m, 7-H), 5.47 (1H, d, J=5.9 Hz, 2'-H), 5.63 (1H, d, J=7 Hz, 2-H), 5.95 (1H, m, 3'-H), 6.12 (1H, bt, J=9 Hz, 13-H), 6.24 (1H, s, 10-H), 6.67 (1H, s, Ar-H), 7.13 (1H, s, Ar-H), 7.2-7.2 (11H, m, Ar-Hs), 7.89 (2H, "d", J=8 Hz, 3'-NHCOPh), 8.11 (2H, "d", J=8 Hz, 2-OCOPh), 8.52 (d, J=9 Hz, NH); MS (FAB/-NOBA+NaI+KI) m/e: 1210 (M+H)$^+$, 1232 (M+Na)$^+$, 1248 (M+K)$^+$; IR (KBr) ν max: 3440, 1750, 1730 (shoulder) cm$^{-1}$.

Anal. calcd for $C_{63}H_{72}NO_{21}P/H_2O$: C, 61.61; H, 6.08; N, 1.14; H$_2$O, 1.47. Found: C, 61.21; H, 5.97; N, 1.03; H$_2$O, 1.78(KF).

Compound Ij (60.5 mg, 0.05 mmol) was dissolved in CH$_3$CN (5 mL) and treated with 0.05M NaHCO$_3$ (1.0 mL, 0.05 mmol). The resulting mixture was diluted with H$_2$O (100 mL). This was sonicated for a few minutes and the organic solvent was removed in vacuo and lyophilized to obtain a monosodium salt of the title compound as a white fluffy powder; HPLC Rt: 3.81 min (purity: >98%, no taxol present; C$_{18}$ a Waters radial pack column; flow rate: 2 mL/min; eluent: 28/72 of A/B, A=0.05M, pH 6.1 ammonium pohosphate buffer, B=80% CH$_3$CN in H$_2$O; UV detection at 254 nm); MS (FAB/NOBA) m/e: 1232 (M+H)$^+$, 1255 (M+Na)$^+$; IR (KBr) ν max: 3432, 1750, 1725(shoulder) cm$^{-1}$; Solubility: ca.5 mg/mL in deionized water at 22° C.

Anal. calcd for $C_{63}H_{71}NO_{21}PNa.2H_2O$: C, 59.67; H, 5.97; N, 1.11; H$_2$O, 2.84. Found: C, 59.20; H, 5.65; N, 1.04; H$_2$O, 2.54(KF).

ALTERNATE RUN monosodium salt

The acid Ij (1.1 g, 0.91 mmol) was suspended in CH$_3$CN (10 mL) and this was treated with a solution of NaHCO$_3$ (90 mg, 1.07 mmol) in H$_2$O (20 mL) to obtain a clear solution. This solution was diluted with H$_2$O (30 mL) and the resulting hazy solution was sonicated and purified on C-18 reverse phase silica gel (eluted with 20-40% CH$_3$CN in H$_2$O) to obtain 720 mg (0.584 mmol, Y: 64.9% from the acid) of the title compound as a monosodium salt in a white fluffy powdery form; HPLC purity: >99%; $[\alpha]_D^{20} = -27.30°$ (c=0.63, 95% EtOH); $^1$H-NMR (acetone-$d_6$/D$_2$O) δ ppm: 1.08 (3H, s, 17-H$_3$), 1.11 (3H, s, 16-H$_3$), 1.20 (3H, t, J=7 Hz, 2'-OCO$_2$CH$_2$CH$_3$), 1.54 (3H, s, 3"-Me), 1.55 (3H, s, 3"-Me), 1.60 (3H, s, 19-H$_3$), 1.86 (3H, s, 18-H$_3$), 2.07 (3H, s, 6'''-Me), 2.12 (3H, s, 10-OAc), 2.39 (3H, s, 4-OAc), 2.44 (3H, s, 4'''-Me), 2.97 (2H, s, 2"-H$_2$), 3.79 (1H, d, J=7.1 Hz, 3-H), 4.08 (2H, s, 20-H$_2$), 4.15 (2H, m, 2'-OCO$_2$CH$_2$CH$_3$), 4.82 (1H, d, J=8.1 Hz, 5-H), 5.39 (1H, dd, J=10.6 and 6.9 Hz, 7-H), 5.44 (1H, d, J=6.8 Hz, 2'-H), 5.58 (1H, d, J=7.1 Hz, 2-H), 5.82 (1H, d, J=6.8 Hz, 3'-H), 6.03 (1H, t, J=9 Hz, 13-H), 6.21 (1H, s, 10-H), 6.45 (1H, s, Ar-H), 7.25 (1H, s, Ar-H), 7.2-7.7 (11H, m, Ar-Hs), 7.86 (2H, "d", J=8 Hz, 3'-NHCOPh), 8.06 (2H, "d", J=8 Hz, 2-OCOPh); MS (FAB/NOBA) m/e: 1232 (M+H)$^+$, 1254 (M+Na)$^+$; IR (KBr) ν max: 3432, 1750, 1726(shoulder) cm$^{-1}$; Solubility: 4 mg/mL in deionized water at 22° C.

Anal. calcd for $C_{63}H_{71}NO_{21}PNa.3.5\ H_2O$: C, 58.33; H, 6.07; N, 1.09; Na, 1.78. Found: C, 58.24; H, 5.55; N, 1.09; Na, 1.74.

ALTERNATE RUN disodium salt

A mixture of compound XXXIa (700 mg, 0.503 mmol) and 10% palladium on activated carbon (140 mg) in absolute EtOH (60 mL) was stirred under 40 psi hydrogen atmosphere for 5 h in a Parr apparatus. The catalyst was filtered off and the solvent was pumped off from the filtrate. The gummy residue, thus obtained (500 mg), was suspended in water (25 mL) and sodium hydrogen carbonate (70 mg, 0.83 mmol, 2 eq.) was added. The mixture was sonicated for 5 min at room temperature; the resultant mixture was found to be cloudy. It became a clear solution by the addition of 5 drops of CH$_3$CN. This solution was passed through a C-18 reverse phase column. The column was successively eluted with water (1L), 10% CH$_3$CN in H$_2$O (300 mL), 20% CH$_3$CN in H$_2$O (200 mL) and then with 40% CH$_3$CN in H$_2$O. The fractions containing the desired compound, as monitored by HPLC, were combined. CH$_3$CN was evaporated off from the combined mixture and the remaining mixture was lyophilized to obtain 380 mg (0.303 mmol, Y: 73.3%) of disodium salt of the title compound as a white puffy powder; HPLC Rt: 3.81 min (purity >98%; C$_{18}$ Waters radial pack column; flow rate: 2 mL/min; eluent: 28/72 of A/B, A=0.05M, pH 6.1 ammonium phosphate buffer, B=80% CH$_3$CN in H$_2$O; UV detection at 254 nm); $[\alpha]_D^{20} = -25.29°$ (c=0.34, 95% EtOH); $^1$H-NMR (acetone-$d_6$/D$_2$O) δ ppm: 1.09 (3H, s, 17-H$_3$), 1.12 (3H, s, 16-H$_3$), 1.21 (3H, t, J=7 Hz, 2'-OCO$_2$CH$_2$CH$_3$), 1.54 (3H, s, 3"-Me), 1.57 (3H, s, 3"-Me), 1.61 (3H, s, 19-H$_3$), 1.87 (3H, s, 18-H$_3$), 2.09 (3H, s, 6'''-Me), 2.14 (3H, s, 10-OAc), 2.39 (3H, s, 4-OAc), 2.44 (3H, s, 4'''-Me), 2.87-2.92-3.11-3.16 (2H, ABq, 2"-H$_2$) 3.78 (1H d J=7 Hz, 3-H) 4.09 (2H bs 20-H$_2$), 4.16 (2H, m, 2'-OCO$_2$CH$_2$CH$_3$), 4.85 (1H, d, J=8.5 Hz, 5-H), 5.38 (1H, dd, 7-H), 5.44 (1H, d, J=7 Hz, 2'-H), 5.57 (1H, d, J=7 Hz, 2-H), 5.81 (1H, d, J=7 Hz, 3'-H), 6.03 (1H, bt, J=8 Hz, 13-H), 6.21 (1H, s, 10-H), 6.39 (1H, s, Ar-H), 7.30 (1H, s, Ar-H), 7.2-7.2 (11H, m), 7.86 (2H, "d", J=8 Hz, 3'-NHCOPh), 8.07 (2H, "d", J=8 Hz, 2-OCOPh); MS (FAB/NOBA+NaI+KI) m/e: 1254 (M+H)$^+$, 1270 (M+Na+K)$^+$; IR (KBr) ν max: 3440, 1750 (shoulder), 1725, 1246 cm$^{-1}$; UV (MeOH:H$_2$O) λ max: 200 (ε 1.41×10$^5$), 226 nm (ε 4.76×10$^4$); Solubility: ca. 5 mg/mL in deionized water at 22° C.; HRMS calcd for $C_{63}H_{71}NO_{21}PNa_2$: 1254.4052, found: 1254.4025.

EXAMPLE 48

2'-O-[[3-(Dimethylamino)phenoxylcarbonyl taxol (Ik)

Taxol ⟶

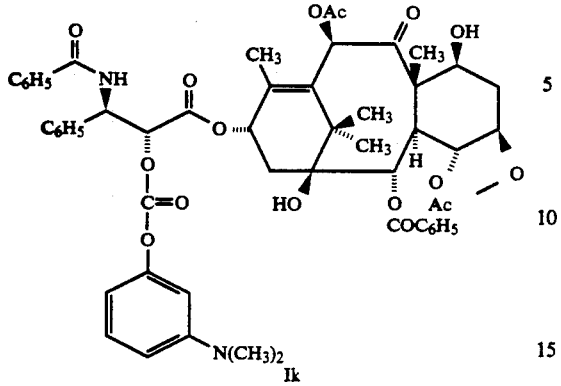

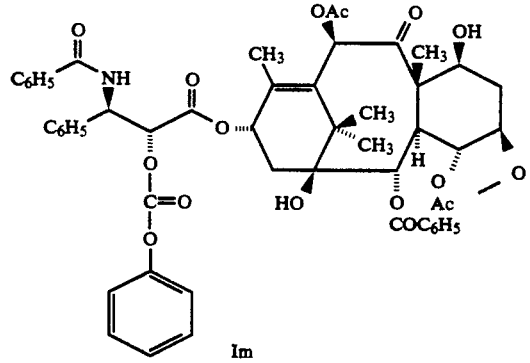

To a cooled (ice bath, 5° C.) solution of m-dimethylaminophenol (0.137 g; 1 mmol) in dry CH₂Cl₂ (10 mL) was added N,N-diisopropylethylamine (0.129 g; 1 mmol) followed by addition of solid triphosgene (0.14 g; 0.35 mmol). The mixture was stirred at 5° C. for 1 h and was added, under N₂, to a cooled (5° C.) solution of taxol (0.43 g; 0.5 mmol) and N,N-diisopropylethylamine (0.129 g; 1 mmol) in dry CH₂Cl₂ (10 mL). The resultant mixture was stirred at 5–10° C. for 2 h. It was concentrated to dryness and the residue was purified by chromatography on a silica gel plate (being eluted with 40% CH₃CN in CH₂Cl₂) to give 0.12 g (Y: 24%) of the title product; 0.2 g of taxol was also recovered. The NMR spectrum of the title product was consistent for the structure.

The free base was dissolved in acetone, treated with 1 equivalent of L-tartaric acid. The mixture was evaporated to dryness, treated with dry ether and filtered to give a white solid; mp, 150–153° C.

Alternate Run

An ice-chilled, stirred solution of 3-dimethylaminophenol (1.65 g, 12 mmol) in 100 mL CH₂Cl₂ under N₂ was treated with diisopropylethylamine (1.55 g, 12 mmol) and triphosgene (1.33 g, 4.5 mmol). Stirring was continued for 1 h. To an an ice chilled solution of taxol (3.41 g, 4 mmol) in 40 mL CH₂Cl₂ was added the freshly prepared solution of the chloroformate and the resultant solution was stirred at 0° C. for 3 h. The cooling bath was removed and stirring under N₂ was continued for 40 h. An additional solution containing 4 mmol of the chloroformate prepared in the same manner as above was added and stirring at ambient temperature was continued for 3 days. The reaction mixture was washed with 100 mL saturated brine, dried over MgSO₄, filtered and concentrated to leave 4.5 g of a crude product. This was partially purified by silica gel column chomatography (being eluted with 3:1 CH₂Cl₂/CH₃CN) to give 2.8 g of an amorphous material (~3:1 mixture of compound Ik and ureidotaxol).

Fractional crystallization from EtOAc removed the insoluble ureidotaxol. Crystallization from Et₂O gave 2.03 g (Y: 50%) of the title compound.

EXAMPLE 49

2'-O-(Phenoxycarbonyl)taxol (Im)

Taxol⟶

Taxol (101 mg, 0.1183 mmol) in anhydrous CH₂Cl₂ (3 mL) at 0° C. was treated with phenylchloroformate (0.030 mL, 0.236 mmol), and the temperature was allowed to equilibrate overnight (18 h). Standard workup (as in Example 41 or 42) and chromatography (being eluted with 60% ethyl acetate in hexane) gave 75 mg (Y: 64%) of the desired product as a white solid; ¹H-NMR (CDCl₃, 300 MHz) δ ppm: 8.13 (m, 2H), 7.73 (m, 2H), 7.58 (m, 1H), 7.56–7.10 (m, 15H), 6.90 (bd, 1H, exchangeable), 6.30–6.25 (m, 2H, includes s at 6.26), 6.03 (dd, 1H), 5.67 (d, 1H), 5.48 (d, 1H), 4.95 (d, 1H), 4.41 (m, 1H), 4.30 (d, 1H), 4.18 (d, 1H), 3.79 (d, 1H), 2.55–2.20 (m, 9H, includes s at 2.46, 3H and at 2.20, 3H), 1.90–1.84 (m, 4H, includes s at 1.88, 3H), 1.66 (s, 3H), 1.61 (s, 3H), 1.23 (s, 3H), 1.20 (s, 3H).

EXAMPLE 50

2'-O-[(1-Methylethenyloxy)carbonyl]taxol (In)

Taxol⟶

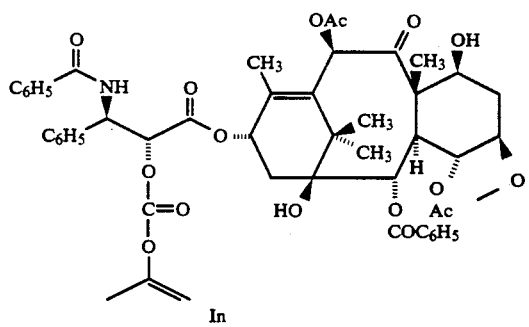

Taxol (0.850 g; 0.998 mmol) in dry methylene chloride (30 mL) was treated with N,N-diisopropylethylamine (0.6 mL) and isopropenylchloroformate (0.24 g, 0.22 mL, 2 mmol) at 0° C. The resulting mixture was allowed to be stirred for 30 min. Standard work up (as in Example 41 or 42) and triturating the solid product with dry ether yielded the title product as a white powder (0.94 g, Y: 74.5%); mp, 165–168° C.; HRMS calcd for C₅₁H₅₆NO₁₆ (MH+): 938.3599, found: 938.3595. The NMR spectrum was consistent for the structure.

EXAMPLE 51

2'-O-(Methoxycarbonyl)taxol (Io)

Taxol⟶

-continued

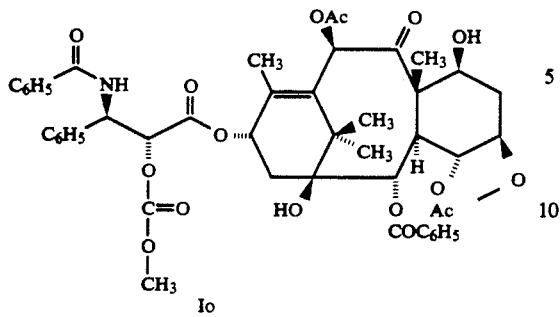

Taxol (0.853 g, 1.0 mmol) in dry methylene chloride (30 mL) was treated with N,N-diisopropylethylamine (0.35 mL) and methyl chloroformate (0.189 g, 0.15 mL, 2 mmol) at 0° C. The resulting mixture was allowed to be stirred for 30 min. Standard work up (as in Example 41 or 42) and triturating the solid product with dry ether yielded the title product as a white powder (0.91 g, Y: 100%); mp, 180–183° C. The NMR spectrum was consistent for the structure.

EXAMPLE 52

2'-O-[(2-Chloroethoxy)carbonyl]taxol (Ip)

Taxol⟶

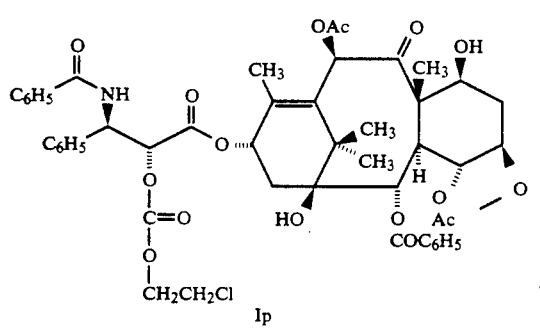

Taxol (0.864 g, 1.1028 mmol) in dry methylene chloride (30 mL) was treated with N,N-diisopropylethylamine (1.0 mL) and chloroethylchloroformate (0.315 g, 0.23 mL, 2.2056 mmol) at 0° C. The resulting mixture was allowed to be stirred for 30 min. Standard work up (as in Example 41 or 42) and triturating the solid with dry ether yielded the title product as a white powder (1.03 g, Y: 97%); mp, 169–172° C.; HRMS calcd for C$_{50}$H$_{55}$NO$_{16}$Cl (MH+): 960.3209, found: 960.3177. The NMR spectrum was consistent for the structure.

EXAMPLE 53

2'-O-[(4-Methylphenoxy)carbonyl]taxol (Iq)

Taxol⟶

-continued

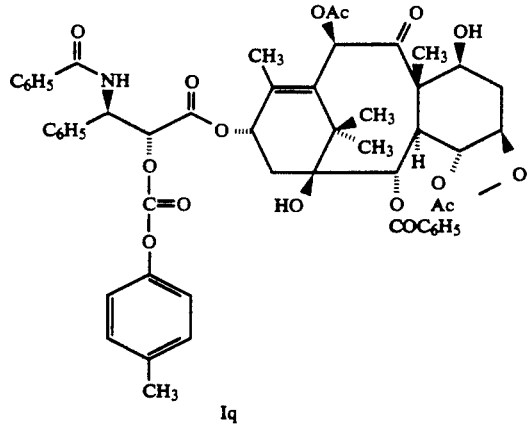

Taxol (0.43 g, 0.5 mmol) in dry methylene chloride (20 mL) was treated with N,N-diisopropylethylamine (0.17 mL) and p-tolylchloroformate (0.177 g, 0.15 mL, 1 mmol) at 0° C. The resulting mixture was allowed to be stirred for 30 min. Standard work up (as in Example 41 or 42) and triturating the solid product with dry ether yielded 0.49 g (Y: 69%) of the title compound as a white powder; mp, 167–170° C. The NMR spectrum was consistent for the structure.

EXAMPLE 54

2'-O-[(Iodomethoxy)carbonyl]taxol (Ir)

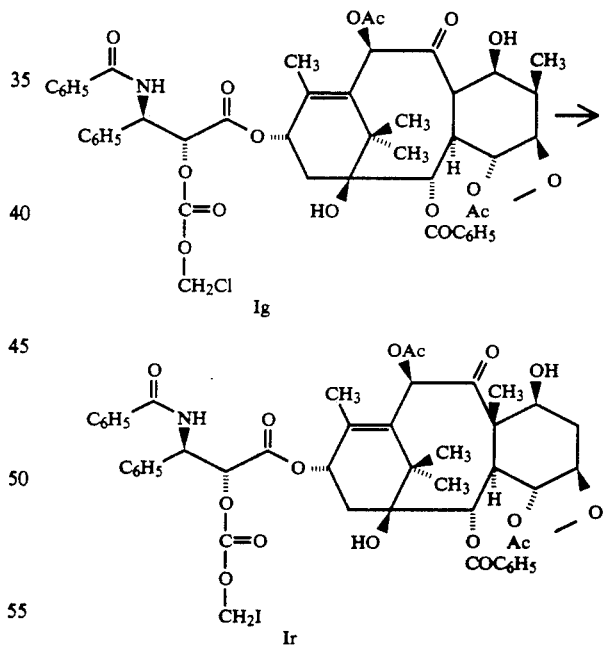

A solution of compound Ig in a dry acetone was stirred at room temperature with 10 eq. of sodium iodide for 60 h. Formation of iodomethyl carbonate Ir was monitored by $^1$H-NMR An increasing intensity of iodomethyl protons and disappearance of chloromethyl protons was observed in the course of the reaction. After 60 h, approximately 75% of compound Ig was converted into compound Ir. In order to isolate the products, the solvent was evaporated to dryness. The residue was extracted with ethyl acetate and purified on a silica gel column, being eluted with methylene chloride:acetone (10:1, v/v). A quantitative amount of compounds Ig and Ir as a mixture (ca. 1:3 ratio) was obtained.

EXAMPLE 55

2'-O-[2''-[(Bisallylphosphonooxy)methyl]benzoyl]taxol (XLIb)

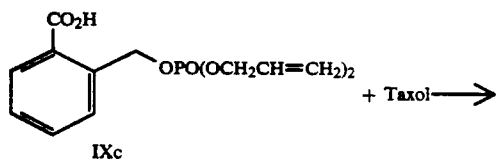

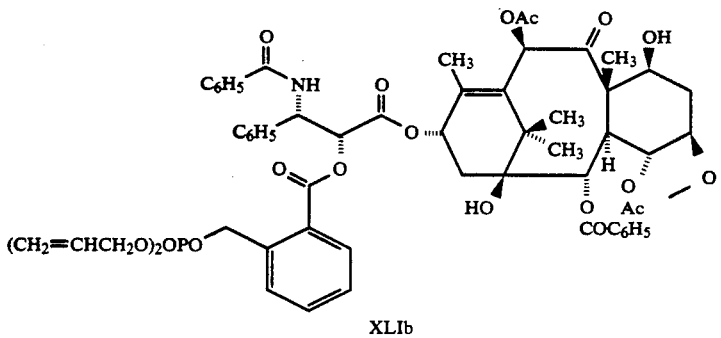

To a solution of taxol (616 mg, 0.721 mmol) and acid IXc (254 mg, 0.814 mmol) in anhydrous $CH_2Cl_2$ (20 mL) was added, at room temperature, N,N-dicyclohexylcarbodiimide (DCC, 171 mg, 0.83 mmol; Aldrich) and 4-dimethylaminopyridine (DMAP, 65 mg, 0.53 mmol; Aldrich). The mixture was stirred at room temperature under anhydrous nitrogen atmosphere for 6 h. The precipitate was filtered and the filtrate was concentrated. The residue was dissolved in acetone. Upon removing insoluble materials, the acetone solution was concentrated. The residue was purified by silica gel column chromatography ($SiO_2$, 100 g, being eluted with 50% EtOAc in hexane) to obtain 482 mg (0.420 mmol, Y: 58.2%*) of the title compound as a white amorphous powder; mp, 133–136° C.; Rf: 0.53 (5% MeOH in $CH_2Cl_2$); $[\alpha]_D^{20} -55.00°$ (c=0.2, $CH_2Cl_2$); IR (KBr) 3430, 1726, 1666 $cm^{-1}$; $^1$H-NMR (300 MHz, acetone-$d_6$) δ ppm: 1.16, 1.18 (6H, 2s, 15-gemMe), 1.65 (3H, s, 8-Me), 1.73–1.84 (1H, m, 6-H), 1.96 (3H, d, J=1.4 Hz, 12-Me), 2.1 (1H, m, 14-H), 2.14 (3H, s, 4-OAc), 2.2–2.35 (1H, m, 14-H), 2.45 (3H, s, 10-OAc), 2.4–2.53 (1H, m, 6-H), 3.52 (1H, d, J=5.9 Hz, 7-OH, disappearing with $D_2O$), 3.83 (1H, d, J=7.3 Hz, 3-H), 4.08–4.11–4.14–4.17 (2H, ABq, 20-H), 4.14 (1H, s, 1-OH, disapp. with $D_2O$), 4.3–4.45 (3H, m, 7-H, $OCH_2$), 4.51–4.56 (2H, m, $OCH_2$), 5.16–5.22 (2H, m, $=CH_2$), 5.27–5.38 (2H, m, $=CH_2$), 5.35–5.37–5.39–5.42, 5.49–5.52–5.54 –5.56 (1H, 2ABq, $ArCH_2OP$), 5.66 (1H, d, J=7.2 Hz, 2-H), 5.79 (1H, d, J=6.5 Hz, 2'-H), 5.91 (2H, m, CH=), 6.1–6.2 (2H, m, 3'-H, 13-H), 6.42 (1H, s, 10-H), 7.25–8.09 (19H, m, Ar-Hs), 8.70 (1H, d, J=9.2 Hz, CONH, disapp. with $D_2O$); MS (FAB/NOBA+NaI+KI) m/e: 1186 (MK+), 1170 (MNa+), 1148 (MH+); UV (MeOH)λ: 204 (ε 4.89×10$^4$), 230 (ε 4.23×10$^4$), 276 nm (ε 4.53×10$^3$); HRMS (FAB/NOBA) calcd for $C_{61}H_{67}NO_{19}P$ 1148.4045, found: 1148.4018.

*The yield was improved from 58.2% to 87.3% by use of 1.5 eq. of benzoic acid IXc and 3 eq. of DCC. Under this condition, the reaction was complete in 1 h at room temperature.

Anal. calcd for $C_{61}H_{66}NO_{19}P$: C, 63.81; H, 5.79; N, 1.22.
Found: C, 63.65; H, 5.80; N, 1.15.

EXAMPLE 56

2'-O-[2'''-(Phosphonooxymethyl)benzoyl]taxol dipotassium salt (Ivv)

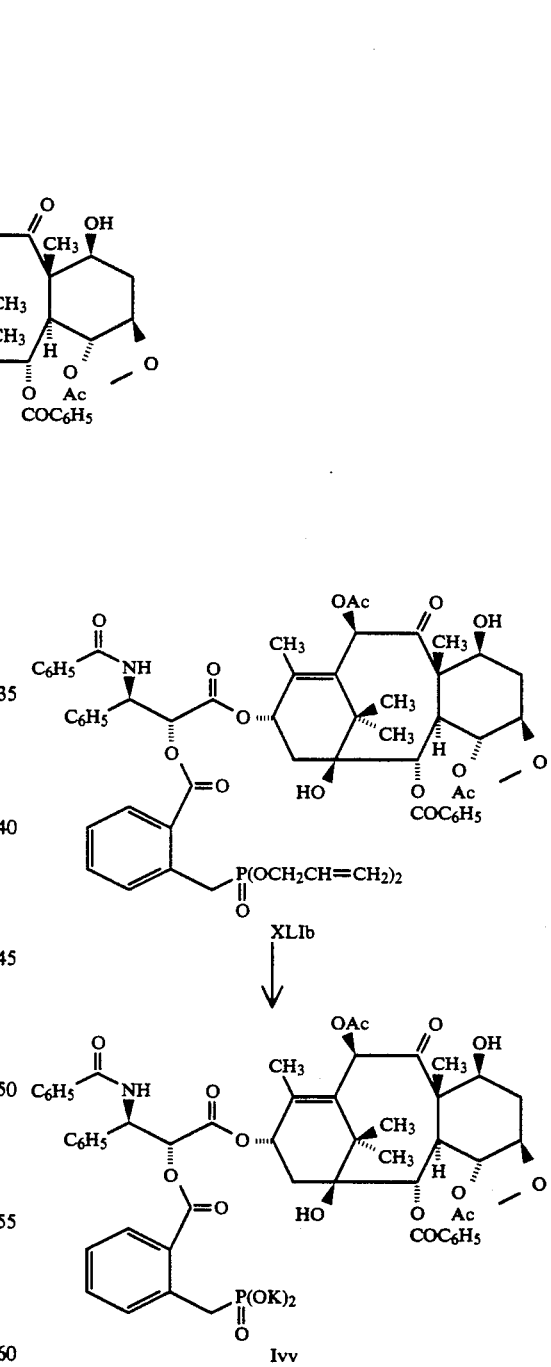

To a solution of compound XLIb (210 mg, 0.183 mmol) in anhydrous $CH_2Cl_2$ (5 mL; Aldrich Sure Seal) under nitrogen atmosphere was added $PPh_3$ (15 mg), $Pd(PPh_3)_4$ (15 mg) and HOAc (55 μL, 0.96 mmol; 5.3 e.g.) followed by $Bu_3SnH$ (120 μL, 0.445 mmol; 2.4 eq). The mixture was stirred at room temperature under nitrogen atmosphere for 20 h. The mixture was concentrated in vacuo to dryness and the residue was dissolved in $CH_2Cl_2$ (ca. 0.5 mL). To the methylene chloride solution, hexane (ca. 3 mL) was added dropwise. The precipitate was collected to obtain 265 mg of an off-white solid which was dissolved in $CH_2Cl_2$ (3 mL). To this solution was added a solution of potassium 2-ethylhexanoate (73 mg, 0.4 mmol) in EtOAc (1 mL; Aldrich Sure Seal). The mixture was sonicated and the resulting cloudy solution was concentrated to dryness, and the residue was triturated with $Et_2O$ to obtain 260 mg of a white powder. This was suspended in $H_2O$ (32 mL), mixed with a solution of $KHCO_3$ (40 mg, 0.4 mmol) in $H_2O$ (5 mL) and then to this was added $CH_3CN$ (4 mL) to obtain a milky solution. This mixture was applied on a C-18 reverse phase silica gel column (Whatman, Partisil 40, ODS-3; d=2.5 cm l=27 cm) and the column was eluted with $H_2O$, 10% $CH_3CN$ in $H_2O$, 20% $CH_3CN$ in $H_2O$ and then with 25% $CH_3CN$ in $H_2O$. Appropriate fractions from 25% $CH_3CN$ in $H_2O$ eluent were combined and lyophilized to obtain 90 mg (0.079 mmol, Y: 43%) of the title compound, Ivv, as a white fluffy powder; Rt: 2.10 min (HPLC purity: >99%; $C_{18}$ Waters Radial Pak column; flow rate: 2 mL/min; eluent: 25% A (0.05M, pH 6.0 ammonium phosphate buffer)/75% B (80% $CH_3CN$ in $H_2O$); UV detection at 227 nm); $[\alpha]_D^{20} = -39.02°$ (c=0.205, 95% EtOH); IR (KBr) 3430 (broad), 1724, 1660, 1244 $cm^{-1}$; $^1H$-NMR (300 MHz; acetone-$d_6$/a few drops of $D_2O$) δ ppm: 1.11 (6H, s 15-$Me_2$), 1.59 (3H, s, 8-Me), 1.95 (3H, s, 12-Me), 2.09 (3H, s, OAc), 2.41 (3H, s, OAc), 3.75 (1H, d, J=7 Hz, 3-H), 4.06–4.09–4.12 (2H, "ABq", 20-H), 4.35 (1H, dd, J=6.5,10.5 Hz, 7-H), 4.95 (1H, d, J=9Hz, 5-H), 5.16 (2H, bs, $ArCH_2OP$), 5.59 (1H, d, J=7 Hz, 2-H), 5.75 (1H, d, J=9 Hz, 2'-H), 5.87 (1H, d, J=9 Hz, 3'-H), 5.99 (1H, "t", J=8.5 Hz, 13-H), 6.42 (1H, s, 10-H), 7.1–8.1 (19H, m, Ar-Hs); MS (FAB/NOBA+NaI +KI) m/e: 1106 (M-K+2H+), 1144 (MH+), 1182 (MK+); HRMS (FAB/NOBA) calcd for $C_{55}H_{57}NO_{19}PK_2$(MH+) 1144.2537, found: 1144.2560; UV (95% EtOH) λ: 204 (ε 189×$10^4$), 234 (ε 2.54×$10^4$), 282 nm (ε 7.8×$10^2$); Solubility: ca. 5 mg/mL in deionized water at 22° C. (hazy solution).

The mono-potassium salt

HPLC Rt: 2.72 min. (94.5% pure; eluent: 30%A/70%B, A and B as defined above; $[\alpha]_D^{20} = -41.74°$ (c=0.23, 95% EtOH); UV (95% EtOH) λmax: 202 (ε 3.05×$10^4$), 232 nm (ε 2.85×$10^4$); MS (FAB/NOBA) m/e: 1106 (MH+), 1090 (M−K+Na), 1068 (M−K+H); HRMS (FAB/NOBA) calcd for $C_{55}H_{58}NO_{19}PK$ (MH+) 1106.2978, found: 1106.3002; Solubility: 4.6 mg/mL in deionized water.

Anal. calcd for $C_{55}H_{58}NO_{19}P/KHCO_3/3H_2O$: C, 55.04; H, 5.37; N, 1.15; K, 3.20; $H_2O$, 4.42. Found: C, 54.66; H, 5.00; N, 1.24; K, 3.88; $H_2O$, 4.14(KF).

EXAMPLE 57

2'-O-[3''-(2'''-Acetoxy-5'''-dibenzylphosphonooxy-4''',6'''-dimethylphenyl)-3'',3''-dimethylpropionyl]taxol (XLIc)

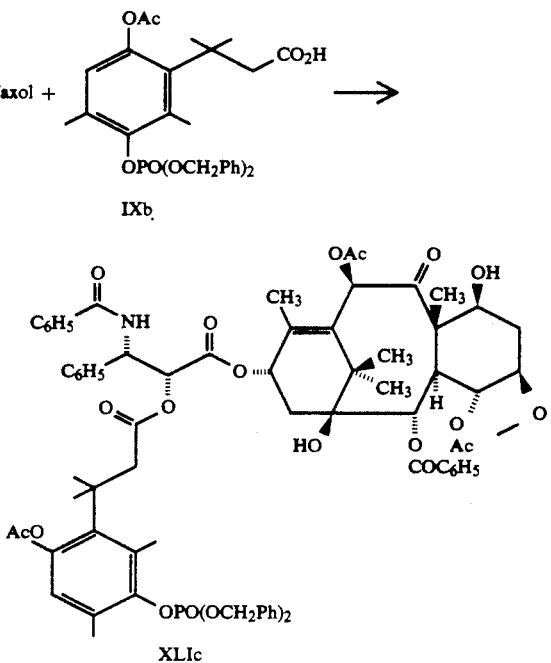

To a solution of phenylpropionic acid IXb (216 mg, 0.40 mmol; crude material) in anhydrous $CH_2Cl_2$ (24 mL) was added at room temperature N,N-dicyclohexylcarbodiimide (DCC, 120 mg, 0.58 mmol; Aldrich) and 4-dimethylaminopyridine (DMAP, 42 mg, 0.34 mmol, Aldrich). The mixture was stirred at room temperature for 15 min under anhydrous nitrogen atmosphere. To this mixture was added taxol (300 mg, 0.36 mmol) and the mixture stirred for 6.5 h. The precipitate was filtered off. The filtrate was washed with $H_2O$ and brine. The organic phase was dried ($Na_2SO_4$) and concentrated. The residue was purified by silica gel column chromatography ($SiO_2$, 50 g, being eluted with 30% EtOAc in hexanes) to obtain 196 mg (0.14 mmol, Y: 39.6%) of the title compound as a white amorphous foam; mp, 118–125° C. (with decomposition); Rf: 0.33 (30% EtOAc in hexanes); $[\alpha]_D^{20} -46.67°$ (c=0.3, $CH_2Cl_2$); IR (KBr) 3434, 1740, 1725(shoulder), 1668 $cm^{-1}$; $^1H$-NMR (300 MHz, acetone-$d_6$) δ ppm: 1.15 (6H, s, 16-$H_3$, 17-$H_3$), 1.49 (6H, s, 3''-Me), 1.63 (3H, s, 19-$H_3$), 1.69–1.97 (m), 1.84 (3H, s, 18-$H_3$), 2.14 (3H, s, OAc), 2.19 (3H, s, OAc), 2.22 (3H, s, Ar-Me), 2.38 (3H, s, 10-OAc), 2.42 (3H, s, Ar-Me), 2.89–2.94–2.98–3.03 (2H, ABq, 2''-$H_2$), 3.49 (1H, d, J=5.7 Hz, 7-OH), 3.79 (1H, d, J=7.1 Hz, 3-H), 3.86 (1H, s, 1-OH), 4.10–4.13–4.14–4.16 (2H, ABq, 20-$H_2$), 4.38 (1H, m, 7-H), 4.91 (1H, d, J=7.7 Hz, 5-H), 5.14 (4H, m, $OCH_2$ph), 5.49 (1H, d, J=6.8 Hz, 2'-H), 5.65 (1H, d, J=7.2 Hz, 2-H), 5.87 (1H, dd, J=8.8, 6.9 Hz, 3'-H), 6.08 (1H, t, J=9 Hz, 13-H), 6.38 (1H, s, 10-H), 6.61 (1H, s, 3'''-H), 7.26 (1H, t, J=7.3 Hz, Ar-H), 7.3–7.7 (20H, m, Ar-Hs), 7.87 (2H, d, J=8 Hz, 3'-NHCOPh), 8.10 (2H, d, J=8 Hz, 2-OCOPh), 8.38 (1H, d, J=9 Hz, NH); MS (FAB/NOBA+NaI+KI) m/e: 1415 (MK+), 1400 (MNa+), 1377 (MH+); UV (MeOH) λmax: 204 (ε6.42×$10^4$), 227 nm (shoulder, ε 4.0×$10^4$).

Anal. calcd for $C_{76}H_{82}NO_{21}P$: C, 66.32; H, 6.01; N, 1.02.
Found: C, 66.46; H, 6.30; N, 0.99.

EXAMPLE 58

2'-O-[3''-(2'''-Acetoxy-4''',6'''-dimethyl-5'''-phosphonooxyphenyl)-3'',3''-dimethylpropionyl]taxol disodium salt (Is)

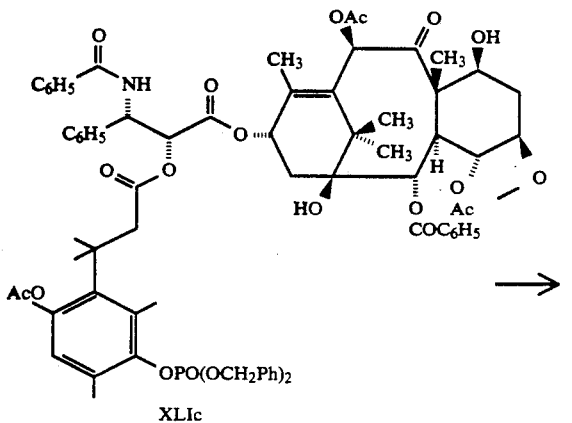

A mixture of compound XLIc (137 mg, 0.0996 mmol) and 10% Pd on carbon (48 mg; Aldrich) in absolute EtOH (15 mL) was stirred in a Parr apparatus under hydrogen atmosphere (40 psi) for 3h. The catalyst was removed and the filtrate was concentrated in vacuo to a gummy residue which was triturated with anhydrous $Et_2O$ to obtain 110 mg (0.092 mmol, crude Y: 92.4%) of the free phosphoric acid form of compound Is as a white powder. A suspension of this material in $H_2O$ (5 mL) was mixed with $NaHCO_3$ (16 mg, 0.19 mmol) and sonicated for 10 min. The resultant solution was purified by reverse phase column chromatography (Lichroprep RP-18, EM Science), being eluted with $H_2O$, to obtain 90 mg (0.075 mmol, Y. 82%) of the title compound as a white puffy powder; Rt: 3.40 min (HPLC purity: ≥99%; $C_{18}$ Waters radial pack column; flow rate: 2 mL/min; eluent: 35/65 of A/B, A=0.05M, pH 6.1 ammonium phosphate buffer, B=80% $CH_3CN$ in $H_2O$; UV detection at 227 nm); $[\alpha]_D^{20}$ −38.18° (c=0.22, $CH_2Cl_2$); IR(KBr) 3430, 1740, 1644 $cm^{-1}$; $^1$H-NMR (300 MHz, acetone-$d_6$/$D_2O$) δ ppm: 1.12 (6H, s, 16-$H_3$, 17-$H_3$), 1.44 (3H, s, 3''-Me), 1.47 (3H, s, 3'''-Me), 1.60 (3H, s, 19-$H_3$), 1.89 (3H, s, 18-$H_3$), 2.11 (3H, s, OAc), 2.12 (3H, s, OAc), 2.26 (3H, s, Ar-Me), 2.35 (3H, s, 10-OAc), 2.51 (3H, s, Ar-Me), 2.58 (s), 2.91 (2H, ABq, 2''-$H_2$), 3.73 (1H, d, J=6.5 Hz, 3-H), 4.10 (2H, s, 20-$H_2$), 4.31 (1H, 7-H), 4.93 (1H, d, J=9 Hz, 5-H), 5.46 (1H, d, J=7.2 Hz, 2'-H), 5.60 (1H, d, J=6.3 Hz, 2-H), 5.80 (1H, d, J=7.5 Hz, 3'-H), 6.02 (1H, t, J=9 Hz, 13-H), 6.35 (1H, s, 10-H), 6.40 (1H, s, 3'''-H), 7.21 (1H, t, J=7.4 Hz, Ar-H), 7.4–7.7 (10H, m, Ar-Hz), 7.87 (2H, d, J=7.8 Hz, 3'-NHCOPh), 8.07 (2H, d, J=8.1 Hz, 2-OCOPh); MS (FAB/NOBA/NaI+KI) m/e: 1240 (MH+); UV (MeOH:$H_2O$=1:1) λmax: 200 (ε 7.18×10⁴), 227 nm (ε 2.6×10⁴); Solubility: ≥1 mg/50 μL in deionized water at 22° C. (clear solution); HRMS (FAB/NOBA) calcd for $C_{62}H_{69}NO_{21}PNa_2$ (MH+): 1240.3895, found: 1240.3869.

EXAMPLE 59

2'-O-[4-(Dibenzylphosphonooxy)butanoyl]taxol (XLId)

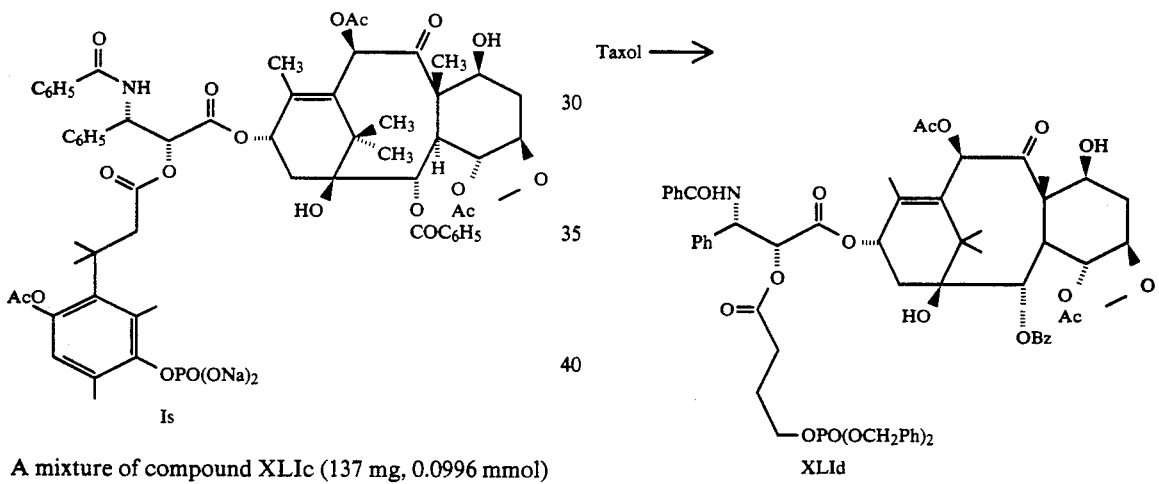

Taxol (71.4 mg, 0.0837 mmol), dicyclohexylcarbodiimide (19.2 mg, 0.093 mmol), acid XXVa (52.1 mg, 0.143 mmol) and 4-dimethylaminopyridine (2 mg, 0.00865 mmol) were dissolved in dry dichloromethane (2 mL) and stirred at room temperature for 1 h. Filtration, evaporation of the filtrate and silica gel chromatography (being eluted with 50% ethyl acetate in hexane) of the residue gave 84.4 mg of the title taxol derivative (Y: 84%) as a foam; $^1$H-NMR (CDCl$_3$, 300 MHz) δ ppm: 8.08 (d, 2H) 7.86 (d, 1H), 7.77 (d, 2H) 7.59–7.16 (m, 21H) 6.22 (s, 1H, H-10) 6.16 (bt, 1H, H-13) 5.97 (dd, 1H, H-3') 5.60 (d, 1H, H-2) 5.40 (d, 1H, H-2') 4.93–4.76 (m, 5H, benzylic+H-5) 4.36 (dd, 1H, H-7) 4.25 (d, 1H, H-20) 4.13 (d, 1H, H-20') 4.15–4.08 (m, 1H) 3.90 (m, 1H) 3.74 (d, 1H, H-3) 2.50–1.06 (m, 26H, including 6 Me singlets).

EXAMPLE 60

2'-O-[4-(Phosphonooxy)butanoyl]taxol (It)

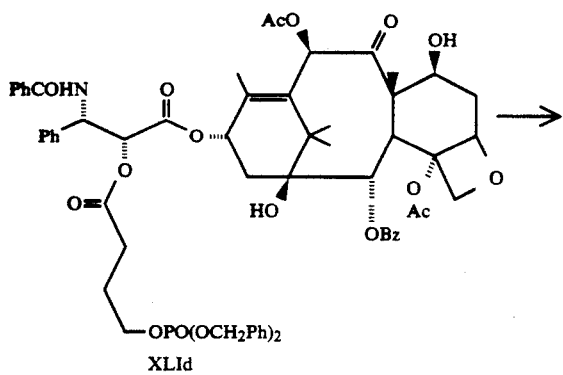

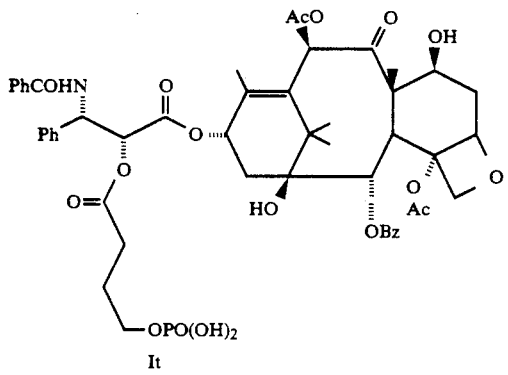

Compound XLId (350 mg, 0.292 mmol) in ethyl acetate (5 mL) was stirred under hydrogen atmosphere (43 psi) in the presence of palladium on carbon (10%, 36 mg) for 20 h. The product was purified by reversed-phase chromatography (C-18, 60% methanol in water). The product was lyophilized to yield 174 mg (Y: 58%) of the title compound as a white solid; $^1$H-NMR (CD$_3$OD, 300 MHz) δ ppm: 8.10 (d, 2H) 7.85 (d, 2H), 7.65–7.18 (m, 12H) 6.43 (s, 1H, H-10) 6.04 (bt, 1H, H-13) 5.82 (d, 1H, H-3') 5.63 (d, 1H, H-2) 5.49 (d, 1H, H-2') 5.02 (d, 1H, H-5) 4.38 (dd, 1H, H-7) 4.22 (s, 2H, H-20s) 3.98 (bs, 2H) 3.82 (d, 1H, H-3) 2.60–1.05 (m, 26H, including 6 Me singlets).

The disodium salt can be made by adding the appropriate amount of aqueous sodium bicarbonate and lyophilizing.

EXAMPLE 61

7-O-[4-(Dibenzylphosphonooxy)butanoyl]taxol (XLb)

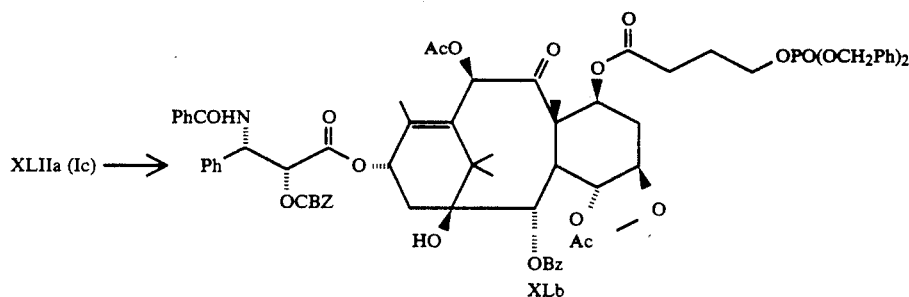

2'-O-(Benzyloxycarbonyl)taxol (XLIIa) (516 mg, 0.523 mmol), dicyclohexylcarbodiimide (167 mg, 0.809 mmol), acid XXVa (335 mg, 0.920 mmol) and 4-dimethylaminopyridine (12 mg, 0.0052 mmol) were dissolved in dry dichloromethane (12 mL) and stirred at room temperature for 96 h. Filtration, evaporation and silica gel chromatography (60% ethyl acetate in hexane) gave the title compound (500 mg, Y: 72%) as a white foam; $^1$H-NMR (CDCl$_3$, 300 MHz) δppm: 8.12 (d, 2H) 7.72 (d, 2H) 7.61–7.25 (m, 26H) 6.89 (d, 1H, NH) 6.23 (m, 2H, H-10 and H-13) 5.96 (dd, 1H, H-3') 5.68 (d, 1H, H-2) 5.44 (dd, 1H, H-7) 5.15 (dd, 2H, Cbz) 5.04–4.92 (m, 1H, Benzyl H's + H-5) 4.33 (d, 1H, H-20) 4.18 (d, 1H-20') 4.02 (m, 2H) 3.94 (d, 1H, H-3) 2.44–1.05 (m, 26H, including 6 Me singlets).

EXAMPLE 62

7-O-[4-(Phosphonooxy)butanoyl]taxol (Iu)

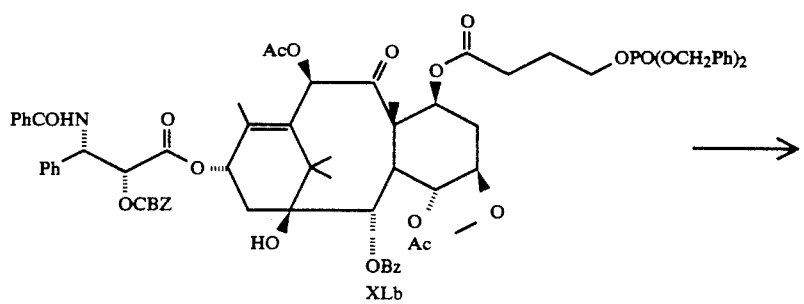

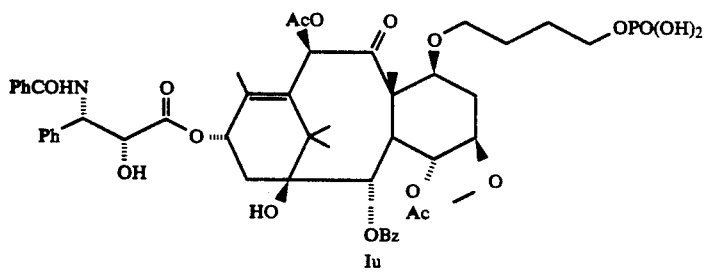

Taxol derivative XLb (400 mg, 0.300 mmol) in ethyl acetate (10 mL) was stirred under 50 psi of hydrogen atmosphere in the presence of palladium on carbon (10%, 59 mg) for 5 h. The product was purified by reverse-phase chromatography (C-18, methanol-water) to afford 117 mg (Y: 38%) of the title product. The mass and NMR spectra were consistent for the structure.

EXAMPLE 63
2'-O-Methoxycarbonyl-7-O-dibenzylphosphonotaxol (XXXIb)

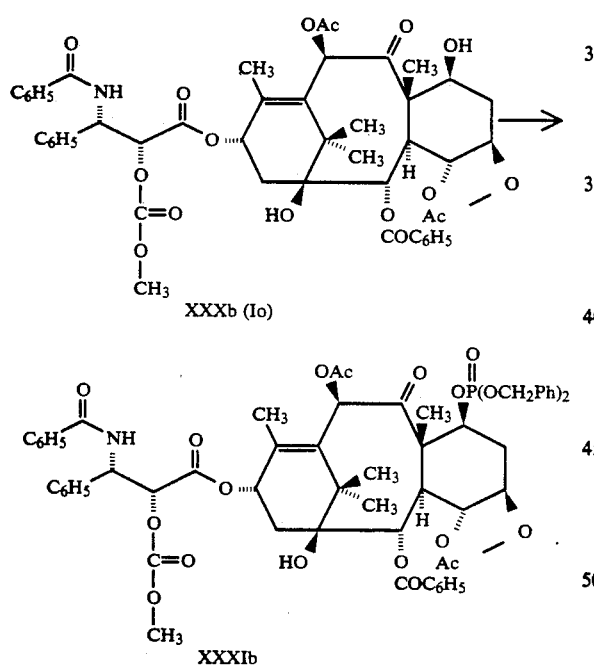

To a cold (−30° C.) solution of compound XXXb (0.73 g, 0.8 mmol) in dry THF (40 mL) was added dropwise freshly prepared LDA (lithium diisopropylamide, 0.1M, 12 mL, 1.2 mmol). The mixture was allowed to be stirred for 30 min followed by addition of tetrabenzylpyrophosphate (XXIVa) (0.65 g, 1.2 mmol) as a solid. The resulting mixture was stirred for 2 h. Standard work up with brine followed by drying and concentrating in vacuo yielded a residue. This residue was purified on a silica gel column (being successively eluted with CH$_2$Cl$_2$, 10% and 20% CH$_3$CN in CH$_2$Cl$_2$) to give the title product (0.46 g, Y: 50%). The NMR spectrum was consistent for the structure. In addition, 0.25 g of the starting carbonate was recovered.

EXAMPLE 64
2'-O-Methoxycarbonyl-7-O-phosphonotaxol (Iv)

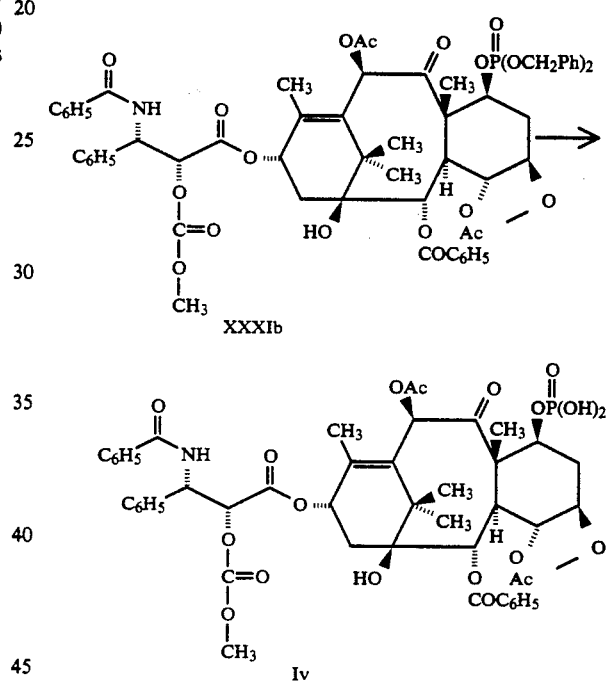

The benzylphosphate XXXIb (0.49 g, 0.3415 mmol) and 10% Pd/carbon (0.40 g) in absolute ethanol (20 mL) were stirred under 40 psi of hydrogen atmosphere for 4 h. The mixture was filtered twice over Celite and concentration in vacuo to give a solid. This was triturated with dry ether to give the title product as a white solid (0.3 g); mp, 204–207° C. The NMR spectrum was consistent for the structure.

EXAMPLE 65
2'-O-[3''-[2'''-(Dibenzylphosphonooxy)phenyl]-3'',3''-dimethylpropionyl]taxol (XLIe)

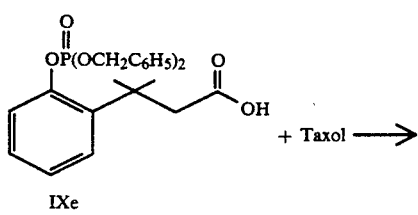

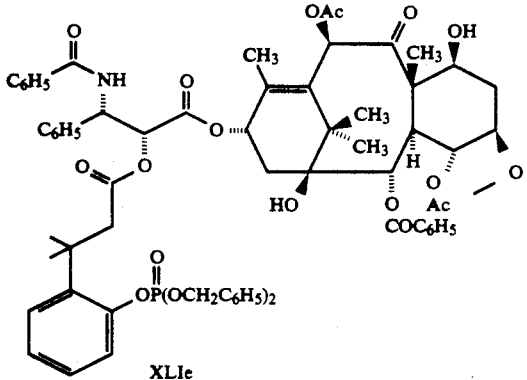

XLIe

A mixture of carboxylic acid IXe (0.5 g; 1.1 mmol, this compound was prepared according the the general method of Scheme A), DCC (0.33 g; 1.6 mmol) and DMAP (0.12 g; 1.0 mmol) in dry CH$_2$Cl$_2$ (40 mL) was stirred at room temperature for 15 min. Then taxol (0.85 g, 1 mmol) was added as solids and the mixture was stirred at room temperature for 18 h. It was evaporated to dryness and purified on a silica gel column (successively eluted with CH$_2$Cl$_2$; CH$_2$Cl$_2$ 10% and 20% in CH$_3$CN) to give 0.66 g of the title compound (Y: 51%). The spectral data was consistent for the expected product; HRMS calcd for C$_{72}$H$_{76}$NO$_{19}$P (MH+): 1290.4827, found: 1290.4844.

EXAMPLE 66

2'-O-[3''-(2'''-Phosphonooxyphenyl)-3'',3''-dimethylpropionyl]taxol (Ix)

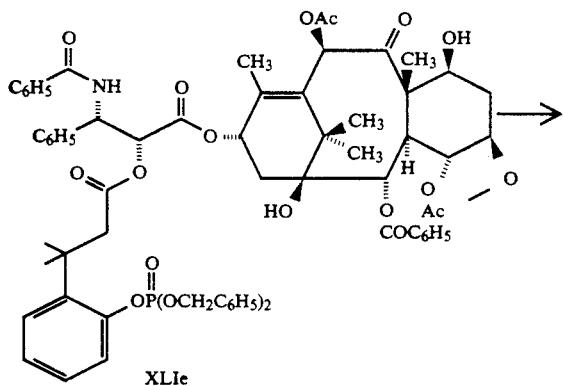

XLIe

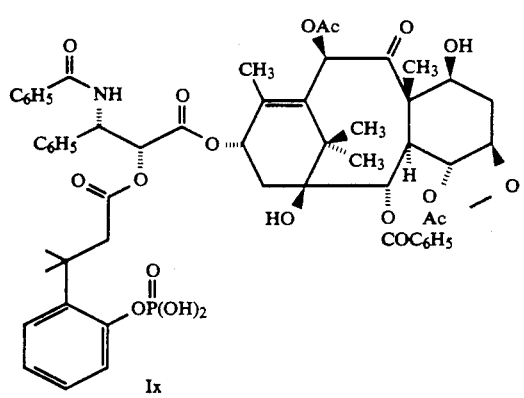

Ix

Compound XLIe (0.6 g; 0.4654 mmol) and 10% Pd/carbon (0.36 g) in absolute ethanol (30 mL) was stirred under 40 psi of hydrogen atmosphere for 4 h. The mixture was filtered through Celite. The filtrate was concentrated to dryness. The solid residue was triturated with dry ether and filtered to give 0.5 g of the title product as a white solid (Y: 96.8%); mp, 190–192° C. Spectral data were consistent for the structure; HRMS calcd for MH+: 1132.3708. Found: 1132.3679.

0.2 g (~0.2 mmol) of the title compound as a white solid was dissolved in acetone (10 ml) and treated at room temperature with solid sodium 2-ethylhexanoate. The resulting mixture was kept at room temperature for 18 h. It was evaporated to dryness, and the residue was triturated with dry ether to give 0.16 g of the sodium salt of the title compound as a white solid; mp, 220–222° C.

EXAMPLE 67

2'-O-(4-Dibenzylphosphonooxy-3,3-dimethylbutanoyl)-taxol (XLIf)

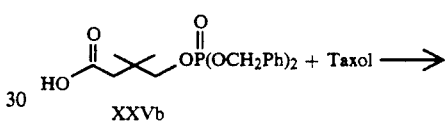

XXVb

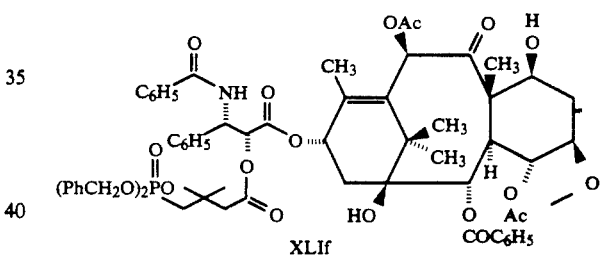

XLIf

Taxol (91.0 mg, 0.106 mg), acid (XXVb (56.0 mg, 0.155 mmol, crude), dicyclohexylcarbodiimide, (24.0 mg, 0.116 mmol), and 4-dimethylaminopyridine (2 mg, 0.0086 mmol) were dissolved in dry dichloromethane (2 ML). The reaction mixture was stirred for 16 h, and then worked up. The solids were filtered and the filtrate concentrated and chromatographed on silica gel (being eluted with 50% ethyl acetate in hexane) to give the title product as an off-white foam (113 mg, Y: 59%); $^1$H-NMR (CDCl$_3$) δ ppm: 8.95 (d, J=9.8 Hz, 1H) 8.16 (d, J=8.7 Hz, 2H) 7.92 (d, J=8.7 Hz, 2H) 7.57–7.21 (m, 21H) 6.28 (s, 1H) 6.23–6.21 (m, 2H) 5.66 (d, J=7.1 Hz, 1H) 5.58 (d, J=3.4 Hz, 1H) 4.96 (d, J=8.3 Hz, 1H) 4.89–4.84 (m, 4H) 4.51–4.40 (m, 1H) 4.25 (ABq, 2H) 4.11–4.06 (m, 1H) 3.81 (d, J=7.1 Hz, 1H) 3.53 (dd, J=9.4 Hz, J'=3.3 Hz, 1H) 2.54–0.75 (m, 32H including singlets at 2.54, 2.20, 1.94, 1.67, 1.20, 1.11, 0.86, 0.75, 3H each); HRMS calcd for C$_{67}$H$_{75}$NO$_{19}$P (MH+): 1228.4671, found: 1228.4691.

EXAMPLE 68

2'-O-(4-Phosphonooxy-3,3-dimethylbutanoyl)taxol disodium salt (Iy)

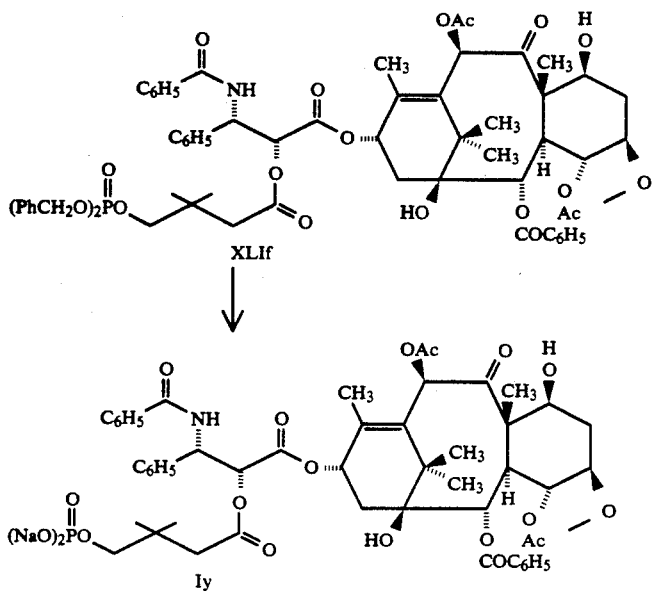

A solution of compound XLIf (979 mg, 0.797 mmol) in ethyl acetate/ethanol (1:1, 100 mL) containing palladium on carbon (10%, 300 mg) was stirred under 65 psi of hydrogen atmosphere for 4 h. The suspension was filtered through Celite; the filtrate was purified by reversed phase (C-18) chromatography using 30%–50% acetonitrile in water as eluent. Lyophilization of the product gave 632 mg (Y: 65%) of the free acid form of the title product as a white foam. Several hydrogenolyses were run and from the combined products, a sample of the acid (371 mg, 0.354 mmol) in water (150 mL) was converted into the sodium salt by addition of sodium bicarbonate (1.0M solution, 0.80 mL, 0.80 mmol). After sonication, the mixture was chromatographed on C-18, eluted first with water, then 15% acetonitrile in water. The acetonitrile was evaporated and the remaining aqueous solution was lyophilized to give a fluffy white solid, 164 mg (Y: 42%); $^1$H-NMR (acetone-$d_6$ and $D_2O$) δ ppm: 8.03 (d, J=8.7 Hz, 2H) 7.82 (d, J=8.7 Hz, 2H) 7.69–7.38 (m, 11H) 7.15 (t, 1H) 6.37 (s, 1H) 5.94 (t, 1H) 5.73 (d, J=7.2 Hz, 1H) 5.55 (d, J=7.1 Hz, 1H) 5.39 (d, J=7.2 Hz, 1H) 4.95 (d, J=7.9 Hz, 1H) 4.40–4.29 (m, 1H) 4.10 (s, 2H) 3.72 (d, J=7.2 Hz, 1H) 3.52–3.44 (m, 2H) 2.48–0.85 (m, 32H, including singlets at 2.42, 2.37, 2.10, 1.86, 1.56, 0.97, 0.85, 3H each, and 1.05, 6H); HRMS calcd for $C_{53}H_{61}NO_{19}PNa_2$ (MH+) 1092.3371, found: 1092.3368.

Anal Calcd for $C_{53}H_{60}NO_{19}PNa_2$: C, 58.29; H, 5.54; N, 1.28; Na, 4.21. Found: C, 55.34; H, 5.74; N, 1.21; Na, 2.84. Water (KF) 9.67%.

EXAMPLE 69

7-O-(4-Dibenzylphosphonooxy-3,3-dimethylbutanoyl)-taxol (XLc)

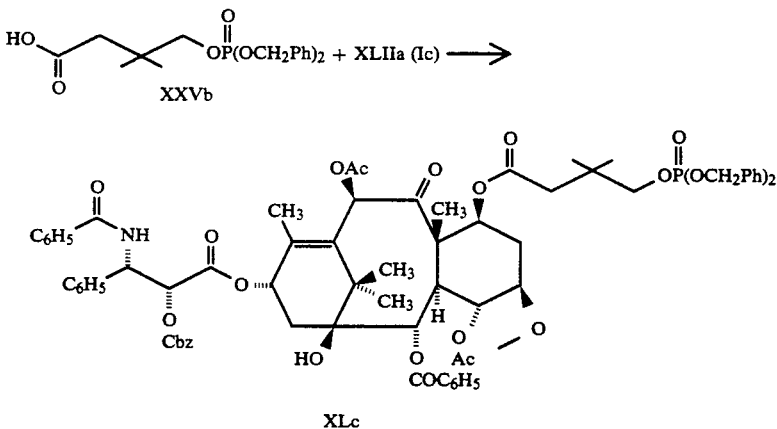

2'-O-(Benzyloxycarbonyl)taxol (1.60 g, 1.62 mmol), acid XXVb (crude, 0.763 g, 1.94 mmol), dicyclohexylcarbodiimide (0.334 g, 1.62 mmol, DCC) and 4-dimethylaminopyridine (0.075 g, 0.324 mmol, DMAP) were dissolved in dry dichloromethane (30 mL). After 24 h at room temperature, the mixture was worked up by filtering off solids followed by drying and concentrating the filtrate. At this time, NMR analysis showed the reaction had only gone to 50% conversion; therefore, an additional amount of acid XXVb (0.600 g, 1.53 mmol), DCC (0.315 g, 1.53 mmol), DMAP (0.075 g, 0.324 mmol) and dry dichloromethane (30 mL) were added. After an additional 24 h, the reaction was worked up as above and chromatographed on silica gel (being eluted with 1:1 ethyl acetate/hexane). 1.53 g (Y: 69%) of the title product was obtained as an off-white foam; $^1$H-NMR (CDCl$_3$) δ ppm: 8.11 (d, J=8.7 Hz, 2H) 7.48 (d, J=8.7 Hz, 2H) 7.62−7.27 (m, 26H) 6.88 (d, J=9.3 Hz, 1H) 6.23 (m, 2H) 5.94 (d, J=9.3 Hz, 1H) 5.66 (d, J=6.9 Hz, 1H) 5.61−5.55 (m, 1H) 5.43 (d, J=2.4 Hz, 1H) 5.14 (dd, 2H) 5.04−5.00 (m, 4H) 4.90 (d, J=9.3 Hz, 1H) 4.31 (d, J=8.4 Hz, 1H) 4.16 (d, 8.4 Hz, 1H) 3.93 (d, J=6.9 Hz, 1H) 3.80–6.69 (m, 2H) 2.63−0.85 (m, 31H, including singlets at 2.43, 2.08, 1.97, 1.78, 1.19, 1.14, 3H each, and 0.93, 6H); HRMS calcd for C$_{75}$H$_{81}$NO$_{21}$P (MH+): 1362.5039, found: 1362.5036.

EXAMPLE 70

7-O-(4-Phosphonooxy-3,3-dimethylbutanoyl)taxol disodium salt (Iz)

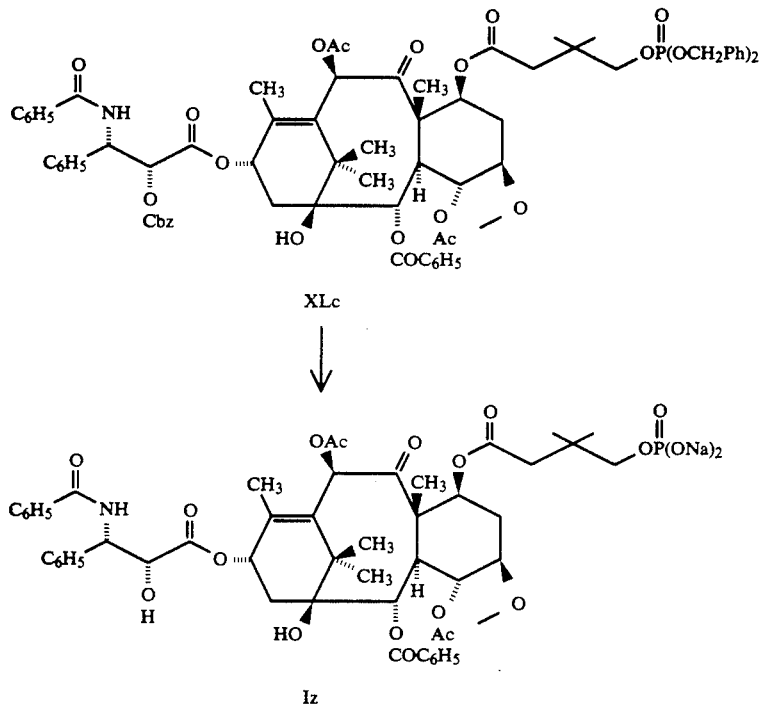

A solution of compound XLc (1.08 g, 0.793 mmol) in ethyl acetate/ethanol (1:1, 10 mL) was stirred under 60 psi of hydrogen atmosphere for 4 h in the presence of palladium on carbon (10%, 400 mg). Filtration and concentration of the filtrate gave 840 mg (Y: 100%) of an off-white foam. The acidic product (460 mg, 0.439 mmol) in water (100 mL) was converted into the sodium salt by addition of sodium bicarbonate (1.0M solution, 0.966 mL, 0.966 mmol) followed by C-18 chromatography (eluted with water followed by 20% acetonitrile in water). After evaporation of the organics and lyophilization, 274 mg (Y: 57%) of a fluffy white foam was obtained. This sample was combined with a similarly obtained lot for analytical purposes; $^1$H-NMR (acetone-d$_6$ and D$_2$O) δ ppm: 7.98 (d, J=8.7 Hz, 2H) 7.80 (d, J=8.7 Hz, 2H) 7.64−7.31 (m, 11H) 7.15 (m, 1H) 6.16 (s, 1H) 5.99 (bt, 1H) 5.53−5.44 (m, 3H) 4.96 (d, J=9.5 Hz, 1H) 4.74 (d, J=6.6 Hz, 1H) 4.10 (s, 2H) 3.78 (d, J=6.0 Hz, 1H) 3.41 (s, 2H) 2.59–0.87 (m, 32H, including singlets at 2.28, 2.09, 1.80, 1.68, 1.05, 1.02, 3H each, and 0.87, 6H); HRMS calcd for C$_{53}$H$_{61}$NO$_{19}$PNa$_2$ (MH+): 1092.3371, found: 1092.3397.

Anal. Calcd for C$_{53}$H$_{60}$NO$_{19}$PNa$_2$: C, 58.30; H, 5.54; N, 1.28; Na, 4.21. Found: C, 56.69; H, 5.64; N, 1.22; Na, 3.31. Water (KF) 2.33%.

EXAMPLE 71

4-(Dibenzylphosphonooxy)butyl 1H-imidazole-1-carboxylate

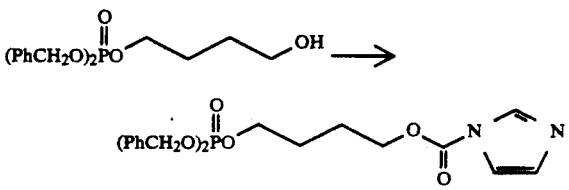

4-(Dibenzylphosphonooxy)-1-butanol (974 mg, 2.78 mmol) in dry dichloromethane (10 mL) was treated with N,N-diisopropylethylamine (0.629 mL, 3.61 mmol). After 5 min, carbonyl diimidazole (586 mg, 3.61 mmol) and 4-dimethylaminopyridine (68.0 mg, 0.556 mmol) were added. The solution was stirred at room temperature for 16 h, then diluted with ethyl acetate. The organics were then washed sequentially with water, 0.1N aqueous HCl, saturated aqueous sodium bicarbonate and brine. The solution was dried and concentrated to give an oil. Chromatography on silica gel (eluted with ethyl acetate) gave 1.16 g (94%) of the title product as an oil; $^1$H-NMR (CDCl$_3$) δ ppm: 8.09 (s, 1H) 7.37−7.29 (m, 11H) 7.04 (s, 1H) 5.08−4.96 (m, 4H) 4.34 (t, 2H) 3.99 (q, 2H) 1.82−1.66 (m, 4H); HRMS calcd for C$_{22}$H$_{26}$N$_2$O$_6$P (MH+): 445.1529, found: 445.1539.

EXAMPLE 72

2'-O-[[4-(Dibenzylphosphonooxy)butoxy]carbonyl]-taxol (XXXc)

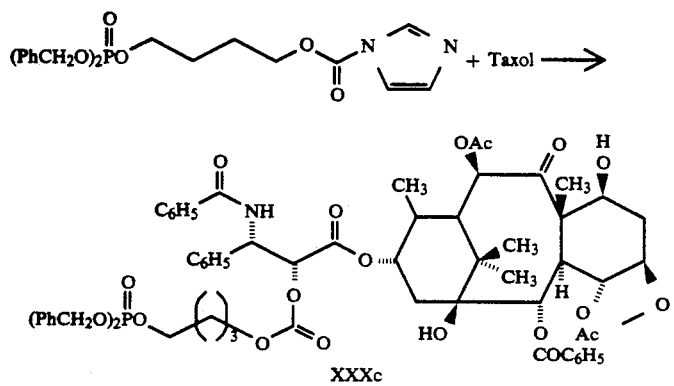

Taxol (1.51 g, 1.77 mmol) in dry dichloromethane (20 mL) was treated with 4-dimethylaminopyridine (492 mg, 2.13 mmol) and 4-(dibenzylphosphonooxy)butyl 1H-imidazole-1-carboxylate (1.16 g, 2.61 mmol). After 4 days at room temperature, the reaction was worked up. The organics were washed with 0.1N aqueous HCl, water and brine, dried and concentrated. Chromatography on silica gel (eluted with 60% ethyl acetate in hexane) gave the title product (905 mg, 42%) as an off-white foam; $^1$H-NMR (CDCl$_3$) δ ppm: 8.12 (d, J=8.7 Hz, 2H) 7.73 (d, J=8.7 Hz, 2H) 7.59–7.31 (m, 21H) 7.08 (d, J=9.0 Hz, 1H) 6.27–6.19 (m, 2H) 5.94 (dd, 1H) 5.66 (d, J=6.0 Hz) 5.39 (d, J=3 Hz, 1H) 5.04–4.93 (m, 4H) 4.48–4.36 (m, 1H) 4.23 (AB q, 2H) 4.13–4.03 (m, 2H) 4.00–3.88 (m, 2H) 3.78 (d, J=6.0 Hz, 1H) 2.51–0.92 (m, 29H, including singlets at 2.43, 2.20, 1.90, 1.21, 1.11, 3H each, and 1.66, 6H); HRMS calcd for C$_{66}$H$_{73}$NO$_{20}$P (MH+): 1230.4464, found: 1230.4434.

EXAMPLE 73

2'-O-[[4-(Phosphonooxy)butoxy]carbonyl]taxol disodium salt (Iaa)

A solution of compound XXXc (876 mg, 0.712 mmol) in ethyl acetate/ethanol (1:1, 10 mL) was stirred under 60 psi of hydrogen atmosphere with palladium on carbon (10%, 200 mg) for 4.5 h. The mixture was filtered through Celite and then concentrated. The resulting free acid (197 mg, 0.188 mmol) in water (15 mL) was converted to its sodium salt by addition of sodium bicarbonate (1M solution, 0.413 mL, 0.413 mmol) followed by C-18 chromatography (being eluted with water followed by 25% acetonitrile in water). The acetonitrile was evaporated and the remaining aqueous solution was lyophilized to give 159 mg (Y: 78%) of a white fluffy powder; $^1$H-NMR (DMSO-d$_6$, D$_2$O) δ ppm: 7.93 (d, J=8.7 Hz, 2H) 7.80 (d, J=8.7 Hz, 2H) 7.71–7.40 (m, 11H) 7.20–7.03 (m, 1H) 6.24 (s, 1H) 5.77 (t, 1H) 5.66–5.28 (m, 3H) 4.89 (d, J=9.0 Hz, 1H) 4.23–4.03 (m, 3H) 3.96 (s, 2H) 3.65–3.47 (m, 3H) 2.30–0.95 (m, 28H, including singlets at 2.20, 2.06, 1.74, 0.95, 3H each, and 1.45, 6H); HRMS calcd for C$_{52}$H$_{59}$NO$_{20}$PNa$_2$ (MH+): 1094.3163, found: 1094.3176.

Anal. Calcd for C$_{52}$H$_{58}$NO$_{20}$PNa$_2$: C, 57.09; H, 5.34; N, 1.28. Found: C, 54.50; H, 5.41; N, 1.16. Water (KF) 2.82%.

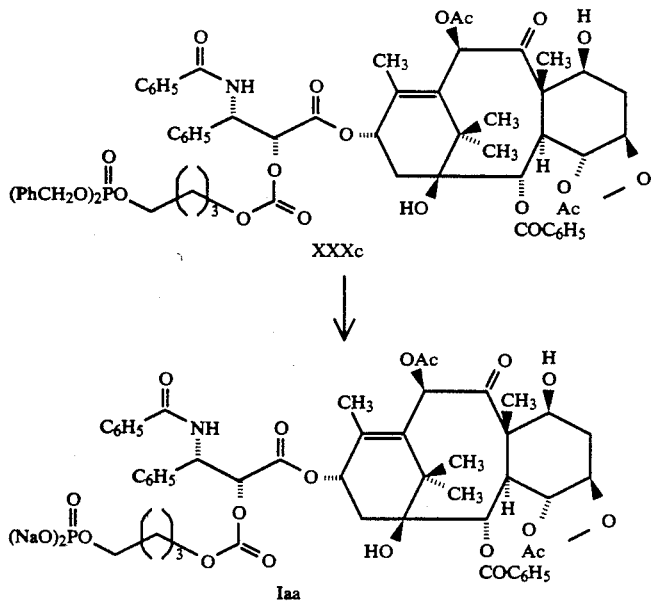

EXAMPLE 74

2'-O-Ethoxycarbonyl-7-O-[[2''-(dibenzylphosphonooxy)phenyl]acetyl]taxol (XXXIc)

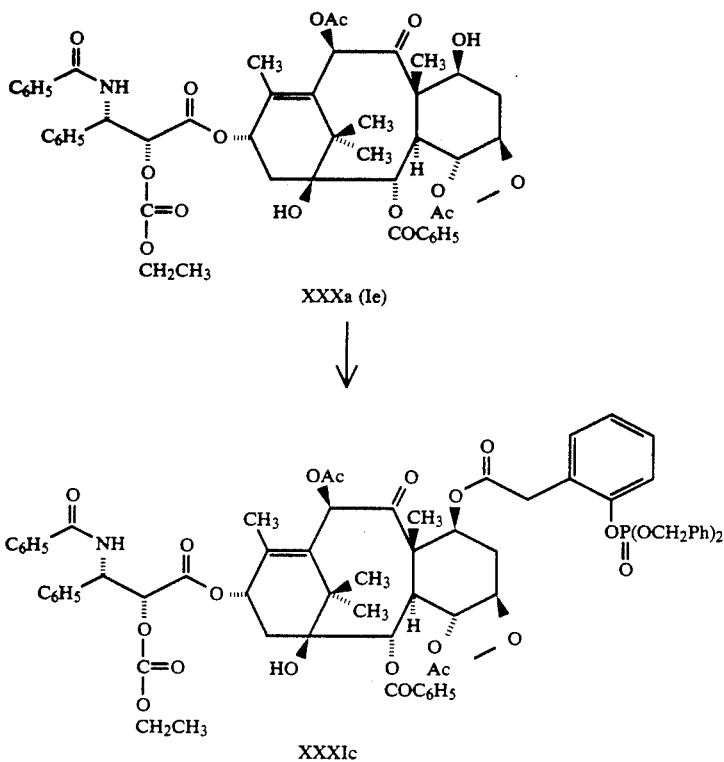

The phenylacetic acid IXd (1.65g, 4 mmol) and dicyclohexylcarbodimide (1.65 g, 8 mmol) were placed together in 30 mL CH$_2$Cl$_2$ under N$_2$ and stirred for 20 min. Then 2'-O-(ethoxycarbonyl)taxol (XXXa) (1.85 g, 2 mmol) and 4-dimethylaminopyridine (122 mg, 1 mmol) were added and stirring was continued for 18 h at room temperature. The CH$_2$Cl$_2$ was removed by evaporation. The residue was suspended in acetone and filtered to remove the insoluble urea. Concentration of the filtrate gave 4.5 g of a yellow amorphous residue. This was purified by silica gel column chromatography (being eluted with 1:1 EtOAc/CH$_2$Cl$_2$). The solid obtained (1.9 g) was again dissolved in acetone and filtered to remove the insoluble material. After concentration of the filtrate, the solid was suspended in Et$_2$O and stored for crystallization. The pure title compound, XXXIc, (1.53 g, Y: 77%) was obtained as off-white crystals; mp, 185–162° C.; HPLC Rt: 7.26 min (purity: >98%; C$_{18}$ Waters radial pack column; flow rate: 2 mL/min; eluent: 80% CH$_3$C≡N in H$_2$O; UV detection at 227 nm); $[\alpha]_D^{20} = -30.14°$ (c=0.335, 95% EtOH); IR MHz, CDCl$_3$) δ ppm: 1.14 (3H, s, Me), 1.19 (3H, s, Me), 1.27 (3H, t, J=7.6 Hz, OCH$_2$CH$_3$), 1.64 (3H, s, Me), 1.68 (3H, s, Me), 1.95 (3H, s, OAc), 2.38 (3H, s, OAc), 1.73–2.52 (4H, m, 6-Hs, 14-Hs), 3.67 (2H, s ArCH$_2$-C=O), 3.90 (1H, d, J=6.9 Hz, 3-H), 4.10–4.29 (4H, m, 20-Hs and CH$_3$CH$_2$O), 4.81 (1H, d, J=8.1 Hz, 5-H); 5.08 (4H, ABq, PhCH$_2$O); 5.39 (1H, d, J=2.7 Hz, 2'-H), 5.53–5.58 (1H, m, 7-H), 5.65 (1H, d, J=6.9 Hz, 2-H), 5.94 (1H, dd J=2.7 and 9.2 Hz, 3'-H), 6.23 (1H, t, 13-H), 6.26 (1H, s, 10-H), 6.90–8.11 (30H, m, ArH's+3'-NH); MS (FAB/NOBA+NaI+KI) m/e: 1320 (MH+), 1342 (MNa+), 1358 (MK+).

Anal. calcd for C$_{72}$H$_{74}$NO$_{21}$P: C, 65.40; H, 5.79; N, 1.06.

Found: C, 65.23; H, 5.65; N, 1.10.

EXAMPLE 75

2'-O-Ethoxycarbonyl-7-O-[(2"-Phosphonooxyphenyl)acetyl]taxol monosodium salt (Ibb)

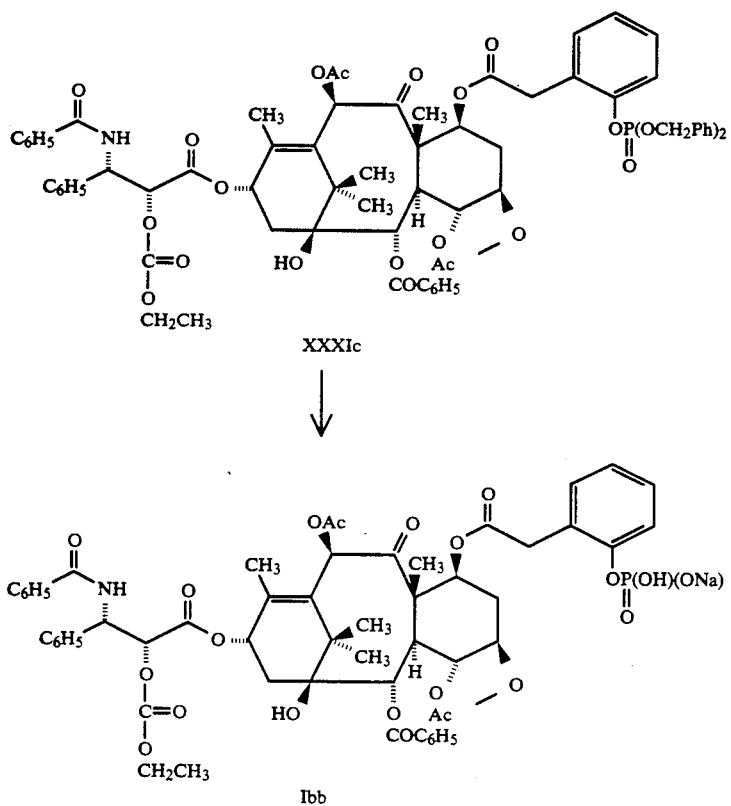

Compound XXXIc (1.19 g, 0.9 mmol) was dissolved in 75 mL EtOAc and 75 mL EtOH, and under $N_2$, 200 mg 10% Pd on carbon was added. The reaction bottle was placed on a Parr hydrogenator, $H_2$ introduced (~40 psi) and the bottle shaken for 3 h. The catalyst was removed by filtration and the filtrate concentrated to leave approximately 1 g (~92% pure by HPLC) of the free acid form of compound Ibb. This was dissolved in $CH_3C\equiv N$ and treated with sodium hydrogen carbonate (151 mg, 1.8 mmol) in $H_2O$. The volume was adjusted to 100 mL (20% $CH_3C\equiv N$ in $H_2O$). This was purified by reverse phase chromatography ($C_{18}$, 20–30% $CH_3C\equiv N$ in $H_2O$). After concentration and lyophilization, the title compound was obtained (410 mg, Y: 35.9%) as a monosodium salt (white fluffy powder); mp, 169–172° C.; HPLC Rt: 9.09 min (purity: ~100%; $C_{18}$ Waters Radial Pak column; flow rate: 2.0 mL/min; eluent 45/55 of A/B, A=0.05M pH 6.0 ammonium phosphate buffer, B=80% $CH_3C\equiv N$ in $H_2O$; UV detection at 227 nm); $[\alpha]_D^{20} = -31.3°$ (c =0.15, 95% EtOH); IR (KBr) 3432, 1748, 1246, 1108 cm$^{-1}$; $^1$H-NMR (300 MHz, acetone-d6/$D_2O$) δ ppm: 1.14 (3H, s, Me); 1.15 (3H, s, Me); 1.17 (3H, t, $CH_3CH_2O$); 1.66 (3H, s, Me); 1.91 (3H, s, Me); 2.12 (3H, s, OAc); 2.40 (3H, s, OAc); 1.66–2.61 (4H, m, 6-Hs, 14H-s); 3.62 (2H, s, ArCH$_2$CO); 3.85 (1H, d, J=3.9 Hz, 3-H); 4.06–4.16 (4H, m, 20-H$_2$, CH$_3$CH$_2$O); 4.86 (1H, d, 5-H); 5.49 (1H, d, J=6.2 Hz, 2'-H); 5.50 (1H, m, 7-H); 5.62 (1H, d, 3.9 Hz, 2-H); 5.90 (1H, d, J=6.2 Hz, 3'-H); 6.10 (1H, t, 13-H); 6.28 (1H, s, 10-H) 6.80–8.11 (20H, m, ArH's+NH); MS (FAB/NOBA) m/e: 1162 (MH+), 1184 (MNa+);

Anal. calcd for $C_{58}H_{61}NO_{21}PNa \cdot 5H_2O$: C, 55.64; H, 5.72; N, 1.12; H$_2$O, 7.19. Found: C, 55.41; H, 5.19; N, 1.16; H$_2$O, 10.21 (KF).

EXAMPLE 76

2'-O-Benzyloxycarbonyl-7-O-[[2''-(dibenzylphosphonooxy)phenyl)acetyl]taxol (XLd)

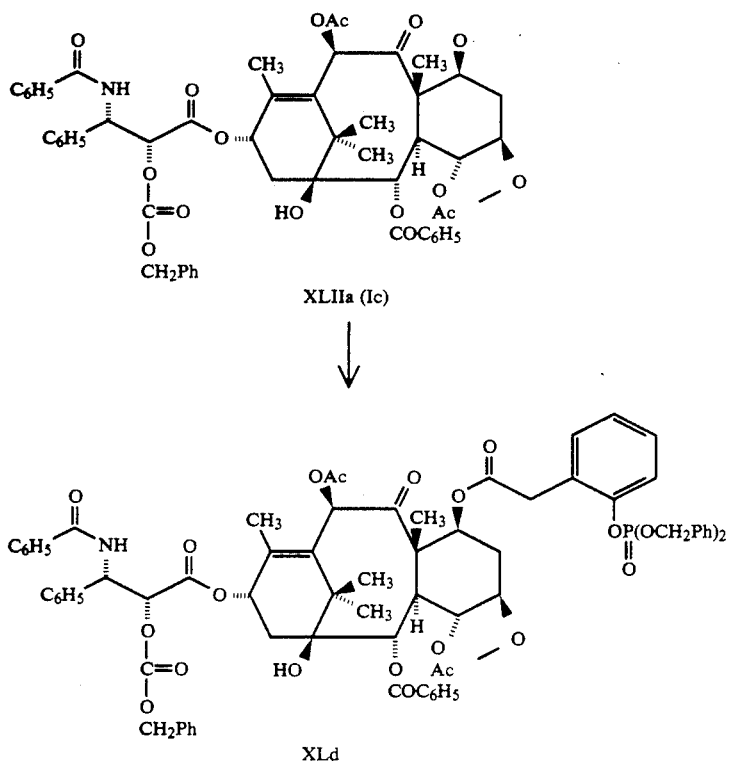

Phenylacetic acid IXd (1.65 g, 2 mmol) and dicyclohexylcarbodiimide (1.65 g, 4 mmol) were placed together in 30 mL CH$_2$Cl$_2$ and stirred for 15 min under N$_2$. Compound XLIIa (1.97 g, 2 mmol) and 4-dimethylaminopyridine (66 mg, 0.5 mmol) were added and stirring was continued. After 2 h the reaction mixture was concentrated. The residue was suspended in acetone and filtered. Concentration of the filtrate gave 4.4 g of a yellow gum. This was purified by silica gel column chromatography (being eluted With 9:1 CH$_2$Cl$_2$:EtOAc) followed by crystallization from Et$_2$O to give 1.5 g (Y: 54%) of the title compound; mp, 183–188° C.; HPLC Rt: 7.7 min (purity: ~100%; C$_{18}$ Water radial pack column; flow rate: 2 mL/min; eluent: 80% CH$_3$C≡N in H$_2$O; UV detection at 227 mmol); [α]$_D^{20}$ = −55.47° (c=0.177, CH$_2$Cl$_2$); IR (KBr) 3440, 1748, 1274, 1240, 1024 cm$^{-1}$; MS (FAB/NOBA+-NaI+KI) m/e: 1382 (MH+), 1404 (MNa+), 1420 (MK+); $^1$H-NMR (300 MHz, CDCl$_3$) δ ppm: 1.14 (3H, s, Me), 1.19 (3H, s, Me), 1.56 (3H, s, Me), 1.69 (3H, s, Me), 2.14 (3H, s, OAc), 2.41 (3H, s, OAc), 1.67–2.60 (4H, m 6Hs, 14 Hs), 3.68 (2H, s, ArCH$_2$O); 3.90 (1H, d, J=6.6 Hz, 3-H); 4.10, 4.13, 4.27, 4.29 (2H, ABq 20-H$_2$), 4.81 (1H, d, J=8.1 Hz, 5-H), 5.07–5.17 (6H, m, ArCH$_2$O), 5.42 (1H, d, J=2.6 Hz, 2'-H), 5.59 (1H, m, 7-H), 5.65 (1H, d, J=6.6 Hz, 2-H), 5.94 (1H, dd, J=2.6 and 9.2 Hz, 3'-H), 6.23 (1H, t, 13-H), 6.26 (1H, s, 10-H), 6.86–8.12 (35H, m, ArH's+NH).

Anal calcd for C$_{77}$H$_{76}$NO$_{21}$P: C, 66.90; H, 5.54; N, 1.01.

Found: C, 67.06; H, 5.70; N, 1.17.

EXAMPLE 77

7-O-[(2''-Phosphonooxyphenyl)acetyl]taxol monosodium salt (Icc)

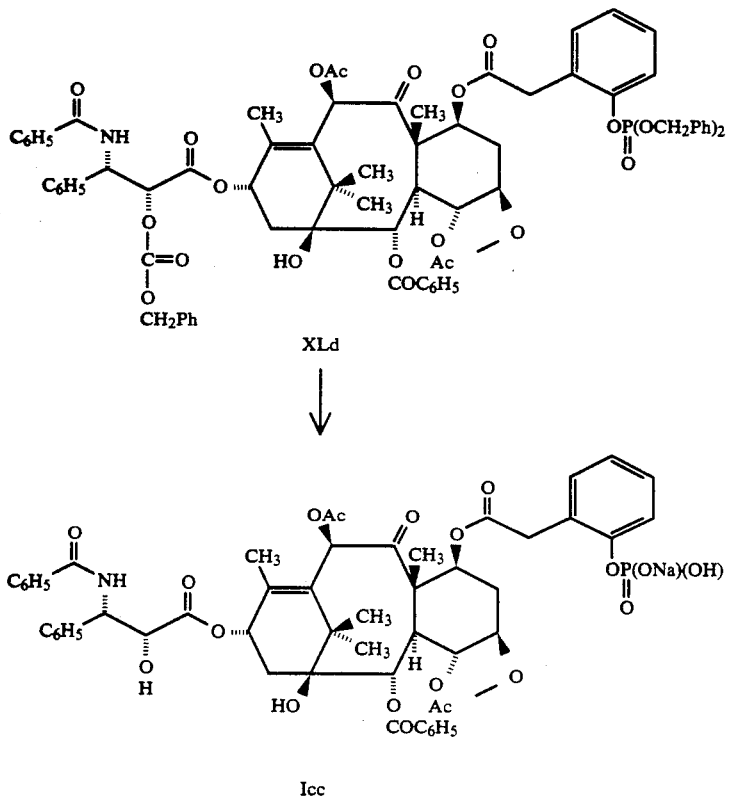

Compound XLd (1.35 g, 0.97 mmol) was dissolved in 75 ml EtOH and 75 ml EtOAc, and under $N_2$, 200 mg 10% Pd on carbon was added. The bottle, under 40 psi of $H_2$ atmosphere, was shaken on a Parr hydrogenator for 3 h. The catalyst was removed by filtration and the filtrate concentrated to leave ~1.0 g of the free acid form of the title compound as an amorphous material. This was dissolved in $CH_3C\equiv N$ and treated with sodium hydrogen carbonate (90 mg, 1.1 mmol) in water. The volume was adjusted to approximately 150 mL (25% $CH_3C\equiv N$ in $H_2O$). This was purified by reverse phase chromatography ($C_{18}$, 20–30% $CH_3C\equiv N$ in $H_2O$). After concentration and lyophilization, 660 mg (Y: 58%) of the title compound was obtained; mp, 173–176° C.; HPLC Rt: 5.02 min (purity: ~100%; $C_{18}$ Waters Radial Pakk column; flow rate: 2.0 mL/min; eluent 45/55 of A/B, A=0.05M pH6.0 ammonium phosphate buffer, B=80% $CH_3C\equiv N$ in $H_2O$; UV detection at 227 nm); $[\alpha]_D^{20}=-34.3°$ (c=0.25, 95% EtOH); IR(KBr) 3432, 1726, 1246, 1146, 1168 cm$^{-1}$; $^1$H-NMR (acetone-d$_6$/D$_2$O) δ ppm: 1.10 (3H, s, Me); 1.14 (3H, s, Me); 1.67 (3H, s, Me); 1.84 (3H, s, Me); 2.16 (3H, s, OAc); 2.34 (3H, s, OAc); 1.67–2.59 (4H, m, 6-Hs, 14-Hs); 3.66 (2H, s, ArCH$_2$C=O); 3.85 (1H, d, J=7.0 Hz, 3-H); 4.10 (2H, s, 20-H$_2$); 4.80 (1H, d, J=5.8 Hz, 2'-H); 4.95 (1H, d, J=9.2 Hz; 5-H); 5.52 (1H, m, 7-H); 5.60 (1H, d, J=7.0 Hz; 2-H); 5.65 (1H, d, J=5.8 Hz, 3'-H); 6.08 (1H, t, 13-H); 6.25 (1H, s, 10-H); 6.82–8.07 (20H, m, ArH's+NH); MS (FAB/NOBA) m/e: 1090 (MH+), 1112 (MNa+).

Anal. calcd for $C_{55}H_{57}NO_{19}PNa/4.5\ H_2O$: C, 56.41; H, 5.68; N, 1.20; H$_2$O, 6.92. Found: C, 55.07; H, 4.88; N, 1.13; H$_2$O, 6.69 (KF).

EXAMPLE 78

2'-O-Acetyl-7-O-[[2''-(dibenzylphosphonooxy)phenyl]acetyl]taxol (XLe)

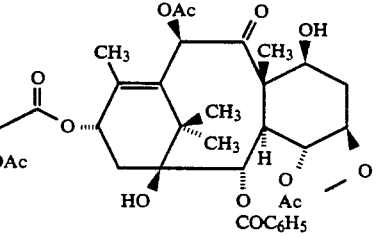

-continued

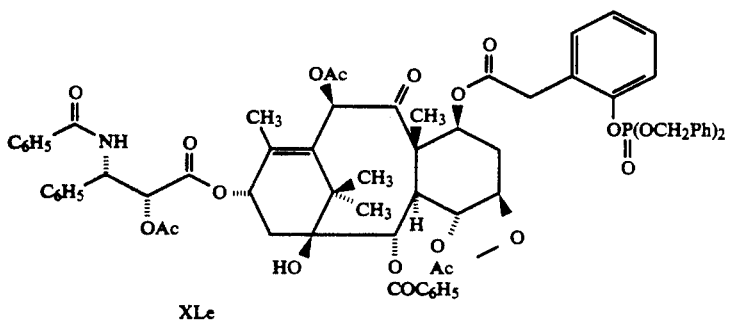

XLe

To a solution of 2'-O-acetyltaxol* (XLIIb) (1.344 g, 150 mmol), 2-(dibenzylphosphonooxy)phenylacetic acid (IXd) (1.237 g, 3.00 mmol) and 1,3-dicyclohexylcarbodiimide (DCC, 1.236 g, 6.00 mmol) in $CH_2Cl_2$ (30 mL, molecular sieves dried) was added 4-dimethylaminopyridine (DMAP, 183 mg, 1.5 mmol) and the mixture was stirred under anhydrous nitrogen atmosphere for 20 h. The white precipitate (urea) was removed and the filtrate was concentrated. The residue was purified by silica gel column chromatography (being eluted with 20% EtOAc in $CH_2Cl_2$) to obtain 1.056 g (0.819 mmol, Y: 54.6%) of the title compound as white crystals after recrystallization from acetone/$Et_2O$; mp, 159°–161° C.; Rf: 0.40 (20% EtOAc in $CH_2Cl_2$); $[\alpha]_D^{20} = -44.52°$ (c=0.155, 95% EtOH); IR(KBr) 3448, 1746 $cm^{-}$, $^1$H-NMR (300 MHz, $CDCl_3$) δ ppm: 1.13 (3H, s, 15-Me), 1.18 (3H, s, 15-Me), 1.68 (3H, s, Me), 1.93 (3H, s, Me), 2.12 (3H, s, OAc), 2.13 (3H, s, OAc), 2.39 (3H, s, OAc), 3.67 (2H, s, $ArCH_2CO$), 3.89 (1H, d, J=6.9 Hz, 3-H), 4.09–4.12–4.25–4.28 (2H, ABq, 20-Hz), 4.81 (1H, d, J=8Hz, 5-H), 5.07 (4H, ABq, $OCH_2Ar$), 5.51 (1H, d, J=3.4 Hz, 2'-H), 5.55 (1H, dd, J=7.2 and 10.7 Hz, 7-H), 5.63 (1H, d, J=7.0 Hz, 2-H), 5.91 (1H, dd, J=3.2 and 9.2 Hz, 3'-H), 6.18 (H, t, J=9.2 Hz, 13-H), 6.25 (1H, s, 10-H), 6.88 (1H, d, J=9.1 Hz, 3'-NH), 7.05–7.65 (15 H, m, Ar-Hs), 7.72 (2H, d, J=7 Hz, 3'-NHCOAr-Ho), 8.09 (2H, d, J=7.1 Hz, 2-OCOAr-Ho); MS (FAB/NOBA+NaI+KI) m/e: 1290 (MH+), 1312 (MNa+), 1328 (MK+); HRMS (FAB/NOBA) calcd for $C_{71}H_{73}NO_{20}P(MH+)$ 1290.4464, found: 1290.4461; UV (MeOH) λmax: 228 nm (ε $2.83 \times 10^4$).

* 2'-O-Acetyltaxol was prepared from taxol by the method described in W. Mellado et al., Biochem. Biophys. Res. Comm., 124, p. 329 (1984).

Anal. calcd for $C_{71}H_{72}NO_{20}P$: C, 66.09; H, 5.62; N, 1.08.

Found: C, 66.07, H, 5.66; N, 1.19.

EXAMPLE 79

2'-O-Acetyl-7-O-[(2'''-phosphonooxyphenyl)acetyl]-taxol monopotassium salt (Idd)

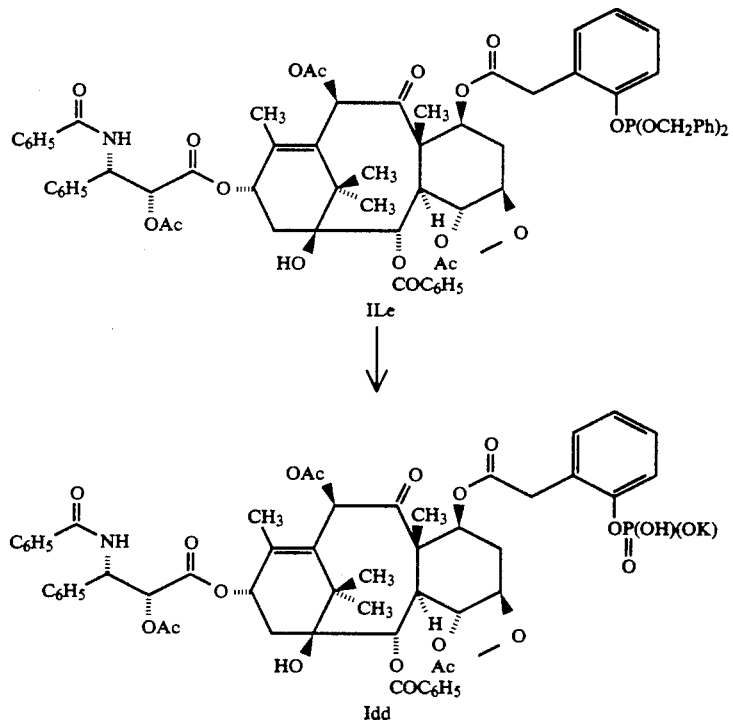

To a solution of compound XLe (924 mg, 0.716 mmol) in EtOAc (50 mL) was added absolute EtOH (50 mL) and 10% Pd on carbon (200 mg; Aldrich). The resultant mixture was stirred under $H_2$ atmosphere (40 psi) for 3¼ h at room temperature in a Parr apparatus. The catalyst was filtered through Celite and the filtrate was concentrated in vacuo to dryness. The residue was triturated with anhydrous Et$_2$O to obtain 783 mg (0.705 mmol, Y: 98.5%) of the free acid form of compound Idd as a white powder; mp, 153°-155° C. (decomposition); Rt: 6.98 min (HPLC purity: 98.7%; eluent: 45% A/55% B, A=0.05M, pH 6.0 ammonium phosphate buffer with 5% CH$_3$CN, B=80% CH$_3$CN in H$_2$O; flow rate: 2 mL/min; detection by UV at 227 nm; column: Waters C-18 RP-Radial Pak); $[\alpha]_D^{20}= -51.35°$ (c=0.185, 95% EtOH); $^1$H-NMR (300 MHz, acetone-d6) δ ppm: 1.17 (3H, s, 15-Me), 1.19 (3H, s, 15-Me), 1.73 (3H, s, 8-Me), 1.8 (1H, m), 1.81 (12-Me), 2.07 (3H, s, OAc), 2.19 (3H, s, OAc), 2.31 (1H, m), 2.43 (3H, s, OAc), 2.57 (1H, m), 3.61-3.67-3.70-3.76 (2H, ABq, CH$_2$CO), 3.92 (1H, d, J=7.0 Hz, 3-H), 4.15 (2H, s, 20-Hz), 4.93 (1H, d, J=8.3 Hz, 5-H), 5.51 (1H, d, J=5.8 Hz, 2'-H), 5.62 (1H, dd, J=7.3 and 10.3 Hz, 7-H), 5.67 (1H, d, J=7.0 Hz, 2-H), 5.93 (1H, m, 3'-H), 6.12 (1H, t, J=8 Hz, 13-H), 6.31 (1H, s, 10-H), 7.05-7.7 (15H, m, Ar-Hs), 7.85 (1H, d, J=7 Hz, Ar-Ho), 8.12 (1H, d, J=7 Hz, Ar-Ho), 8.42 (1H, d, J=9.1 Hz, 3'-NH); MS (FAB/NOBA+NaI+KI) m/e: 1132 (MNa+), 1148 (MK+); HRMS (FAB/NOBA) calcd for C$_{57}$H$_{61}$NO$_{20}$P(MH+) 1110.3525, found: 1110.3495; UV (95% EtOH) λmax: 230 (ε 2.54×10$^4$), 268 nm (ε 3.24×10$^3$).

Anal. calcd for C$_{57}$H$_{60}$NO$_{20}$P.H$_2$O: C, 60.69; H, 5.55; N, 1.25; H$_2$O, 1.60. Found: C, 60.56; H, 5.36; N, 1.27; H$_2$O, 1.48 (KF).

A solution of the above free acid (673 mg, 0.676 mmol as monohydrate) in acetone (25 mL) was mixed with a solution of KHCO$_3$ (68 mg, 0.68 mmol) in H$_2$O (100 mL, deionized) and sonicated to obtain a cloudy solution. This was concentrated in vacuo to remove the acetone and the aqueous solution was lyophilized to obtain 782 mg (0.681 mmol, Y: ~100%) of the title compound as a white fluffy powder; Rt: 4.52 min (HPLC purity: 99.6%; eluent: 40% A/60% B; A, B and other conditions are as defined above); $[\alpha]_D^{20}= -31.3°$ (c=0.23, 95% EtOH, rotation at equilibrium, initial $[\alpha]_D^{20}$ was −62.2°); IR (KBr) 3432, 1732 cm$^{-1}$; $^1$H-NMR (300 MHz, acetone-d$_6$/D$_2$O) δ ppm: 1.12 (3H, s, 15-Me), 1.14 (3H, s, 15-Me), 1.68 (3H, s, 8-Me), 1.88 (3H, s, 12-Me), 2.07 (3H, s, OAc), 2.16 (3H, s, OAc), 2.39 (3H, s, OAc), 2.64 (1H, m), 3.58-3.63-3.67-3.73 (2H, ABq, ArCH$_2$CO), 3.86 (1H, d, J=6.9 Hz, 3-H), 4.10 (2H, s, 20-H$_2$), 4.95 (1H, d, J=8.8 Hz, 5-H), 5.48 (1H, d, J=6.7 Hz, 2'-H), 5.57 (1H, m, 7-H), 5.62 (1H, d, J=7.2 Hz, 2-H), 5.83 (1H, d, J=6.7 Hz, 3'-H), 6.05 (1H, t, J=8.4 Hz, 13-H), 6.28 (1H, s, 10-H), 6.88 (1H, t, J=7.4 Hz, Ar-H), 7.08 (1H, t, Ar-H), 7.17 (1H, d, J=7.4 Hz, Ar-H), 7.25 (1H, t, J=7.4 Hz, Ar-H), 7.35-7.7 (11H, m, Ar-Hs), 7.86 (2H, d, J=7.1 Hz, 3'-NHCOAr-Ho), 8.08 (2H, d, J=7 Hz, 2-OCOAr-Ho); MS(FAB/NOBA) m/e: 1148 (MH+), 1186 (MK+); HRMS (FAB/NOBA) calcd for C$_{57}$H$_{60}$NO$_{20}$PK(MH+) 1148.3083, found: 1148.3082; UV (95% EtOH) λmax: 230 (ε 3.03×10$^4$), 268 nm (ε 6.88×10$^3$); Solubility: estimated to be ca. 5 mg/mL in deionized water.

Anal. calcd for C$_{57}$H$_{59}$NO$_{20}$PK/3.5H$_2$O: C, 56.53; H, 5.50; N, 1.16; P, 2.56; K, 3.23; H$_2$O, 5.21. Found: C, 56.83; H, 5.12; N, 1.17; p, 3.63; K, 2.15; H$_2$O, 5.55.

EXAMPLE 80

2'-O-[2''-(Dibenzylphosphonooxy)phenyl]acetyl]taxol (XLIg)

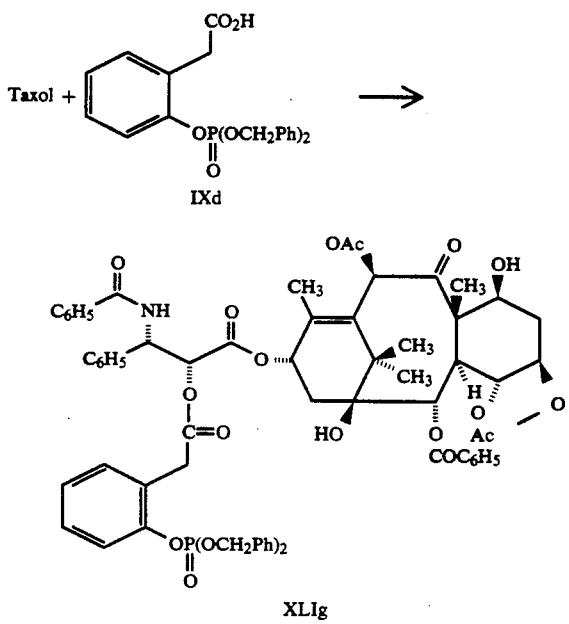

Taxol (5.98 g, 7 mmol) and 4-dimethylaminopyridine (DMAP, 122 mg, 1 mmol) were dissolved in 60 mL CH$_2$Cl$_2$ under N$_2$ and cooled in an ice bath. Simultaneously, to this stirring mixture was added at approximately equal rates, over a period of 15 min, a suspension of phenylacetic acid IXd (3.17 g, 7.7 mmol) in 20 mL CH$_2$Cl$_2$ and a solution of dicyclohexylcarbodiimide (DCC, 1.58 g, 7.7 mmol) in 20 mL CH$_2$Cl$_2$. After ¼ h at 0° C., an additional amount (1 mmol) of phenylacetic acid IXd and DCC each in 10 mL CH$_2$Cl$_2$ were added. Within ½ h, HPLC indicated that no taxol remained. The reaction mixture was concentrated and the residue was suspended in acetone and filtered to remove the insoluble urea. Concentration of the acetone mixture gave 9.4 g of a crude product. This was chromatographed on silica gel (being eluted with 3:2 EtOAc/hexanes) to give 8.7 g of an amorphous material (~10:1 mixture of 2'-acylated compound XLIg and 2',7-bisacylated compound). Further purification was performed by reverse phase chromatography (C$_{18}$, eluted with 75% CH$_3$CN in H$_2$O) to give 6.58 g (5.27 mmol, Y: 75%) of the title compound; mp, 102–107° C.; HPLC Rt: 4.75 min (purity: ~100%; C$_{18}$ Waters radial pack column; flow rate: 2 mL/min; eluent 80% CH$_3$CN in H$_2$O; UV detection at 227 nm); $[\alpha]_D^{20}= -27.83°$ (c=0.6, 95% EtOH); $^1$H-NMR (300 MHz, CDCl$_3$) δ ppm: 1.09 (3H, s, Me), 1.18 (3H, s, Me), 1.58 (3H, s, Me), 1.64 (3H, s, Me), 2.20 (3H, s, OAc), 2.37 (3H, s, OAc), 2.47 (1H, d, 7-OH), 1.60-2.50 (4H, m, 6-H and 14-H), 3.57-3.62-3.76-3.81 (2H, ABq, ArCH$_2$C=O), 3.75 (1H, d, J=6 Hz, 3-H), 4.13-4.16-4.24-4.27 (2H, ABq, 20-H's), 4.40 (1H, m, 7-H), 4.90 (1H, d, J=8.7 Hz, 5-H), 4.97-5.14 (4H, m, ArCH$_2$O), 5.28 (1H, d, J=5.4 Hz, 2'-H), 5.61 (1H, d, J=7.2 Hz, 2-H), 5.72 (1H, dd, J=5.3 and 8.2 Hz, 3'H), 6.09 (1H, t, 13-H), 6.24 (1H, s 10-H), 7.02-8.14 (30H, m, Ar-H's, 3'-NH); MS (FAB/NOBA+NaI+KI) m/e: 1247 (MH+), 1270 (MNa+), 1286 (MK+); IR (KBr) 3438, 1744, 1726, 1272, 1242, 1018 cm$^{-1}$.

Anal. calcd for $C_{69}H_{70}NO_{19}P$: C, 66.39; H, 5.65; N, 1.12.

Found: C, 66.18; H, 5.59; N, 0.96.

EXAMPLE 81

2'-O-[(2''-Phosphonooxyphenyl)acetyl]taxol monosodium salt (Iee)

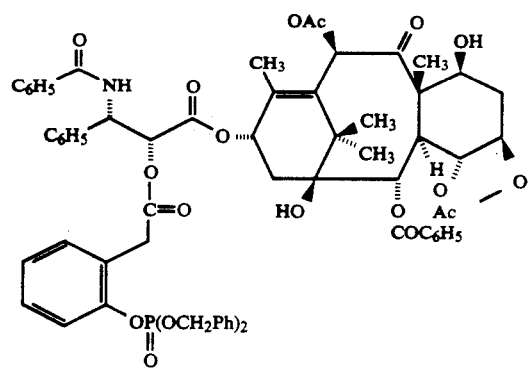

XLIg

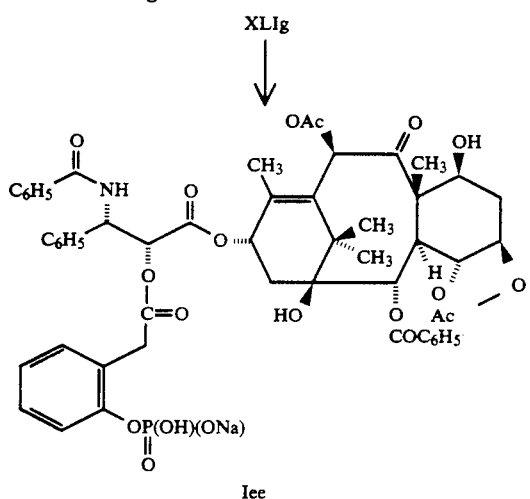

Iee

Compound XLIg(3.9 g, 3.12 mmol) was dissolved in 100 mL EtOAc and 100 mL EtOH, and under $N_2$, 300 mg 10% Pd on carbon was added. The reaction bottle was placed on a Parr hydrogenator and $H_2$ was introduced (~40 psi). After shaking for 3 h, the debenzylation was complete. The catalyst was removed by filtration and the filtrate concentrated to leave a glass. This was triturated with dry $Et_2O$ under $N_2$; the supernatant was decanted; and the residue was vacuum dried to give the free acid form of the title compound (2.97 g, Y: 89%); mp, 153-159° C. (decomposition); HPLC purity: ~94%. This acid (4.7 g, 4.4 mmol) was divided into 3 parts and treated as follows. The acid was dissolved in 20 ml $CH_3C≡N$ and treated with sodium hydrogen carbonate (2 equiv.) in 80 mL of water. The resultant solution was purified by chromatography ($C_{18}$, eluted with 20-36% $CH_3C≡N$ in $H_2O$). Purified fractions were concentrated to remove $CH_3C≡N$, combined and lyophilized to give the title compound (2.7 g, Y; 53%, purified); HPLC Rt: 3.40 min (purity: >97%; $C_{18}$ Waters radial pack column; flow rate: 2.0 mL/min; eluent: 40/60 of A/B, A=0.05M pH 6.0 ammonium phosphate buffer, B=80% $CH_3C≡N$ in $H_2O$; UV detection at 227 nm); $[\alpha]_D^{20} = -38.71°$ (c=0.46, 95% EtOH); IR (KBr) 3440, 1726, 1244, 1180, 1070 cm$^{-1}$; $^1$H-NMR (300 MHz acetone-$d_6$/$D_2O$) δ ppm: 1.10 (6H, s); 1.58 (3H, s); 1.86 (3H, s); 2.06 (3H, s, OAc); 2.36 (3H, s, OAc); 1.58-2.50 (4H, m, 6-Hs, 14-Hs); 3.69 (1H, d, J=7.2 Hz, 3-H); 3.79 (2H, q, $ArCH_2C=O$); 4.07 (2H, s, 20-H); 4.31 (1H, m, 7-H); 4.92 (1H, d, J=9.6 Hz, 5-H); 5.52 (1H, d, J=8.6 Hz, 2'-H); 5.57 (1H, d, J=7.2 Hz, 2-H); 5.64 (1H, d, J=8.6, 3'-H); 5.96 (1H, t, 13H), 6.39 (1H, s, 10-H); 6.58-8.07 (20H, m, ArH's+NH); MS (FAB/NOBA) m/e: 1090 (MH+).

Anal. calcd for $C_{55}H_{57}NO_{19}PNa$.5.5 $H_2O$: C, 55.50; H, 5.77; N, 1.18; $H_2O$, 8.33. Found: C, 55.09; H, 4.95; N, 1.16; $H_2O$, 8.18(KF).

EXAMPLE 82

2'-O-[3-(Dimethylamino)phenoxy]carbonyl-7-O-[3''-(2'''-dibenzylphosphonooxy-4''',6'''-dimethylphenyl)-3'',3''-dimethylpropionyl]taxol (XXXId)

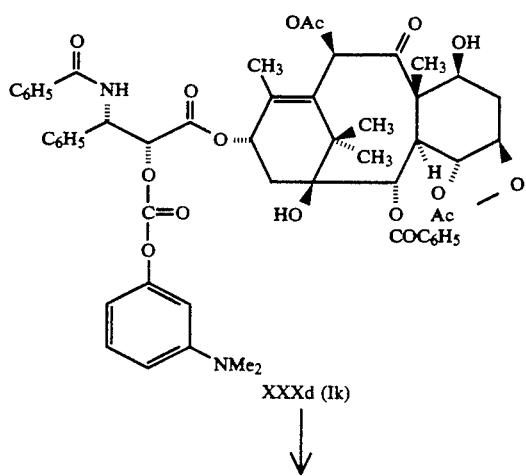

XXXd (Ik)

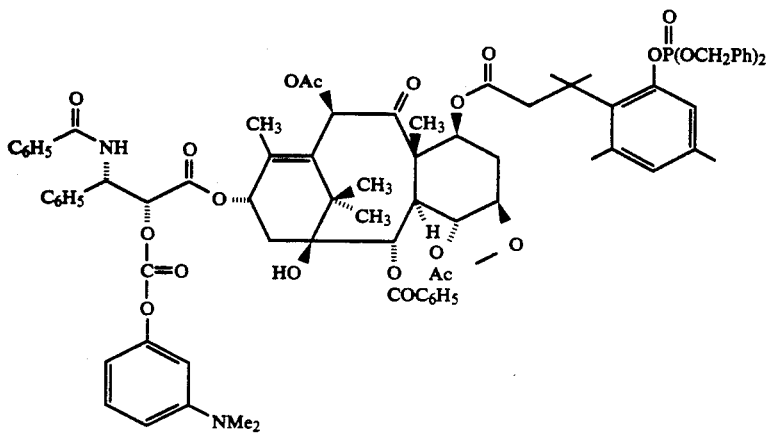

XXXId

Phenylpropanoic acid IXa (1.08 g, 2.25 mmol) was dissolved in 30 mL CH$_2$Cl$_2$ under N$_2$, and with stirring dicyclohexylcarbodiimide (DCC, 555 mg, 2.7 mmol) and 4-dimethylaminopyridine (201 mg, 1.64 mmol) were added. After 20 min compound XXXd (1.52 g, 1.5 mmol) was added and stirring, under N$_2$ was continued for 4 days. The reaction mixture was concentrated to remove CH$_2$Cl$_2$ and the residue was suspended in acetone and filtered to remove insoluble material. Concentration of the filtrate gave 3.4 g of a crude product. This was partially purified by silica gel column chromatography (being eluted with 9:1 CH$_2$Cl$_2$/EtOAc) to give 1.3 g of an amorphous material (a 5:1 mixture, containing the ureido derivative). Further purification was performed by reverse phase chromatography (C$_{18}$, eluted with 80% CH$_3$C≡N in H$_2$O) followed by trituration from Et$_2$O to give 910 mg (Y: 41%) of the title compound; mp, 130–134° C.; Rt: 8.01 min (HPLC purity: 98.9%; eluent: 80% CH$_3$CN in H$_2$O; column: C$_{18}$ reverse phase Waters Radial Pak column; flow rate: 2 mL/min; UV detection at 227 nm); $[\alpha]_D^{20} = -28.86°$ (c=0.395, CH$_2$Cl$_2$); IR (KBr) 3430, 1748, 1725 (shoulder) cm$^{-1}$; $^1$H-NMR (300 MHz, CDCl$_3$) δ ppm: 1.10 (3H, s, 15-Me), 1.17 (3H, s, 15-Me), 1.49 (3H, s, 8-Me), 1.58 (6H, s, gem-Me), 1.89 (3H, s, 12-Me), 2.02 (3H, s, 4-OAc), 2.08 (3H, s, Ar-Me), 2.16 (1H, dd, J=8.8, 15.1 Hz, 14-H), 2.34 (1H, dd, J=9.2, 15.1 Hz, 14-H), 2.41 (3H, s, 10-OAc), 2.46 (3H, s, Ar-Me), 2.66 (1H, d, J=14.5 Hz, COCH$_2$), 2.89 (6H, s, NMe$_2$), 3.09 (1H, d, J=14.5 Hz, COCH$_2$), 3.83 (1H, d, J=7.0 Hz, 3-H), 4.05–4.08–4.21–4.24 (2H, ABq, 20-H$_2$), 4.74 (1H, d, J=8.3 Hz, 5-H), 5.10 (2H, ABq, OCH$_2$Ph), 5.13 (2H, d, J=7.9 Hz, OCH$_2$Ph), 5.36 (1H, dd, J=6.8, 10.6 Hz, 7-H), 5.47 (1H, d, J=2.9 H, 2'-H), 5.60 (1H, d, J=7.1 Hz, 2-H), 5.98 (1H, dd, J=2.8, 9.3 Hz, 3'-H), 6.14 (1H, s, 10-H), 6.22 (1H, t, 13-H), 6.45–6.65 (3H, m, Ar-Hs), 6.65 (1H, s, Ar-H), 6.93 (1H, d, J=9.5 Hz, 3'-NH), 7.03 (1H, s, Ar-H), 7.16 (1H, t, J=8.1 Hz, Ar-H), 7.25–7.60 (21H, m, Ar-Hs), 7.73 (2H, d, J=7.1 Hz, 3'-NHCOAr-Hs), 8.09 (2H, d, J=7.1 Hz, 2-OCOAr-Hs); MS (FAB/-NOBA+NaI+KI) m/e: 1481 (MH+), 1503 (MNa+), 1519 (MK+).

Anal. calcd for C$_{83}$H$_{89}$N$_2$O$_{21}$P: C, 67.29; H, 6.05; N, 1.89. Found: C, 67.07; H, 6.08; N, 1.89.

EXAMPLE 83

2'-O-[3-(Dimethylamino)phenoxy]carbonyl-7-O-[3″-(2‴-phosphonooxy-4‴,6‴-dimethylphenyl)-3″,3″-dimethylpropionyl]taxol monosodium salt (Igg)

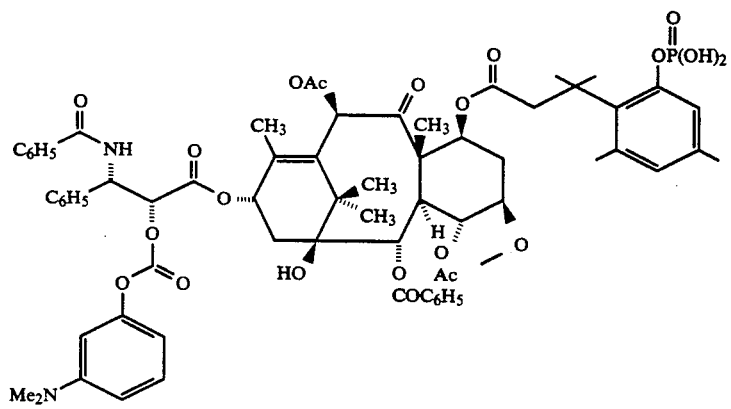

XXXId

-continued

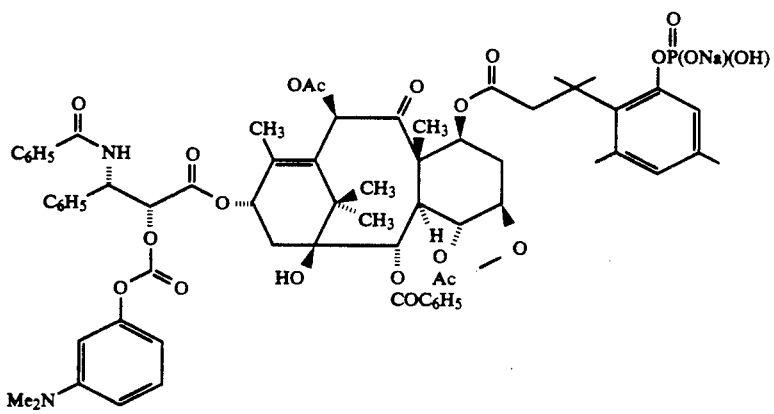

Igg

Compound XXXId (840 mg, 0.567 mmol) was dissolved in 50 mL EtOAc and 50 mL EtOH, and under N₂ was treated with 100 mg 10% Pd on carbon. The mixture was placed on a Parr hydrogenator and shaken for 4 h under 40 psi of H₂ atmosphere. The catalyst was removed by filtration and the filtrate was concentrated to leave an amorphous solid. This was triturated with Et₂O to give, after drying, 650 mg (0.50 mmol, Y: 88%) of the free acid form of the title compound as a solid.

The acid was suspended in CH₃C≡N (10 mL) and was treated with sodium hydrogen carbonate (50 mg, 0.59 mmol) in 50 mL H₂O. A suspension resulted. The suspension was chromatographed (C₁₈, eluted with 20% CH₃C≡N in H₂O) to give, after careful concentration and lyophilization, 320 mg (0.23 mmol, Y: 46%) of the mono sodium salt, Igg, as a white fluffy solid; Rt: 6.86 min (HPLC purity: 96.5%; eluent: 30% A/70% B, A=0.05M, pH 6.0 ammonium phosphate buffer, B=80% CH₃CN/H₂O; flow rate: 2 mL/min; detection by UV at 227 nm; column: Waters C-18 RP-Radial Pak); $[\alpha]_D^{20} = -26.45°$ (c=0.155, 95% EtOH); IR (KBr) 3430, 1750 (shoulder), 1730 cm⁻¹; ¹H-NMR (acetone-d₆/D₂O) δ ppm: 1.11 (3H, s, 15-Me), 1.14 (3H, s, 15-Me), 1.54 (6H, s, gem Me), 1.62 (3H, s, 8-Me), 1.86 (3H, s, 12-Me), 2.07 (3H, s, Ar-Me), 2.12 (3H, s, 4-OAc), 2.42 (3H, s, 10-OAc), 2.44 (3H, s, Ar-Me), 2.87 (6H, s, NMe₂), 2.97 (2H, ABq, COCH₂), 3.81 (1H, d, J=6.8 Hz, 3-H), 4.09 (2H, s, 20-H₂), 4.82 (1H, d, 5-H), 5.39 (1H, m, 7-H), 5.60 (2H, d, J=6.2 Hz, 2-H, 2'-H), 5.96 (1H, d, J=5.9 Hz, 3'-H), 6.11 (1H, t, 13-H), 6.21 (1H, s, 10-H), 6.38 (2H, m, Ar-H), 6.44 (1H, s, Ar-H), 6.59 (1H, d, J=9.8 Hz, Ar-H), 7.1–7.7 (12H, m, Ar-Hs), 7.90 (2H, d, J=7 Hz, 3'-NHCOAr-Hs), 8.09 (2H, d, J=7 Hz, 2-OCOAr-Hs); MS (FAB/NOBA) m/e: 1323 (MH+), 1345 (MNa+); Solubility: 1 mg/mL (H₂O), 4.8 mg/mL (10% EtOH).

Anal. calcd for C₆₉H₇₆N₂O₂₁PNa.4H₂O: C, 59.39; H, 6.07; N, 2.01; Na, 1.69; H₂O, 5.16. Found: C, 59.34; H, 5.62; N, 2.02; Na, 1.59; H₂O, 5.42 (KF).

EXAMPLE 84

2'-O-(Isopropyloxycarbonyl)taxol (Ihh)

Taxol →

-continued

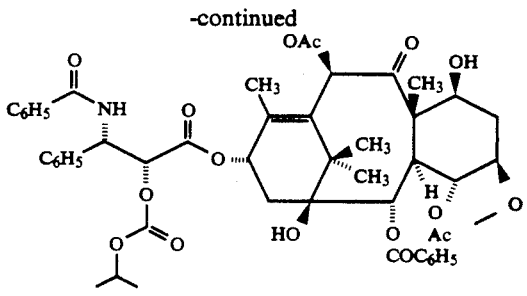

Ihh

Taxol (2.56 g, 3 mmol) was dissolved in 50 mL CH₂Cl₂, and diisopropylethylamine (1.57 mL, 9 mmol) was added. The resultant solution was stirred and cooled in an ice bath. 1M solution of isopropyl chloroformate in toluene (9 mL) was added over a period of 10 min. The reaction was monitored by HPLC. After 1.5 h the ice bath was removed and stirring at ambient conditions was continued for 7 days. Saturated brine 20 mL was added and the layers were separated. The CH₂Cl₂ layer was dried over MgSO₄, filtered and concentrated to leave a gummy solid which was washed with Et₂O and vacuum dried to give 2.9 g of a crude product. This was purified by silica gel chromatography (being eluted with 2:1 CH₂Cl₂/EtOAc) and Et₂O trituration to give 2.17 g (2.71 mmol, Y: 77%) of the title compound; mp, 177–181° C.; $[\alpha]_D^{20} = -62.77°$ (c=0.505, CH₂Cl₂); IR (KBr) 3510, 3450, 1750, 1730 cm⁻¹; ¹H-NMR (300 MHz, acetone-d₆) δ ppm: 1.18 (3H, s, Me), 1.19 (3H, s, Me), 1.22 (3H, d, J=6.2 Hz, Me), 1.26 (3H, d, J=6.2 Hz, Me), 1.66 (3H, s, 8-Me), 1.78 (1H, m, 6-H), 1.95 (3H, s, 12-Me), 2.1 (1H, m, 14-H), 2.15 (3H, s, OAc), 2.3–2.5 (2H, m, 6-H, 14-H), 2.49 (3H, s, OAc), 3.52 (1H, d, J=5.9 Hz, 7-OH), 3.85 (1H, d, J=7.2 Hz, 3-H), 3.90 (1H, s, 1-OH), 4.17 (2H, s, 20-H), 4.42 (1H, m, 7-H), 4.83 (1H, m, OCH), 4.97 (1H, d, J=7.6 Hz, 5-H), 5.51 (1H, d, J=5.8 Hz, 2'-H), 5.68 (1H, d, J=7.2 Hz, 2-H), 5.99 (1H, dd, J=5.8, 9 Hz, 3'-H), 6.16 (1H, t, J=9.2 Hz, 13-H), 6.41 (1H, s, 10-H), 7.25–7.67 (11H, m, Ar-Hs), 7.90 (2H, m, 3'-NHCOAr-Hs), 8.14 (2H, m, 2-OCOAr-Hs), 8.51 (1H, d, J=9.1 Hz, 3'-NH); MS (FAB/NOBA) m/e: 940 (MH+).

Anal. calcd for C₅₁H₅₇NO₁₆/0.5H₂O: C, 64.55; H, 6.16; N, 1.40; H₂O, 0.95. Found: C, 64.33; H, 6.05; N, 1.38; H₂O, 0.81 (KF).

EXAMPLE 85

2'-O-Isopropyloxycarbonyl-7-O-[3''-(2'''-dibenzylphosphonooxy-4''',6'''-dimethylphenyl)-3'',3''-dimethylpropionyl]taxol (XXXIe)

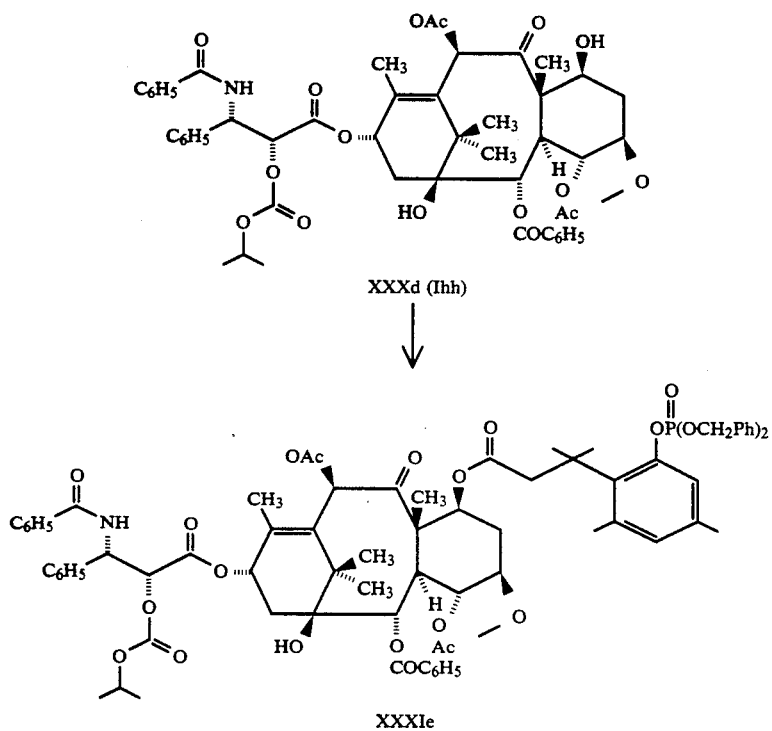

To 40 mL CH$_2$Cl$_2$ was added with stirring dicyclohexylcarbodiimide (DCC, 555 mg, 2.55 mmol), phenylpropanoic acid IXa (1.08 g, 2.25 mmol) and 4-dimethylaminopyridine (DMAP, 201 mg, 1.65 mmol). After stirring for 20 min, compound XXXd (1.41 g, 1.5 mmol) was added and the reaction mixture was stirred under N$_2$ for 3 days. The mixture was concentrated to remove CH$_2$Cl$_2$ and the residue was suspended in acetone. This suspension was filtered to remove a solid and the filtrate was concentrated to leave an amorphous solid. This was purified by silica gel column chromatography (being eluted with 17:3 CH$_2$Cl$_2$/EtOAc) to give 1.8 g of an amorphous product which was crystallized from 50 mL Et$_2$O. After collecting and drying, 1.39 g (9.90 mmol, Y: 66%) of the title compound was obtained; mp, 167–169° C.; tlc Rf: 0.5 (17:3 CH$_2$Cl$_2$/EtOAc); $[\alpha]_D^{20} = -42.96°$ (c=0.54, CH$_2$Cl$_2$); IR (KBr) 3430, 1748, 1730 (shoulder) cm$^{-1}$; $^1$H-NMR (acetone-d6) δ ppm: 1.14 (3H, s, 15-Me), 1.17 (3H, s, 15-Me), 1.22 (3H, d, J=6.3 Hz, Me), 1.25 (3H, d, J=6.2 Hz, Me), 1.52 (1H, s, 8-Me), 1.65 (6H, s, gem-Me), 1.91 (3H, s, 12-Me), 2.09 (3H, s, 4-OAc), 2.30 (1H, dd, J=9.4, 15.5 Hz, 14-H), 2.44 (3H, s, 10-OAc), 2.51 (3H, s, Ar-Me), 2.65 (1H, d, J=14.5 Hz, CH$_2$CO), 3.16 (1H, d, J=14.5 Hz, CH$_2$CO), 3.85 (1H, d, J=8.7 Hz, 3-H), 3.93 (1H, s, 1-OH, D$_2$O-exchanged), 4.10 (2H, s, 20-H$_2$), 4.79 (1H, d, J=6.8 Hz, 5-H), 4.82 (1H, m, OCH), 5.18–5.19–5.21–5.22 (2H, ABq, OCH$_2$), 5.25 (2H, d, J=7.8 Hz, OCH$_2$), 5.45 (1H, m, 7-H), 5.48 (1H, d, J=5.9 Hz, 2'-H), 5.63 (1H, d, J=7.1 Hz, 2-H), 5.95 (1H, dd, J=5.9, 8.9 Hz, 3'-H), 6.11 (1H, t, J=8.8 Hz, 13-H), 6.21 (1H, s, 10-H), 6.70 (1H, s, Ar-H), 7.08 (1H, s, Ar-H), 7.27–7.7 (11H, m, Ar-Hs), 7.89 (2H, d, J=7 Hz, 3'-NHCOAr-Hs), 8.12 (2H, d, J=7 Hz, 2-OCOAr-Hs), 8.50 (1H, d, J=9 Hz, 3'-NH); MS (FAB/NOBA) m/e: 1405 (MH$^+$), 1428 (MNa$^+$).

Anal. calcd for C$_{78}$H$_{86}$NO$_{21}$P: C, 66.42; H, 5.87; N, 1.02.

Found: C, 66.16; H, 6.17; N, 0.98.

EXAMPLE 86

2'-O-Isopropylcarbonyl-7-O-[3''-(2'''-phosphonooxy-4''',6'''-dimethylphenyl)-3'',3''-dimethylpropionyl]taxol (Iii)

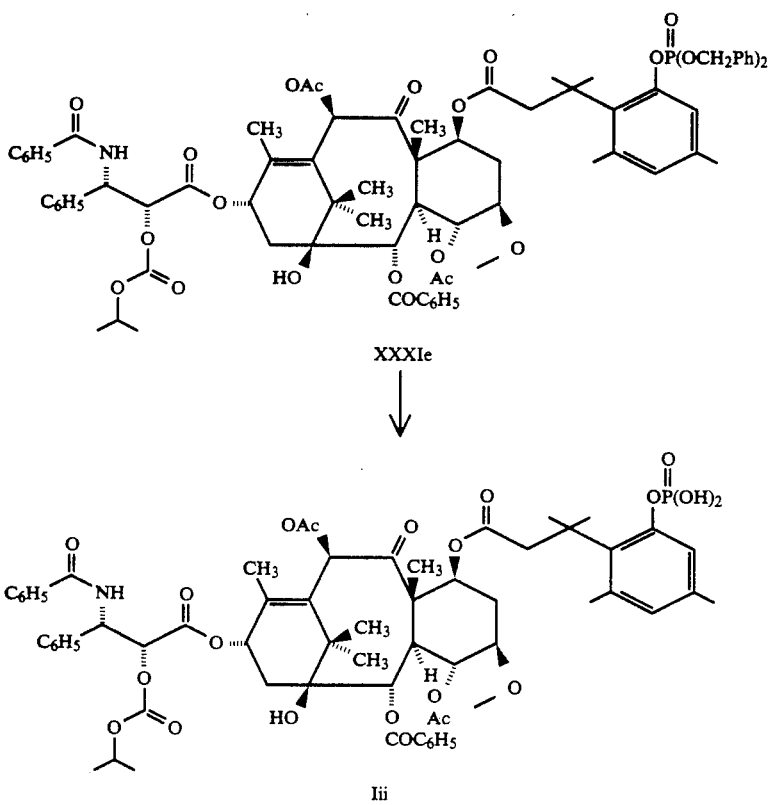

Compound XXXIe (1.2 g, 0.854 mmol) was dissolved in 50 mL EtOAc and 50 mL EtOH, and under $N_2$, 200 mg 10% Pd on carbon was added. The mixture was shaken on a Parr apparatus for 5 h under 40 psi of $H_2$ atmosphere. Upon removal of the catalyst by filtration and concentration, 1.1 g of an amorphous material was obtained. Trituration with $Et_2O$ gave 805 mg (0.643 mmol, Y: 75%) of the title acid Iii as a hydrate; IR (KBr) 3440, 1750, 1730 (shoulder) $cm^{-1}$; $^1$H-NMR (acetone-d6) δ ppm: 1.14 (3H, s, 15-Me), 1.17 (3H, s, 15-Me), 1.22 (3H, d, J=6.3 Hz, Me), 1.25 (3H, d, J=6.2 Hz, Me), 1.55 (3H, s, 8-Me), 1.64 (6H, s, gem-Me), 1.91 (3H, s, 12-Me), 2.12 (3H, s, Ar-Me), 2.13 (3H, s, 4-OAc), 2.3 (1H, dd, J=9.8 Hz, 14-H), 2.43 (3H, s, 10-OAc), 2.51 (3H, s, Ar-Me), 2.72 (1H, d, J=15 Hz, $COCH_2$), 3.11 (1H, d, J=15.4 Hz, $COCH_2$), 3.85 (1H, d, J=7.0 Hz, 3-H), 4.11 (2H, s, 20-$H_2$), 4.82 (2H, m, OCH, 5-H), 5.46 (1H, m, 7-H), 5.47 (1H, d, J=6.0 Hz, 2'-H), 5.63 (1H, d, J=7.2 Hz, 2-H), 5.95 (1H, m, 3'-H), 6.11 (1H, t, 13-H), 6.24 (1H, s, 10-H), 6.65 (1H, s, Ar-H), 7.17 (1H, s, Ar-H), 7.29 (1H, t, J=6.4 Hz, Ar-H), 7.35–7.7 (10H, m, Ar-Hs), 7.89 (2H, d, J=7 Hz, 3'-NHCOAr-Hs), 8.11 (2H, d, J=7 Hz, 2-OCOAr-Hs), 8.51 (1H, d, J=9 Hz, 3'-NH); MS (FAB/NOBA+NaI+KI) m/e: 1224 ($MH^+$), 1246 ($MNa^+$), 1262 ($MK^+$).

Anal. calcd for $C_{64}H_{74}NO_{21}P$ 1.5 $H_2O$: C, 61.44; H, 6.20; N, 1.12. Found: C, 61.44; H, 5.95; N, 1.09.

EXAMPLE 87

2'-O-Isopropylcarbonyl-7-O-[3''-(2'''-phosphonooxy-4''',6'''-dimethylphenyl)-3'',3''-dimethylpropionyl]taxol disodium salt (Ikk).

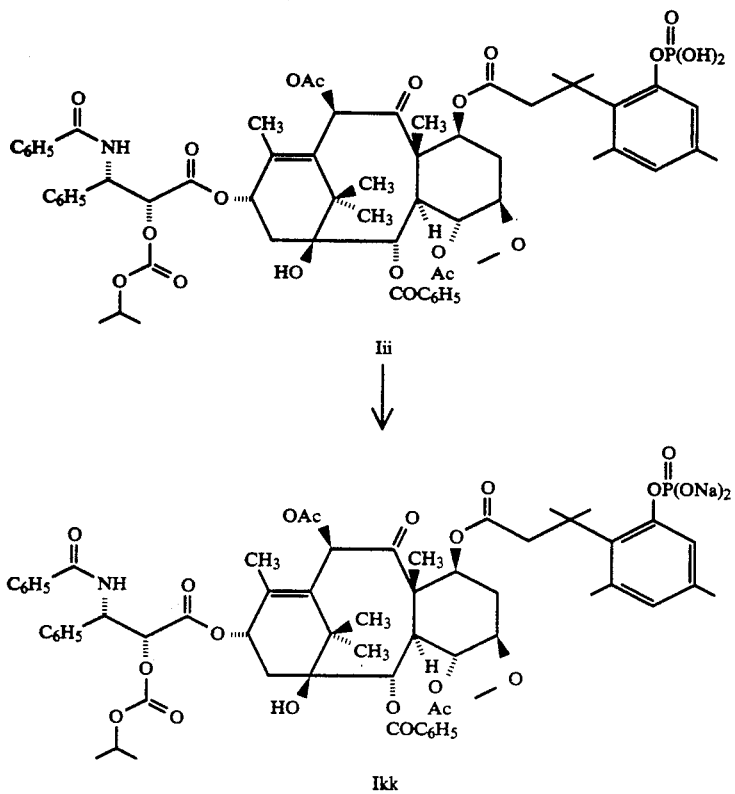

Compound Iii (620 mg, 0.495 mmol) dissolved in 15 mL $CH_3CN$ was treated with $NaHCO_3$ (80 mg, 0.94 mmol) in 19 mL $H_2O$. An additional 15 mL of $CH_3CN$ was added to achieve a near solution. This was filtered, diluted further with 100 mL $H_2O$ and concentrated without warming to remove $CH_3CN$. The solution was frozen and lyophilized to give 650 mg of the title compound as a white fluffy powder; mp, 185–188° C.; $[\alpha]_D^{20} = -24.12°$ (c=0.34, 95% EtOH); IR (KBr) 3440, 1750, 1730 (shoulder) $cm^{-1}$; $^1H$-NMR (acetone-$d_6$) δ ppm: 1.11 (3H, s, 15-Me), 1.14 (3H, s, 15-Me), 1.17 (3H, d, J=6.2 Hz, Me), 1.21 (3H, d, J=6.2 Hz, Me), 1.51 (3H, s, Me), 1.55 (3H, s, Me), 1.61 (3H, s, Me), 1.89 (3H, s, 12-Me), 2.10 (3H, s, 4-OAc), 2.42 (3H, s, 10-OAc), 2.43 (3H, s, Ar-Me), 2.85 (1H, d, J=15 Hz, $COCH_2$), 3.82 (1H, d, J=7 Hz, 3-H), 4.09 (2H, s, 20-$H_2$), 4.81 (2H, m, OCH, 5-H), 5.40 (1H, t, 7-H), 5.46 (1H, d, J=5.9 Hz, 2'-H), 5.61 (1H, d, J=7.3 Hz, 2-H), 5.92 (1H, d, J=5.8 Hz, 3'-H), 6.10 (1H, t, 13-H), 6.24 (1H, s, 10-H), 6.37 (1H, s, Ar-H), 7.25–7.65 (12H, m, Ar-Hs), 7.88 (2H, d, J=7.1 Hz, 3'-NHCOAr-Hs), 8.10 (2H, d, J=7 Hz, 2-OCOAr-Hs); MS (FAB/NOBA) m/e: 1269 (MH+); Solubility: 4.5 mg/mL ($H_2O$), >10 mg/mL (10% EtOH).

Anal calcd for $C_{64}H_{72}NO_{21}PNa_2 \cdot 3H_2O$: C, 58.14; H, 5.95; N, 1.06; $H_2O$, 4.08. Found: C, 58.09; H, 5.57; N, 1.10; $H_2O$, 4.97 (KF).

EXAMPLE 88

2'-O-Acetyl-7-O-[3''-(2'''-dibenzylphosphonooxy-4''',6'''-dimethylphenyl)-3'',3''-dimethylpropionyl]taxol (XLf)

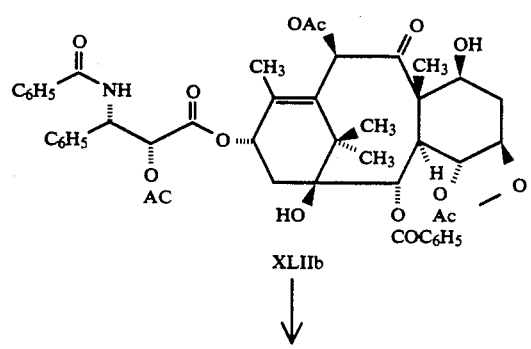

-continued

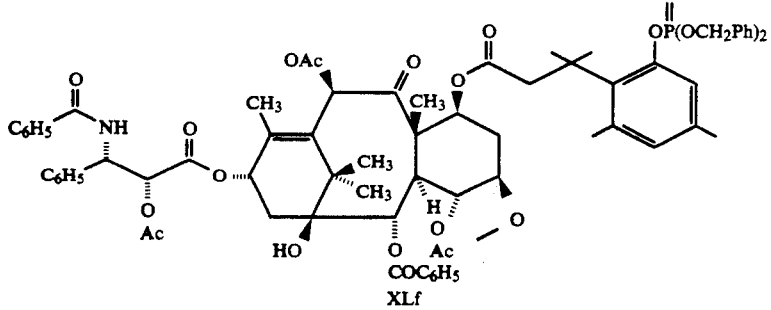

To a solution of 2'-O-acetyltaxol (XLIIb) (1.50 g, 1.67 mmol) and phenylpropionic acid IXa (1.612 g, 3.34 mmol, 2 eq.) in CH$_2$Cl$_2$ (30 mL, anhydrous) was added successively N,N'-dicyclohexylcarbodiimide (DCC, 1.376 g, 6.68 mmol, 4 eq.) and 4-dimethylaminopyridine (DMAP, 204 mg, 1.67 mmol), and the mixture was stirred at room temperature under anhydrous nitrogen atmosphere for 5 days. The white precipitate (urea) was filtered off and the filtrate concentrated in vacuo. The residue was purified by silica gel column chromatography (being eluted with 20% EtOAc in CH$_2$Cl$_2$) and then by crystallization from acetone-Et$_2$O to obtain 1.84 g (1.35 mmol, Y: 81.0%) of the title compound as white crystals; mp, 136–138° C.; Rf: 0.45 (20% EtOAc in CH$_2$Cl$_2$); $[\alpha]_D^{20} = -34.00°$ (c=0.275, MeOH); IR (KBr) 3430, 1744, 1725 (shoulder) cm$^{-1}$; $^1$H-NMR (300 MHz, acetone-d$_6$) δ ppm: 1.13 (3H, s, 15-Me), 1.16 (3H, s, 15-Me), 1.52 (3H, s, Me), 1.64 (6H, s, Me), 1.89 (3H, s, 12-Me), 2.08 (3H, s, OAc), 2.09 (3H, s, 6'''-Me), 2.41 (3H, s, OAc), 2.50 (3H, s, 4'''-Me), 2.64 (1H, d, J=14.5 Hz, COCH$_2$), 3.16 (1H, d, J=14.5 Hz, COCH$_2$), 3.84 (1H, d, J=7.2 Hz, 3-H), 3.93 (1H, s, 1-OH, D$_2$O-exchanged), 4.10 (2H, s, 20-H$_2$), 4.78 (2H, d, J=7.9 Hz, 5-H), 5.1–5.3 (4H, m, OCH$_2$), 5.44 (1H, dd, J=6.9 and 10.7 Hz, 7-H), 5.48 (1H, d, J=5.9 Hz, 2'-H), 5.62 (1H, d, J=7.1 Hz, 2-H), 5.92 (1H, dd, J=5.8 and 9 Hz, 3'-H), 6.09 (1H, t, 13-H), 6.20 (1H, s, 10-H), 6.70 (1H, s, Ar-H), 7.08 (1H, s, Ar-H), 7.25–7.75 (11H, m, Ar-Hs), 7.84 (2H, d, J=7 Hz, 3'-NHCOAr-Ho), 8.11 (2H, d, J=7 Hz, 2-OCOAr-Ho), 8.43 (1H, d, J=8.9 Hz, 3'-NH); MS (FAB/NOBA+NaI+KI) m/e: 1360 (MH+), 1383 (MNa+), 1399 (MK+); HRMS (FAB/NOBA) calcd for C$_{76}$H$_{83}$NO$_{20}$P(MH+): 1360.5246, found: 1360.5262; UV (MeOH) λmax: 227 nm (shoulder, ε 3.2×10$^4$).

Anal. calcd for C$_{76}$H$_{82}$NO$_{20}$P: C, 67.10; H, 6.08; N, 1.04.

Found: C, 67.09; H, 6.14; N, 1.02.

EXAMPLE 89

2'-O-Acetyl-7-O-[3''-(4''',6'''-dimethyl-2'''-phosphonooxyphenyl)-3'',3''-dimethylpropionyl]taxol (Imm)

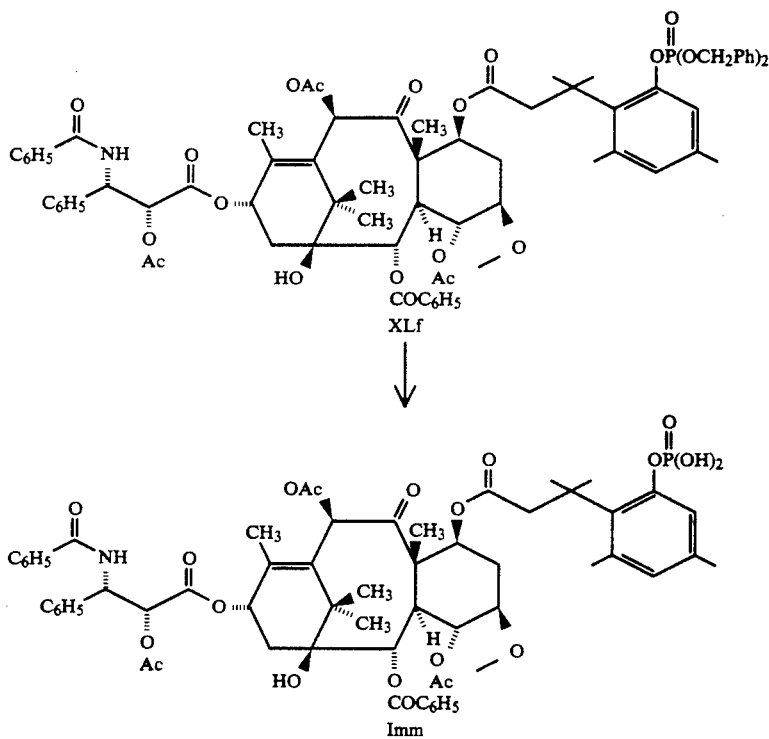

To a suspension of compound XLf (1.225 g, 0.901 mmol) in EtOAc (75 mL) and absolute EtOH (75 ml) was added 10% Pd on carbon (300 mg; Aldrich), and the mixture was stirred under 40 psi of hydrogen atmosphere in a Parr apparatus at room temperature for 4 h. The catalyst was filtered off over Celite and the filtrate concentrated. The residue was triturated with anhydrous Et$_2$O to obtain 1.015 g (0.86 mmol, Y: 95.5%) of the title compound as a white powder; mp, 157°–160° C.

EXAMPLE 90

2,-O-Acetyl-7-O-[3''-(4''',6'''-dimethyl-2'''-phosphonooxyphenyl)-3'',3''-dimethylpropionyl]taxol monopotassium salt (Inn)

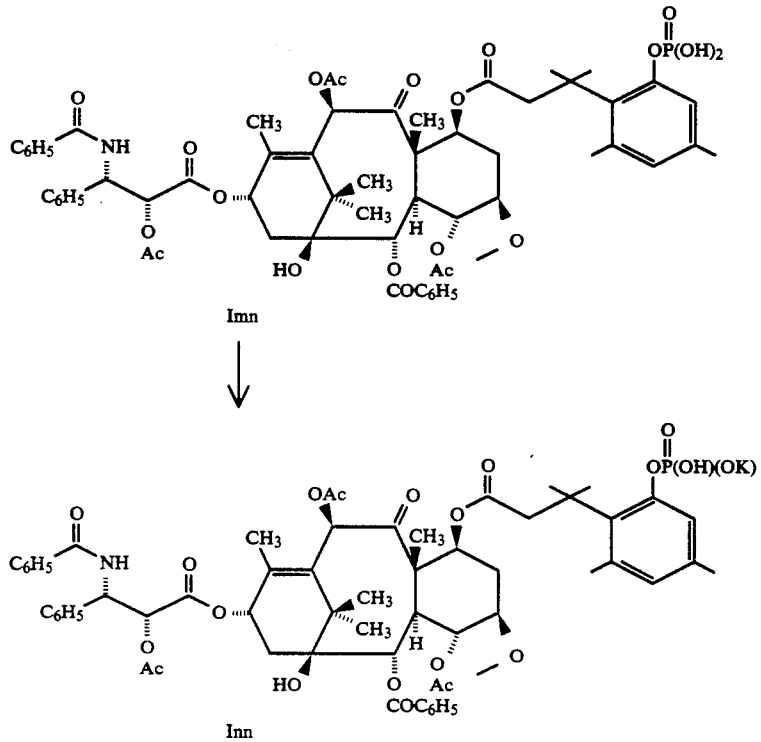

(decomposition); Rt: 3.24 min (HPLC purity: 100%; eluent: 25% A/75% B, A=0.05M, pH6.0 ammonium phosphate buffer with 5% CH$_3$CN, B=80% CH$_3$CN in H$_2$O; flow rate: 2 mL/min; UV detection at 227 nm; Waters C-18 Reverse Phase Radial Pak column); [°]$_D^{20}$=−34.40° (c=0.25, MeOH); IR (KBr) 3438, 1748, 1730 cm$^{-1}$; $^1$H-NMR (300 MHz, acetone-d$_6$) δ ppm: 1.14 (3H, s, 15-Me), 1.16 (3H, s, 15-Me), 1.30 (1H, t, J=12.6 Hz, 14-H), 1.55 (3H, s, 8-Me), 1.63 (3H, s, Me), 1.64 (3H, s, Me), 1.90 (3H, s, 12-Me), 2.07 (3H, s, OAc), 2.12 (3H, s, 6''-Me), 2.13 (3H, s, OAc), 2.27 (1H, dd, J=9.5 and 15.2 Hz, 6-H), 2.40 (3H, s, OAc), 2.51 (3H, s, 4'''-Me), 2.72 (1H, d, J=15.2 Hz, COCH), 3.11 (1H, d, J=15.2 Hz, COCH), 3.84 (1H, d, J=7.1 Hz, 3-H), 4.11 (2H, s, 20-H$_2$), 4.82 (1H, d, J=9.2 Hz, 5-H), 5.44 (1H, dd, J=7 and 10 Hz, 7-H), 5.49 (1H, d, J=5.9 Hz, 2'-H), 5.62 (1H, d, J=7.1 Hz, 2-H), 5.91 (1H, m, 3'-H), 6.09 (1H, t, 13-H), 6.23 (1H, s, 10-H), 6.65 (1H, s, Ar-H), 7.15 (1H, s, Ar-H), 7.29 (1H, t, J=7.3 Hz, Ar-H), 7.39–7.69 (10H, m, Ar-H), 7.84 (2H, d, J=7 Hz, 3'-NHCOAr-Ho), 8.11 (1H, d, J=7 Hz, 2-OCOAr-Ho), 8.42 (1H, d, J=9 Hz, 3'-NH); MS (FAB/NOBA) m/e: 1180 (MH$^+$); HRMS (FAB/NOBA) calcd for C$_{62}$H$_{71}$NO$_{20}$P(MH$^+$) 1180.4307, found: 1180.4289; UV (MeOH) λmax: 226 nm (ε 3.6×10$^4$).

Anal. calcd for C$_{62}$H$_{70}$NO$_{20}$P.H$_2$O: C, 62.15; H, 6.06; N, 1.17; P, 2.59; H$_2$O, 1.50. Found: C, 62.19; H, 5.89; N, 1.20; p, 3.06; H$_2$O, 0, 1.41 (KF).

To a solution of compound Imm (472 mg, 0.394 mmol; monohydrate) in acetone (20 mL) was added a solution of KHCO$_3$ (39.4 mg, 0.394 mmol) in H$_2$O (100 mL) and the mixture sonicated to obtain a hazy solution. This was concentrated in vacuo to remove acetone and lyophilized to obtain 496 mg (0.393 mmol, Y: 99.7%; calculated as hydrate) of the title compound as a white fluffy powder; Rt: 7.07 min (HPLC purity: 97.0%; eluent: 35% A/65%B; A, B and other HPLC conditions as defined for compound Imm); [α]$_D^{20}$=−28.23° (c=0.255, 95% EtOH); IR (KBr) 3432, 1750 (shoulder), 1730 cm$^{-1}$; $^1$H-NMR (300 MHz, acetone-d$_6$/D$_2$O) δ ppm: 1.09 (3H, s, 15-Me), 1.11 (3H, s, 15-Me), 1.17 (1H, m, 6-H), 1.53 (3H, s, 3''-Me), 1.55 (3H, s, 3''-Me), 1.60 (3H, s, 8-Me), 1.86 (3H, s, 12-Me), 1.9 (1H, m, 14-H), 2–2.2 (2H, m, 6-H and 14-H), 2.06 (3H, s, Me), 2.07 (3H, s, Me), 2.11 (3H, s, OAc), 2.37 (3H, s, OAc), 2.45 (3H, s, 4'''-Me), 2.88–2.93–3.03–3.08 (2H, ABq, COCH$_2$), 3.78 (1H, d, J=6.9 Hz, 3-H), 4.07 (2H, s, 20-H$_2$), 4.82 (1H, d, J=8.8 Hz, 5-H), 5.4 (1H, m, 7-H), 5.44 (1H, d, J=6.7 Hz, 2'-H), 5.57 (1H, d, J=6.9 Hz, 2-H), 5.91 (1H, d, J=6.6 Hz, 3'-H), 6.02 (1H, t, J=9.1 Hz, 13-H), 6.21 (1H, s, 10-H), 6.44 (1H, s, Ar-H), 7.2–7.7 (12H, m, Ar-H), 7.84 (2H, d, J=8 Hz, 3'-NHCOAr-Ho), 8.06 (2H, d, J=7.5 Hz, 2-OCOAr-Ho); MS(FAB/NOBA) m/e: 1218 (MH$^+$), 1256 (MK$^+$); HRMS (FAB/NOBA) calcd for C$_{62}$H$_{70}$NO$_{20}$PK(MH$^+$): 1218.3866, found: 1218.3851; UV (95% EtOH) λmax: 228 (ε 3.13×10$^4$), 274 nm (ε 3.41×10$^3$); Solubility: 3 mg/mL (in deionized water).

Anal. calcd for C_{62}H_{69}NO_{20}PK.2.5H_2O: C, 58.95; H, 5.91; N, 1.11; K, 3.10. Found: C, 58.85; H, 5.64; N, 1.12; K, 3.21.

EXAMPLE 91

2'-O-Ethoxycarbonyl-7-O-[2''-[(bisallylphosphonooxy)-methyl]benzoyl]taxol (XXXIf)

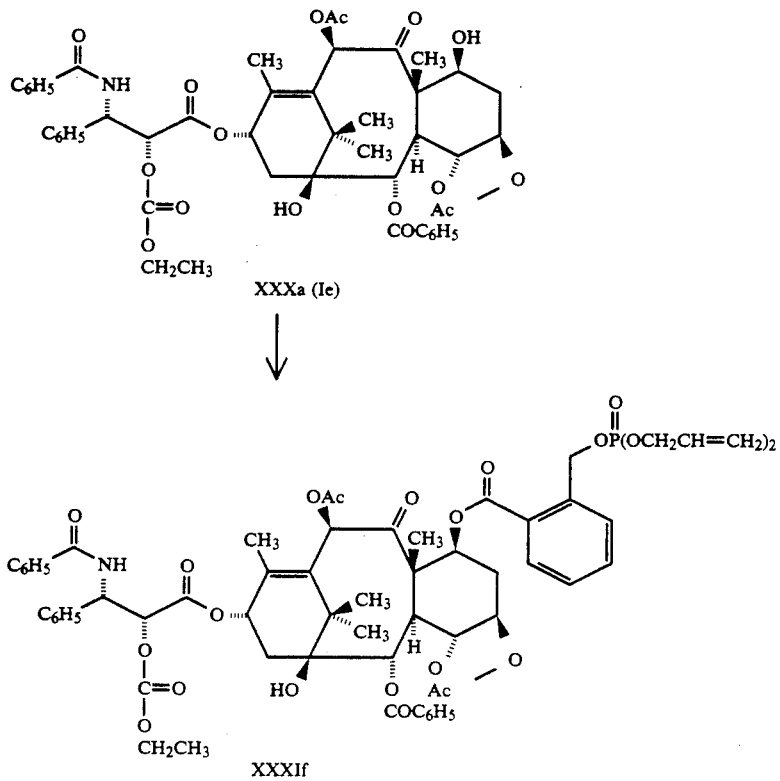

To a solution of 2'-O-(ethoxycarbonyl)taxol (XXXa) (1.50 g, 1.62 mmol) and 2-[(bisallylphosphonooxy)methyl]benzoic acid (IXc) (1.01 g, 3.24 mmol, 2 eq.) in CH_2Cl_2 (30 mL; Aldrich Sure Seal) was added dicyclohexylcarbodiimide (DCC, 1.335 g, 6.48 mmol, 4 eq.) and 4-dimethylaminopyridine (DMAP, 198 mg, 1.62 mmol), and the mixture was stirred at room temperature under anhydrous nitrogen atmosphere for 15 h. The precipitate was filtered off and the filtrate was concentrated in vacuo. The residue was dissolved in a small amount of acetone, and insoluble materials were removed. The acetone solution was concentrated and the residue was purified by silica gel column chromatography (SiO_2, 200 g; eluted with 10–30% EtOAc in CH_2Cl_2) to obtain 1.406 g (1.15 mmol, Y: 71.1%) of the title compound as white crystals after crystallization from acetone-Et_2O; mp, 146–148° C.; Rf: 0.27 (20% EtOAc in CH_2Cl_2); Rt: 18.3 min (HPLC purity: 100%; 25% A/75% B, A=H_2O, B=80% CH_3CN in H_2O; flow rate: 2 mL/min); [α]_D^{20}=−15.47° (c=0.265, MeOH); IR(KBr) 3422, 1750, 1726, 1668, 1250 cm^{−1}; ¹H-NMR (300 MHz, acetone-d_6) δ ppm: 1.18, 1.19 (6H, 2s, 15-gem Me), 1.25 (3H, t, J=7.1 Hz, OCH_2CH_3), 1.92 (3H, s, 12-Me), 1.95 (3H, s, 8-Me), 1.9–2.0 (1H, m, 6-H), 2.08 (3H, s, OAc), 2.0–2.1 (1H, m, 14-H), 2.38 (1H, dd, J=9.5 and 15.5 Hz, 14-H), 2.66 (3H, s, OAc), 2.71 (1H, m, 6-H), 4.03 (1H, s, 1-OH, D_2O-exchanged), 4.04 (1H, d, J=7.2 Hz, 3-H), 4.15–4.3 (4H, m, 20-H_2, OCH_2CH_3), 4.56–4.61 (4H, m, OCH_2C=), 5.04 (1H, d, J=7.9 Hz, 5-H), 5.21 (2H, d, J=10.5 Hz, =CH), 5.37 (2H, d, J=17.2 Hz, =CH_2), 5.5–5.6 (3H, m, ArCH_2O, 2'-H), 5.74 (1H, d, J=7.1 Hz, 2-H), 5.85–6.1 (4H, m, 7-H, CH=, 3'-H), 6.14 (1H, t, J=9.5 Hz, 13-H), 6.43 (1H, s, 10-H), 7.32 (1H, t, J=7.4 Hz, Ar-H), 7.4–7.75 (13H, m, Ar-Hs), 7.88 (1H, dd, J=1.2 and 7.3 Hz, 7-OCOAr-Ho), 7.91 (2H, dd, J=1.5 and 7 Hz, 3'-NHCOAr-Ho), 8.16 (2H, dd, J=1.6 and 8.5 Hz, 2-OCOAr-Ho), 8.55 (1H, d, J=9.0 Hz, NH, D_2O-exchanged); MS (FAB/NOBA+-NaI+KI) m/e: 1220 (MH^+), 1242 (MNa^+), 1258 (MK^+); HRMS (FAB/NOBA) calcd for C_{64}H_{71}NO_{21}P (MH^+): 1220.4256, found: 1220.4239; UV (MeOH) λ_{max}: 206 (ε 1.26×10^5), 230 nm (ε 4.51×10^4).

Anal. calcd for C_{64}H_{70}NO_{21}P: C, 63.00; H, 5.78; N, 1.15; P, 2.54. Found: C, 62.96; H, 5.77; N, 1.10; P, 2.80.

EXAMPLE 92

2'-O-Ethoxycarbonyl-7-O-[2'''-(phosphonooxymethyl)-benzoyl]taxol monopotassium salt (Igg)

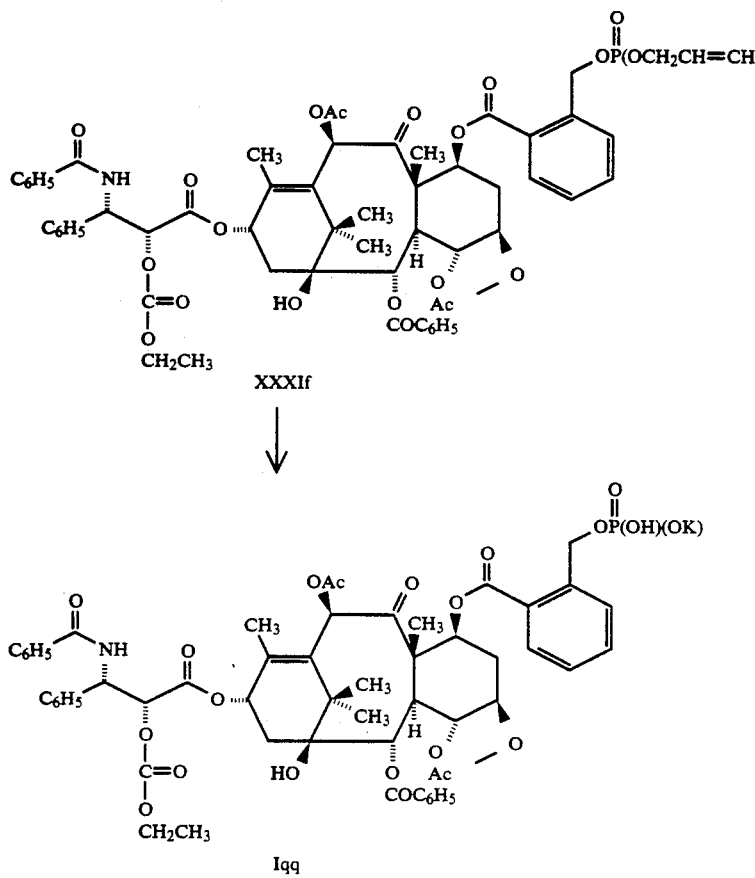

To a solution of compound XXXIf (1.098 g, 0.9 mmol), triphenylphosphine (82 mg) and Pd(PPh$_3$)$_4$ (82 mg; Aldrich) in CH$_2$Cl$_2$ (25 mL, anhydrous, Aldrich Sure Seal) was injected acetic acid (274 μL, 4.79 mmol; 5.3 eq, glacial) and then Bu$_3$SnH (590 μL, 2.19 mmol; 2.4 eq, Aldrich). The resulting mixture was stirred under anhydrous nitrogen atmosphere at room temperature for 5 days, being monitored by HPLC. The solvent was evaporated in vacuo and the residual solid was triturated with anhydrous Et$_2$O to obtain 1.63 g of an off-white powder which was redissolved in CH$_2$Cl$_2$. The solution was washed with 0.1N HCl (x3), dried (Na$_2$SO$_4$) and concentrated to obtain a solid which was triturated with Et$_2$O to yield 1.17 g of an off-white powder. The powder was dissolved in CH$_2$Cl$_2$ (30 mL, anhydrous), mixed with a solution of potassium 2-ethyl-hexanoate (364 mg, 2 mmol) in EtOAc (6 mL) and sonicated for 5 min. This cloudy solution was concentrated in vacuo to dryness to obtain 1.47 g of a solid. A solution of this solid in CH$_3$CN (10 mL) was mixed with a solution of KHCO$_3$ (150 mg, 1.5 mmol) in H$_2$O (40 mL) and sonicated. This milky solution was purified by C-18 reverse phase silica gel column chromatography (Whatman, Partisil 40, ODS-3; d=4.5 cm, l=28 cm; 20–30% CH$_3$CN in H$_2$O) to obtain 407 mg (0.303 mmol, Y: 33.7%, purity: 85.5% by HPLC) of the title compound as a white fluffy powder (contaminated with ca. 15% of 2'-OH compound). An analytical sample was also obtained during the column purification; Rt: 4.64 min (98.8% pure by HPLC; 35% A (0.05M, pH6, ammonium phosphate buffer)/65% B (80% CH$_3$CN in H$_2$O); about 1% of 2'-hydroxy compound was detected as an impurity at Rt 3.40 min); $[\alpha]_D^{20} = -18.18°$ (c=0.275, MeOH); IR (KBr) 3432, 1750, 1724, 1670, 1250 cm$^{-1}$; $^1$H-NMR (300 MHz, acetone-d$_6$/D$_2$O) δ ppm: 1.13 (6H, s, 15-Me$_2$), 1.18 (3H, t, J=7.1 Hz, OCH$_2$CH$_3$), 1.85 (3H, s, 8-Me), 1.93 (3H, s, 12-Me), 1.96 (3H, s, OAc), 2.24 (1H, m, 14-H), 2.46 (3H, s, OAc), 2.73 (1H, m, 6-H), 3.96 (1H, d, J=6.9 Hz, 3-H), 4.1–4.25 (4H, m, 20-H$_2$, OCH$_2$CH$_3$), 4.99 (1H, d, J=9.7 Hz, 5-H), 5.23 (2H, bs, ArCH$_2$O), 5.50 (1H, d, J=6.5 Hz, 2'-H), 5.69 (1H, d, J=7.0 Hz, 2-H), 5.7 (1H, m, 7-H), 5.88 (1H, d, J=6.4 Hz, 3'-H), 6.09 (1H, t, 13-H), 6.41 (1H, s, 10-H), 7.15–7.75 (14H, m, Ar-Hs), 7.80 (1H, d, J=7.8 Hz, 7-OCOAr-Ho), 7.89 (2H, d, J=7 Hz, 3'-NHCOAr-Ho), 8.11 (2H, d, J=7 Hz, 2-OCOAr-Ho); MS (FAB/-NOBA) m/e: 1178 (MH+), 1216 (MK+); Solubility: 2.6 mg/mL in H$_2$O, >10 mg/mL in 10% EtOH.

Anal. calcd for C$_{58}$H$_{61}$NO$_{21}$PK.2H$_2$O (MW 1214.23): C, 57.38; H, 5.40; N, 1.16; p, 2.56; K, 3.23; H$_2$O, 2.98.

Found: C, 57.09; H, 5.21; N, 1.17; P, 2.34; K, 3.30; H$_2$O, 2.67 (KF).

7-O-[2'''-(Phosphonooxymethyl)benzoyl]taxol (2'-hydroxy compound) was also isolated during the column purification; Rt: 3.80 min (HPLC purity: >99%; eluent: 40% A/60% B, A, B as defined above); IR (KBr) 3422, 1722, 1650, 1250 cm$^{-1}$; $^1$H-NMR (300 MHz, acetone-d$_6$/D$_2$O) δ ppm: 1.11 (6H, s, 15-Me$_2$), 1.85 (3H, s, 8-Me), 1.92 (3H, s, 12-Me), 1.94 (3H, s, OAc), 2.18 (1H, m, 14-H), 2.35 (3H, s, OAc), 2.75 (1H, m, 6-H), 3.94 (1H, d, J=6.7 Hz, 3-H), 4.16 (2H, s, 20-H₂), 4.83 (1H, d, J=6.1 Hz, 2'-H), 5.02 (1H, d, J=8.6 Hz, 5-H), 5.18 (2H, m, OCH₂Ar), 5.62 (1H, d, J=6.1 Hz, 2-H), 5.6-5.75 (2H, m, 3'-H, 7-H), 6.07 (1H, t, 13-H), 6.37 (1H, s, 10-H), 7.1-7.7 (14H, m, Ar-Hs), 7.89 (3H, m, Ar-Hs), 8.06 (2H, d, J=7 Hz, 2-OCOAr-Ho); MS(FAB/NOBA) m/e: 1106 (MH+), 1144 (MK+).

EXAMPLE 93

2',7-O-Bis[[(2''-dibenzylphosphonooxy)phenyl]acetyl]-taxol (LXXIV)

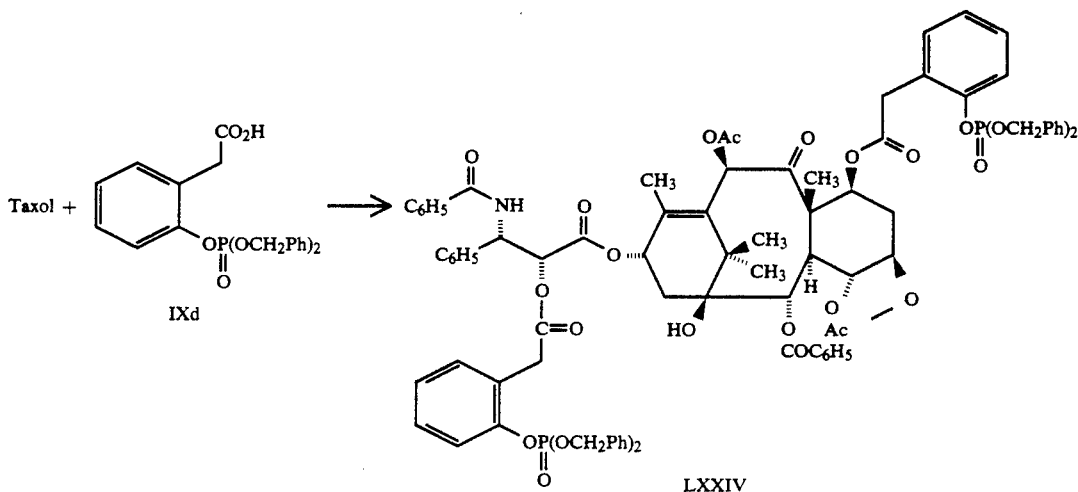

Taxol (5.98 g, 7 mmol) and 4-dimethylaminopyridine (DMAP, 122 mg, 1 mmol) were dissolved in 60 mL CH₂Cl₂ under N₂ atmosphere and cooled in an ice bath. Simultaneously to this stirred mixture was added at approximately equal rates over a period of 15 min a suspension of phenylacetic acid IXd (3.17 g, 7.7 mmol) in 20 mL CH₂Cl₂ and a solution of dicyclohexylcarbodiimide (DCC, 1.58 g, 7.7 mmol) in 20 mL CH₂Cl₂. After ½ h at 0° C., an additional 1 mmol of phenylacetic acid IXd and DCC, each in 10 mL CH₂Cl₂, were added. Within ½ h, HPLC indicated that no taxol remained. The reaction mixture was concentrated and the residue was suspended in acetone and filtered to remove the insoluble urea. Concentration of the acetone gave 9.4 g of a crude product. This was chromatographed on silica gel (eluted with 3:2 EtOAc/hexanes) to give 8.7 g of an amorphous material (about 10:1 mixture of 2'-acylated compound and 2',7-bis-acylated compound). Further purification was performed by reverse phase chromatography (C₁₈, eluted with 75% CH₃CN in H₂O) to give 6.58 g (5.27 mmol, Y: 75%) of 2'-O-[[2''-(dibenzylphosphonooxy)phenyl]acetyl]taxol; mp, 102-107° C.; HPLC Rt: 4.75 min (purity: ~100%; C₁₈ Waters Radial Pak column; flow rate: 2 mL/min; eluent: 80% CH₃CN in H₂O; UV detection at 227 nm); $[\alpha]_D^{20}=-27.38°$ (c=0.6, 95% EtOH); ¹H-NMR (300 MHz, CDCL₃) δ ppm: 1.09 (3H, s, Me), 1.18 (3H, s, Me), 1.58 (3H, s, Me), 1.64 (3H, s, Me), 2.20 (3H, s, OAc), 2.37 (3H, s, OAc), 2.47 (1H, d, 7-OH), 1.60-2.50 (4H, m, 6-H and 14-H), 3.57-3.62-3.76-3.81 (2H, ABq, ArCH₂C=O), 3.75 (1H, d, J=6 Hz, 3-H), 4.13-4.16-4.24-4.27 (2H, ABq, 20-H's), 4.40 (1H, m, 7-H), 4.90 (1H, d, J=8.7 Hz, 5-H), 4.97-5.14 (4H, m, ArCH₂O), 5.28 (1H, d, J=5.4 Hz, 2'-H), 5.61 (1H, d, J=7.2 Hz, 2-H), 5.72 (1H, dd, J=5.3 and 8.2 Hz, 3'-H), 6.09 (1H, t, 13-H), 6.24 (1H, s, 10-H), 7.02-8.14 (30H, m, Ar-H's, 3'-NH); MS (FAB/NOBA+NaI+KI) m/e: 1247 (MH+), 1270 (MNa+), 1286 (MK+); IR (KBr) 3438, 1744, 1726, 1272, 1242, 1018 cm⁻¹.

Anal. calcd for C₆₉H₇₀NO₁₉P: C, 66.39; H, 5.65; N, 1.12.
Found: C, 66.18; H, 5.59; N, 0.96.

Further elution of the C₁₈ column with 90% CH₃C≡N in H₂O followed by concentration to remove CH₃C≡N and extraction with CH₂Cl₂ gave 800 mg of the bis-acylated product. This was further purified by reverse phase chromatography (C₁₈, 90% CH₃C≡N in H₂O). Removal of the CH₃C≡N was followed by extraction into CH₂Cl₂, drying over anhydrous MgSO₄, filtration, concentration and drying under vacuum. 710 mg (0.432 mmol, Y: 6.2%) of the title product was obtained as an amorphous solid; HPLC Rt: 4.39 min (purity: 99.5%; C₁₈ Waters Radial Pak column; flow rate: 2 mL/min; eluent: 90% CH₃C≡N in H₂O; UV detection at 227 nm); $[\alpha]_D^{20}=-40.0°$ (c=0.22, CH₂Cl₂); IR (KBr) 3432, 1746, 1272, 1240, 1038, 1020 cm⁻¹; MS (FAB/NOBA+NaI+KI) m/e: 1641 (MH+), 1664 (MNa+), 1680 (MK+); ¹H-NMR (300 MHz, CDCl₃) δ ppm: 1.11 (3H, s, Me), 1.16 (3H, s, Me), 1.59 (3H, s, Me), 1.67 (3H, s, Me), 2.13 (3H, s, OAc), 2.35 (3H, s, OAc), 1.61-2.46 (4H, m, 6-H, 14-H), 3.67 (2H, s, 7-PhCH₂C=O); 3.54-3.79 (2H, ABq, 2'-PhCH₂C=O); 3.84 (1H, d, J=7.0 Hz, 3-H); 4.07, 4.10, 4.22, 4.24 (2H, ABq 20-H); 4.73 (1H, d, J=8.1 Hz, 5-H); 4.98-5.16 (8H, m, ArCH₂O (4x)); 5.29 (1H, d, J=8.4 Hz; 2'-H); 5.51-5.61 (1H, m, 7-H); 5.59 (1H, d, J=7.0 Hz, 2-H); 5.71 (1H, dd, 3'-H); 6.07 (1H, t, 13-H); 6.24 (1H, s, 10-H); 7.00-8.13 (44H, m, ArHs+NH).

Anal. calcd for C₉₁H₈₉NO₂₄P₂: C, 66.54; H, 5.47; N, 0.86. Found: C, 66.12; H, 5.42; N, 0.86.

EXAMPLE 94

2',7-O-Bis[(2''-phosphonooxyphenyl)acetyl]taxol monosodium salt (Irr)

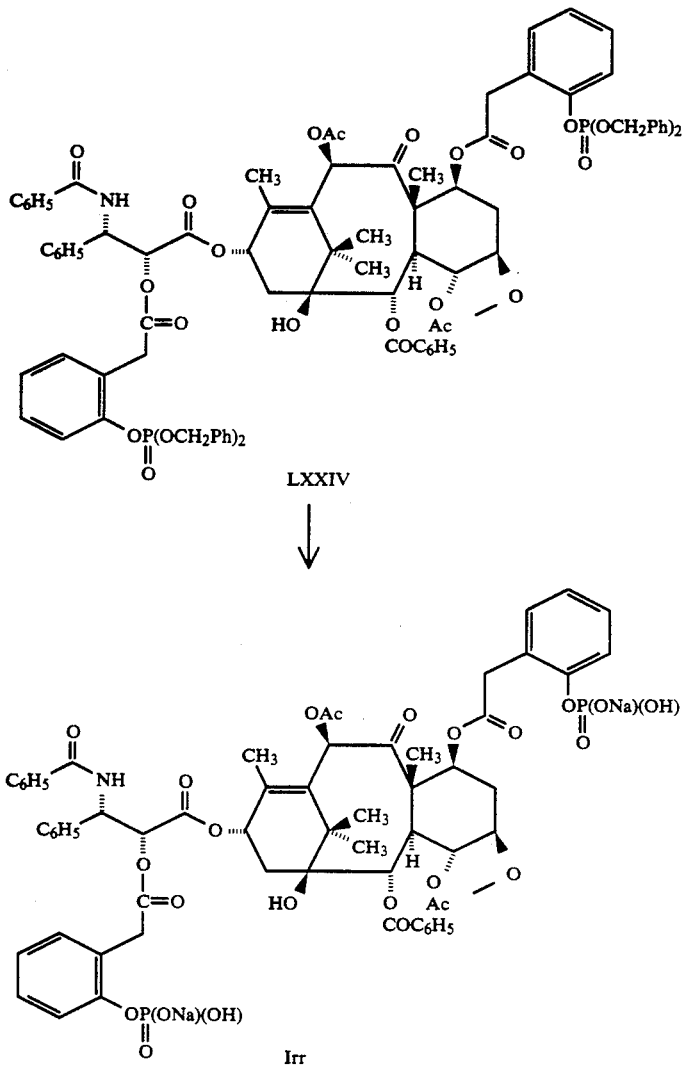

LXXIV

↓

Irr

The bis-dibenzyl compound LXXIV (641 mg, 0.39 mmol) was dissolved in 50 mL EtOAc and 50 mL EtOH, and under $N_2$, 200 mg 10% Pd on carbon was added. The mixture was placed on a Parr hydrogenator and 40 psi of $H_2$ was introduced. After shaking for 3 h under hydrogen, the catalyst was removed by filtration and the filtrate concentrated to leave 2',7-O-bis[(2''-phosphonooxyphenyl)acetyl]taxol as a solid. This was suspended in 10 mL of $CH_3C{\equiv}N$ and treated with sodium hydrogen carbonate (65 mg, 0.78 mmol) dissolved in 40 mL of $H_2O$. The near solution was diluted with 20% $CH_3C{\equiv}N$ in $H_2O$ to a total volume of 100 mL, filtered and concentrated without warming to remove $CH_3C{\equiv}N$. The aqueous solution was frozen and lyophilized to give 505 mg (0.38 mmol, Y: 98%) of the title compound as a white fluffy solid; Rt: 3.43 min (HPLC purity: 98.5%; eluent: 45%A/55%B, A=0.05M, pH 6.0 ammonium phosphate buffer, B=80% $CH_3C{\equiv}N$ in $H_2O$; flow rate=2 mL/min; column: Water $C_{18}$ Radial Pak; detection by UV at 227 nm); $[\alpha]_D^{20}=-21.62°$ (c=0.148, 95% EtOH); IR (KBr) 3430, 1728, 1246 $cm^{-1}$; $^1H$-NMR (300 Mz, acetone-$d_6$/$D_2O$) δ ppm 1.06 (3H, s, $CH_3$); 1.08 (3H, s, $CH_3$); 1.61 (3H, s, $CH_3$); 1.83 (3H, s, $CH_3$); 2.15 (3H, s, OAc); 2.37 (3H, s, OAc); 1.37-2.70 (4H, m, 6-H, 14-H); 3.58-3.80 (5H, m, 3-H and $ArCH_2{=}O$); 3.99 (2H, s, 20-H); 5.03 (1H, d, J=8.7, 5-H); 5.40 (1H, d, J=10.5 Hz, 2'-H); 5.49 (2H, m, 2-H, 3'-H); 5.60 (1H, m, 7-H); 5.83 (1H, t, 13-H); 6.22 (1H, s, 10-H); 6.61-7.98 (24H, m, ArH's+NH); MS (FAB/NOBA+NaI+KI) m/e: 1326 (MH+).

Anal. calcd for $C_{63}H_{63}NO_{24}P_2Na_2/8.5$ $H_2O$: C, 51.16; H, 5.45; N, 0.95; Na, 3.11; $H_2O$, 10.35. Found: C, 50.91; H, 4.54; N, 0.91; Na, 3.16; $H_2O$, 10.5 (KF).

SCHEME X
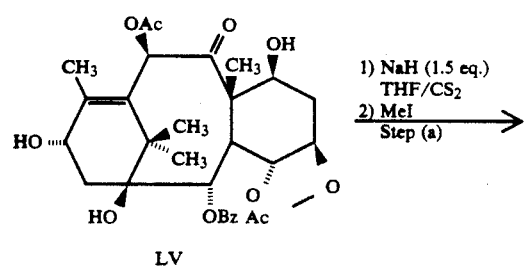
LV
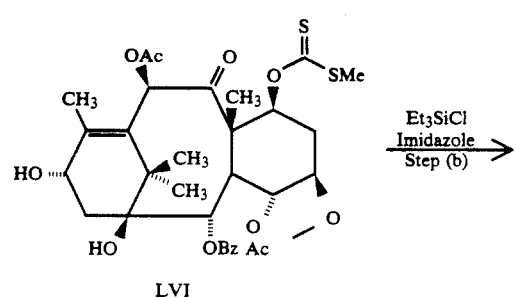
LVI
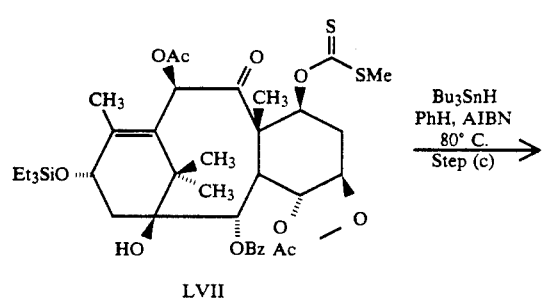
LVII
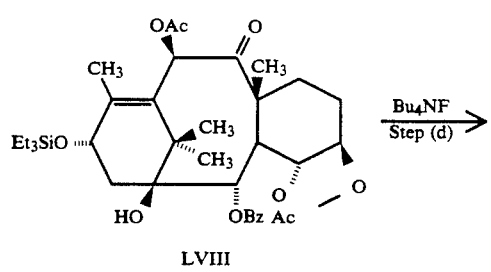
LVIII
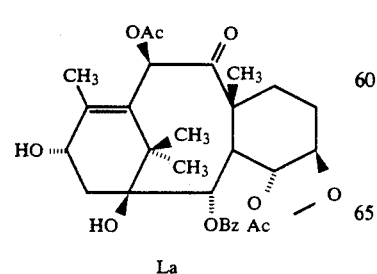
La
SCHEME XI
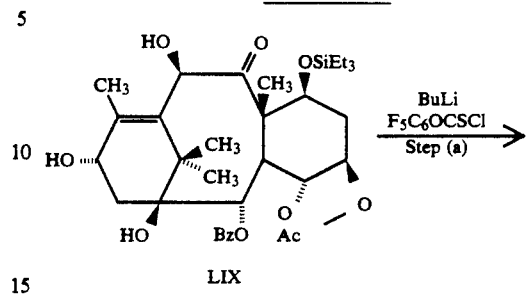
LIX
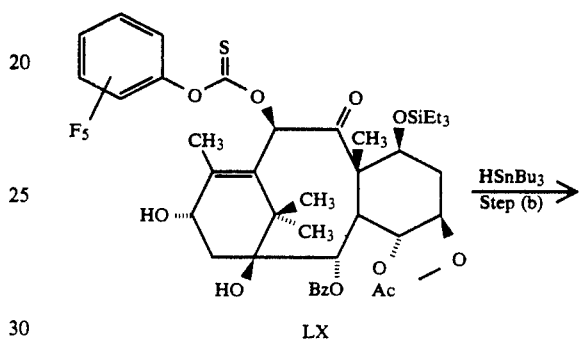
LX
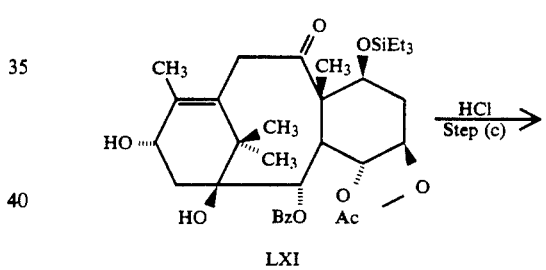
LXI
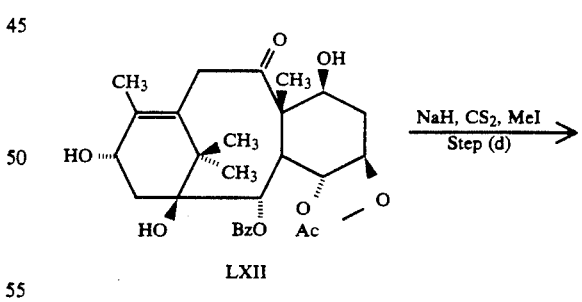
LXII
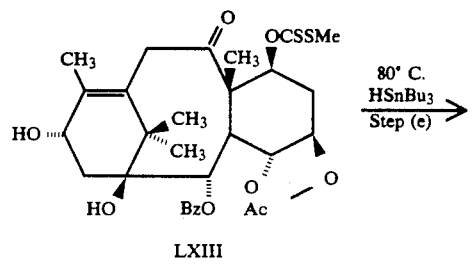
LXIII

SCHEME XI -continued

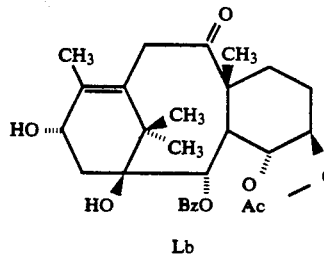

Lb

SCHEME XII

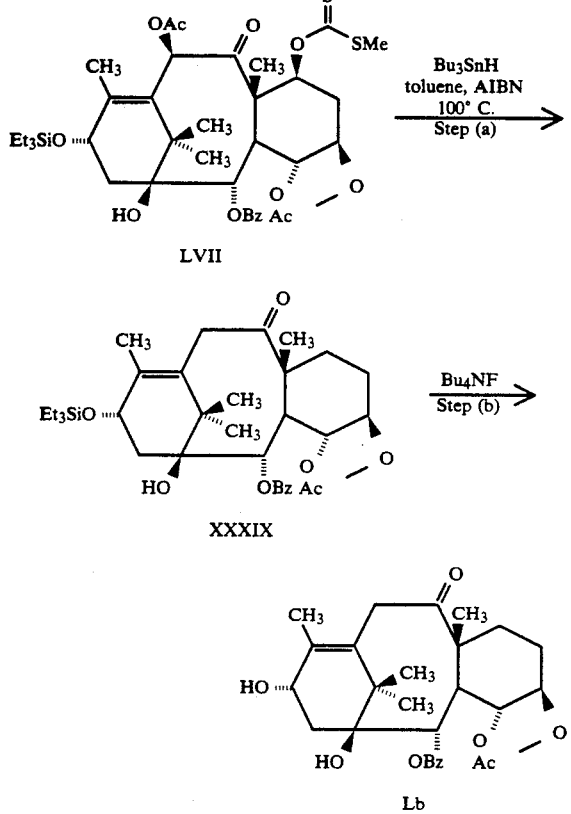

For Examples 95-104 and 118, refer to Schemes X, XI and XII.

EXAMPLE 95

7-[(Methylthio)carbonothioyloxy]baccatin III (LVI)

Baccatin III (750 mg, 1.278 mmol) was dissolved in dry THF (20 mL) and imidazole (8.7 mg, 0.128 mmol) was added in one lot. Sodium hydride (50% in mineral oil, 77 mg, 1.597 mmol) was added at room temperature. When gas evolution had ceased (10 min), carbon disulfide (4.6 mL) was added at once. After 3 h at room temperature, the yellow solution was treated with methyl iodide (0.238 mL, 3.835 mmol) and stirred overnight. Work-up with ethyl acetate and water gave the title xanthate LVI as a crude oil. A fraction of this was purified by silica gel flash chromatography (being eluted with 1:1 ethyl acetate/hexane) for characterization (white solid); $^1$H-NMR (CDCl$_3$) δ ppm: 8.08 (d, J=8.3 Hz, 2H) 7.58 (bt, 1H) 7.45 (m, 2H) 6.35 (m, 1H) 6.29 (s, 1H) 5.63 (d, J=7.0 Hz, 1H) 4.97 (d, J=8.7 Hz, 1H) 4.69 (bq, 1H) 4.31 (d, J=8.3 Hz, 1H) 4.15 (d, J=8.3 Hz, 1H) 4.03 (d, J=7.0 Hz, 1H) 2.91 (m, 1H) 2.44 (s, 3H) 2.29−1.50 (m, 16H, including singlets at 2.27, 2.13, 2.08, 1.89, 3H each) 1.12 (s, 3H) 1.05 (s, 3H).

Alternate Run

Baccatin III (394 mg, 0.672 mmol) was dissolved in THF (5 mL) and CS$_2$ (1 mL). To this solution was added NaH (40.3 mg, 60%, 1.009 mmol). A catalytic amount of imidazole was also added. The reaction was stirred at room temperature for 1.5 h. Then MeI (122.8 μL, 2.016 mmol) was added. After 40 min, the solvent was removed in vacuo, the residue was chromatographed on silica gel (eluted with 20%-50%-60% ethyl acetate in hexanes) to afford 260 mg (Y: 57.2%) of the title product together with 98.5 mg (25%) of the 7-epi baccatin.

EXAMPLE 96

7-(Methylthio)carbonothioyloxy]-13-triethylsilyloxybaccatin III (LVII)

Compound LVI of Example 95 as a crude oil was dissolved in dry DMF (5 mL) and treated with imidazole (870 mg, 12.78 mmol) and triethylsilyl chloride (2.10 mL, 12.78 mmol) at room temperature for 15 h. Addition of water was followed by extraction into ethyl acetate. The organic layer was washed extensively with water, and then dried. Silica gel flash chromatography (being eluted with 20% ethyl acetate in hexanes) gave compound LVII as a glassy solid (Y: 209 mg, 20% yield over two steps); $^1$H-NMR (CDCl$_3$) δ ppm: 8.08 (d, J=8.3 Hz, 2H) 7.58 (bt, 1H) 7.44 (m, 2H) 6.34 (m, 1H) 6.30 (s, 1H) 5.62 (d, J=7.0 Hz, 1H) 4.99−4.83 (m, 2H) 4.30 (d, J=8.3 Hz, 1H) 4.15 (d, J=8.3 Hz, 1H) 4.03 (d, J=7.0 Hz, 1H) 2.91 (m, 1H) 2.44 (s, 3H) 2.30−1.60 (m, 15H, including singlets at 2.27, 2.10, 2.05, 1.90, 3H each) 1.15−1.00 (m, 15H) 0.65 (m, 6H); MS calcd for C$_{31}$H$_{55}$O$_{11}$S$_2$Si: 790, found: 790.

Alternate Run

Compound LVI (193.4 mg, 0.286 mmol) was dissolved in dry DMF (2.86 mL). To this solution was added imidazole (77.9 mg, 1.14 mmol), followed by triethylsilyl chloride (192 μL, 1.14 mmol). The reaction was stirred overnight at room temperature. After 12 h, the reaction mixture was diluted with EtOAc (150 mL); the organic layer was washed with water (3×10mL) and brine (1×10 mL). The organic layer was then dried and concentrated in vacuo. The residue was chromatographed on silica gel (eluted with 20% EtOAc in hexanes) to afford 163 mg (Y: 72.0%) of the title product.

EXAMPLE 97

7-Deoxy-13-triethylsilyloxybaccatin III (LVIII)

Compound LVII (182 mg, 0.230 mmol) in dry benzene (5 mL) was heated to 80° C. in the presence of tributyltin hydride (0.310 mL, 1.150 mmol) and AIBN (2,2'-azobisisobutyronitrile, 10 mg). After 3 h the solution was cooled and evaporated in vacuo. Silica gel chromatography (being eluted with 20% ethyl acetate in hexane) gave compound LVIII as an oil.

EXAMPLE 98

7-Deoxybaccatin III (La)

Compound LVIII was dissolved in THF (5 mL) and treated with tetrabutylammonium fluoride (1M in THF, 0.50 mL, 0.50 mmol) for 2 h at room temperature. Dilution with ethyl acetate and washing with water and brine, followed by silica gel chromatography (being eluted with 1:1 ethyl acetate/hexane) gave compound La as a white glassy solid (Y: 63 mg, 58% over two steps); $^1$H-NMR (CDCl$_3$) δ ppm: 8.10 (d, J=8.3 Hz, 2H) 7.59 (bt, 1H) 7.48 (m, 2H) 6.46 (s, 1H) 5.60 (d, J=7.4 Hz, 1H) 4.95 (bd, 1H) 4.84 (m, 1H) 4.30 (d, J=8.3 Hz, 1H) 4.16 (d, J=8.3 Hz, 1H) 3.83 (d, J=7.4 Hz, 1H) 2.45−1.00 (m, 26H, including singlets at 2.31, 2.23, 2.03, 1.71, 1.10, 1.06, 3H each); HRMS, calcd for C$_{31}$H$_{39}$O$_{10}$ (MH+) 571.2543, found: 571.2528.

EXAMPLE 99

7-Triethylsilyloxy-10-deacetylbaccatin III (LIX)

10-Deacetylbaccatin III (from Taxus baccata, 628.0 mg, 1.150 mmol) was dissolved in dry DMF (6 mL), cooled to 0° C., and treated with imidazole (312.8 mg, 4.595 mmol) and chlorotriethylsilane (0.772 mL, 4.60 mmol). The mixture was stirred at 0° C. for 4 h, then diluted with ethyl acetate (150 mL) and washed exhaustively with water and brine. The organic layer was dried and concentrated. The residue was puried by silica gel chromatography (being eluted with 50% ethyl acetate in hexane) to afford the title product as a foam (Y: 586 mg, 77%). This compound was described by Greene et al. in the *J. Am. Chem. Soc.*, 110, p 5917 (1988).

EXAMPLE 100

10-Pentafluorophenylthionocarbonate-7-triethylsilyloxybaccatin III (LX)

Compound LIX (319 mg, 0.485 mmol) was dissolved in dry THF (5 mL), cooled to −40° C., and treated with n-butyllithium (1.58M in hexanes, 0.384 mL, 0.606 mmol). After 40 min at this temperature, pentafluorophenyl chlorothionoformate (0.086 mL, 0.536 mmol) was added neat by syringe. The reaction mixture was stirred at −20° C. for 90 min, then quenched with saturated ammonium chloride solution, and extracted with ethyl acetate. The ethyl acetate layer was dried and concentrated. The residue was purified by silica gel chromatography (being eluted with 40% ethyl acetate in hexane) to afford compound LX as a foam (Y: 320 mg, 74%); $^1$H-NMR (CDCl$_3$) δ ppm: 8.09 (d, 2H) 7.56 (t, 1H) 7.44 (m, 2H) 6.78 (s, 1H) 5.64 (d, J=6.9 Hz, 1H) 4.96−4.89 (m, 2H) 4.49 (dd, J=10.2 Hz, J'=6.6 Hz, 1H) 4.12 (AB q, 2H) 3.80 (d, J=6.9 Hz, 1H) 2.55−0.44 (m, 43H); MS: 884 (MH+).

EXAMPLE 101

10-Deacetyloxy-7-triethylsilyloxybacctain III (LXI)

Thionocarbonate LX (119 mg, 0.135 mmol) was dissolved in dry toluene (3 mL) and treated with AIBN (2 mg). The solution was degassed with dry nitrogen, then tributyltin hydride (0.055 mL, 0.202 mmol) was added. Subsequently, the solution was heated at 90° C. for 1 h. The solvent was evaporated and silica gel chromatography of the residue (being eluted with 40% ethyl acetate in hexane) gave compound LXI (Y: 87 mg, 99%) as a colorless foam; $^1$H-NMR (CDCl$_3$) δ ppm: 8.07 (d, J=8.2 Hz, 2H) 7.56 (bt, 1H) 7.44 (m, 2H) 5.57 (d, J=6.7 Hz, 1H) 4.92 (d, J=9.3 Hz, 1H) 4.78 (bs, 1H) 4.48 (dd, J=10.4 Hz, J'=6.6 Hz, 1H) 4.09 (AB q, 2H) 4.06 (d, J=6.7 Hz, 1H) 3.74 (d, J=14.8 Hz, 1H) 3.35 (bd, 1H) 2.44 (m, 1H) 2.25 (s, 3H) 2.22−0.45 (m, 42H); MS: 642 (MH+).

EXAMPLE 102

10-Deacetyloxybaccatin III (LXII)

Compound LXI (120 mg, 0.187 mmol) was dissolved in acetonitrile (3.5 mL) and the solution was cooled to −10° C. Concentrated HCl (36%, 0.060 mL) was added, and the solution was stirred for 30 min. The mixture was diluted with ethyl acetate (75 mL), washed with saturated aqueous sodium bicarbonate and brine, dried and then concentrated. The residue was purified by flash silica chromatography (being eluted with 70% ethyl acetate in hexane) to afford desilylated 10-deacetyloxybaccatin III (LXII) as a foam (Y: 75 mg, 76%); $^1$H-NMR (CDCl$_3$) δ ppm: 8.10 (d, J=7.3 Hz, 2H) 7.60 (m, 1H) 7.45 (m, 2H) 5.64 (d, J=6.9 Hz, 1H) 4.97 (bd, J=9.4 Hz, 1H) 4.81 (bt, 1H) 4.36−4.28 (m, 2H) 4.17−4.07 (m, 3H) 3.82 (d, J=15.6 Hz, 1H) 3.43 (bd, J=15.6 Hz, 1H) 2.60 (m, 1H) 2.28−1.73 (m, 14 H, including singlets at 2.27, 1.93, 1.62, 3H each) 1.11 (s, 3H) 1.04 (s, 3H); HRMS calcd for C$_{29}$H$_{37}$O$_9$ (MH+) 529.2438, found: 529.2432.

EXAMPLE 103

7-(Methylthio)carbonothioyloxy]-10-deacetyloxybaccatin III (LXIII)

Compound LXII (75 mg, 0.142 mmol) was dissolved in dry THF (2 mL) and carbon disulfide (0.5 mL). Sodium hydride (60% in mineral oil, 8.5 mg, 0.213 mmol) was then added, and the mixture was stirred at room temperature for 2 h. Iodomethane (0.026 mL, 0.426 mmol) was added, and the reaction was allowed to proceed overnight. The solvent was then removed and the residue was purified by silica gel chromatography (being eluted with 50–70% ethyl acetate in hexane) to give xanthate LXIII as a foam (Y: 46.4 mg, 53%); $^1$H-NMR (CDCl$_3$) δ ppm: 8.10 (d, J=7.3 Hz, 2H) 7.59 (m, 1H) 7.44 (m, 2H) 6.44 (dd, J=10.4 Hz, J'=7.3 Hz, 1H) 5.63 (d, J=6.8 Hz, 1H) 4.97 (bd, J=9.4 Hz, 1H) 4.78 (bt, 1H) 4.31 (d, J=8.4 Hz, 1H) 4.26 (d, J=6.8 Hz, 1H) 4.13 (d, J=8.4 Hz, 1H) 3.83 (d, J=15.4 Hz, 1H) 3.35 (bd, J=15.4 Hz, 1H) 2.55 (m, 1H) 2.49 (s, 3H) 2.28 (m, 14 H, including singlets at 2.27, 1.95, 1.83, 3H each) 1.1 (s, 3H) 1.07 (s, 3H); HRMS calcd for C$_{31}$H$_{39}$O$_9$S$_2$ (MH+) 619.2036, found: 619.2017.

EXAMPLE 104

7-Deoxy-10-deacetyloxybaccatin III (Lb)

Xanthate LXIII (36 mg, 0.058 mmol) was refluxed in benzene (1 mL) in the presence of AIBN (2 mg) and tributyltin hydride (0.079 mL, 0.290 mmol) under an argon atmosphere for 3 h. Concentration of the reaction mixture and flash silica gel chromatography of the residue (being eluted with 40% ethyl acetate in hexanes) followed by HPLC (high pressure liquid chromatography) separation from other components afforded compound Lb as a foam (16.8 mg, Y: 56%); $^1$H-NMR (CDCl$_3$) δ ppm: 8.10 (d, J=7.3 Hz, 2H) 7.56 (m, 1H) 7.45 (m, 2H) 5.62 (d, J=7.2 Hz, 1H) 4.94 (bd, 1H) 4.79 (bs, 1H) 4.29 (d, J=8.0 Hz, 1H) 4.18 (d, J=8.0 Hz, 1H) 4.09 (d, J=7.2 Hz, 1H) 3.83 (d, J=16.2 Hz, 1H) 3.34 (bd, J=16.2 Hz, 1H) 2.35−1.40 (m, 17H, including singlets at 2.27, 1.90, 1.67, 3H each) 1.06 (s, 3H) 1.02 (s, 3H); HRMS calcd for C$_{29}$H$_{37}$O$_8$ (MH+): 513.2488, found: 513.2502.

ALTERNATE METHOD

Compound XXXIX (160 mg, 0.255 mmol) was dissolved in dry THF (2 mL). To this solution at room temperature was added tetrabutylammonium fluoride (766 uL, 1M, 0.766 mmol). The reaction was stirred for 1 h at room temperature. The solvent was removed and the residue was chromatographed on silica gel (eluted with 50-70% ethyl acetate in hexanes) to afford 115 mg (Y: 87.9%) of the desired title product.

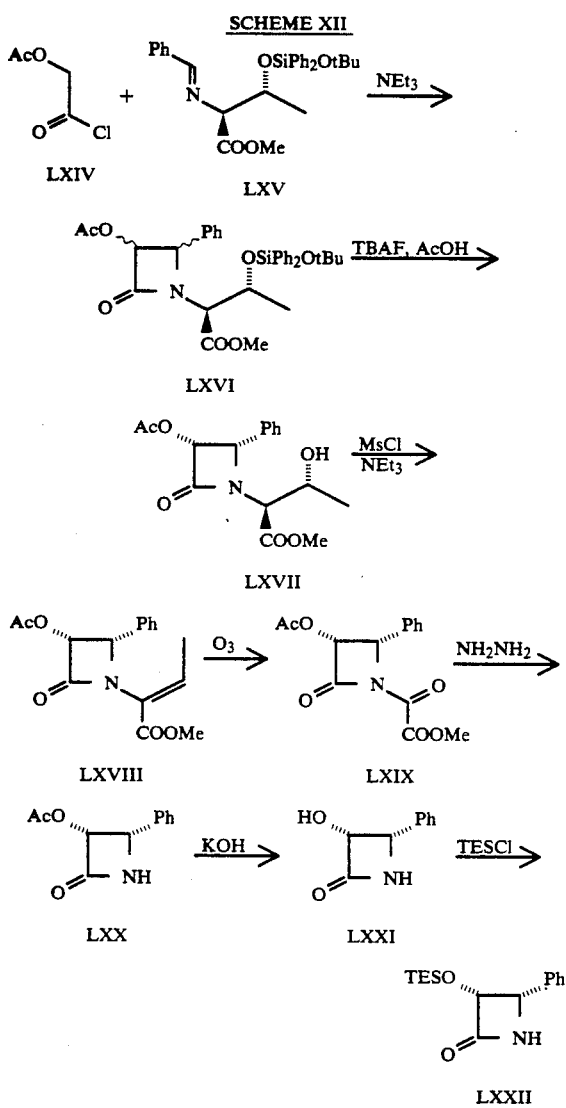

EXAMPLE 105

(3R, 4S)-4-Phenyl-3-triethylsilyloxy-2-azetidinone (LXXII)

(L)-Threonine methyl ester hydrochloride (1.26 g, 7.44 mmol) in anhydrous dichloromethane (15 mL) was stirred with imidazole (1.01 g, 14.89 mmol) and t-butoxydiphenylsilyl chloride (2.274 g, 7.816 mmol) for 16 h at room temperature. The reaction mixture was partitioned between water and dichloromethane. The organic phase was washed with 5% aqueous sodium bicarbonate and water, dried and concentrated to give 2.88 g of a crude oil, which was used directly in the next step; $^1$H-NMR (CDCl$_3$) δ ppm: 7.70−7.25 (m, 10H) 4.44 (m, 1H) 3.62 (s, 3H) 3.31 (d, J=3 Hz, 1H) 2.12 (bs, 2H) 1.3−1.5 (m, 12H).

The foregoing oil (548 mg, 1.414 mmol) in anhydrous dichloromethane (10 mL) was treated with benzaldehyde (0.158 mL, 1.55 mmol) at room temperature overnight in the presence of 4Å molecular sieves to afford compound of formula LXV in situ. Upon cooling the solution containing compound LXV to −40° C., triethylamine (0.20 mL, 1.698 mmol) was added, followed by acetoxyacetyl chloride (LXIV) (0.182 mL, 1.698 mmol) over 10 min. The mixture was allowed to reach room temperature over 4 h and the product was partitioned between dichloromethane and water. The organic phase was further washed with water and brine, dried and concentrated. Silica gel chromatography (being eluted with 1:4 EtOAc/hexane) gave 411 mg of compound LXVI as a ca. 10:1 mixture of 3R,4S:3S,4R diastereomers.

This mixture of diastereomers (245.1 mg, 0.414 mmol) in dry THF (2 mL) was treated with acetic acid (0.15 mL) and tetrabutylammonium fluoride (TBAF, 1M in THF, 1.20 mL). The solution was stirred for 14 h at room temperature, then partitioned between ethyl acetate and 5% aqueous sodium bicarbonate. The organic phase was dried and concentrated. Flash silica gel chromatography using 1:1 ethyl acetate/hexane as eluent gave 66 mg (Y: 50%) of compound LXVII (one diastereomer) as a foam; $^1$H-NMR (CDCl$_3$) δ ppm: 7.42−7.25 (m, 5H) 5.90 (d, J=4.8 Hz, 1H) 5.09 (d, J=4.8 Hz, 1H) 4.28 (m, 1H) 4.01 (d, J=4.8 Hz, 1H) 3.70 (s, 3H) 1.73 (s, 3H) 1.19 (d, J=6.6 Hz, 3H).

Compound of formula LXVII (9.8 g, 0.0305 mol) in dry dichloromethane (100 mL) was treated at −78° C. with triethylamine (9.40 mL, 0.0671 mol) and methanesulfonyl chloride (MsCl, 3.50 mL, 0.0457 mol). The solution was allowed to reach room temperature overnight. The reaction mixture was partitioned between water and dichloromethane. The organic layer was washed with 5% aqueous sodium bicarbonate, dilute aqueous HCl, water and brine, and concentrated to afford compound LXVIII as a crude oily residue. The crude residue (10.0 g) was dissolved in dichloromethane (250 mL) and ozone was passed through the solution at −78° C. until the solution retained blue color. Addition of methyl sulfide (11 mL) and concentration of the reaction mixture gave compound of formula LXIX (crude).

Compound of formula LXIX was dissolved in THF (150 mL) and treated at −78° C. with hydrazine hydrate (10 mL). After 2 h, the mixture was poured into dilute aqueous HCl and ethyl acetate, and the two phases were separated. The organic phase was washed with more acid, water and brine and concentrated to afford a crude product, which was purified by silica gel chromatography using 1-5% methanol in methylene chloride as eluent to yield 4.40 g (Y: 71%) of compound of formula LXX; $^1$H-NMR (CDCl$_3$) δ ppm: 7.38−7.24 (m, 5H) 6.31 (bs, 1H) 5.87 (bm, 1H) 5.04 (d, J=4.8 Hz, 1H) 1.67 (s, 3H).

To a cooled (−5° C.) mixture of 1M aqueous KOH (140 mL) and acetonitrile (100 mL), a solution of compound LXX (2.39 g, 11.22 mmol) in acetonitrile (130 mL) was added dropwise. The mixture was stirred at 0° C. for 1 h and diluted with ethyl acetate (300 mL), water (50 mL) and saturated aqueous bicarbonate (50 mL). The organic phase was separated, and the aqueous layer further extracted with ethyl acetate (3×200 mL).

The organic phases were combined, dried, filtered and concentrated to give compound of formula LXXI (crude), which was recrystallized from hexane/acetone (mp, 184–6° C.); yield, 1.53 g (Y: 82%).

To azetidinone LXXI (580 mg, 3.55 mmol) in dry THF (5.0 mL) was added imidazole (265.5 mg, 3.90 mmol), followed by triethylsilyl chloride (TESCl, 0.654 mL, 3.90 mmol). The mixture was allowed to be stirred for 1 h. Ethyl acetate was added and the organic layer was washed with brine, 10% aqueous HCl and dried. Silica gel chromatography (being eluted with 25% ethyl acetate in hexane) gave 670 mg (Y: 68%) of compound LXXII as a foam.

EXAMPLE 106

(3R, 4S)-1-t-Butoxycarbonyl-4-phenyl-3-triethylsilyloxy-2-azetidinone (ILa)

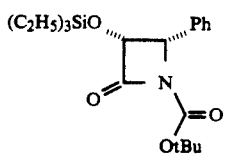

To a stirred solution of (3R, 4S)-4-phenyl-3-triethylsilyloxy-2-azetidinone (LXXII) (2.200 g, 7.92 mmol) in dry THF (25 mL) was added N,N-diisopropylethylamine (1.65 mL, 9.510 mmol, 1.2 equiv) at 0° C. under an argon atmosphere. The solution was stirred for 5 min followed by the addition of di-t-butyl carbonate (2.080 g, 9.510 mmol, 1.2 equiv) and 4-dimethylaminopyridine (193.6 mg, 1.581 mmol, 0.20 equiv). The reaction mixture was stirred at 0° C. for 60 min. The solution was diluted by adding ethyl acetate (25 mL). The resulting solution was washed with brine, 10% NaHCO$_3$, 10% HCl solution, dried (MgSO$_4$), and concentrated to give a crude compound (oil). The compound was further purified by silica gel flash chromatography (being eluted with 15% ethyl acetate in hexanes) to afford 2.4 g (Y: 83%) of the title β-lactam as a white solid; $^1$H-NMR (CDCl$_3$) δ ppm: 7.28 (m, 5H) 5.03 (m, 2H) 1.39 (s, 9H) 0.76 (t, J=7.6 Hz, 9H) 0.43 (m, 6H).

EXAMPLE 107

(3R, 4S)-1-Benzoyl-4-phenyl-3-triethylsilyloxy-2-azetidinone (ILb)

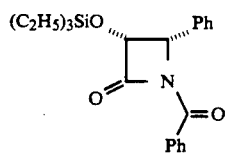

To a stirred solution of (3R, 4S)-4-phenyl-3-triethylsilyloxy-2-azetidinone (LXXII) (1.000 g, 3.601 mmol) in dry CH$_2$Cl$_2$ (25 mL) was added N,N-diisopropylethylamine (0.689 mL, 3.961 mmol, 1.1 equiv) at 0° C. under an argon atmosphere. The solution was stirred for 5 min followed by the addition of benzoyl chloride (0.459 mL, 3.961 mmol, 1.1 equiv) and 4-dimethylaminopyridine (96.5 mg, 0.790 mmol, 0.20 equiv). The reaction mixture was stirred at room temperature for 1 h, then it was diluted with ethyl acetate (25 mL). The resulting solution was washed with brine, 10% NaHCO$_3$, 10% HCl solution, dried (MgSO$_4$), and concentrated to give a crude compound as an oil. The compound was further purified by silica gel flash chromatography (being eluted with 15% ethyl acetate in hexanes) which afforded 1.04 g (Y: 80%) of 8.07–8.00 (m, 2H) 7.59–7.45 (m, 3H) 7.37–7.31 (m, 5H) 5.41 (d, J=6.1 Hz, 1H) 0.83–0.77 (m, 9H) 0.54–0.42 (m, 6H).

EXAMPLE 108

N-Debenzoyl-N-t-butoxycarbonyl-2'-O-triethylsilyl-7deoxytaxol (LIa)

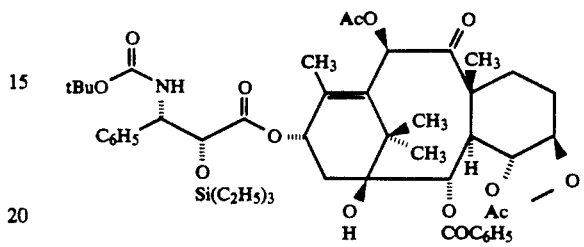

In a two-necked flask under an argon atmosphere was placed 7-deoxybaccatin III (La) (24 mg, 0.042 mmol). The flask was evacuated and purged with argon three times. Using a syringe, THF (1.0 mL) was added and the resulting clear solution was cooled to −40° C. (acetonitrile/dry ice bath) and stirred. To the stirred solution, n-butyllithium (16M solution in hexanes, 32.5 mL, 0.052 mmol) was added followed by azetidinone ILa (31.7 mg, 0.084 mmol) in THF (0.5 mL) over a period of 2 min. The reaction mixture was immediately warmed to 0° C. and stirred for 40 min before being quenched with a saturated solution of NH$_4$Cl (3.0 mL). The aqueous solution was extracted with ethyl acetate; the organic phase was dried (anhydrous magnesium sulfate) and concentrated in vacuo to give an oil. The crude product after silica gel flash chromatography (being eluted with 25% ethyl acetate in hexanes) afforded the title compound LIa (Y: 19.5 mg, 52%); $^1$H-NMR (CDCl$_3$) δ ppm: 8.11 (d, J=8.2 Hz, 2H) 7.62–7.28 (m, 8H) 6.45 (s, 1H) 6.28 (bt, J=8.9 Hz, 1H) 5.66 (d, J=8.4 Hz, 1H) 5.45 (bd, 1H) 5.25 (bd, 1H) 4.95 (dd, J=8.2 Hz, J'=2.6 Hz, 1H) 4.53 (d, J=2.0 Hz, 1H) 4.34 (d, J=8.5 Hz, 1H) 4.20 (d, J=8.5 Hz, 1H) 3.78 (d, J=8.4 Hz, 1H) 2.52 (s, 3H) 2.47–2.25 (m, 2H) 2.22 (s, 3H) 2.19–1.40 (m, 11H) 1.34–1.20 (m, 12H) 1.14 (s, 3H) 0.62 (t, J=8.4 Hz, 9H) 0.22–0.48 (m, 6H).

EXAMPLE 109

N-Debenzoyl-N-t-butoxycarbonyl-7-deoxytaxol (XXXVIIa)

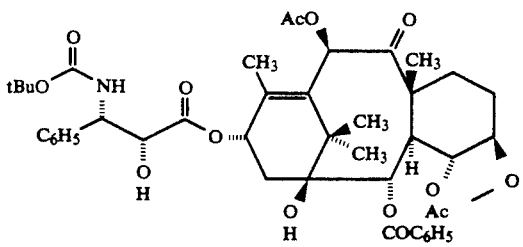

To a stirred solution of compound LIa (13.5 mg, 0.0142 mmol) in acetonitrile (1.0 mL), at −5° C., was added aqueous HCl (2.6 mL, 36% solution). The reaction mixture was stirred for 10 min. Thin layer chromatography at this point indicated consumption of the starting material. The reaction was stopped and the mixture was diluted with ethyl acetate (2 mL). The combined solution was washed with brine, 10% aqueous sodium bicarbonate solution, dried (anhydrous magnesium sulfate) and concentrated under vacuum to afford a crude product. Purification by silica gel flash chromatography (being eluted with 30% ethyl acetate in hexanes) afforded 10.2 mg (Y: 86.4%) of title compound XXXVIIa; $^1$H-NMR (CDCl$_3$) δ ppm: 8.11 (d, J=8.2 Hz, 2H) 7.66−7.23 (m, 8H) 6.47 (s, 1H) 6.20 (bt, J=8.3 Hz, 1H) 5.64 (d, J=8.4 Hz, 1H) 5.39−5.17 (m, 2H) 4.92 (dd, J=8.5 Hz, J'=2.5 Hz, 1H) 4.60 (m, 1H) 4.31 (d, J=8.4 Hz, 1H) 4.18 (d, J=8.4 Hz, 1H) 3.76 (d, J=8.4 Hz, 1H) 3.27 (d, J=4.2 Hz, 1H) 2.46−1.92 (m, 11H) 1.87 (s, 3H) 1.74 (s, 3H) 1.64−1.39 (m, 2H) 1.3 (s, 9H) 1.24 (s, 3H) 1.15 (s, 3H); HRMS calcd for C$_{45}$H$_{56}$NO$_{14}$ (MH+): 834.3701, found: 834.3691.

EXAMPLE 110

2'-O-Triethylsilyl-7-deoxytaxol (LIb)

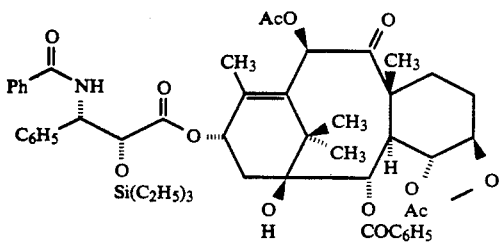

In a two-necked flask under an argon atmosphere was placed 7-deoxybaccatin III (La) (62 mg, 0.108 mmol). The flask was evacuated and purged with argon three times. Using a syringe, THF (1.0 mL) was added and the resulting clear solution was cooled to −40° C. (acetonitrile/dry ice bath). To this stirred solution, n-butyllithium (1.43M solution in hexanes, 91 mL, 0.173 mmol) was added followed by azetidinone ILb (66.3 mg, 0.174 mmol) in THF (0.5 mL). The solution was immediately warmed to 0° C. and stirred for 45 min before being quenched with a saturated solution of NH$_4$Cl (3.0 mL). The aqueous solution was extracted with ethyl acetate; the organic phase was dried (anhydrous magnesium sulfate) and concentrated under vacuum to give an oil. The crude oil after silica gel flash chromatography (being eluted with 25% ethyl acetate and hexanes) afforded the title compound (LIb) as a foam (Y: 63 mg, 61%); $^1$H-NMR (CDCl$_3$) δ ppm: 8.14 (d, J=7.6 Hz, 2H) 7.73 (d, J=7.6 Hz, 2H) 7.64−7.29 (m, 11H) 7.12 (d, J=8.8 Hz, 1H) 6.46 (s, 1H) 6.25 (t, J=8.8 Hz, 1H) 5.73−5.67 (m, 2H) 4.95 (dd, J=8.2 Hz, J'=2.6 Hz, 1H) 4.68 (d, J=2.0 Hz, 1H) 4.33 (d, J=8.4 Hz, 1H) 4.26 (d, J=8.4 Hz, 1H) 3.78 (d, J=7.3 Hz, 1H) 2.56 (s, 3H) 2.50−2.25 (m, 1H) 2.22 (s, 3H) 2.18−2.06 (m, 2H) 1.91 (s, 3H) 1.86−1.71 (m, 6H) 1.58 (dd, J=13.2 Hz, J'=7.5 Hz, 1H) 1.23 (s, 3H) 1.14 (s, 3H) 0.87−0.76 (m, 9H) 0.58−0.35 (m, 6H).

EXAMPLE 111

7-Deoxytaxol (XXXVIIb)

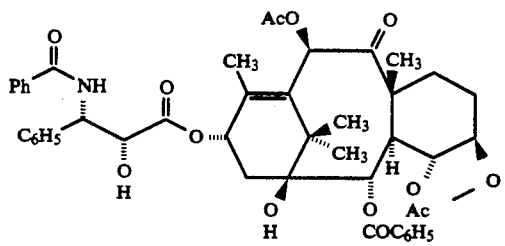

To a stirred solution of compound LIb (60 mg, 0.063 mmol) in acetonitrile (1.0 mL), at −5° C., was added aqueous HCl (15.8 mL, 36% solution). The reaction mixture was stirred for 15 min. Thin layer chromatography at this point indicated consumption of the starting material. The reaction was stopped and the mixture diluted with ethyl acetate (2 mL). The combined solution was washed with brine, 10% aqueous sodium bicarbonate, dried (anhydrous magnesium sulfate) and concentrated under vacuum to afford a crude product. Purification by silica gel flash chromatography (being eluted with 30% ethyl acetate hexanes) afforded 45 mg (Y: 87%) of title product, XXXVIIb, as a foam; $^1$H-NMR (CDCl$_3$) δ ppm: 8.15 (d, J=7.6 Hz, 2H) 7.70 (d, J=7.6 Hz, 2H) 7.63−7.30 (m, 11H) 7.02 (d, J=8.9 Hz, 1H) 6.42 (s, 1H) 6.21 (bt, J=8.8 Hz, 1H) 5.79 (dd, J=8.9 Hz, J'=2.7 Hz, 1H) 5.66 (d, J=7.3 Hz, 1H) 4.91 (dd, J=9.0 Hz, J'=2.2 Hz, 1H) 4.77 (dd, J=5.2 Hz, J'=2.7 Hz, 1H) 4.31 (d, J=8.3 Hz, 1H) 4.23 (d, J=8.3 Hz, 1H) 3.76 (d, J=7.3 Hz, 1H) 3.59 (d, J=5.2 Hz, 1H) 2.35−2.05 (m, 10H) 2.00−1.83 (m, 2H) 1.80 (s, 3H) 1.77−1.70 (m, 3H) 1.55 (dd, J=13.0 Hz, J'=7.5 Hz, 1H) 1.20 (s, 3H) 1.15 (s, 3H); HRMS calcd for C$_{47}$H$_{52}$NO$_{13}$ (MH+) 838.3439, found: 838.3436.

EXAMPLE 112

N-Debenzoyl-N-t-butoxycarbonyl-2'-O-triethylsilyl-7-deoxy-10-deacetyloxytaxol (LIc)

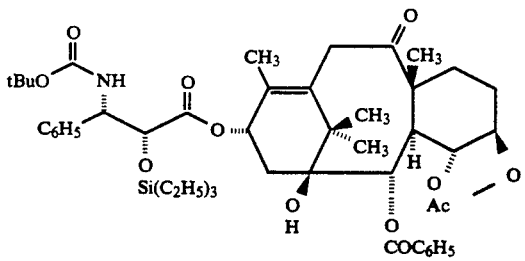

In a two-necked flask under argon atmosphere was placed 7-deoxy-10-deacetyloxybaccatin III (Lb) (39.0 mg, 0.076 mmol). The flask was evacuated and purged with argon three times. Using a syringe, THF (1.0 ml) was added and the resulting clear solution was cooled to −40° C. (acetonitrile/dry ice bath). To this stirred solution, n-butyllithium 0.061 ml 0.083 mmol, 1.35M solution in hexanes) was added followed by azetidinone ILa (43.0 mg, 0.114 mmol) in THF (0.5 ml) over a period of 2 min. The reaction mixture was immediately warmed to 0° C. and stirred for 45 min before being quenched with a saturated solution of NH$_4$Cl (3.0 ml). The aqueous solution was extracted with ethyl acetate;

the organic phase was dried (anhydrous magnesium sulfate) and concentrated in vacuo to give an oil. The crude product after silica gel flash chromatography (being eluted with 25% ethyl acetate in hexanes) afforded the title compound (LIc) (Y: 37 mg, 55.3%); $^1$H-NMR (CDCl$_3$) δ ppm: 8.19–8.08 (m, 2H) 7.62–7.19 (m, 8H) 6.17 (bt, 1H) 5.70 (d, J=7.1 Hz, 1H) 5.49 (d, J=9.5 Hz, 1H) 5.27 (d, J=9.0 Hz, 1H) 4.94 (dd, J=9.0, J'=2.1 Hz, 1H) 4.51 (d, J=1.6 Hz, 1H) 4.32 (d, J=8.4 Hz, 1H) 4.23 (d, J=8.4 Hz, 1H) 3.98 (d, J=7.1 Hz, 1H) 3.84 (d, J=16.5 Hz, 1H) 3.35 (d, J=16.5 Hz, 1H), 2.54–1.08 (m, 31H, including singlets at 2.53, 3H; 1.75, 3H; 1.71, 3H; 1.62, 3H; 1.35, 9H; 1.19, 3H; 1.12, 3H) 0.86–0.65 (m, 9H) 0.48–0.26 (m, 6H),

EXAMPLE 113

N-Debenzoyl-N-t-butoxycarbonyl-7-deoxy-10-deacetyloxytaxol (XXXVIIc)

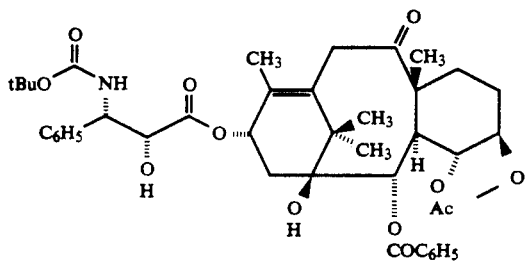

To a stirred solution of compound LIc (30.0 mg, 0.033 mmol) in acetonitrile (1.0 ml), at −5° C., was added aqueous HCl (0.0063 ml, 36% solution). The reaction mixture was stirred for 10 min. Thin layer chromatography at this point indicated consumption of the starting material. The reaction was stopped and the mixture was diluted with ethyl acetate (2 ml). The combined solution was washed with brine, 10% aqueous sodium bicarbonate solution, dried (anhydrous magnesium sulfate) and evaporated in vacuo to afford a crude product. Purification by silica gel flash chromatography (being eluted with 30% ethyl acetate in hexanes) afforded 20 mg (Y: 77%) of the title product; $^1$H-NMR (CDCl$_3$) δ ppm: 8.14–8.11 (m, 2H) 7.63–7.30 (m, 8H) 6.13 (bt, 1H) 5.67 (d, J=7.1 Hz, 1H) 5.42 (d, J=9.5 Hz, 1H) 5.26 (d, J=8.9 Hz, 1H) 4.94 (dd, J=8.9, J'=2.1 Hz, 1H) 4.60 (bd, J=1.6 Hz, 1H) 4.31 (d, J=8.3 Hz, 1H) 4.21 (d, J=8.3 Hz, 1H) 3.96 (d, J=7.1 Hz, 1H) 3.83 (d, J=16.5 Hz, 1H) 3.38–3.32 (m, 2H), 2.37–1.08 (m, 31H, including singlets at 2.37, 3H; 1.72, 3H; 1.71, 3H; 1.67, 3H; 1.33, 9H; 1.19, 3H; 1.12, 3H).

EXAMPLE 114

2'-O-Triethylsilyl-7-deoxy-10-deacetyloxytaxol (LId)

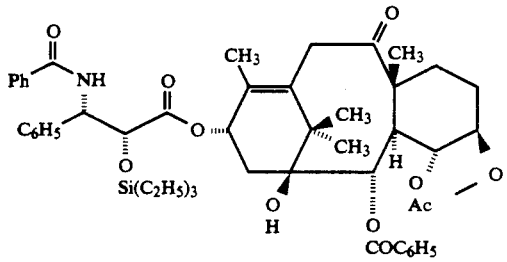

In a two-necked flask under argon atmosphere was placed 7-deoxy-10-deacetylbaccatin III (Lb) (45 mg, 0.087 mmol). The flask was evacuated and purged with argon three times. Using a syringe, THF (1.0 ml) was added and the resulting clear solution was cooled to −40° C. (acetonitrile/dry-ice bath). To a stirred solution, n-butyllithium (0.066 ml, 0.10 mmol, 1.52M solution in hexanes) was added followed by azetidinone IIb (59.6 mg, 0.16 mmol) in THF (0.5 ml). The solution was immediately warmed to 0° C. and stirred for 45 min. Thin layer chromatography at this point indicated only a trace amount of the product. An additional amount of n-BuLi (0.066 ml, 0.10 mmol, 1.52M solution in hexanes) was added. The reaction mixture was stirred for an additional 60 min before being quenched with a saturated solution of NH$_4$Cl (3.0 ml). The aqueous solution was extracted with ethyl acetate; the organic phase was dried (anhydrous magnesium sulfate) and concentrated in vacuo to give an oil. The crude oil after silica gel flash chromatography (being eluted with 30% ethyl acetate in hexanes) afforded the title compound (LId) (Y: 18 mg, 23%) along with the starting compound (Lb) (recovered yield: 25 mg). Yield based on the recovered starting material was 51%; $^1$H-NMR (CDCl$_3$) δ ppm: 8.15–8.12 (m, 2H) 7.73 (d, J=7.2 Hz, 2H) 7.72–7.24 (m, 6H) 7.13 (d, J=8.7 Hz, 1H) 6.16 (bt, J=8.0 Hz, 1H) 5.69–5.65 (m, 2H) 4.95 (dd, J=7.0 Hz, J'=2.0 Hz, 1H) 4.66 (bd, J=2.0 Hz, 1H) 4.34 (d, J=8.6 Hz, 1H) 4.26 (d, J=8.6 Hz, 1H) 3.97 (d, J=7.1 Hz, 1H) 3.83 (d, J=16.5 Hz, 1H) 3.34 (d, J=16.5 Hz, 1H), 2.53–1.04 (m, 27H, including singlets at 2.52, 3H; 1.76, 3H; 1.71, 6H; 1.14, 3H; 100, 3H) 0.85–0.78 (m, 9H) 0.52–0.37 (m, 6H).

EXAMPLE 115

7-Deoxy-10-deacetyloxytaxol (XXXVIId)

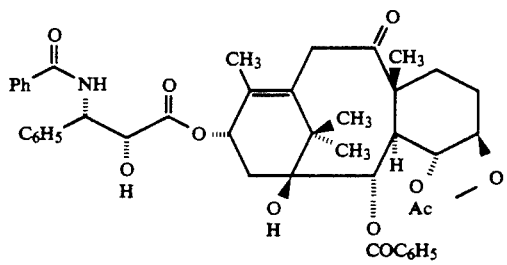

To a stirred solution of compound LId (18.5 mg, 0.02 mmol) in acetonitrile (1.0 ml), at −5° C., was added aqueous HCl (0.004 ml, 36% solution). The reaction mixture was stirred for 10 min. Thin layer chromatography at this point indicated consumption of the starting material. The reaction was stopped and the mixture diluted with ethyl acetate (2 ml). The combined solution was washed with brine, 10% aqueous sodium bicarbonate solution, dried (anhydrous magnesium sulfate) and concentrated in vacuo to afford a crude product. Purification by silica gel flash chromatography (being eluted with 50% ethyl acetate in hexanes) afforded 7.5 mg (Y: 47%) of compound XXXVIId; $^1$H-NMR (CDCl$_3$) δ ppm: 8.16–8.13 (m, 2H) 7.75–7.72 (m, 2H) 7.61–7.26 (m, 6H) 7.05 (d, J=8.9 Hz, 1H) 6.11 (bt, J=8.0 Hz, 1H) 5.78 (dd, J=8.9, J'=2.5 Hz, 1H) 5.67 (d, J=7.2 Hz, 1H) 4.92 (dd, J=9.0, J'=2.5 Hz, 1H) 4.76 (bs, 1H) 4.30 (d, J=8.3 Hz, 1H) 4.24 (d, J=8.3 Hz, 1H) 3.94 (d, J=7.0 Hz, 1H) 3.80 (d, J=16.5 Hz, 1H) 3.58 (d, J=4.7 Hz, 1H) 3.35 (d, J=16.5 HZ, 1H) 2.43–1.07 (m, 27H, including singlets at 2.37, 3H; 1.71, 3H; 1.68, 3H; 1.65, 3H; 1.15, 3H; 1.11, 3H).

EXAMPLE 116

N-Debenzoyl-N-t-butyoxycarbonyl-10-deacetyloxytaxol (XXXVIIe)

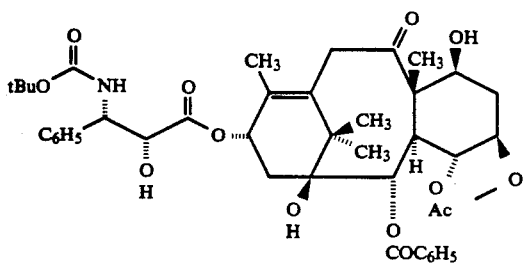

Compound LXI (100 mg, 0.156 mmol) was placed in a flask under argon and dissolved in dry THF (1.5 mL). Upon cooling to −40° C., n-butyllithium (1.45M in hexanes, 0.119 mL, 0.170 mmol) was added dropwise, followed by (3R,4S)-1-tert-butoxycarbonyl-4-phenyl-3-triethylsilyloxy-2-azetidinone (IIa) (94.2 mg, 0.25 mmol) in THF (0.5 mL) over a period of 2 min. The mixture was immediately warmed to 0° C. and stirred for 45 min before being quenched with saturated ammonium chloride (3 mL). The mixture was extracted with ethyl acetate, dried, and concentrated. Silica gel chromatography (eluted with 30% ethyl acetate in hexane) afforded N-debenzoyl-N-t-butyoxycarbonyl-10-deacetyloxy-2″,7-bis-O-(triethylsilyl)taxol as a foam (Y: 125 mg, 76%). This compound (100 mg, 0.098 mmol) was immediately dissolved in acetonitrile (2 mL) at −5° C. and treated with hydrochloric acid (0.037 mL, 36%, 12M). The mixture was stirred for 2 h at −5° C., then it was quenched with aqueous bicarbonate, extracted with ethyl acetate, and dried. Evaporation of the solvent was followed by silica gel chromatography (eluted with 75% ethyl acetate in hexane) to afford the title compound as a foam (Y: 80.5 mg, 80%); $^1$H-NMR(CDCl$_3$) δ ppm: 8.10 (d, J=8.2 Hz, 2H) 7.64−7.29 (m, 8H) 6.11 (bt, 1H) 5.68 (d, J=6.9 Hz, 1H) 5.43 (bd, 1H) 5.25 (bd, 1H) 4.93 (d, J=7.7 Hz, 1H) 4.60 (bs, 1H) 4.30−4.18 (m, 3H) 4.02 (d, J=7.7 Hz, 1H) 3.80 (d, J=15.8 Hz, 1H) 3.46−3.40 (m, 2H) 2.62 (m, 1H) 2.35 (s, 3H) 2.35−2.25 (m, 2H) 1.89−1.65 (m, 5H) 1.63 (s, 3H) 1.35 (s, 9H) 1.19 (s, 3H) 1.16 (s, 3H).

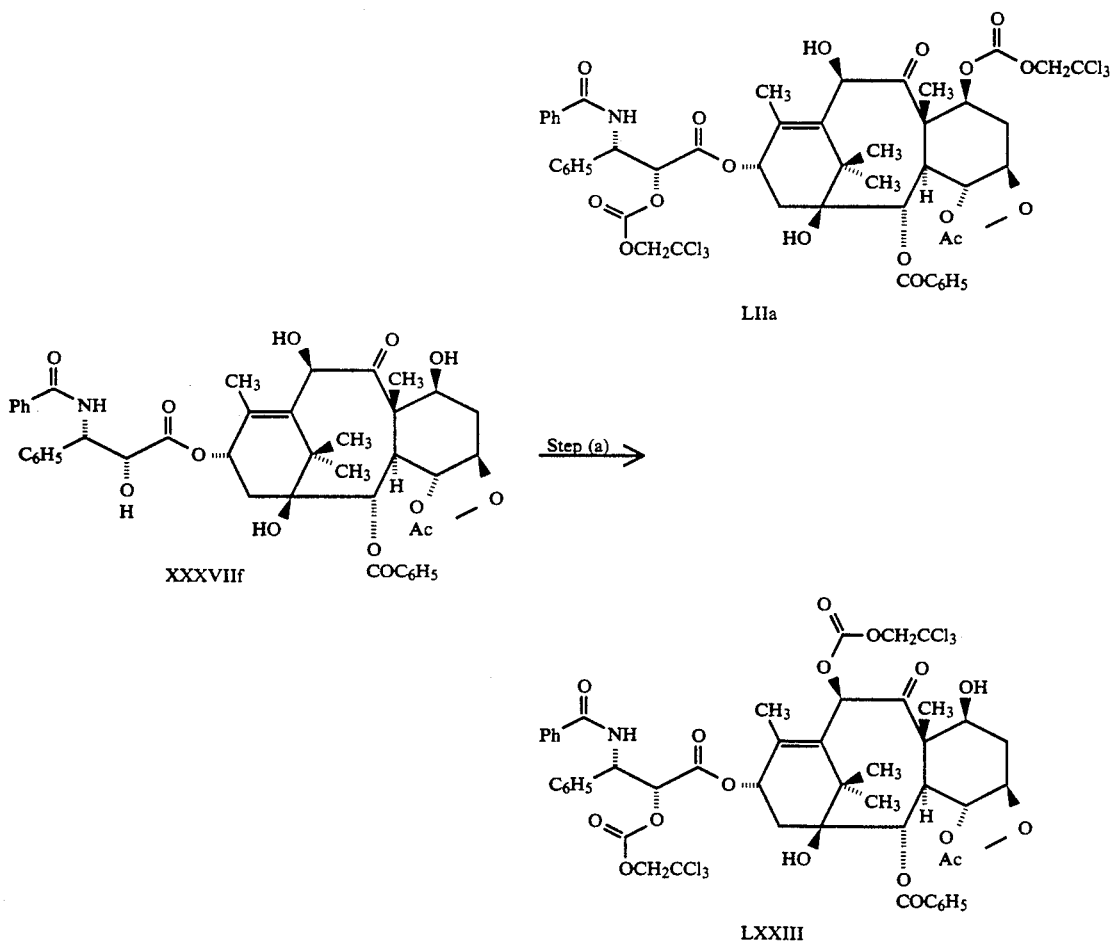

SCHEME XIII

-continued
SCHEME XIII

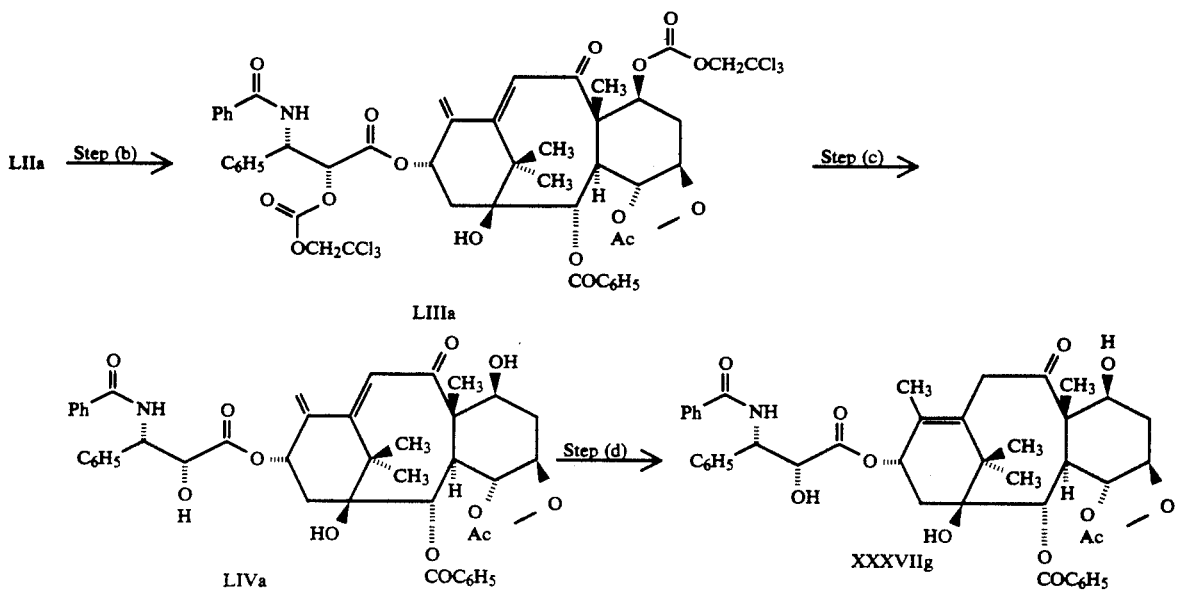

EXAMPLE 117
10-Deacetyloxytaxol (XXXVIIg)

10-Deacetyltaxol (XXXVIIf) (140 mg, 0.173 mmol) in dry dichloromethane (3.5 mL) was treated at 0° C. with pyridine (0.028 mL, 0.346 mmol) and trichloroethyl chloroformate (0.0724 mL, 0.260 mmol). After 1 h at this temperature, the cold bath was removed and the mixture was stirred at room temperature overnight. The solvent was evaporated and the residue chromatographed on a silica gel column (being eluted with 30–50% ethyl acetate in hexane) to afford 92.3 mg (Y: 46%) of compound LIIa as a foam. Continued elution also afforded compound LXXIII in 16% yield as a foam.

Compound LIIa (92.3 mg, 0.079 mmol) in dry dichloromethane (2 mL) was treated with 1,1,2-trifluoro-2-chlorotriethylamine (0.0384 mL, 0.238 mmol). The solution was stirred overnight, the solvent evaporated, and the residue purified by silica gel chromatography (being eluted with 25% ethyl acetate in hexane) to yield 42.8 mg (Y: 47%) of compound LIIIa as a white solid.

Dienone LIIIa (39 mg, 0.034 mmol) was dissolved in methanol (0.5 mL) and acetic acid (0.5 mL). Zinc dust (66.4 mg, 1.02 mmol) was added, and temperature of the mixture was maintained at 40° C. for 1 h. The insoluble matter was removed by filtration. The filtrate was concentrated and silica gel chromatography of the residue (being eluted with 60% ethyl acetate in hexane) gave 22 mg (Y: 81.5%) of compound LIVa as a foam.

Dienone LIVa (22 mg, 0.028 mmol) in ethyl acetate (0.7 mL) was hydrogenated at slightly over one atmospheric pressure of hydrogen in the presence of 10% palladium on charcoal (14.7 mg) for 5.5 h at room temperature. Removal of the catalyst by filtration, and purification of the product by silica gel chromatography (being eluted with 1:1 ethyl acetate/hexane) gave 15 mg (Y: 68%) of compound XXXVIIg as a foam.

EXAMPLE 118
7-Deoxy-10-deacetyloxy-13-triethylsilyloxybaccatin III (XXXIX)

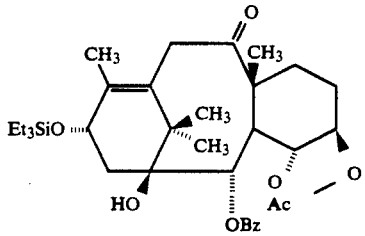

Compound LVII (416.3 mg, 0.527 mmol) was dissolved in dry toluene (10.5 mL), to this solution was added catalytic amount of AIBN and the resulting solution was degassed with dry $N_2$ for 5 min. Tributyltin hydride (708.7 uL, 2.63 mmol) was added. The reaction mixture was heated at 100° C. for 2 h. Then another portion of tributyltin hydride (425.3 uL, 1.581 mmol) was added. The reaction was heated for 5.5 h at 100° C. The reaction was complete by this time. The reaction mixture was cooled to room temperature and silica gel chromatography (eluted with 20% ethyl acetate in hexanes) afforded 320 mg (Y: 97%) of the title product.

EXAMPLE 119
3-(2'-Dibenzylphosphonooxy-4',6'-dimethylphenyl)-3,3-dimethylpropionic acid pentafluorophenylester

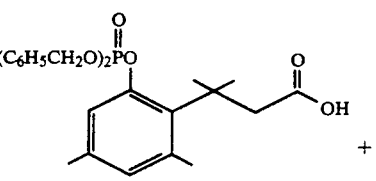

+

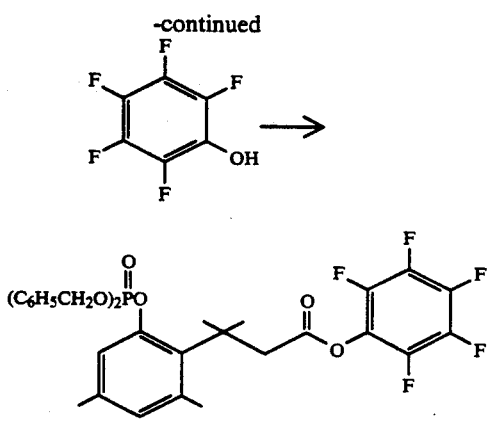

Pentafluorophenol (0.801 g, 4.35 mmol) was combined with acid IXa (2.50 g, 5.18 mmol), dicyclohexylcarbodiimide (1.08 g, 5.23 mmol), and 4-dimethylaminopyridine (0.107 g, 0.872 mmol). Dichloromethane (30 mL) was added and the mixture stirred under argon for 5 h. The solids were filtered off and the solution was washed sequentially with 0.1N HCl, saturated NaHCO$_3$ and brine. The solution was dried, concentrated, and the residue was chromatographed on silica gel (being eluted with 15% ethyl acetate in hexane) to give 3-(2'-dibenzylphosphonooxy-4',6'-dimethylphenyl)-3,3-dimethylpropionic acid pentafluorophenylester (2.44 g Y: 86%) as an off-white oil; $^1$H-NMR (CDCl$_3$, 300 MHz) δ ppm: 7.32−7.23 (m, 10H), 7.11 (s, 1H), 6.72 (s, 1H), 5.11 (d, J=8.4 Hz, 4H), 3.21 (s, 2H), 2.51 (s, 3H), 2.16 (s, 3H), 1.64 (s, 6H).

EXAMPLE 120

10-Deacetyl-10-O-[3'-(2''-dibenzylphophonooxy-4'',6'' dimethylphenyl)-3',3'-dimethylpropionyl]-7-triethylsilyloxybaccatin III (LXXVa)

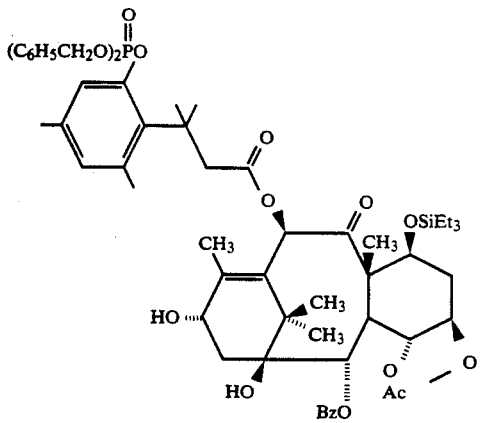

Butyl lithium (1.27M in hexane 0.110 mL 0.140 mmol) was added to a pre-cooled (−40° C.) solution of 7-triethylsilyloxy-10-deacetylbaccatin III (LIX, 83.7 mg, 0.127 mmol) in anhydrous THF (4 mL) and the resulting solution was stirred for 20 min at −40° C. under argon. A solution of 3-(2'-dibenzylphosphonooxy-4',6'-dimethylphenyl)-3,3-dimethylpropionic acid pentafluorophenylester (105 mg, 0.159 mmol) in THF (1 mL) was then added dropwise followed by a THF rinse (1 mL). After 1 h at −40° C., the reaction was allowed to warm up to 10° C., then worked up by addition of ethyl acetate and aqueous bicarbonate. The organic phase was separated, washed with brine, dried and concentrated. Following chromatography on silica gel (eluted with 40% ethyl acetate in hexane), 70 mg of derivative LXXVa (Y: 49%) was obtained as a white solid; $^1$H-NMR (CDCl$_3$) δ ppm: 8.08 (d, J=8.9 Hz, 2H), 7.56 (t, 1H), 7.45 (t, 2H), 7.33−7.26 (m, 10H), 7.07 (s, 1H), 6.70 (s, 1H), 6.41 (s, 1H), 5.57 (d, J=7.0 Hz, 1H), 5.12−5.08 (m, 4H), 4.92 (d, J=7.9 Hz, 1H), 4.66 (m, 1H), 4.50−4.38 (dd, J=10.4 Hz, J'=6.6 Hz, 1H), 4.27 (d, J=8.4 Hz, 1H), 4.12 (d, J=8.4 Hz, 1H), 3.81 (d, J=7.0 Hz, 1H), 3.05 (s, 2H), 2.56−0.48 (m, 47H including singlets at 2.56, 2.25, 2.13, 1.67, 1.63, 1.57, and 0.97, 3H each; singlet at 2.03, 6H).

EXAMPLE 121

N-Debenzoyl-N-t-butoxycarbonyl-2'-O-triethylsilyl-7-O-triethylsilyl-10-deacetyl-10-O-[3''-(2'''-dibenzylphosphonooxy-4''',6'''-dimethylphenyl)-3'',3''-dimethylpropionyl]taxol (LXXIXa)

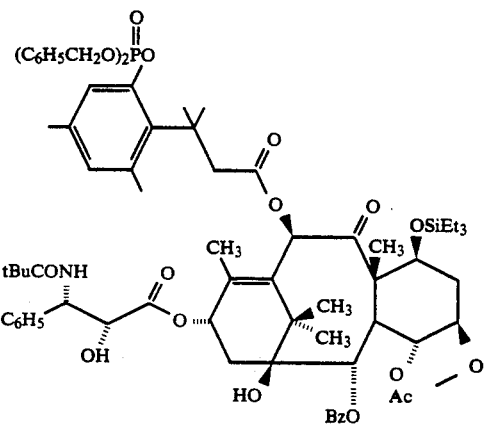

Butyl lithium (1.27M in hexane, 0.067 mL, 0.0851 mmol) was added to a pre-cooled (−40 ° C.) solution of compound LXXVa (76.6 mg, 0.0682 mmol) in anhydrous THF (1 mL) under argon. After 25 min, β-lactam ILa (90 mg, 0.238 mmol) in dry THF (1 mL) was added dropwise followed by a THF rinse (1 mL) and the solution was placed in a 0° C. bath. After 1 h at 0° C., the reaction mixture was quenched into a saturated aqueous ammonium chloride solution and extracted with ethyl acetate. The organics were dried and then concentrated. The residue was chromatographed on silica gel (eluted with 30% ethyl acetate in hexane) to give the title product, LXXIXa, (66.3 mg, Y: 65%) as a white foam; $^1$H-NMR (CDCl$_3$) δ ppm: 8.09 (d, J=7.2 Hz, 2H), 7.60−7.25 (m, 18H), 7.09 (s, 1H), 6.69 (s, 1H), 6.42 (s, 1H), 6.21 (t, 1H), 5.64 (d, J=7.0 Hz, 1H), 5.46 (bd, 1H), 5.28 (bd, 1H), 5.14−5.10 (m, 4H), 4.92 (d, J=8.1 Hz, 1H), 4.54 (bd, 1H), 4.46−4.41 (m, 1H), 4.29 (d, J=8.3 Hz, 1H), 4.15 (d, J=8.3 Hz, 1H), 3.79 (d, J=7.0 Hz, 1H), 3.09 (d, J=15.0 Hz, 1H), 2.95 (d, J=15.0 Hz, 1H), 2.56−0.29 (m, 79H including singlets at 2.55, 2.51, 2.14, 1.90, 1.71, 1.04, and 0.99, 3H each; singlets at 1.64, 6H, and 1.29, 9H).

EXAMPLE 122

The following compounds are some examples which can be made using the processes described in this application.

2-40   -O-[3'''-(2''''-phosphonooxy-4''''',6'''''-dimethylphenyl)-3''',3'''-dimethylpropionyl]-7-deoxytaxol.

2'-O-[2"-(phosphonooxymethyl)benzoyl]-7-deoxytaxol.
2'-O-[3"-(2'''-acetoxy-4''',6'''-dimethyl-5'''-phosphonooxyphenyl)-3",3"-dimethylpropionyl]-7-deoxytaxol.
2'-O-[4-(phosphonooxy)butanoyl]-7-deoxytaxol.
2'-O-[3"-(2'''-phosphonooxyphenyl)-3",3"-dimethylpropionyl]-7-deoxytaxol.
2'-O-(4-phosphonooxy-3,3-dimethylbutanoyl)-7-deoxytaxol.
2'-O-[(2"-phosphonooxyphenyl)acetyl]-7-deoxytaxol.
2'-O-[3"-(2'''-phosphonooxy-4''',6'''-dimethylphenyl)-3",3"-dimethylpropionyl]-7-deoxy-10-deacetyloxytaxol.
2'-O-[2"-(phosphonooxymethyl)benzoyl]-7-deoxy-10-deacetyloxytaxol.
2'-O-[3"-(2'''-acetoxy-4''',6'''-dimethyl-5'''-phosphonooxyphenyl)-3",3"-dimethylpropionyl]-7-deoxy-10-deacetyloxytaxol.
2'-O-[4-(phosphonooxy)butanoyl]-7-deoxy-10-deacetyloxytaxol.
2'-O-[3"-(2'''-phosphonooxyphenyl)-3",3"-dimethylpropionyl]-7-deoxy-10-deacetyloxytaxol.
2'-O-(4-phosphonooxy-3,3-dimethylbutanoyl)-7-deoxy-10-deacetyloxytaxol.
2'-O-[(2"-phosphonooxyphenyl)acetyl]-7-deoxy-10-deacetyloxytaxol.
7-O-[3"-(2'''-phosphonooxy-4''',6'''-dimethylphenyl)-3",3"-dimethylpropionyl]-10-deacetyloxytaxol.
7-O-[2"-(phosphonooxymethyl)benzoyl]-10-deacetyloxytaxol.
7-O-[3"-(2'''-acetoxy-4''',6'''-dimethyl-5'''-phosphonooxyphenyl)-3",3"-dimethylpropionyl]-10-deacetyloxytaxol.
7-O-[4-(phosphonooxy)butanoyl]-10-deacetyloxytaxol.
7-O-[3"-(2'''-phosphonooxyphenyl)-3",3"-dimethylpropionyl]-10-deacetyloxytaxol.
7-O-(4-phosphonooxy-3,3-dimethylbutanoyl)-10-deacetyloxytaxol.
7-O-[(2"-phosphonooxyphenyl)acetyl]-10-deacetyloxytaxol.
10-deacetyl-10-O-[3"-(2'''-phosphonooxy-4''',6'''-dimethylphenyl)-3",3"-dimethylpropionyl]-7-deoxytaxol.
10-deacetyl-10-O-[2"-(phosphonooxymethyl)benzoyl]-7-deoxytaxol.
10-deacetyl-10-O-[3"-(2'''-acetoxy-4''',6'''-dimethyl-5'''-phosphonooxyphenyl)-3",3"-dimethylpropionyl]-7-deoxytaxol.
10-deacetyl-10-O-[4-(phosphonooxy)butanoyl]-7-deoxytaxol.
10-deacetyl-10-O-[3"-(2'''-phosphonooxyphenyl)-3",3"-dimethylpropionyl]-7-deoxytaxol.
10-deacetyl-10-O-(4-phosphonooxy-3,3-dimethylbutanoyl)-7-deoxytaxol.
10-deacetyl-10-O-[(2"-phosphonooxyphenyl)acetyl]-7-deoxytaxol.
2'-O-[3"-(2'''-phosphonooxy-4''',6'''-dimethylphenyl)-3",3"-dimethylpropionyl]-7-deoxy-10-deacetyl-10-O-(benzyloxycarbonyl)taxol.
2'-O-[2"-(phosphonooxymethyl)benzoyl]-7-deoxy-10-deacetyl-10-O-(benzyloxycarbonyl)taxol.
2'-O-[3"-(2'''-acetoxy-4''',6'''-dimethyl-5'''-phosphonooxyphenyl)-3",3"-dimethylpropionyl]-7-deoxy-10-deacetyl-10-O-(benzyloxycarbonyl)taxol.
2'-O-[4-(phosphonooxy)butanoyl]-7-deoxy-10-deacetyl-10-O-(benzyloxycarbonyl)taxol.
2'-O-[3"-(2'''-phosphonooxyphenyl)-3",3"-dimethylpropionyl]-7-deoxy-10-deacetyl-10-O-(benzyloxycarbonyl)taxol.
2'-O-(4-phosphonooxy-3,3-dimethylbutanoyl)-7-deoxy-10-deacetyl-10-O-(benzyloxycarbonyl)taxol.
2'-O-[(2"-phosphonooxyphenyl)acetyl]-7-deoxy-10-deacetyl-10-O-(benzyloxycarbonyl)taxol.
2'-O-[3"-(2'''-phosphonooxy-4''',6'''-dimethylphenyl)-3",3"-dimethylpropionyl]-7-deoxy-10-deacetyl-10-O-(ethoxycarbonyl)taxol.
2'-O-[2"-(phosphonooxymethyl)benzoyl]-7-deoxy-10-deacetyl-10-O-(ethoxycarbonyl)taxol.
2'-O-[3"-(2'''-acetoxy-4''',6'''-dimethyl-5'''-phosphonooxyphenyl)-3",3"-dimethylpropionyl]-7-deoxy-10-deacetyl-10-O-(ethoxycarbonyl)taxol.
2'-O-[4-(phosphonooxy)butanoyl]-7-deoxy-10-deacetyl-10-O-(ethoxycarbonyl)taxol.
2'-O-[3"-(2'''-phosphonooxyphenyl)-3",3"-dimethylpropionyl]-7-deoxy-10-deacetyl-10-O-(ethoxycarbonyl)taxol.
2'-O-(4-phosphonooxy-3,3-dimethylbutanoyl)-7-deoxy-10-deacetyl-10-O-(ethoxycarbonyl)taxol.
2'-O-[(2"-phosphonooxyphenyl)acetyl]-7-deoxy-10-deacetyl-10-O-(ethoxycarbonyl)taxol.
2'-O-[3"-(2'''-phosphonooxy-4''',6'''-dimethylphenyl)-3",3"-dimethylpropionyl]-7-deoxy-10-deacetyl-10-O-(vinyloxycarbony)taxol.
2'-O-[2"-(phosphonooxymethyl)benzoyl]-7-deoxy-10-deacetyl-10-O-(vinyloxycarbonyl)taxol.
2'-O-[3"-(2'''-acetoxy-4''',6'''-dimethyl-5'''-phosphonooxyphenyl)-3",3"-dimethylpropionyl]-7-deoxy-10-deacetyl-10-O-(vinyloxycarbonyl)taxol.
2'-O-[4-(phosphonooxy)butanoyl]-7-deoxy-10-deacetyl-10-O-(vinyloxycarbonyl)taxol.
2'-O-[3"-(2'''-phosphonooxyphenyl)-3",3"-dimethylpropionyl]-7-deoxy-10-deacetyl-10-O-(vinyloxycarbonyl)taxol.
2'-O-(4-phosphonooxy-3,3-dimethylbutanoyl)-7-deoxy-10-deacetyl-10-O-(vinyloxycarbonyl)taxol.
2'-O-[(2"-phosphonooxyphenyl)acetyl]-7-deoxy-10-deacetyl-10-O-(vinyloxycarbonyl)taxol.
2'-O-[3"-(2'''-phosphonooxy-4''',6'''-dimethylphenyl)-3",3"-dimethylpropionyl]-10-deacetyl-10-O-(benzyloxycarbony)taxol.
2'-O-[2"-(phosphonooxymethyl)benzoyl]-10-deacetyl-10-O-(benzyloxycarbonyl)taxol.
2'O-[3"-(2'''-acetoxy-4''',6'''-dimethyl-5'''-phosphonooxyphenyl)-3",3"-dimethylpropionyl]-10-deacetyl-10-O-(benzyloxycarbonyl)taxol.
2'-O-[4-(phosphonooxy)butanoyl]-10-deacetyl-10-O-(benzyloxycarbonyl)taxol.
2'-O-[3"-(2'''-phosphonooxyphenyl)-3",3"-dimethylpropionyl]-10-deacetyl-10-O-(benzyloxycarbonyl)taxol.
2'-O-(4-phosphonooxy-3,3-dimethylbutanoyl)-10-deacetyl-10-O-(benzyloxycarbonyl)taxol.
2'-O-[(2"-phosphonooxyphenyl)acetyl]-10-deacetyl-10-O-(benzyloxycarbonyl)taxol.
2'-O-[3"-(2'''-phosphonooxy-4''',6'''-dimethylphenyl)-3",3"-dimethylpropionyl]-10-deacetyl-10-O-(ethoxycarbonyl)taxol.
2'-O-[2"-(phosphonooxymethyl)benzoyl]-10-deacetyl-10-O-(ethoxycarbonyl)taxol.
2'-O-[3"-(2'''-acetoxy-4''',6'''-dimethyl-5'''-phosphonooxyphenyl)-3",3"-dimethylpropionyl]-10-deacetyl-10-O-(ethoxycarbonyl)taxol.
2'-O-[4-(phosphonooxy)butanoyl]-10-deacetyl-10-O-(ethoxycarbonyl)taxol.
2'-O-[3"-(2'''-phosphonooxyphenyl)-3",3"-dimethylpropionyl]-10-deacetyl-10-O-(ethoxycarbonyl)taxol.
2'-O-(4-phosphonooxy-3,3-dimethylbutanoyl)-10-deacetyl-10-O-(ethoxycarbonyl)taxol.

2'-O-[(2'''-phosphonooxyphenyl)acetyl]-10-deacetyl-10-O-ethoxycarbonyl)taxol.
2'-O-[3''-(2''''-phosphonooxy-4''',6'''-dimethylphenyl)-3'',3''-dimethylpropionyl]-10-deacetyl-10-O-(vinyloxycarbony)taxol.
2'-O-[2''-(phosphonooxymethyl)benzoyl]-10-deacetyl-10-O-(vinyloxycarbonyl)taxol.
2'-O-[3''-(2''''-acetoxy-4''',6'''-dimethyl-5'''-phosphonooxyphenyl)-3'',3''-dimethylpropionyl]-10-deacetyl-10-O-(vinyloxycarbonyl)taxol.
2'-O-[4-(phosphonooxy)butanoyl]-10-deacetyl-10-O-(vinyloxycarbonyl)taxol.
2'-O-[3''-(2''''-phosphonooxyphenyl)-3'',3''-dimethylpropionyl]-10-deacetyl-10-O-(vinyloxycarbonyl)taxol.
2'-O-(4-phosphonooxy-3,3-dimethylbutanoyl)-10-deacetyl-10-O-(vinyloxycarbonyl)taxol.
2'-O-[(2''-phosphonooxyphenyl)acetyl]-10-deacetyl-10-O-(vinyloxycarbonyl)taxol.
7-O-[3''-(2''''-phosphonooxy-4''',6'''-dimethylphenyl)-3'',3''-dimethylpropionyl]-10-deacetyl-10-O-(benzyloxycarbony)taxol.
7-O-[2''-(phosphonooxymethyl)benzoyl]-10-deacetyl-10-O-(benzyloxycarbonyl)taxol.
7-O-[3''-(2''''-acetoxy-4''',6'''-dimethyl-5'''-phosphonooxyphenyl)-3'',3''-dimethylpropionyl]-10-deacetyl-10-O-(benzyloxycarbonyl)taxol.
7-O-[4-(phosphonooxy)butanoyl]-10-deacetyl-10-O-(benzyloxycarbonyl)taxol.
7-O-[3''-(2''''-phosphonooxyphenyl)-3'',3''-dimethylpropionyl]-10-deacetyl-10-O-(benzyloxycarbonyl)taxol.
7-O-(4-phosphonooxy-3,3-dimethylbutanoyl)-10-deacetyl-10-O-(benzyloxycarbonyl)taxol.
7-O-[(2''-phosphonooxyphenyl)acetyl]-10-deacetyl-10-O-(benzyloxycarbonyl)taxol.
7-O-[3''-(2''''-phosphonooxy-4''',6'''-dimethylphenyl)-3'',3''-dimethylpropionyl]-10-deacetyl-10-O-(ethoxycarbony)taxol.
7-O-[2''-(phosphonooxymethyl)benzoyl]-10-deacetyl-10-O-(ethoxycarbonyl)taxol.
7-O-[3''-(2''''-acetoxy-4''',6'''-dimethyl-5'''-phosphonooxyphenyl)-3'',3''-dimethylpropionyl]-10-deacetyl-10-O-(ethoxycarbonyl)taxol.
7-O-[4-(phosphonooxy)butanoyl]-10-deacetyl-10-O(ethoxycarbonyl)taxol.
7-O-[3''-(2''''-phosphonooxyphenyl)-3'',3''-dimethylpropionyl]-10-deacetyl-10-O-(ethoxycarbonyl)taxol.
7-O-(4-phosphonooxy-3,3-dimethylbutanoyl)-10-deacetyl-10-O-(ethoxycarbonyl)taxol.
7-O-[(2''-phosphonooxyphenyl)acetyl]-10-deacetyl-10-O-(ethoxycarbonyl)taxol.
7-O-[3''-(2''''-phosphonooxy-4''',6'''-dimethylphenyl)-3'',3''-dimethylpropionyl]-10-deacetyl-10-O-(vinyloxycarbony)taxol.
7-O-[2''-(phosphonooxymethyl)benzoyl]-10-deacetyl-10-O-(vinyloxycarbonyl)taxol.
7-O-[3''-(2''''-acetoxy-4''',6'''-dimethyl-5'''-phosphonooxyphenyl)-3'',3''-dimethylpropionyl]-10-deacetyl-10-O-(vinyloxycarbonyl)taxol.
7-O-[4-(phosphonooxy)butanoyl]-10-deacetyl-10-O-(vinyloxycarbonyl)taxol.
7-O-[3''-(2''''-phosphonooxyphenyl)-3'',3''-dimethylpropionyl]-10-deacetyl-10-O-(vinyloxycarbonyl)taxol.
7-O-(4-phosphonooxy-3,3-dimethylbutanoyl)-10-deacetyl-10-O-(vinyloxycarbonyl)taxol.
7-O-[(2''-phosphonooxyphenyl)acetyl]-10-deacetyl-10-O-(vinyloxycarbonyl)taxol.
N-debenzoyl-N-t-butoxycarbonyl-2'-O-[3''-(2''''-phosphonooxy-4''',6'''-dimethylphenyl)-3'',3''-dimethylpropionyl]-7-deoxytaxol.
N-debenzoyl-N-t-butoxycarbonyl-2'-O-[2''-(phosphonooxymethyl)benzoyl]-7-deoxytaxol.
N-debenzoyl-N-t-butoxycarbonyl-2'-O-[3''-(2''''-acetoxy-4''',6'''-dimethyl-5'''-phosphonooxyphenyl)-3'',3''-dimethylpropionyl]-7-deoxytaxol.
N-debenzoyl-N-t-butoxycarbonyl-2'-O-[4-(phosphonooxy)butanoyl]-7-deoxytaxol.
N-debenzoyl-N-t-butoxycarbonyl-2'-O-[3''-(2''''-phosphonooxyphenyl)-3'',3''-dimethylpropionyl]-7deoxytaxol.
N-debenzoyl-N-t-butoxycarbonyl-2'-O-(4-phosphonooxy-3,3-dimethylbutanoyl)-7-deoxytaxol.
N-debenzoyl-N-t-butoxycarbonyl-2'-O-[(2''-phosphonooxyphenyl)acetyl]-7-deoxytaxol.
N-debenzoyl-N-t-butoxycarbonyl-2'-O-[3''-(2''''-phosphonooxy-4''',6'''-dimethylphenyl)-3'',3''-dimethylpropionyl]-7-deoxy-10-deacetyloxytaxol.
N-debenzoyl-N-t-butoxycarbonyl-2'-O-2''-(phosphonooxymethyl)benzoyl]-7-deoxy-10-deacetyloxytaxol.
N-debenzoyl-N-t-butoxycarbonyl-2'-O-[3''-(2''''-acetoxy-4''',6'''-dimethyl-5'''-phosphonooxyphenyl)-3'',3''-dimethylpropionyl]-7-deoxy-10-deacetyloxytaxol.
N-debenzoyl-N-t-butoxycarbonyl-2'-O-[4-(phosphonooxy)butanoyl]-7-deoxy-10-deacetyloxytaxol.
N-debenzoyl-N-t-butoxycarbonyl-2'-O-[3''-(2''''-phosphonooxyphenyl)-3'',3''-dimethylpropionyl]-7-deoxy-10-deacetyloxytaxol.
N-debenzoyl-N-t-butoxycarbonyl-2'-O-(4-phosphonooxy-3,3-dimethylbutanoyl)-7-deoxy-10-deacetyloxytaxol.
N-debenzoyl-N-t-butoxycarbonyl-2'-O-[(2''-phosphonooxyphenyl)acetyl]-7-deoxy-10-deacetyloxytaxol.
N-debenzoyl-N-t-butoxycarbonyl-7-O-[3''-(2''''-phosphonooxy-4''',6'''-dimethylphenyl)-3'',3''-dimethylpropionyl]-10-deacetyloxytaxol.
N-debenzoyl-N-t-butoxycarbonyl-7-O-[2''-(phosphonooxymethyl)benzoyl]-10-deacetyloxytaxol.
N-debenzoyl-N-t-butoxycarbonyl-7-O-[3''-(2''''-acetoxy-4''',6'''-dimethyl-5'''-phosphonooxyphenyl)-3'',3''-dimethylpropionyl]-10-deacetyloxytaxol.
N-debenzoyl-N-t-butoxycarbonyl-7-O-[4-(phosphonooxy)butanoyl]-10-deacetyloxytaxol.
N-debenzoyl-N-t-butoxycarbonyl-7-O-[3''-(2''''-phosphonooxyphenyl)-3'',3''-dimethylpropionyl]-10-deacetyloxytaxol.
N-debenzoyl-N-t-butoxycarbonyl-7-O-(4-phosphonooxy-3,3-dimethylbutanoyl)-10-deacetyloxytaxol.
N-debenzoyl-N-t-butoxycarbonyl-7-O-[2''-phosphonooxyphenyl)acetyl]-10-deacetyloxytaxol.
N-debenzoyl-N-t-butoxycarbonyl-10-deacetyl-10-O-[3''-2''-phosphonooxy-4''',6'''-dimethylphenyl)-3'',3''-dimethylpropionyl]-7-deoxytaxol.
N-debenzoyl-N-t-butoxycarbonyl-10-deacetyl-10-O-2''-(phosphonooxymethyl)benzoyl]-7-deoxytaxol.
N-debenzoyl-N-t-butoxycarbonyl-10-deacetyl-10-O-[3''-(2''''-acetoxy-4''',6'''-dimethyl-5'''-phosphonooxyphenyl)-3'',3''-dimethylpropionyl]-7deoxytaxol.
N-debenzoyl-N-t-butoxycarbonyl-10-deacetyl-10-O-[4-(phosphonooxy)butanoyl]-7-deoxytaxol.

N-debenzoyl-N-t-butoxycarbonyl-10-deacetyl-10-O-[3''-(2'''-phosphonooxyphenyl)-3'',3''-dimethylpropionyl]-7-deoxytaxol.

N-debenzoyl-N-t-butoxycarbonyl-10-deacetyl-10-O-(4-phosphonooxy-3,3-dimethylbutanoyl)-7-deoxytaxol.

N-debenzoyl-N-t-butoxycarbonyl-10-deacetyl-10-O-[(2''-phosphonooxyphenyl)acetyl]-7-deoxytaxol.

N-debenzoyl-N-t-butoxycarbonyl-2'-O-[3''-(2'''-phosphonooxy-4''',6'''-dimethylphenyl)-3'',3''-dimethylpropionyl]-7-deoxy-10-deacetyl-10-O-(benzyloxycarbony)taxol.

N-debenzoyl-N-t-butoxycarbonyl-2'-O-2''-(phosphonooxymethyl)benzoyl]-7-deoxy-10-deacetyl-10-O-(benzyloxycarbonyl)taxol.

N-debenzoyl-N-t-butoxycarbonyl-2'-O-[3''-(2'''-acetoxy-4''',6'''-dimethyl-5'''-phosphonooxyphenyl)-3'',3''-dimethylpropionyl]-7-deoxy-10-deacetyl-10-O-(benzyloxycarbonyl)taxol.

N-debenzoyl-N-t-butoxycarbonyl-2'-O-[4-(phosphonooxy)butanoyl]-7-deoxy-10-deacetyl-10-O-(benzyloxycarbonyl)taxol.

N-debenzoyl-N-t-butoxycarbonyl-2'-O-[3''-(2'''-phosphonooxyphenyl)-3'',3''-dimethylpropionyl]-7-deoxy-10-deacetyl-10-O-(benzyloxycarbonyl)taxol.

N-debenzoyl-N-t-butoxycarbonyl-2'-O-(4-phosphonooxy-3,3-dimethylbutanoyl)-7-deoxy-10-deacetyl-10-O-(benzyloxycarbonyl)taxol.

N-debenzoyl-N-t-butoxycarbonyl-2'-O-[(2''-phosphonooxyphenyl)acetyl]-7-deoxy-10-deacetyl-10-O-(benzyloxycarbonyl)taxol.

N-debenzoyl-N-t-butoxycarbonyl-2'-O-[3''-(2'''-phosphonooxy-4''',6'''-dimethylphenyl)-3'',3''-dimethylpropionyl]-7-deoxy-10-deacetyl-10-O-(ethoxycarbony)taxol.

N-debenzoyl-N-t-butoxycarbonyl-2'-O-[2''-(phosphonooxymethyl)benzoyl]-7-deoxy-10-deacetyl-10-O-(ethoxycarbonyl)taxol.

N-debenzoyl-N-t-butoxycarbonyl-2'-O-[3''-(2'''-acetoxy-4''',6'''-dimethyl-5'''-phosphonooxyphenyl)-3'',3''-dimethylpropionyl]-7-deoxy-10-deacetyl-10-O-(ethoxycarbonyl)taxol.

N-debenzoyl-N-t-butoxycarbonyl-2'-O-[4-(phosphonooxy)butanoyl]-7-deoxy-10-deacetyl-10-O-(ethoxycarbonyl)taxol.

N-debenzoyl-N-t-butoxycarbonyl-2'-O-[3''-(2'''-phosphonooxyphenyl)-3'',3''-dimethylpropionyl]-7-deoxy-10-deacetyl-10-O-(ethoxycarbonyl)taxol.

N-debenzoyl-N-t-butoxycarbonyl-2'-O-(4-phosphonooxy-3,3-dimethylbutanoyl)-7-deoxy-10-deacetyl-10-O-(ethoxycarbonyl)taxol.

N-debenzoyl-N-t-butoxycarbonyl-2'-O-[(2''-phosphonooxyphenyl)acetyl]-7-deoxy-10-deacetyl-10-O-(ethoxycarbonyl)taxol.

N-debenzoyl-N-t-butoxycarbonyl-2'-O-[3''-(2'''-phosphonooxy-4''',6'''-dimethylphenyl)-3'',3''-dimethylpropionyl]-7-deoxy-10-deacetyl-10-O-(vinyloxycarbony)taxol.

N-debenzoyl-N-t-butoxycarbonyl-2'-O-[2''-(phosphonooxymethyl)benzoyl]-7-deoxy-10-deacetyl-10-O-(vinyloxycarbonyl)taxol.

N-debenzoyl-N-t-butoxycarbonyl-2'-O-[3''-(2'''-acetoxy-4''',6'''-dimethyl-5'''-phosphonooxyphenyl)-3'',3''-dimethylpropionyl]-7-deoxy-10-deacetyl-10-O-(vinyloxycarbonyl)taxol.

N-debenzoyl-N-t-butoxycarbonyl-2'-O-[4-(phosphonooxy)butanoyl]-7-deoxy-10-deacetyl-10-O-(vinyloxycarbonyl)taxol.

N-debenzoyl-N-t-butoxycarbonyl-2'-O-[3''-(2'''-phosphonooxyphenyl)-3'',3''-dimethylpropionyl]-7-deoxy-10-deacetyl-10-O-(vinyloxycarbonyl)taxol.

N-debenzoyl-N-t-butoxycarbonyl-2'-O-(4-phosphonooxy-3,3-dimethylbutanoyl)-7-deoxy-10-deacetyl-10-O-(vinyloxycarbonyl)taxol.

N-debenzoyl-N-t-butoxycarbonyl-2'-O-[(2''-phosphonooxyphenyl)acetyl]-7-deoxy-10-deacetyl-10-O-(vinyloxycarbonyl)taxol.

N-debenzoyl-N-t-butoxycarbonyl-2'-O-[3''-(2'''-phosphonooxy-4''',6'''-dimethylphenyl)-3'',3''-dimethylpropionyl]-10-deacetyl-10-O-(benzyloxycarbony)taxol.

N-debenzoyl-N-t-butoxycarbonyl-2'-O-[2''-(phosphonooxymethyl)benzoyl]-10-deacetyl-10-O-(benzyloxycarbonyl)taxol.

N-debenzoyl-N-t-butoxycarbonyl-2'-O-[3''-(2'''-acetoxy-4''',6'''-dimethyl-5'''-phosphonooxyphenyl)-3'',3''-dimethylpropionyl]-10-deacetyl-10-O-(benzyloxycarbonyl)taxol.

N-debenzoyl-N-t-butoxycarbonyl-2'-O-[4-(phosphonooxy)butanoyl]-10-deacetyl-10-O-(benzyloxycarbonyl)taxol.

N-debenzoyl-N-t-butoxycarbonyl-2'-O-[3''-(2'''-phosphonooxyphenyl)-3'',3''-dimethylpropionyl]-10-deacetyl-10-O-(benzyloxycarbonyl)taxol.

N-debenzoyl-N-t-butoxycarbonyl-2'-O-(4-phosphonooxy-3,3-dimethylbutanoyl)-10-deacetyl-10-O-(benzyloxycarbonyl)taxol.

N-debenzoyl-N-t-butoxycarbonyl-2'-O-[(2''-phosphonooxyphenyl)acetyl]-10-deacetyl-10-O-(benzyloxycarbonyl)taxol.

N-debenzoyl-N-t-butoxycarbonyl-2'-O-[3''-(2'''-phosphonooxy-4''',6'''-dimethylphenyl)-3'',3''-dimethylpropionyl]-10-deacetyl-10-O-(ethoxycarbony)taxol.

N-debenzoyl-N-t-butoxycarbonyl-2'-O-[2''-(phosphonooxymethyl)benzoyl]-10-deacetyl-10-O-(ethoxycarbonyl)taxol.

N-debenzoyl-N-t-butoxycarbonyl-2'-O-[3''-(2'''-acetoxy-4''',6'''-dimethyl-5'''-phosphonooxyphenyl)-3'',3''-dimethylpropionyl]-10-deacetyl-10-O-(ethoxycarbonyl)taxol.

N-debenzoyl-N-t-butoxycarbonyl-2'-O-[4-(phosphonooxy)butanoyl]-10-deacetyl-10-O-(ethoxycarbonyl)taxol.

N-debenzoyl-N-t-butoxycarbonyl-2'-O-[3''-(2'''-phosphonooxyphenyl)-3'',3''-dimethylpropionyl]-10-deacetyl-10-O-(ethoxycarbonyl)taxol.

N-debenzoyl-N-t-butoxycarbonyl-2'-O-(4-phosphonooxy-3,3-dimethylbutanoyl)-10-deacetyl-10-O-(ethoxycarbonyl)taxol.

N-debenzoyl-N-t-butoxycarbonyl-2'-O-[(2''-phosphonooxyphenyl)acetyl]-10-deacetyl-10-O-(ethoxycarbonyl)taxol.

N-debenzoyl-N-t-butoxycarbonyl-2'-O-[3''-(2'''-phosphonooxy-4''',6'''-dimethylphenyl)-3'',3''-dimethylpropionyl]-10-deacetyl-10-O-(vinyloxycarbony)taxol.

N-debenzoyl-N-t-butoxycarbonyl-2'-O-[2''-(phosphonooxymethyl)benzoyl]-10-deacetyl-10-O-(vinyloxycarbonyl)taxol.

N-debenzoyl-N-t-butoxycarbonyl-2'-O-[3''-(2'''-acetoxy-4''',6'''-dimethyl-5'''-phosphonooxyphenyl)-3'',3''-dimethylpropionyl]-10-deacetyl-10-O-(vinyloxycarbonyl)taxol.

N-debenzoyl-N-t-butoxycarbonyl-2'-O-[4-(phosphonooxy)butanoyl]-10-deacetyl-10-O-(vinyloxycarbonyl)taxol.

N-debenzoyl-N-t-butoxycarbonyl-2'-O-[3''-(2'''-phosphonooxyphenyl)-3'',3''-dimethylpropionyl]-10-deacetyl-10-O-(vinyloxycarbonyl)taxol.

N-debenzoyl-N-t-butoxycarbonyl-2'-O-(4-phosphonooxy-3,3-dimethylbutanoyl)-10-deacetyl-10-O-(vinyloxycarbonyl)taxol.

N-debenzoyl-N-t-butoxycarbonyl-2'-O-[(2''-phosphonooxyphenyl)acetyl]-10-deacetyl-10-O-(vinyloxycarbonyl)taxol.

N-debenzoyl-N-t-butoxycarbonyl-7-O-[3''-(2'''-phosphonooxy-4''',6'''-dimethylphenyl)-3'',3''-dimethylpropionyl]-10-deacetyl-10-O-(benzyloxycarbony)taxol.

N-debenzoyl-N-t-butoxycarbonyl-7-O-[2''-(phosphonooxymethyl)benzoyl]-10-deacetyl-10-O-(benzyloxycarbonyl)taxol.

N-debenzoyl-N-t-butoxycarbonyl-7-O-[3''-(2'''-acetoxy-4''',6'''-dimethyl-5'''-phosphonooxyphenyl)-3'',3''-dimethylpropionyl]-10-deacetyl-10-O-(benzyloxycarbonyl)taxol.

N-debenzoyl-N-t-butoxycarbonyl-7-O-[4-(phosphonooxy)butanoyl]-10-deacetyl-10-O-(benzyloxycarbonyl)taxol.

N-debenzoyl-N-t-butoxycarbonyl-7-O-[3''-(2'''-phosphonooxyphenyl)-3'',3''-dimethylpropionyl]-10-deacetyl-10-O-(benzyloxycarbonyl)taxol.

N-debenzoyl-N-t-butoxycarbonyl-7-O-(4-phosphonooxy-3,3-dimethylbutanoyl)-10-deacetyl-10-O-(benzyloxycarbonyl)taxol.

N-debenzoyl-N-t-butoxycarbonyl-7-O-[(2''-phosphonooxyphenyl)acetyl]-10-deacetyl-10-O-(benzyloxycarbonyl)taxol.

N-debenzoyl-N-t-butoxycarbonyl-7-O-[3''-(2'''-phosphonooxy-4''',6'''-dimethylphenyl)-3'',3''-dimethylpropionyl]-10-deacetyl-10-O-(ethoxycarbony)taxol.

N-debenzoyl-N-t-butoxycarbonyl-7-O-[2''-(phosphonooxymethyl)benzoyl]-10-deacetyl-10-O-(ethoxycarbonyl)taxol.

N-debenzoyl-N-t-butoxycarbonyl-7-O-[3''-(2'''-acetoxy-4''',6'''-dimethyl-5'''-phosphonooxyphenyl)-3'',3''-dimethylpropionyl]-10-deacetyl-10-O-(ethoxycarbonyl)taxol.

N-debenzoyl-N-t-butoxycarbonyl-7-O-[4-(phosphonooxy)butanoyl]-10-deacetyl-10-O-(ethoxycarbonyl)taxol.

N-debenzoyl-N-t-butoxycarbonyl-7-O-[3''-(2''-phosphonooxyphenyl)-3'',3''-dimethylpropionyl]-10-deacetyl-10-O-(ethoxycarbonyl)taxol.

N-debenzoyl-N-t-butoxycarbonyl-7-O-(4-phosphonooxy-3,3-dimethylbutanoyl)-10-deacetyl-10-O-(ethoxycarbonyl)taxol.

N-debenzoyl-N-t-butoxycarbonyl-7-O-[(2''-phosphonooxyphenyl)acetyl]-10-deacetyl-10-O-(ethoxycarbonyl)taxol.

N-debenzoyl-N-t-butoxycarbonyl-7-O-[3''-(2'''-phosphonooxy-4''',6'''-dimethylphenyl) -3'',3''-dimethylpropionyl]-10-deacetyl-10-O-(vinyloxycarbony)taxol.

N-debenzoyl-N-t-butoxycarbonyl-7-O-[2''-(phosphonooxymethyl)benzoyl]-10-deacetyl-10-O-(vinyloxycarbonyl)taxol.

N-debenzoyl-N-t-butoxycarbonyl-7-O-[3''-(2'''-acetoxy-4''',6'''-dimethyl-5'''-phosphonooxyphenyl)-3'',3''-dimethylpropionyl]-10-deacetyl-10-O-(vinyloxycarbonyl)taxol.

N-debenzoyl-N-t-butoxycarbonyl-7-O-[4-(phosphonooxy)butanoyl]-10-deacetyl-10-O-(vinyloxycarbonyl)taxol.

N-debenzoyl-N-t-butoxycarbonyl-7-O-[3''-(2'''-phosphonooxyphenyl)-3'',3''-dimethylpropionyl]-10-deacetyl-10-O-(vinyloxycarbonyl)taxol.

N-debenzoyl-N-t-butoxycarbonyl-7-O-(4-phosphonooxy-3,3-dimethylbutanoyl)-10-deacetyl-10-O-(vinyloxycarbonyl)taxol.

N-debenzoyl-N-t-butoxycarbonyl-7-O-](2''-phosphonooxyphenyl)acetyl]-10-deacetyl-10-O-(vinyloxycarbonyl)taxol.

BIOLOGICAL DATA

Mice M109 Model

Balb/c×DBA/2 $F_1$ hybrid mice were implanted intraperitoneally, as described by William Rose in Evaluation of Madison 109 Lung Carcinoma as a Model for Screening Antitumor Drugs, *Cancer Treatment Reports*, 65, No. 3–4 (1981), with 0.5 mL of a 2% (w/v) brei of M109 lung carcinoma.

Mice were treated with compound under study by receiving intraperitoneal injections of various doses on either days 1, 5 and 9 post-tumor implant or days 5 and 8 post-implant. Mice were followed daily for survival until approximately 75–90 days post-tumor implant. One group of mice per experiment remained untreated and served as the control group.

Median survival times of compound-treated (T) mice were compared to the median survial time of the control (C) mice. The ratio of the two values for each compound-treated group of mice was multiplied by 100 and expressed as a percentage (i.e. % T/C) in Table I for representative compounds.

TABLE I

| Compound | IP M109 data |
|---|---|
| | % T/C (dose in mg/kg/injection; schedule) |
| Is | 138 (80; d. 5 + 8) |
| Id | 156 (140; d. 5 + 8) |
| Ix dissodium salt | 135 (160; d. 5 + 8) |
| Ib | 144 (100; d. 1, 5 + 9) |
| | 138 (40; d. 1, 5 + 9) |
| Ic | 310 (50; d. 1, 5 + 9) |
| | (1/6 cured) |
| Ie | >450 (60; d. 1, 5 + 9) |
| | (6/6 cured) |
| If | 197 (90; d. 5 + 8) |
| Ig | 275 (60; d. 1, 5 + 9) |
| Ih | 294 (60; d. 1, 5 + 9) |
| | (1/6 cured) |
| Ii | >475 (60; d. 1, 5 + 9) |
| | (4/6 cured) |
| Ij dissodium salt | 185 (80; d. 5 + 8) |
| Ik tartarate salt | 226 (80; d. 5 + 8) |
| Im | 203 (80; d. 5 + 8) |
| In | 235 (80; d. 5 + 8) |
| Io | 162 (90; d. 5 + 8) |
| Ip | 203 (40; d. 5 + 8) |
| Iq | 168 (180; d. 5 + 8) |
| Ivv | 206 (80; d. 5 + 8) |
| Iv | 185 (180; d. 5 + 8) |
| Ihh | 247 (100; d. 5 + 8) |

Sc M109 Protocol

Balb/c×DBAl$_2$ $F_1$ hybrid mice were implanted subcutaneously (sc), as described by W. Rose in Evaluation of Madison 109 Lung Carcinoma as a Model for Screening Antitumor Drugs, *Cancer Treatment Reports*, 65, No. 3-4 (1981), with 0.1 ml of a 2% (w/v) brei of M109 lung carcinoma.

Mice were treated with the compounds under study by receiving intravenous injections (or intraperitoneal injections if not sufficiently soluble) of various doses on Days 4, 5, 6, 7, and 8 post-implant (i.e., qd 4-8). Mice were followed daily for survival until their death or Day 75, whichever occurred first. One group of mice per experiment remained untreated and served as the control. Tumors were also measured once or twice weekly and the size in mm was used to estimate tumor weight according to the published procedure (ibid).

Median survival times of compound-treated (T) mice were compared to the median survival time of parallel control (C) mice. The ratio of the two values for each compound-treated group of mice was multiplied by 100 and expressed as a percentage (i.e., % T/C) in Table II for representative compounds. Additionally, the relative median times for T and C groups of mice to grow tumors of 1 gm, expressed as T-C values in days, are also shown in Table II. The greater the T-C value, the greater was the delay in primary tumor growth caused by each compound.

Activity in this model was reflected by a % T/C of ≧125% and/or typically a T-C of ≧4.0 days, depending upon control titration data generated in each experiment (ibid).

TABLE II

| Compound | Maximum % T/C | T-C (days) | Dose (mg/kg/m;), Route |
|---|---|---|---|
| Id | 254 | 34.8 | 36, iv |
| Ic | 112 | 2.3 | 13, ip |
| Ie | 168 | 16.0 | 30, iv |
| Ii | 127 | 12.0 | 48, ip |
| Ij dissodium salt | 138 | 18.0 | 40, iv |
| Ivv | 114 | 6.0 | 23, iv |
| It dissodium salt | 164 | 12.0 | 40, iv |
| Iy | 129 | 9.0 | 61, iv |
| Iz | 111 | 8.3 | 46, iv |
| Iaa | 144 | 10.3 | 40, iv |
| Ibb | 106 | 1.5 | 33, iv |
| Idd | 110 | 1.5 | 34, iv |
| Iee | 142 | 16.5 | 51, iv |
| Igg | 100 | 5.8 | 20, iv |
| Ikk | 137 | 7.8 | 56, iv |
| Inn | 139 | 16.8 | 50, iv |

The compounds of the instant invention have tumor inhibiting activities in mammals. Thus, another aspect of the instant invention concerns with a method for inhibiting mammalian tumors sensitive to a compound of formula I.

The present invention also provides pharmaceutical formulations (compositions) containing a compound of formula I in combination with one or more pharmaceutically acceptable, inert or physiologically active, carriers, excipients, diluents or adjuvants. Examples of formulating taxol or its related derivatives (including a possible dosage) are described in numerous literatures, for example in U.S. Pat. Nos. 4,960,790 and 4,814,470, and such examples may be followed to formulate the compounds of this invention. For example, the new compounds are administrable in the form of tablets, pills, powder mixtures, capsules, injectables, solutions, suppositories, emulsions, dispersions, food premix, and in other suitable forms. The pharmaceutical preparation which contains the compound is conveniently admixed with a nontoxic pharmaceutical organic carrier or a nontoxic pharmaceutical inorganic carrier, usually about 0.01 mg up to 2500 mg, or higher per dosage unit, preferably 50-500 mg. Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The compounds of present invention can be used as taxol for treating mammalian tumors. The mode, dosage and schedule of administration of taxol in human cancer, patients have been extensively studied. See, for example *Ann. Int. Med.*, 111, pp 273-279 (1989). For the compounds of this invention, the dose to be administered, whether a single dose, multiple dose, or a daily dose, will of course vary with the particular compound employed because of the varying potency of the compound, the chosen route of administration, the size of the recipient and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. The dosage to be administered will be generally in the range of 0.8 to 8 mg/kg of body weight or about 50-275 mg/m$^2$ of the patient. An oncologist skilled in the art of cancer treatment will be able to ascertain, without undue experimentation, appropriate protocols for effective administration of the compounds of this present invention such as by referring to the earlier studies of taxol and its derivatives.

What is claimed is:

1. A compound of formula I

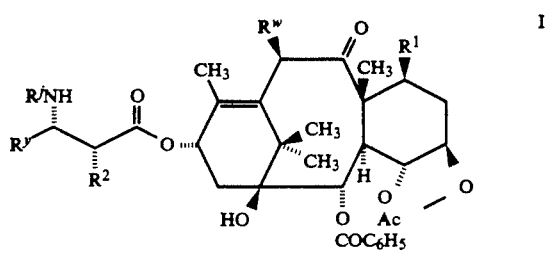

or a pharmaceutically acceptable salt thereof, in which $R^j$ is —COR² in which R² is t-butyloxy, $C_{1-6}$ alkyl, $C_{2-6}$ alkenyl, $C_{2-6}$ alkynyl, $C_{3-6}$ cycloalkyl, or phenyl, optionally substituted with one to three same or different $C_{1-6}$ alkyl, $C_{1-6}$ alkoxy, halogen or —CF₃ groups;

$R^y$ is $C_{1-6}$ alkyl, $C_{2-6}$ alkenyl, $C_{2-6}$ alkynyl, $C_{3-6}$ cycloalkyl, or a radical of the formula —W—R$^x$ in which W is a bond, $C_{2-6}$ alkenediyl, or —(CH₂)$_t$—, in which t is one to six; and R$^x$ is naphthyl, furyl, thienyl or phenyl, and furthermore R$^x$ can be optionally substituted with one to three same or different $C_{1-6}$ alkyl, $C_{1-6}$ alkoxy, halogen or —CF₃ groups;

$R^w$ is hydrogen, hydroxy, acetyloxy, —OC(=O)OY or —OZ;

$R^1$ is hydrogen, hydroxy, —OC(=O)OY or —OZ; $R^2$ is hydroxy, —OC(=O)OY, —OC(=O)R or —OZ, with the proviso at least one of $R^1$, $R^2$ or $R^w$ is —OC(=O)OY or —OZ;

R is $C_{1-6}$ alkyl;

Z is of the formula

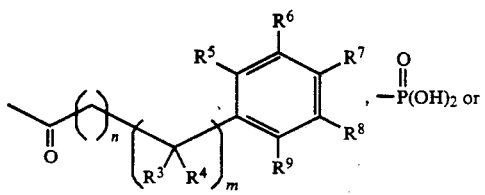, —P̈(OH)₂ or

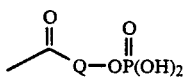

wherein $R^3$ and $R^4$ are independently hydrogen or $C_{1-6}$ alkyl, or $R^3$ and $R^4$ taken together with the carbon atom to which they are attached form $C_{3-6}$ cycloalkylidene;

$R^5$ is —OC(=O)R, —OP=O(OH)₂ or —CH₂OP=O(OH)₂;

$R^6$, $R^7$, $R^8$ and $R^9$ are independently halogen, $C_{1-6}$ alkyl, $C_{1-6}$ alkoxy or hydrogen; or one of $R^6$, $R^7$, $R^8$ and $R^9$ is —OC(=O)R, —OP=O(OH)₂ or hydroxy, and the others are independently halogen, $C_{1-6}$ alkyl, $C_{1-6}$ alkoxy or hydrogen; but when $R^5$ is —OC(=O)R, one of $R^6$, $R^7$, $R^8$ or $R^9$ must be —OP=O(OH)₂;

Q is —(CH₂)$_q$—, optionally substituted with one to six same or different $C_{1-6}$ alkyl or $C_{3-6}$ cycloalkyl, or a carbon atom of said —(CH₂)$_q$— group can also be a part of $C_{3-6}$ cycloalkylidene;

q is 2 to 6; n is 0, and m is 1 or 0 when $R^5$ is —CH₂OP=O(OH)₂; n is 1 or 0, and m is 1 when $R^5$ is —OC(=O)R or —OP=O(OH)₂;

Y is $C_{1-6}$ alkyl (optionally substituted with —OP=O(OH)₂ or one to six same or different halogen atoms), $C_{3-6}$ cycloalkyl, $C_{2-6}$ alkenyl, or a radical of the formula

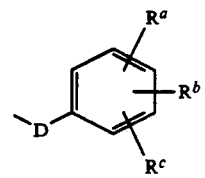

in which

D is a bond or —(CH₂)$_r$—, optionally substituted with one to six same or different $C_{1-6}$ alkyl; and R$^a$, R$^b$ and R$^c$ are independently hydrogen, amino, $C_{1-6}$alkylamino, di-$C_{1-6}$alkylamino, halogen, $C_{1-6}$ alkyl, or $C_{1-6}$ alkoxy; and with the further proviso that R² cannot be —OP=O(OH)₂; Y cannot be —CH₂CCl₃; and R¹ cannot be

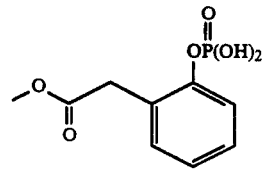

2. A compound of claim 1 in which R$^j$ is benzoyl or t-butyloxycarbonyl; and R$^y$ is phenyl.

3. A compound of claim 2 in which $R^3$ and $R^4$ are independently hydrogen or $C_{1-6}$ alkyl; $R^6$, $R^7$, $R^8$ and $R^9$ are independently $C_{1-6}$ alkyl or hydrogen; but when $R^5$ is —OC(=O)R, one of $R^6$, $R^7$, $R^8$ or $R^9$ must be —OP=O(OH)₂, and the others are independently $C_{1-6}$ alkyl or hydrogen; Q is —(CH₂)$_q$—, optionally substituted with one to six same or different $C_{1-6}$ alkyl; Y is $C_{1-6}$ alkyl (optionally substituted with —OP=O(OH)₂ or one to six same or different halogen atoms), $C_{2-6}$ alkenyl, or a radical of the formula

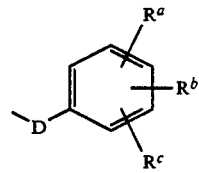

in which

D is a bond or —(CH₂)$_r$—; and R$^a$, R$^b$ and R$^c$ are independently hydrogen, di-$C_{1-6}$alkylamino, or $C_{1-6}$ alkyl.

4. A compound of claim 3 in which R$^j$ is benzoyl; and R$^w$ is acetyloxy.

5. A compound of claim 4 in which R¹ is hydroxy or —OZ, and R² is hydroxy or —OZ, with the proviso that at least one of R¹ or R² is —OZ.

6. The compound of claim 5 that is 2′-O-[3″-(2‴-phosphonooxy-4‴,6‴-dimethylphenyl)-3″,3″-dimethylpropionyl]taxol.

7. The compound of claim 5 that is 7-O-[3″-(2‴-phosphonooxy-4‴,6‴-dimethylphenyl)-3″,3″-dimethylpropionyl]taxol.

8. The compound of claim 5 that is 2″-O-[2″-(phosphonooxymethyl)benzoyl]taxol.

9. The compound of claim 5 that is 2′-O-[3″-(2‴-acetoxy-4‴,6‴-dimethyl-5‴-phosphonooxyphenyl)-3″,3″-dimethylpropionyl]taxol.

10. The compound of claim 5 that is 2'-O-[4(phosphonooxy)butanoyl]taxol.

11. The compound of claim 5 that is 7-O-[4-(phosphonooxy)butanoyl]taxol.

12. The compound of claim 5 that is 2'-O-[3''-(2'''-phosphonooxyphenyl)-3'',3''-dimethylpropionyl]taxol.

13. The compound of claim 5 that is 2'-O-(4-phosphonooxy-3,3-dimethylbutanoyl)taxol.

14. The compound of claim 5 that is 7-O-(4-phosphonooxy-3,3-dimethylbutanoyl)taxol.

15. The compound of claim 5 that is 2'-O-[(2''-phosphonooxyphenyl)acetyl]taxol.

16. A compound of claim 4 in which R is hydroxy, and $R^2$ is —OC(=O)OY.

17. The compound of claim 16 that is 2'-O-(benzyloxycarbonyl)taxol.

18. The compound of claim 16 that is 2'-O-(ethoxycarbonyl)taxol.

19. The compound of claim 16 that is 2'-O-(allyloxycarbonyl)taxol.

20. The compound of claim 16 that is 2'-O-[(chloromethoxy)carbonyl]taxol.

21. The compound of claim 16 that is 2'-O-[(1-chloroethoxy)carbonyl]taxol.

22. The compound of claim 16 that is 2'-O-(vinyloxycarbonyl)taxol.

23. The compound of claim 16 that is 2'-O-[[3-(dimethylamino)phenoxy]carbonyl]taxol.

24. The compound of claim 16 that is 2'-O-(phenoxycarbonyl)taxol.

25. The compound of claim 16 that is 2'-O-[(1-methylethenyloxy)carbonyl]taxol.

26. The compound of claim 16 that is 2'-O-(methoxycarbonyl)taxol.

27. The compound of claim 16 that is 2'-O-[(2-chloroethoxy)carbonyl]taxol.

28. The compound of claim 16 that is 2'-O-[(4-methylphenoxy)carbonyl]taxol.

29. The compound of claim 16 that is 2'-O-[(iodomethoxy)carbonyl]taxol.

30. The compound of claim 16 that is 2'-O-[[4-(phosphonooxy)butoxy]carbonyl]taxol.

31. The compound of claim 16 that is 2'-O-(isopropyloxycarbonyl)taxol.

32. A compound of claim 4 in which $R^1$ is —OZ, and $R^2$ is —OC(=O)OY.

33. The compound of claim 32 that is 2'-O-ethoxycarbonyl-7-O-[3''-(2'''-phosphonooxy-4''',6'''-dimethylphenyl)-3'',3''-dimethylpropionyl]taxol.

34. The compound of claim 32 that is 2'-O-methoxycarbonyl-7-O-phosphonotaxol.

35. The compound of claim 32 that is 2'-[O-3-(dimethylamino)phenoxy]carbonyl-7-O-3''-(2'''-phosphonooxy-4''',6'''-dimethylphenyl)-3'',3''-dimethylpropionyl]taxol.

36. The compound of claim 32 that is 2'-O-isopropylcarbonyl-7-O-[3''-(2'''-phosphonooxy-4''',6'''-dimethylphenyl)-3'',3''-dimethylpropionyl]taxol.

37. The compound of claim 32 that is 2'-O-ethoxycarbonyl-7-O-[2''-(phosphonooxymethyl)benzoyl]taxol.

38. A compound of claim 4 in which $R^1$ is —OZ, and $R^2$ is —OC(=O)R.

39. The compound of claim 38 that is 2'-O-acetyl-7-O-[3''-(4''',6'''-dimethyl-2'''-phosphonooxyphenyl)-3'',3''-dimethylpropionyl]taxol.

40. A compound of formula I

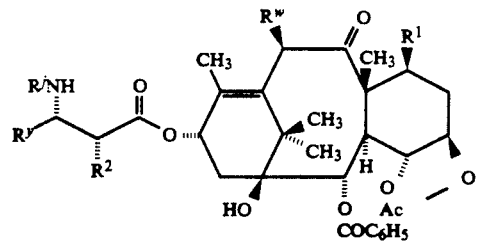

or a pharmaceutically acceptable salt thereof, in which $R^j$ is —$COR^z$ in which $R^z$ is t-butyloxy, $C_{1-6}$ alkyl, $C_{2-6}$ alkenyl, $C_{2-6}$ alkynyl, $C_{3-6}$ cycloalkyl, or phenyl, optionally substituted with one to three same or different $C_{1-6}$ alkyl, $C_{1-6}$ alkoxy, halogen or —$CF_3$ groups;

$R^y$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, furyl, thienyl or phenyl, and furthermore $R^x$ can be optionally substituted with one to three same or different $C_{1-6}$ alkyl, $C_{1-6}$ alkoxy, halogen or —$CF_3$ groups;

$R^w$ is hydrogen, hydroxy, acetyloxy, —OC(=O)OY or —OZ;

$R^1$ is of the formula

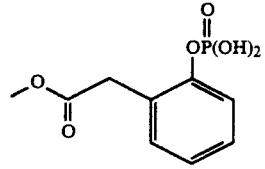

$R^2$ is hydroxy, —OC(=O)OY, —OC(=O)R or —OZ;

R is $C_{1-6}$ alkyl;

Z is of the formula

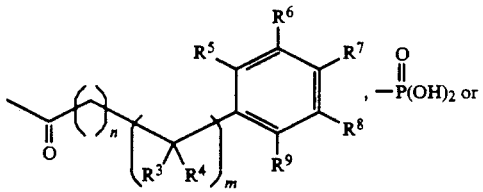

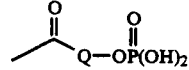

wherein $R^3$ and $R^4$ are independently hydrogen or $C_{1-6}$ alkyl, or $R^3$ and $R^4$ taken together with the carbon atom to which they are attached form $C_{3-6}$ cycloalkylidene;

$R^5$ is —OC(=O)R, —OP=O(OH)$_2$ or —CH$_2$OP=O(OH)$_2$;

$R^6$, $R^7$, $R^8$ and $R^9$ are independently halogen, $C_{1-6}$ alkyl, $C_{1-6}$ alkoxy or hydrogen; or one of $R^6$, $R^7$, $R^8$ and $R^9$ is —OC(=O)R, —OP=O(OH)$_2$ or hydroxy, and the others are independently halogen, $C_{1-6}$ alkyl, $C_{1-6}$ alkoxy or hydrogen; but when $R^5$ is —OC(=O)R, one of $R^6$, $R^7$, $R^8$ or $R^9$ must be —OP=O(OH)$_2$;

Q is —(CH$_2$)$_q$—, optionally substituted with one to six same or different C$_{1-6}$ alkyl or C$_{3-6}$ cycloalkyl, or a carbon atom of said —(CH$_2$)$_q$— group can also be a part of C$_{3-6}$ cycloalkylidene;

q is 2 to 6; n is 0, and m is 1 or 0 when $R^5$ is —CH$_2$OP=O(OH)$_2$; n is 1 or 0, and m is 1 when $R^5$ is —OC(=O)R or —OP=O(OH)$_2$;

Y is C$_{1-6}$ alkyl (optionally substituted with —OP=O(OH)$_2$ or one to six same or different halogen atoms), C$_{3-6}$ cycloalkyl, C$_{2-6}$ alkenyl, or a radical of the formula

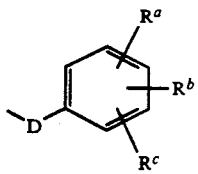

in which

D is a bond or —(CH$_2$)$_r$—, optionally substituted with one to six same or different C$_{1-6}$ alkyl; and $R^a$, $R^b$ and $R^c$ are independently hydrogen, amino, C$_{1-6}$alkylamino, di-C$_{1-6}$alkylamino, halogen, C$_{1-6}$ alkyl, or C$_{1-6}$ alkoxy; and with the further proviso that $R^2$ cannot be —OP=O(OH)$_2$; and Y cannot be —CH$_2$CCl$_3$.

41. A compound of claim 1 in which $R^j$ is benzoyl or t-butyloxycarbonyl; and $R^y$ is phenyl.

42. A compound of claim 41 in which $R^3$ and $R^4$ are independently hydrogen or C$_{1-6}$ alkyl; $R^6$, $R^7$, $R^8$ and $R^9$ are independently C$_{1-6}$ alkyl or hydrogen; but when $R^5$ is —OC(=O)R, one of $R^6$, $R^7$, $R^8$ or $R^9$ must be —OP=O(OH)$_2$, and the others are independently C$_{1-6}$ alkyl or hydrogen; Q is —(CH$_2$)$_q$—, optionally substituted with one to six same or different C$_{1-6}$ alkyl; Y is C$_{1-6}$ alkyl (optionally substituted with —OP=O(OH)$_2$ or one to six same or different halogen atoms), C$_{2-6}$ alkenyl, or a radical of the formula

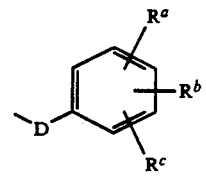

in which

D is a bond or —(CH$_2$)$_r$—; and $R^a$, $R^b$ and $R^c$ are independently hydrogen, di-C$_{1-6}$alkylamino, or C$_{1-6}$ alkyl.

43. A compound of claim 42 in which $R^j$ is benzoyl; and $R^w$ is acetyloxy.

44. A compound of claim 43 in which $R^2$ is hydroxy or —OZ.

45. The compound of claim 44 that is 7-O-[(2″-phosphonooxyphenyl)acetyl]taxol.

46. The compound of claim 44 that is 2′,7-O-bis[(2″-phosphonooxyphenyl)acetyl]taxol.

47. A compound of claim 43 in which $R^2$ is —OC(=O)OY.

48. The compound of claim 47 that is 2′-O-ethoxycarbonyl-7-O-[(2″-phosphonooxyphenyl)acetyl]taxol.

49. A compound of claim 43 in which $R^2$ is —OC(=O)R.

50. The compound of claim 49 that is 2′-O-acetyl-7-O-[(2″-phosphonooxyphenyl)acetyl]taxol.

51. A pharmaceutical formulation which comprises as an active ingredient a compound as claimed in any one of claims 1 to 50, or a pharmaceutically acceptable salt thereof, associated with one or more pharmaceutically acceptable carriers, excipients or diluents therefor.

52. A method for treating mammalian tumors which comprises administering to a mammal a tumor sensitive amount of a compound as claimed in any one of claims 1 to 50.

* * * * *

UNITED STATES PATENT AND TRADEMARK OFFICE
CERTIFICATE OF CORRECTION

PATENT NO. : 5,272,171

DATED : December 21, 1993

INVENTOR(S): Yasutsugu Ueda, Henry Wong, Vittorio Farina, Amarendra Mikkilineni, Dolatria M. Vyas, and Terrence Doyle It is certified that errors appears in the above-identified patent and that said Letters Patent is hereby corrected as shown below:

Columns 156 and 160 of taxane structures of formula I

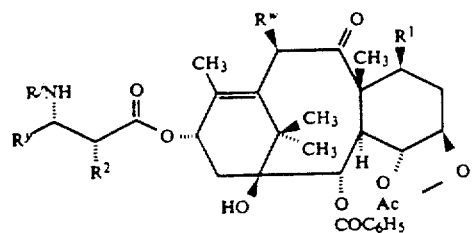   should read   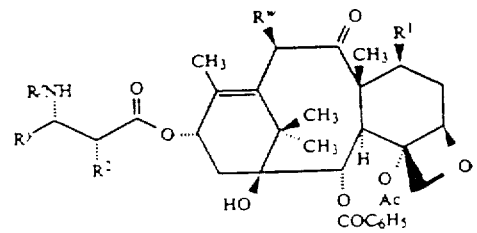

UNITED STATES PATENT AND TRADEMARK OFFICE
CERTIFICATE OF CORRECTION

PATENT NO. : 5,272,171

DATED : December 21, 1993

INVENTOR(S) : Yasutsugu Ueda, Henry Wong, Vittorio Farina, Amarendra Mikkilineni, Dolatria M. Vyas, and Terrence Doyle It is certified that error appears in the above-identified patent and that said Letters Patent is hereby corrected as shown below:

Likewise, the same error in the structural formulas of taxanes appears throughout the entire specification; thus, all taxane structures should include a bond from the $C_4$ position to form an oxetane ring.

Signed and Sealed this

Seventeenth Day of May, 1994

BRUCE LEHMAN

*Attest:*

*Attesting Officer*   *Commissioner of Patents and Trademarks*